(12) United States Patent
Kuo et al.

(10) Patent No.: US 11,912,776 B2
(45) Date of Patent: Feb. 27, 2024

(54) CHIMERIC ANTIGEN RECEPTORS TARGETING B-CELL MATURATION ANTIGEN

(71) Applicant: Pfizer Inc., New York, NY (US)

(72) Inventors: Tracy Chia-Chien Kuo, San Mateo, CA (US); Bijan Andre Boldajipour, San Francisco, CA (US); Javier Fernando Chaparro Riggers, San Mateo, CA (US); Philippe Duchateau, Draveil (FR); Roman Galetto, Paris (FR); Alexandre Juillerat, New York, NY (US); Thomas Charles Pertel, San Mateo, CA (US); Arvind Rajpal, San Francisco, CA (US); Barbra Johnson Sasu, San Francisco, CA (US); Cesar Adolfo Sommer, San Mateo, CA (US); Julien Valton, Charenton le Pont (FR); Thomas John Van Blarcom, Oakland, CA (US)

(73) Assignee: PFIZER INC., New York, NY (US)

( * ) Notice: Subject to any disclaimer, the term of this patent is extended or adjusted under 35 U.S.C. 154(b) by 141 days.

(21) Appl. No.: 17/695,769

(22) Filed: Mar. 15, 2022

(65) Prior Publication Data
US 2022/0340671 A1  Oct. 27, 2022

Related U.S. Application Data

(62) Division of application No. 16/384,719, filed on Apr. 15, 2019, now Pat. No. 11,312,782, which is a division of application No. 15/085,317, filed on Mar. 30, 2016, now Pat. No. 10,294,304.

(60) Provisional application No. 62/301,177, filed on Feb. 29, 2016, provisional application No. 62/286,473, filed on Jan. 25, 2016, provisional application No. 62/146,825, filed on Apr. 13, 2015.

(51) Int. Cl.
| | | |
|---|---|---|
| C07K 14/705 | (2006.01) | |
| C07K 16/28 | (2006.01) | |
| A61K 39/395 | (2006.01) | |
| A61K 39/00 | (2006.01) | |
| C12N 5/10 | (2006.01) | |
| C07K 14/725 | (2006.01) | |
| A61K 31/7076 | (2006.01) | |
| C12N 15/63 | (2006.01) | |
| A61K 35/17 | (2015.01) | |
| C12N 5/0783 | (2010.01) | |
| A61K 38/00 | (2006.01) | |

(52) U.S. Cl.
CPC ...... *C07K 16/2878* (2013.01); *A61K 31/7076* (2013.01); *A61K 35/17* (2013.01); *A61K 39/0011* (2013.01); *A61K 39/46* (2023.05); *A61K 39/4631* (2023.05); *A61K 39/464417* (2023.05); *C07K 14/7051* (2013.01); *C07K 14/70517* (2013.01); *C07K 14/70578* (2013.01); *C07K 16/2896* (2013.01); *C12N 5/0636* (2013.01); *C12N 5/10* (2013.01); *C12N 15/63* (2013.01); *A61K 38/00* (2013.01); *A61K 2039/505* (2013.01); *A61K 2039/5156* (2013.01); *C07K 16/2863* (2013.01); *C07K 2317/56* (2013.01); *C07K 2317/565* (2013.01); *C07K 2317/569* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01); *C12N 2510/02* (2013.01)

(58) Field of Classification Search
CPC .......... C07K 2317/622; C07K 2319/03; C07K 2319/74; C07K 2319/00; C07K 2317/56; C07K 2317/565; C07K 2317/569; C07K 14/70578; C07K 16/2878; C07K 16/2896; C07K 16/2866; C07K 14/70596; C07K 2319/02; C07K 2319/32; A61K 39/3955; A61K 39/39558; A61K 2039/505; A61K 39/46; A61K 39/4631; A61K 39/464417
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |

(Continued)

FOREIGN PATENT DOCUMENTS

| | | |
|---|---|---|
| EP | 2762497 A1 | 8/2014 |
| EP | 3023437 A1 | 5/2016 |

(Continued)

OTHER PUBLICATIONS

Chiu et al. Hodgkin lymphoma cells express TACI and BCMA receptors and generate survival and proliferation signals in response to BAFF and April. Blood 109: 729-739, 2007.*

(Continued)

*Primary Examiner* — Bridget E Bunner

(57) ABSTRACT

The invention provides CARs (CARs) that specifically bind to BCMA (B-Cell Maturation Antigen). The invention further relates to engineered immune cells comprising such CARs, CAR-encoding nucleic acids, and methods of making such CARs, engineered immune cells, and nucleic acids. The invention further relates to therapeutic methods for use of these CARs and engineered immune cells for the treatment of a condition associated with malignant cells expressing BCMA (e.g., cancer).

24 Claims, 2 Drawing Sheets
Specification includes a Sequence Listing.

(56) References Cited

U.S. PATENT DOCUMENTS

| | | | |
|---|---|---|---|
| 4,816,567 A | 3/1989 | Cabilly et al. | |
| 5,037,743 A | 8/1991 | Welch et al. | |
| 5,143,830 A | 9/1992 | Holland et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,750,373 A | 5/1998 | Garrard et al. | |
| 5,858,358 A | 1/1999 | June et al. | |
| 5,883,223 A | 3/1999 | Gray | |
| 6,352,694 B1 | 3/2002 | June et al. | |
| 6,534,055 B1 | 3/2003 | June et al. | |
| 6,692,964 B1 | 2/2004 | June et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,067,318 B2 | 6/2006 | June et al. | |
| 7,083,785 B2 | 8/2006 | Browning et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 9,243,058 B2 | 1/2016 | Armitage et al. | |
| 9,765,342 B2 | 9/2017 | Kochenderfer | |
| 9,969,809 B2 | 5/2018 | Kuo et al. | |
| 10,040,860 B2 | 8/2018 | Kuo et al. | |
| 10,294,304 B2 | 5/2019 | Kuo et al. | |
| 10,793,635 B2* | 10/2020 | Kuo | A61K 39/39558 |
| 11,155,630 B2* | 10/2021 | Kuo | A61P 35/02 |
| 11,312,782 B2 | 4/2022 | Kuo et al. | |
| 2006/0121005 A1 | 6/2006 | Berenson et al. | |
| 2008/0267965 A1 | 10/2008 | Kalled et al. | |
| 2012/0082661 A1 | 4/2012 | Kalled et al. | |
| 2013/0280280 A1 | 10/2013 | Algate et al. | |
| 2014/0161828 A1 | 6/2014 | Armitage et al. | |
| 2014/0288275 A1 | 9/2014 | Moore et al. | |
| 2015/0051266 A1 | 2/2015 | Kochenderfer | |
| 2015/0093401 A1 | 4/2015 | Pule et al. | |
| 2015/0284467 A1 | 10/2015 | Lipp et al. | |
| 2015/0368351 A1 | 12/2015 | Vu et al. | |
| 2016/0297885 A1 | 10/2016 | Kuo et al. | |
| 2018/0298108 A1 | 10/2018 | Kuo et al. | |
| 2019/0241669 A1 | 8/2019 | Kuo et al. | |
| 2020/0261503 A1 | 8/2020 | Chang et al. | |

FOREIGN PATENT DOCUMENTS

| | | |
|---|---|---|
| EP | 3029068 A1 | 6/2016 |
| EP | 3283520 B1 | 5/2020 |
| EP | 3757128 A1 | 12/2020 |
| JP | 2017/513478 A | 6/2017 |
| JP | 2017/527271 A | 9/2017 |
| WO | WO-1987/004462 A1 | 7/1987 |
| WO | WO-1999/058572 A1 | 11/1999 |
| WO | WO-2010/104949 A2 | 9/2010 |
| WO | WO-2010/104949 A3 | 9/2010 |
| WO | WO 2012/007576 A1 | 1/2012 |
| WO | WO-2012/058458 A2 | 5/2012 |
| WO | WO-2012/066058 A1 | 5/2012 |
| WO | WO-2013/072406 A1 | 5/2013 |
| WO | WO-2013/072415 A1 | 5/2013 |
| WO | WO-2013/154760 A1 | 10/2013 |
| WO | WO-2013/158856 A2 | 10/2013 |
| WO | WO-2013/158856 A3 | 10/2013 |
| WO | WO-2014/039523 A1 | 3/2014 |
| WO | WO-2014/068079 A1 | 5/2014 |
| WO | WO-2014/089335 A2 | 6/2014 |
| WO | WO-2014/089335 A3 | 6/2014 |
| WO | WO-2014/122143 A1 | 8/2014 |
| WO | WO-2014/122144 A1 | 8/2014 |
| WO | WO-2014/140248 A1 | 9/2014 |
| WO | WO-2014/152177 A1 | 9/2014 |
| WO | WO-2014/172584 A1 | 10/2014 |
| WO | WO-2014/184143 A1 | 11/2014 |
| WO | WO-2014/184741 A1 | 11/2014 |
| WO | WO-2014/184744 A1 | 11/2014 |
| WO | WO-2014/191128 A1 | 12/2014 |
| WO | WO-2015/052536 A1 | 4/2015 |
| WO | WO-2015/052538 A1 | 4/2015 |
| WO | WO-2015/128653 A2 | 9/2015 |
| WO | WO-2015/128653 A3 | 9/2015 |
| WO | WO-2015/158671 A1 | 10/2015 |
| WO | WO-2015/166073 A1 | 11/2015 |
| WO | WO-2016/014565 A2 | 1/2016 |
| WO | WO-2016/014565 A3 | 1/2016 |
| WO | WO-2016/014789 A2 | 1/2016 |
| WO | WO-2016/014789 A3 | 1/2016 |
| WO | WO-2016/090320 A1 | 6/2016 |
| WO | WO-2016/094304 A2 | 6/2016 |
| WO | WO-2016/094304 A3 | 6/2016 |
| WO | WO-2016/120216 A1 | 8/2016 |
| WO | WO 2016/166630 A1 | 10/2016 |

OTHER PUBLICATIONS

Maia et al. Aberrant expression of functional BAFF-system receptors by malignant B-cell precursors impacts leukemia cell survival. PLoS ONE 6(6): e20787, 2011.*

Novak et al. Aberrant expression of B-lymphocyte stimulator by B chronic lymphocytic leukemia cells: a mechanism for survival. Blood 100: 2973-2979, 2002.*

Novak et al. Expression of BCMA, TACI, and BAFF-R in multiple myeloma: a mechanism for growth and survival. Blood 103: 689-694, 2004.*

Carpenter et al., "B-cell Maturation Antigen is a Promising Target for Adoptive T-cell Therapy of Multiple Myeloma," Clin. Cancer Res., 2013, vol. 19, No. 8, p. 2048-2060.

European Office Action for European Patent Application No. 20172811.0, dated Aug. 25, 2022, 9 pages.

Extended European Search Report for European Patent Application No. 20172811.0, dated Nov. 6, 2020, 11 pages.

Sievers et al., "CARs: Beyond T cells and T cell-derived signaling domains," Int. J. Mol. Sci. 2020, 21, 3525, 30 pages. (Apr. 5, 2012; Kalled et al.); White, C.A. et al. (2001).

White et al. (2001) "Antibody-Targeted Immunotherapy for Treatment of Malignancy," Ann. Rev. Med. 52: 125-145.

Yang Min et al., "B-cell maturation antigen can induce NF-κb activation," Journal of the Fourth Military Medical University, 2003, pp. 1729-1732.

Substantive Examination Adverse Report for Malaysian Application No. PI2021003979 dated Feb. 24, 2023, 7 pgs.

Examination Report for Australian Application No. 2020256365 dated Feb. 17, 2023, 3 pgs.

Abdiche et al., "Expanding the ProteOn XPR36 biosensor into a 36-ligand array expedites protein interaction analysis." *Analytical biochemistry* 411.1 (2011): 139-151.

Accelrys Software, Inc: ""Abm" 0 results found", Accelrys.com Search Tool, Aug. 10, 2018 (Aug. 10, 2018), Retrieved from the Internet: URL:~1ttp:i/search.accelrys .com/solr/collection 1 /browse?fq=u rl%3A%22http0/.03A%2F0io2Faccelrys.com%22&q=Abm &btnG:::Search [retrieved on Aug. 10, 2018].

Al-Lazikani, et al. "Standard conformations for the canonical structures of immunoglobulins." *Journal of molecular biology* vol. 273,4 (1997): 927-48.

Atkins et al., "A case for "StopGo": Reprogramming translation to augment codon meaning of GGN by promoting unconventional termination (Stop) after addition of glycine and then allowing continued translation (Go)," Cold Spring Harbor Laboratory Press 13: pp. 803-810, 2007.

Bierer, Barbara E., et al. "Cyclosporin A and FK506: molecular mechanisms of immunosuppression and probes for transplantation biology." *Current opinion in immunology* 5.5 (1993): 763-773.

Bird, et al. "Single-chain antigen-binding proteins." *Science* 242. 4877 (1988): 423-426.

(56) References Cited

OTHER PUBLICATIONS

Boerner, et al. "Production of antigen-specific human monoclonal antibodies from in vitro-primed human splenocytes." *The Journal of Immunology* 147.1 (1991): 86-95.
Brenner et al., NIH Public Access Author Manuscript (May 12, 2011) of "Adoptive T Cell Therapy of Cancer," published in Current Opinion in Immunology 22(2): 251-257 (2010).
Canadian Office Action for Canadian Patent Application No. 2,925,589, dated Mar. 28, 2022, 4 pages.
Capel, et al., "Heterogeneity of human IgG Fc receptors." *Immunomethods* 4.1 (1994): 25-34.
Chothia et al., "Conformations of immunoglobulin hypervariable regions," Nature Publishing Group, vol. 342, pp. 877-883, Dec. 1989.
Cole et al., "The EBV-Hybridoma Technique and its Application to Human Lung Cancer," Monoclonal Antibodies and Cancer Therapy, Alan R. Liss, p. 77-96, 1985.
Dayhoff, M.O. (ed.), "A model of evolutionary change in proteins," Atlas of Protein Sequence and Structure, National Biomedical Research Foundation, Washington DC vol. 5, Suppl. 3, pp. 345-358, 1978.
De Haas, M. "Fc gamma receptors of phagocytes." *J Lab Clin Med* 126.4 (1995): 330-341.
Diamond, B. et al. (1984). "Somatic mutation of the T15 heavy chain gives rise to an antibody with autoantibody specificity," PNAS 81: 5841-5844.
Donnelly and Elliott, "Nuclear Localization and Shuttling of Herpes Simplex Virus Tegument Protein VP13/14," Journal of Virology, vol. 75, No. 6, p. 2566-2574, Mar. 2001.
Doronina et al., "Site-Specific Release of Nascent Chains from Ribosomes at a Sense Codon," Molecular and Cellular Biology, vol. 28, No. 13, pp. 4227-4239, Jul. 2008.
Dubel et al. (2014) 9.8.3 Automated Modeling Tools In "Handbook of Therapeutic Antibodies—vol. 3 (2nd ed)," Wiley Blackwell, Weinheim (Germany) ISBN: 978-3-527-32937-3; p. 217.
Eshhar et al., "Specific activation and targeting of cytotoxic lymphocytes through chimeric single chains consisting of antibody-binding domains and the [gamma] or [zeta] subunits of the immunoglobulin and T-cell receptors," Proc Natl. Acad. Sci. USA 90(2): 720-724 (1993).
Fellouse, et al. "High-throughput generation of synthetic antibodies from highly functional minimalist phage-displayed libraries." *Journal of molecular biology* 373.4 (2007): 924-940.
Glienke et al. Advantages and applications of CAR-expressing natural killer cells. Front Pharmacol 6: 21, 2015 (7 total pages).
Guyer, Koshland, and Knopf. "Immunoglobulin binding by mouse intestinal epithelial cell receptors." *The Journal of Immunology* 117.2 (1976): 587-593.
Hein, "[39] Unified approach to alignment and phylogenies." Methods in Enzymology (1990): vol. 183, pp. 626-645.
Henderson, D. J., et al. "Comparison of the effects of FK-506, cyclosporin A and rapamycin on IL-2 production." *Immunology* 73.3 (1991): 316-321.
Higgins and Sharp, "Fast and sensitive multiple sequence alignments on a microcomputer," IRL Press, vol. 5, No. 2, pp. 151-153, 1989.
Hoogenboom, Hennie R., and Greg Winter. "By-passing immunisation: human antibodies from synthetic repertoires of germline VH gene segments rearranged in vitro." *Journal of molecular biology* 227.2 (1992): 381-388.
International Search Report for International Appln. No. PCT/IB2016/051808 completed on May 24, 2016, 6 pages.
International Search Report dated Aug. 30, 2016, for PCT Application No. PCT/IB2016/051801, filed on Mar. 30, 2016, 8 pages.
Jacobsohn, DA et al. (2007). "Acute graft versus host disease," Orphanet J Rare Dis. 2:35.
Jayasena, "Aptamers: An Emerging Class of Molecules That Rival Antibodies in Diagnostics," Clinical Chemistry, vol. 45, No. 9, pp. 1628-1650, 1999.

Jeger, L. (1990). Klinicheskaja immunologija I allergologija, 2nd ed.; M.: Meditsina, 3 volumes, vol. 1, pp. 219-222 (with English translation), 4 total pages.
Jones et al. Improving the safety of cell therapy products by suicide gene transfer. Front Pharmacol 5: 254, 2014 (8 total pages).
Kim et al, "Localization of the site of the murine IgG1 molecule that is involved in binding to the murine intestinal Fc receptor," Eur. J. Immunol, 24:2429-2434, 1994.
Kohler and Milstein, "Continuous cultures of fused cells secreting antibody of predefined specificity," Nature Publishing Group, vol. 256, pp. 495-497, Aug. 1975.
Koiko, R. et al., (2008). Irnmunologiya, M.: Akademiya, pp. 156, 160 (with English translation), 4 total pages.
Lin et al. Increasing the safety and efficacy of chimeric antigen receptor T cell therapy. Protein Cell 8(8): 573-589, 2017.
Liu et al., "Inhibition of T cell signaling by immunophilin-ligand complexes correlates with loss of calcineurin phosphatase activity." *Biochemistry* 31.16 (1992): 3896-3901.
Lonial et al., "Treatment Options for Relapsed and Refractory Multiple Myeloma," Clinical Cancer Res. 17(6): 1264-1277 (2011).
MacCallum, et al. "Antibody-antigen interactions: contact analysis and binding site topography." *Journal of molecular biology* vol. 262,5 (1996): 732-745.
Makabe et al., "Thermodynamic consequences of mutations in vernier zone residues of a humanized anti-human epidermal growth factor receptor murine antibody, 528," Journal of Biological Chemistry, vol. 283, iss. 2, pp. 1156-1166, Jan. 2008.
Marks et al., "By-passing Immunization. Human Antibodies from V-gene Libraries Displayed on Phage," J. Mol. Biol., vol. 222, pp. 581-597, 1991.
McCafferty, et al., "Phage antibodies: filamentous phage displaying antibody variable domains." *Nature* vol. 348, pp. 552-554, 1990.
Myers and Miller, "Optimal alignments in linear space." *Bioinformatics* 4.1 (1988): 11-17.
Myszka, "Improving biosensor analysis." *Journal of molecular recognition: JMR* vol. 12: 279-284 (1999).
Ohno, S. et. al. (1985). "Antigen-binding specificities of antibodies are primarily determined by seven residues of VH," PNAS 82:2945-2949.
Peru Office Action for Peruvian Patent Application No. 001979-2017/DIN, dated Apr. 19, 2022, 5 pages.
Qin et al. Chimeric antigen receptor beyond CAR-T cells. Cancers 13: 404, 2021 (17 total pages).
Rajkumar, NIH Public Access Author Manuscript (Sep. 15, 2013) of "Treatment of multiple myeloma," published in Nature Rev. Clinical Oncol. 8(8): 479-491 (2011).
Ramadoss, N, et al. (2015). "An anti-B ceil maturation antigen bispecific antibody for multiple myeloma," J. Am. Chem. Soc. 137:5288-5291.
Ravetch and Kinet "Fc receptors." *Annual review of immunology* 9.1 (1991): 457-492.
Robinson, "Comparison of Labeled Trees with Valency Three," Journal of Combinatorial Theory 11, pp. 105-119, 1971.
Rosenberg et al., NIH Public Access Author Manuscript (Sep. 25, 2008) of "Adoptive cell transfer: a clinical path to effective cancer immunotherapy," published in Nature Reviews Cancer 8(4): 299-308 (2008).
Rudikoff, S. et al. (1982) "Single amino acid substitution altering antigen-binding specificity," PNAS 79:1979-1983.
Russian Patent Application 2019136144 Mar. 30, 2016, pp. 1-2.
Sadelain et al., HHS Public Access Author manuscript (Aug. 8, 2017) of "The promise and potential pitfalls of chimeric antigen receptors," published in Curr. Opin. Immunol. 21(2): 215-233 (2009).
Saitou and Nei. "The Neighbor-joining method: a new method for reconstructing phylogenetic trees." *Molecular biology and evolution* vol. 4,4 (1987): 406-25.
Sheets et al., "Efficient construction of a large nonimmune phage antibody library: The production of high-affinity human single-chain antibodies to protein antigens," Proc. Natl. Acad. Sci. USA, vol. 95, pp. 6157-6162, May 1998.
Tang, Q. et al. (2008). "The Foxp3+ regulatory T cell: A jack of all trades, master of regulation," Nat. Immunol. 9:239-244.

(56) References Cited

OTHER PUBLICATIONS

Torikai, H., et al. (2012). "A foundation for universal T-cell based immunotherapy: T cells engineered to express a CD19-specific chimeric-antigen-receptor and eliminate expression of endogenous TCR," Blood 119:5697-5705.

Vaughan et al., "Human Antibodies with Sub-nanomolar Affinities Isolated from a Large Non-immunized Phage Display Library," Nature Publishing Group, vol. 14, pp. 309-314, Mar. 1996.

Ward et al., "Binding activities of a repertoire of single immunoglobulin variable domains secreted from *Escherichia coli*," Nature Publishing Group, vol. 341, pp. 544-546, Oct. 1989.

Wilbur and Lipman, "Rapid similarity searches of nucleic acid and protein data banks," Proc. Natt Acad. Sci. USA, vol. 80, pp. 726-730, Feb. 1983.

Written Opinion for International Appln. No. PCT/IB2016/051808 completed on May 24, 2016, 10 pages.

Written Opinion of the International Searching Authority dated Aug. 30, 2016, for PCT Appln. No. PCT/IB2016/051801, filed on Mar. 30, 2016, 18 pages.

Yang, Y. et al. (2015). CD4 CART cells mediate CDS-like cytotoxic anti-leukemic effects resulting in leukemic clearance and are less susceptible to attenuation by endogenous TCR activation than CD8 CART cells, Blood 126:100, 5 total pages.

Yarilin AA, "Osnovy immunologli", M.: Meditsina, 1999, pp. 172-174 (with English summary).

Zhang, C. et al. (2017). "Engineering CAR-T cells," *Biomaker Res.* 5:22, 6 total pages.

Zhong, X.S et al. (2010). "Chimeric Antigen Receptors Combining 4-1 BB and CD28 Signaling Domains Augment PI3kinase/AKT/Bcl-XL Activation and cos+ T cell-mediated Tumor Eradication," Mol. Ther. 18:413-420.

* cited by examiner

SEQUENCE LISTING

```
<160> NUMBER OF SEQ ID NOS: 401

<210> SEQ ID NO 1
<211> LENGTH: 109
<212> TYPE: PRT
<213> ORGANISM: Artificial Sequence
<220> FEATURE:
<223> OTHER INFORMATION: Synthetic Construct

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Pro Pro
                85                  90                  95

Ser Phe Thr Phe Gly Gln Gly Thr Lys Val Glu Ile Lys
            100                 105

<210> SEQ ID NO 2
<211> LENGTH: 119
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30
```

Ala Met Thr Trp Val Arg Gln Ala Pro Gly Lys Gly Leu Glu Trp Val
            35                  40                  45

Ser Ala Ile Ser Gly Ser Gly Gly Asn Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Gly Asn Thr Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ala Gln Met Asp Tyr Trp Gly Gln Gly
            100                 105                 110

Thr Leu Val Thr Val Ser Ser
        115

<210> SEQ ID NO 4
<211> LENGTH: 109
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys His Tyr Gly Trp Pro Pro

```
                    85                  90                  95

Ser Phe Thr Phe Gly Gln Gly Thr Lys Val Glu Ile Lys
                100                 105

<210> SEQ ID NO 5
<211> LENGTH: 109
<212> TYPE: PRT
<213> ORGANISM: Artificial Sequence
<220> FEATURE:
<223> OTHER INFORMATION: Synthetic Construct

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
                100                 105

<210> SEQ ID NO 6
<211> LENGTH: 109
<212> TYPE: PRT
<213> ORGANISM: Artificial Sequence
<220> FEATURE:
<223> OTHER INFORMATION: Synthetic Construct

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
                100                 105

<210> SEQ ID NO 7
<211> LENGTH: 121
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Val Ser Pro Ile Ala Ala Leu Met Asp Tyr Trp Gly
            100                 105                 110

Gln Gly Thr Leu Val Thr Val Ser Ser
            115                 120

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ala Pro Met Asp Tyr Trp Gly Gln Gly
            100                 105                 110

Thr Leu Val Thr Val Ser Ser
        115

<210> SEQ ID NO 9
<211> LENGTH: 109
<212> TYPE: PRT
<213> ORGANISM: Artificial Sequence
<220> FEATURE:
<223> OTHER INFORMATION: Synthetic Construct

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80

Pro Glu Asp Phe Ala Val Tyr Tyr Cys Gln His Tyr Pro Tyr Pro Pro
                    85                  90                  95

Ser Phe Thr Phe Gly Gln Gly Thr Lys Val Glu Ile Lys
                100                 105

<210> SEQ ID NO 10
<211> LENGTH: 109
<212> TYPE: PRT
<213> ORGANISM: Artificial Sequence
<220> FEATURE:
<223> OTHER INFORMATION: Synthetic Construct

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Phe
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                    85                  90                  95

Ser Phe Thr Phe Gly Gln Gly Thr Lys Val Glu Ile Lys
                100                 105

<210> SEQ ID NO 11
<211> LENGTH: 109
<212> TYPE: PRT
<213> ORGANISM: Artificial Sequence
<220> FEATURE:
<223> OTHER INFORMATION: Synthetic Construct

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys His Tyr Gly Trp Pro Pro
                    85                  90                  95

Ser Phe Thr Phe Gly Gln Gly Thr Lys Val Glu Ile Lys
                100                 105

<210> SEQ ID NO 12
<211> LENGTH: 109
<212> TYPE: PRT
<213> ORGANISM: Artificial Sequence
<220> FEATURE:
<223> OTHER INFORMATION: Synthetic Construct

<400> SEQUENCE: 12
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105

<210> SEQ ID NO 13
<211> LENGTH: 109
<212> TYPE: PRT
<213> ORGANISM: Artificial Sequence
<220> FEATURE:
<223> OTHER INFORMATION: Synthetic Construct

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
            100                 105

<210> SEQ ID NO 14
<211> LENGTH: 109
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Asp Phe
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro

```
                    85                  90                  95

Ser Phe Thr Phe Gly Gln Gly Thr Lys Val Glu Ile Lys
                100                 105

<210> SEQ ID NO 15
<211> LENGTH: 109
<212> TYPE: PRT
<213> ORGANISM: Artificial Sequence
<220> FEATURE:
<223> OTHER INFORMATION: Synthetic Construct

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Lys His Tyr Gly Trp Pro Pro
                85                  90                  95

Ser Phe Thr Phe Gly Gln Gly Thr Lys Val Glu Ile Lys
                100                 105

<210> SEQ ID NO 16
<211> LENGTH: 109
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
                100                 105

<210> SEQ ID NO 17
<211> LENGTH: 109
<212> TYPE: PRT
<213> ORGANISM: Artificial Sequence
<220> FEATURE:
<223> OTHER INFORMATION: Synthetic Construct

<400> SEQUENCE: 17

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asn Tyr Pro Pro
                85                  90                  95

Ser Phe Thr Phe Gly Gln Gly Thr Lys Val Glu Ile Lys
            100                 105

<210> SEQ ID NO 18
<211> LENGTH: 109
<212> TYPE: PRT
<213> ORGANISM: Artificial Sequence
<220> FEATURE:
<223> OTHER INFORMATION: Synthetic Construct

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Pro Ser Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105

<210> SEQ ID NO 19
<211> LENGTH: 109
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
```

<210> SEQ ID NO 20
<211> LENGTH: 109
<212> TYPE: PRT
<213> ORGANISM: Artificial Sequence
<220> FEATURE:
<223> OTHER INFORMATION: Synthetic Construct

<400> SEQUENCE: 20

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105
```

<210> SEQ ID NO 21
<211> LENGTH: 109
<212> TYPE: PRT
<213> ORGANISM: Artificial Sequence
<220> FEATURE:
<223> OTHER INFORMATION: Synthetic Construct

<400> SEQUENCE: 21

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro His
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Pro Tyr Pro Pro
                85                  90                  95

Ser Phe Thr Phe Gly Gln Gly Thr Lys Val Glu Ile Lys
            100                 105
```

<210> SEQ ID NO 22
<211> LENGTH: 109
<212> TYPE: PRT
<213> ORGANISM: Artificial Sequence
<220> FEATURE:
<223> OTHER INFORMATION: Synthetic Construct

<400> SEQUENCE: 22

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30
```

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Lys Tyr Tyr Pro Tyr Pro Pro
                 85                  90                  95

Ser Phe Thr Phe Gly Gln Gly Thr Lys Val Glu Ile Lys
            100                 105

<210> SEQ ID NO 23
<211> LENGTH: 109
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Lys Phe Tyr Pro Tyr Pro Pro
                 85                  90                  95

Ser Phe Thr Phe Gly Gln Gly Thr Lys Val Glu Ile Lys
            100                 105

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
            35                  40                  45

Ser Ala Ile Ser Gly Ser Gly Asn Thr Phe Tyr Ala Asp Gln Arg
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Pro Ile Ala Ser Gly Met Asp Tyr Trp Gly Gln Gly
            100                 105                 110

Thr Leu Val Thr Val Ser Ser

115

<210> SEQ ID NO 25
<211> LENGTH: 119
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Asp Tyr Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Tyr Gln Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Artificial Sequence
<220> FEATURE:
<223> OTHER INFORMATION: Synthetic Construct

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Leu Thr Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115
```

<210> SEQ ID NO 28
<211> LENGTH: 119
<212> TYPE: PRT
<213> ORGANISM: Artificial Sequence
<220> FEATURE:
<223> OTHER INFORMATION: Synthetic Construct

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser His Ala Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Ala Ser Gly Met Asp Tyr Trp Gly Gln Gly
            100                 105                 110

Thr Leu Val Thr Val Ser Ser
        115
```

<210> SEQ ID NO 29
<211> LENGTH: 119
<212> TYPE: PRT
<213> ORGANISM: Artificial Sequence
<220> FEATURE:
<223> OTHER INFORMATION: Synthetic Construct

<400> SEQUENCE: 29

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Gln Leu
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Pro Ile Ala Ser Gly Met Asp Tyr Trp Gly Gln Gly
                100                 105                 110

Thr Leu Val Thr Val Ser Ser
            115

<210> SEQ ID NO 30
<211> LENGTH: 119
<212> TYPE: PRT
<213> ORGANISM: Artificial Sequence
<220> FEATURE:
<223> OTHER INFORMATION: Synthetic Construct

<400> SEQUENCE: 30

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Tyr
                20                  25                  30

Ala Met Thr Trp Val Arg Gln Ala Pro Gly Lys Gly Leu Glu Trp Val
            35                  40                  45

Ser Ala Ile Ser Gly Ser Gly Gly Asn Thr Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Pro Ile Tyr Ala Gly Met Asp Tyr Trp Gly Gln Gly
                100                 105                 110

Thr Leu Val Thr Val Ser Ser
            115

<210> SEQ ID NO 31
<211> LENGTH: 119
<212> TYPE: PRT
<213> ORGANISM: Artificial Sequence
<220> FEATURE:
<223> OTHER INFORMATION: Synthetic Construct

<400> SEQUENCE: 31

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Tyr
                20                  25                  30

Ala Met Thr Trp Val Arg Gln Ala Pro Gly Lys Gly Leu Glu Trp Val
            35                  40                  45

Ser Ala Ile Ser Gly Ser Gly Gly Asn Thr Phe Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ser Pro Ile Ala Ala Glu Met Asp Tyr Trp Gly Gln Gly
                100                 105                 110
```

```
Thr Leu Val Thr Val Ser Ser
        115

<210> SEQ ID NO 32
<211> LENGTH: 119
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Val Ser Pro Ile Ala Ala Gln Met Asp Tyr Trp Gly Gln Gly
            100                 105                 110

Thr Leu Val Thr Val Ser Ser
        115

<210> SEQ ID NO 33
<211> LENGTH: 115
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
    115

<210> SEQ ID NO 34
<211> LENGTH: 108
<212> TYPE: PRT
<213> ORGANISM: Artificial Sequence
<220> FEATURE:
<223> OTHER INFORMATION: Synthetic Construct
```

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Leu Thr Phe Gly Gln Gly Thr Lys Val Glu Ile Lys
            100                 105

<210> SEQ ID NO 35
<211> LENGTH: 115
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Ala Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

<210> SEQ ID NO 36
<211> LENGTH: 108
<212> TYPE: PRT
<213> ORGANISM: Artificial Sequence
<220> FEATURE:
<223> OTHER INFORMATION: Synthetic Construct

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Arg Trp Pro
                 85                  90                  95

Leu Thr Phe Gly Gln Gly Thr Lys Val Glu Ile Lys
            100                 105

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Ser Asp Ser Gly Gly Ser Met Trp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ser Leu Trp Gly Gln Gly Thr Leu Val Thr
            100                 105                 110

Val Ser Ser
        115

<210> SEQ ID NO 38
<211> LENGTH: 108
<212> TYPE: PRT
<213> ORGANISM: Artificial Sequence
<220> FEATURE:
<223> OTHER INFORMATION: Synthetic Construct

<400> SEQUENCE: 38

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
                 85                  90                  95

Leu Thr Phe Gly Gln Gly Thr Lys Val Glu Ile Lys
            100                 105

<210> SEQ ID NO 39
<211> LENGTH: 115
<212> TYPE: PRT
<213> ORGANISM: Artificial Sequence
```

```
<220> FEATURE:
<223> OTHER INFORMATION: Synthetic Construct

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Phe Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
            100                 105                 110

Val Ser Ser
        115

<210> SEQ ID NO 40
<211> LENGTH: 108
<212> TYPE: PRT
<213> ORGANISM: Artificial Sequence
<220> FEATURE:
<223> OTHER INFORMATION: Synthetic Construct

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asp Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Thr Trp Pro
                85                  90                  95

Leu Thr Phe Gly Gln Gly Thr Lys Val Glu Ile Lys
            100                 105

<210> SEQ ID NO 41
<211> LENGTH: 108
<212> TYPE: PRT
<213> ORGANISM: Artificial Sequence
<220> FEATURE:
<223> OTHER INFORMATION: Synthetic Construct

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Leu
            20                  25                  30

Tyr Leu Ala Trp Tyr Gln Gln Lys Pro Gly Gln Ala Pro Arg Leu Leu
        35                  40                  45
```

```
Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Gly Trp Pro
                    85                  90                  95

Leu Thr Phe Gly Gln Gly Thr Lys Val Glu Ile Lys
                100                 105
```

<210> SEQ ID NO 42
<211> LENGTH: 115
<212> TYPE: PRT
<213> ORGANISM: Artificial Sequence
<220> FEATURE:
<223> OTHER INFORMATION: Synthetic Construct

<400> SEQUENCE: 42

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ala Ile Thr Ala Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                 90                  95

Ala Arg Tyr Trp Pro Met Ser Leu Trp Gly Gln Gly Thr Leu Val Thr
                100                 105                 110

Val Ser Ser
        115
```

<210> SEQ ID NO 43
<211> LENGTH: 108
<212> TYPE: PRT
<213> ORGANISM: Artificial Sequence
<220> FEATURE:
<223> OTHER INFORMATION: Synthetic Construct

<400> SEQUENCE: 43

```
Glu Ile Val Leu Thr Gln Ser Pro Gly Thr Leu Ser Leu Ser Pro Gly
 1               5                   10                  15

Glu Arg Ala Thr Leu Ser Cys Arg Ala Ser Gln Ser Val Ser Ala Tyr
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Glu Arg Trp Pro
                    85                  90                  95

Leu Thr Phe Gly Gln Gly Thr Lys Val Glu Ile Lys
                100                 105
```

<210> SEQ ID NO 44

<211> LENGTH: 115
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

<210> SEQ ID NO 45
<211> LENGTH: 108
<212> TYPE: PRT
<213> ORGANISM: Artificial Sequence
<220> FEATURE:
<223> OTHER INFORMATION: Synthetic Construct

<400> SEQUENCE: 45

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Val Trp Pro
                85                  90                  95

Leu Thr Phe Gly Gln Gly Thr Lys Val Glu Ile Lys
            100                 105

<210> SEQ ID NO 46
<211> LENGTH: 115
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Asn Trp Val Arg Gln Ala Pro Gly Lys Gly Leu Glu Trp Val
            35                  40                  45

Ser Ala Ile Ser Asp Ser Gly Gly Ser Arg Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
            100                 105                 110

Val Ser Ser
        115

<210> SEQ ID NO 47
<211> LENGTH: 108
<212> TYPE: PRT
<213> ORGANISM: Artificial Sequence
<220> FEATURE:
<223> OTHER INFORMATION: Synthetic Construct

<400> SEQUENCE: 47

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Leu Asp Trp Pro
                85                  90                  95

Leu Thr Phe Gly Gln Gly Thr Lys Val Glu Ile Lys
            100                 105

<210> SEQ ID NO 48
<211> LENGTH: 115
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ala Val Leu Asp Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
            100                 105                 110
```

-continued

Val Ser Ser
        115

<210> SEQ ID NO 49
<211> LENGTH: 108
<212> TYPE: PRT
<213> ORGANISM: Artificial Sequence
<220> FEATURE:
<223> OTHER INFORMATION: Synthetic Construct

<400> SEQUENCE: 49

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Val Trp Pro
                85                  90                  95

Leu Thr Phe Gly Gln Gly Thr Lys Val Glu Ile Lys
            100                 105

<210> SEQ ID NO 50
<211> LENGTH: 115
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Arg Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Asp Trp Gly Gln Gly Thr Leu Val Thr
            100                 105                 110

Val Ser Ser
        115

<210> SEQ ID NO 51
<211> LENGTH: 108
<212> TYPE: PRT
<213> ORGANISM: Artificial Sequence
<220> FEATURE:
<223> OTHER INFORMATION: Synthetic Construct

<400> SEQUENCE: 51

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Leu Ala Trp Pro
                85                  90                  95

Leu Thr Phe Gly Gln Gly Thr Lys Val Glu Ile Lys
            100                 105
```

<210> SEQ ID NO 52
<211> LENGTH: 115
<212> TYPE: PRT
<213> ORGANISM: Artificial Sequence
<220> FEATURE:
<223> OTHER INFORMATION: Synthetic Construct

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Gly Ser Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115
```

<210> SEQ ID NO 53
<211> LENGTH: 108
<212> TYPE: PRT
<213> ORGANISM: Artificial Sequence
<220> FEATURE:
<223> OTHER INFORMATION: Synthetic Construct

<400> SEQUENCE: 53

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Phe Thr Trp Pro
                85                  90                  95

Leu Thr Phe Gly Gln Gly Thr Lys Val Glu Ile Lys
            100                 105

<210> SEQ ID NO 54
<211> LENGTH: 115
<212> TYPE: PRT
<213> ORGANISM: Artificial Sequence
<220> FEATURE:
<223> OTHER INFORMATION: Synthetic Construct

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 55
<211> LENGTH: 108
<212> TYPE: PRT
<213> ORGANISM: Artificial Sequence
<220> FEATURE:
<223> OTHER INFORMATION: Synthetic Construct

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Tyr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Arg Trp Pro
                85                  90                  95

Leu Thr Phe Gly Gln Gly Thr Lys Val Glu Ile Lys
            100                 105

<210> SEQ ID NO 56
<211> LENGTH: 115
<212> TYPE: PRT
<213> ORGANISM: Artificial Sequence
<220> FEATURE:
<223> OTHER INFORMATION: Synthetic Construct
```

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Ser Gly Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115

<210> SEQ ID NO 57
<211> LENGTH: 108
<212> TYPE: PRT
<213> ORGANISM: Artificial Sequence
<220> FEATURE:
<223> OTHER INFORMATION: Synthetic Construct

<400> SEQUENCE: 57

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Glu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Arg Trp Pro
                85                  90                  95

Leu Thr Phe Gly Gln Gly Thr Lys Val Glu Ile Lys
            100                 105

<210> SEQ ID NO 58
<211> LENGTH: 115
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Val Leu Asp Ser Gly Gly Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ser Leu Trp Gly Gln Gly Thr Leu Val Thr
            100                 105                 110

Val Ser Ser
        115

<210> SEQ ID NO 59
<211> LENGTH: 108
<212> TYPE: PRT
<213> ORGANISM: Artificial Sequence
<220> FEATURE:
<223> OTHER INFORMATION: Synthetic Construct

<400> SEQUENCE: 59

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Glu Leu
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Phe Gly Trp Pro
                 85                  90                  95

Leu Thr Phe Gly Gln Gly Thr Lys Val Glu Ile Lys
            100                 105

<210> SEQ ID NO 60
<211> LENGTH: 115
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ala Ile Ser Asp Ser Gly Gly Ser Cys Trp Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Thr Pro Trp Gly Gln Gly Thr Leu Val Thr
            100                 105                 110

Val Ser Ser
        115
```

```
<210> SEQ ID NO 61
<211> LENGTH: 108
<212> TYPE: PRT
<213> ORGANISM: Artificial Sequence
<220> FEATURE:
<223> OTHER INFORMATION: Synthetic Construct

<400> SEQUENCE: 61
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Glu Met Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala His Trp Pro
                85                  90                  95

Leu Thr Phe Gly Gln Gly Thr Lys Val Glu Ile Lys
            100                 105

```
<210> SEQ ID NO 62
<211> LENGTH: 115
<212> TYPE: PRT
<213> ORGANISM: Artificial Sequence
<220> FEATURE:
<223> OTHER INFORMATION: Synthetic Construct

<400> SEQUENCE: 62
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Phe Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Thr Pro Trp Gly Gln Gly Thr Leu Val Thr
            100                 105                 110

Val Ser Ser
        115

```
<210> SEQ ID NO 63
<211> LENGTH: 108
<212> TYPE: PRT
<213> ORGANISM: Artificial Sequence
<220> FEATURE:
<223> OTHER INFORMATION: Synthetic Construct

<400> SEQUENCE: 63
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Arg Trp Pro
                85                  90                  95

Leu Thr Phe Gly Gln Gly Thr Lys Val Glu Ile Lys
            100                 105

<210> SEQ ID NO 64
<211> LENGTH: 115
<212> TYPE: PRT
<213> ORGANISM: Artificial Sequence
<220> FEATURE:
<223> OTHER INFORMATION: Synthetic Construct

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Trp Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 65
<211> LENGTH: 108
<212> TYPE: PRT
<213> ORGANISM: Artificial Sequence
<220> FEATURE:
<223> OTHER INFORMATION: Synthetic Construct

<400> SEQUENCE: 65

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Gln
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Arg Trp Pro
                85                  90                  95

Leu Thr Phe Gly Gln Gly Thr Lys Val Glu Ile Lys

<210> SEQ ID NO 66
<211> LENGTH: 115
<212> TYPE: PRT
<213> ORGANISM: Artificial Sequence
<220> FEATURE:
<223> OTHER INFORMATION: Synthetic Construct

<400> SEQUENCE: 66

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Asn Trp Val Arg Gln Ala Pro Gly Lys Gly Leu Glu Trp Val
        35                  40                  45
Ser Ala Ile Met Ser Ser Gly Gly Pro Leu Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Trp Pro Met Ala Leu Trp Gly Gln Gly Thr Leu Val Thr
            100                 105                 110
Val Ser Ser
        115
```

<210> SEQ ID NO 67
<211> LENGTH: 108
<212> TYPE: PRT
<213> ORGANISM: Artificial Sequence
<220> FEATURE:
<223> OTHER INFORMATION: Synthetic Construct

<400> SEQUENCE: 67

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ala Leu
            20                  25                  30
Tyr Leu Ala Trp Tyr Gln Gln Lys Pro Gly Gln Ala Pro Arg Leu Leu
        35                  40                  45
Met Tyr Asp Ala Ser Ile Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gln Val Trp Pro
                85                  90                  95
Leu Thr Phe Gly Gln Gly Thr Lys Val Glu Ile Lys
            100                 105
```

<210> SEQ ID NO 68
<211> LENGTH: 115
<212> TYPE: PRT
<213> ORGANISM: Artificial Sequence
<220> FEATURE:
<223> OTHER INFORMATION: Synthetic Construct

<400> SEQUENCE: 68

```
Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
                35                  40                  45

Ser Ala Ile Leu Met Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
                100                 105                 110

Val Ser Ser
        115
```

<210> SEQ ID NO 69
<211> LENGTH: 108
<212> TYPE: PRT
<213> ORGANISM: Artificial Sequence
<220> FEATURE:
<223> OTHER INFORMATION: Synthetic Construct

<400> SEQUENCE: 69

```
Glu Ile Val Leu Thr Gln Ser Pro Gly Thr Leu Ser Leu Ser Pro Gly
 1               5                   10                  15

Glu Arg Ala Thr Leu Ser Cys Gly Pro Ser Gln Ser Val Ser Ser Ser
            20                  25                  30

Tyr Leu Ala Trp Tyr Gln Gln Lys Pro Gly Gln Ala Pro Arg Leu Leu
                35                  40                  45

Met Tyr Asp Ala Ser Ile Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
                100                 105
```

<210> SEQ ID NO 70
<211> LENGTH: 115
<212> TYPE: PRT
<213> ORGANISM: Artificial Sequence
<220> FEATURE:
<223> OTHER INFORMATION: Synthetic Construct

<400> SEQUENCE: 70

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
                35                  40                  45

Ser Ala Ile Ser Asp Ser Gly Gly Tyr Arg Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

85                  90                  95

Ala Arg Tyr Trp Pro Met Ser Leu Trp Gly Gln Gly Thr Leu Val Thr
                100                 105                 110

Val Ser Ser
        115

<210> SEQ ID NO 71
<211> LENGTH: 108
<212> TYPE: PRT
<213> ORGANISM: Artificial Sequence
<220> FEATURE:
<223> OTHER INFORMATION: Synthetic Construct

<400> SEQUENCE: 71

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Trp Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Ser Trp Pro
                85                  90                  95

Leu Thr Phe Gly Gln Gly Thr Lys Val Glu Ile Lys
                100                 105

<210> SEQ ID NO 72
<211> LENGTH: 115
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Leu Ser Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ile Trp Gly Gln Gly Thr Leu Val Thr
                100                 105                 110

Val Ser Ser
        115

<210> SEQ ID NO 73
<211> LENGTH: 108
<212> TYPE: PRT
<213> ORGANISM: Artificial Sequence
<220> FEATURE:

<223> OTHER INFORMATION: Synthetic Construct

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Gly Gly Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ser Trp Pro
                85                  90                  95

Leu Thr Phe Gly Gln Gly Thr Lys Val Glu Ile Lys
            100                 105

<210> SEQ ID NO 74
<211> LENGTH: 115
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Leu Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Pro Trp Gly Gly Gly Thr Leu Val Thr
            100                 105                 110

Val Ser Ser
        115

<210> SEQ ID NO 75
<211> LENGTH: 108
<212> TYPE: PRT
<213> ORGANISM: Artificial Sequence
<220> FEATURE:
<223> OTHER INFORMATION: Synthetic Construct

<400> SEQUENCE: 75

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Phe Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser

```
                    50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Trp Pro
                    85                  90                  95

Leu Thr Phe Gly Gln Gly Thr Lys Val Glu Ile Lys
                100                 105

<210> SEQ ID NO 76
<211> LENGTH: 115
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Pro Met Ser Trp Val Arg Gln Ala Pro Gly Lys Gly Leu Glu Trp Val
                35                  40                  45

Ser Ala Ile Gly Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
                100                 105                 110

Val Ser Ser
        115

<210> SEQ ID NO 77
<211> LENGTH: 108
<212> TYPE: PRT
<213> ORGANISM: Artificial Sequence
<220> FEATURE:
<223> OTHER INFORMATION: Synthetic Construct

<400> SEQUENCE: 77

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
                35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Thr Ser Pro
                85                  90                  95

Leu Thr Phe Gly Gln Gly Thr Lys Val Glu Ile Lys
                100                 105

<210> SEQ ID NO 78
<211> LENGTH: 115
```

```
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 79
<211> LENGTH: 108
<212> TYPE: PRT
<213> ORGANISM: Artificial Sequence
<220> FEATURE:
<223> OTHER INFORMATION: Synthetic Construct

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Pro Glu
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Val Trp Pro
                85                  90                  95

Leu Thr Phe Gly Gln Gly Thr Lys Val Glu Ile Lys
            100                 105

<210> SEQ ID NO 80
<211> LENGTH: 108
<212> TYPE: PRT
<213> ORGANISM: Artificial Sequence
<220> FEATURE:
<223> OTHER INFORMATION: Synthetic Construct

<400> SEQUENCE: 80

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Leu Gly Ser Phe Tyr
            20                  25                  30

Leu Ala Trp Tyr Gln Gln Lys Pro Gly Gln Ala Pro Arg Leu Leu Ile
```

```
                35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln His Tyr Asn Tyr Pro Pro Ser
                 85                  90                  95

Phe Thr Phe Gly Gln Gly Thr Lys Val Glu Ile Lys
            100                 105
```

<210> SEQ ID NO 81
<211> LENGTH: 108
<212> TYPE: PRT
<213> ORGANISM: Artificial Sequence
<220> FEATURE:
<223> OTHER INFORMATION: Synthetic Construct

<400> SEQUENCE: 81

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Arg Trp Pro
                 85                  90                  95

Leu Thr Phe Gly Gln Gly Thr Lys Val Glu Ile Lys
            100                 105
```

<210> SEQ ID NO 82
<211> LENGTH: 108
<212> TYPE: PRT
<213> ORGANISM: Artificial Sequence
<220> FEATURE:
<223> OTHER INFORMATION: Synthetic Construct

<400> SEQUENCE: 82

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Pro Leu
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Ala Phe Pro
                 85                  90                  95

Leu Thr Phe Gly Gln Gly Thr Lys Val Glu Ile Lys
            100                 105
```

<210> SEQ ID NO 83
<211> LENGTH: 115

<212> TYPE: PRT
<213> ORGANISM: Artificial Sequence
<220> FEATURE:
<223> OTHER INFORMATION: Synthetic Construct

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Trp Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 84
<211> LENGTH: 108
<212> TYPE: PRT
<213> ORGANISM: Artificial Sequence
<220> FEATURE:
<223> OTHER INFORMATION: Synthetic Construct

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Trp Leu Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Glu Trp Pro
                85                  90                  95

Leu Thr Phe Gly Gln Gly Thr Lys Val Glu Ile Lys
            100                 105

<210> SEQ ID NO 85
<211> LENGTH: 108
<212> TYPE: PRT
<213> ORGANISM: Artificial Sequence
<220> FEATURE:
<223> OTHER INFORMATION: Synthetic Construct

<400> SEQUENCE: 85

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu

```
                35                  40                  45
Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Ser Trp Pro
                 85                  90                  95

Leu Thr Phe Gly Gln Gly Thr Lys Val Glu Ile Lys
            100                 105

<210> SEQ ID NO 86
<211> LENGTH: 108
<212> TYPE: PRT
<213> ORGANISM: Artificial Sequence
<220> FEATURE:
<223> OTHER INFORMATION: Synthetic Construct

<400> SEQUENCE: 86

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Leu
                20                  25                  30

Phe Leu Ala Trp Tyr Gln Gln Lys Pro Gly Gln Ala Pro Arg Leu Leu
            35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ser Ala Trp Pro
                 85                  90                  95

Leu Thr Phe Gly Gln Gly Thr Lys Val Glu Ile Lys
            100                 105

<210> SEQ ID NO 87
<211> LENGTH: 115
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Pro Met Ser Trp Val Arg Gln Ala Pro Gly Lys Gly Leu Glu Trp Val
            35                  40                  45

Ser Ala Thr Val Gly Ser Gly Gly Ser Ile Gly Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ser Trp Gly Gln Gly Thr Leu Val Thr
            100                 105                 110

Val Ser Ser
        115
```

<210> SEQ ID NO 88
<211> LENGTH: 108
<212> TYPE: PRT
<213> ORGANISM: Artificial Sequence
<220> FEATURE:
<223> OTHER INFORMATION: Synthetic Construct

<400> SEQUENCE: 88

```
Glu Ile Val Leu Thr Gln Ser Pro Gly Thr Leu Ser Leu Ser Pro Gly
1               5                   10                  15

Glu Arg Ala Thr Leu Ser Cys Ala Cys Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Trp Pro
                85                  90                  95

Leu Thr Phe Gly Gln Gly Thr Lys Val Glu Ile Lys
            100                 105
```

<210> SEQ ID NO 89
<211> LENGTH: 108
<212> TYPE: PRT
<213> ORGANISM: Artificial Sequence
<220> FEATURE:
<223> OTHER INFORMATION: Synthetic Construct

<400> SEQUENCE: 89

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Cys Asp Val Ser Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Arg Ser Pro
                85                  90                  95

Leu Thr Phe Gly Gln Gly Thr Lys Val Glu Ile Lys
            100                 105
```

<210> SEQ ID NO 90
<211> LENGTH: 108
<212> TYPE: PRT
<213> ORGANISM: Artificial Sequence
<220> FEATURE:
<223> OTHER INFORMATION: Synthetic Construct

<400> SEQUENCE: 90

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Glu Ala Val Pro Ser Thr
            20                  25                  30

Tyr Leu Ala Trp Tyr Gln Gln Lys Pro Gly Gln Ala Pro Arg Leu Leu
```

```
                35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Phe Pro
                85                  90                  95

Leu Thr Phe Gly Gln Gly Thr Lys Val Glu Ile Lys
                100                 105
```

<210> SEQ ID NO 91
<211> LENGTH: 108
<212> TYPE: PRT
<213> ORGANISM: Artificial Sequence
<220> FEATURE:
<223> OTHER INFORMATION: Synthetic Construct

<400> SEQUENCE: 91

```
Glu Ile Val Leu Thr Gln Ser Pro Gly Thr Leu Ser Leu Ser Pro Gly
1               5                   10                  15

Glu Arg Ala Thr Leu Ser Cys Cys Ser Ser Gln Ser Val Ser Ser Thr
                20                  25                  30

Tyr Leu Ala Trp Tyr Gln Gln Lys Pro Gly Gln Ala Pro Arg Leu Leu
            35                  40                  45

Ile Tyr Asp Ala Ser Ser Arg Ala Pro Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Phe Pro
                85                  90                  95

Leu Thr Phe Gly Gln Gly Thr Lys Val Glu Ile Lys
                100                 105
```

<210> SEQ ID NO 92
<211> LENGTH: 115
<212> TYPE: PRT
<213> ORGANISM: Artificial Sequence
<220> FEATURE:
<223> OTHER INFORMATION: Synthetic Construct

<400> SEQUENCE: 92

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ser Ala Ile Ser Asp Ser Gly Gly Ser Arg Trp Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Tyr Trp Pro Met Asp Ile Trp Gly Gln Gly Thr Leu Val Thr
                100                 105                 110

Val Ser Ser
        115
```

<210> SEQ ID NO 93
<211> LENGTH: 108
<212> TYPE: PRT
<213> ORGANISM: Artificial Sequence
<220> FEATURE:
<223> OTHER INFORMATION: Synthetic Construct

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Val Arg Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Lys Trp Pro
                85                  90                  95

Leu Thr Phe Gly Gln Gly Thr Lys Val Glu Ile Lys
            100                 105

<210> SEQ ID NO 94
<211> LENGTH: 108
<212> TYPE: PRT
<213> ORGANISM: Artificial Sequence
<220> FEATURE:
<223> OTHER INFORMATION: Synthetic Construct

<400> SEQUENCE: 94

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Ala
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Cys Trp Pro
                85                  90                  95

Leu Thr Phe Gly Gln Gly Thr Lys Val Glu Ile Lys
            100                 105

<210> SEQ ID NO 95
<211> LENGTH: 115
<212> TYPE: PRT
<213> ORGANISM: Artificial Sequence
<220> FEATURE:
<223> OTHER INFORMATION: Synthetic Construct

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val

```
                35                  40                  45
Ser Ala Ile Gly Gly Ser Gly Gly Ser Ile His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 96
<211> LENGTH: 108
<212> TYPE: PRT
<213> ORGANISM: Artificial Sequence
<220> FEATURE:
<223> OTHER INFORMATION: Synthetic Construct

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Trp Gly Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Cys Trp Pro
                85                  90                  95

Leu Thr Phe Gly Gln Gly Thr Lys Val Glu Ile Lys
            100                 105

<210> SEQ ID NO 97
<211> LENGTH: 115
<212> TYPE: PRT
<213> ORGANISM: Artificial Sequence
<220> FEATURE:
<223> OTHER INFORMATION: Synthetic Construct

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala His Ile Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110
```

<210> SEQ ID NO 98
<211> LENGTH: 108
<212> TYPE: PRT
<213> ORGANISM: Artificial Sequence
<220> FEATURE:
<223> OTHER INFORMATION: Synthetic Construct

<400> SEQUENCE: 98

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Thr
            20                  25                  30
Tyr Leu Ala Trp Tyr Gln Gln Lys Pro Gly Gln Ala Pro Arg Leu Leu
        35                  40                  45
Met Tyr Asp Ala Ser Ile Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gln Ser Trp Pro
                85                  90                  95
Leu Thr Phe Gly Gln Gly Thr Lys Val Glu Ile Lys
            100                 105
```

<210> SEQ ID NO 99
<211> LENGTH: 115
<212> TYPE: PRT
<213> ORGANISM: Artificial Sequence
<220> FEATURE:
<223> OTHER INFORMATION: Synthetic Construct

<400> SEQUENCE: 99

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Pro Met Ser Trp Val Arg Gln Ala Pro Gly Lys Gly Leu Glu Trp Val
        35                  40                  45
Ser Ala Ile Gly Gly Ser Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Tyr Trp Pro Met Asp Pro Trp Gly Gln Gly Thr Leu Val Thr
            100                 105                 110
Val Ser Ser
        115
```

<210> SEQ ID NO 100
<211> LENGTH: 108
<212> TYPE: PRT
<213> ORGANISM: Artificial Sequence
<220> FEATURE:
<223> OTHER INFORMATION: Synthetic Construct

<400> SEQUENCE: 100

```
Glu Ile Val Leu Thr Gln Ser Pro Gly Thr Leu Ser Leu Ser Pro Gly
```

```
            1               5                  10                  15
        Glu Arg Ala Thr Leu Ser Cys Arg Ala Ser Gln Ser Val Ser Pro
                        20                  25                  30

Tyr Leu Ala Trp Tyr Gln Gln Lys Pro Gly Gln Ala Pro Arg Leu Leu
                        35                  40                  45

Met Tyr Asp Ala Ser Ile Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
        65                  70                  75                  80

Pro Glu Asp Phe Ala Val Tyr Tyr Cys Gln Gln Tyr Gln Ser Trp Pro
                        85                  90                  95

Leu Thr Phe Gly Gln Gly Thr Lys Val Glu Ile Lys
                        100                 105

<210> SEQ ID NO 101
<211> LENGTH: 115
<212> TYPE: PRT
<213> ORGANISM: Artificial Sequence
<220> FEATURE:
<223> OTHER INFORMATION: Synthetic Construct

<400> SEQUENCE: 101

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Ser Tyr
                        20                  25                  30

Pro Met Ser Trp Val Arg Gln Ala Pro Gly Lys Gly Leu Glu Trp Val
                        35                  40                  45

Ser Ala Ile Gly Gly Ser Gly Gly Ser Leu Gly Tyr Ala Asp Ser Val
                    50                  55                  60

Lys Gly Arg Phe Thr Ile Ser Arg Asp Asn Ser Lys Asn Thr Leu Tyr
        65                  70                  75                  80

Leu Gln Met Asn Ser Leu Arg Ala Glu Asp Thr Ala Val Tyr Tyr Cys
                        85                  90                  95

Ala Arg Tyr Trp Pro Met Asp Ser Trp Gly Gln Gly Thr Leu Val Thr
                        100                 105                 110

Val Ser Ser
                115

<210> SEQ ID NO 102
<211> LENGTH: 108
<212> TYPE: PRT
<213> ORGANISM: Artificial Sequence
<220> FEATURE:
<223> OTHER INFORMATION: Sequence Listing

<400> SEQUENCE: 102

Glu Ile Val Leu Thr Gln Ser Pro Gly Thr Leu Ser Leu Ser Pro Gly
        1               5                   10                  15

Glu Arg Ala Thr Leu Ser Cys Arg Ala Ser Gln Ser Val Ser Pro Leu
                        20                  25                  30

Tyr Leu Ala Trp Tyr Gln Gln Lys Pro Gly Gln Ala Pro Arg Leu Leu
                        35                  40                  45

Met Tyr Asp Ala Ser Ile Arg Ala Thr Gly Ile Pro Asp Arg Phe Ser
                    50                  55                  60

Gly Ser Gly Ser Gly Thr Asp Phe Thr Leu Thr Ile Ser Arg Leu Glu
        65                  70                  75                  80
```

```
Pro Glu Asp Phe Ala Val Tyr Tyr Cys Gln Gln Tyr Lys Ala Trp Pro
                85                  90                  95

Leu Thr Phe Gly Gln Gly Thr Lys Val Glu Ile Lys
            100                 105
```

<210> SEQ ID NO 103
<211> LENGTH: 108
<212> TYPE: PRT
<213> ORGANISM: Artificial Sequence
<220> FEATURE:
<223> OTHER INFORMATION: Synthetic Construct

<400> SEQUENCE: 103

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Glu Trp Pro
                85                  90                  95

Leu Thr Phe Gly Gln Gly Thr Lys Val Glu Ile Lys
            100                 105
```

<210> SEQ ID NO 104
<211> LENGTH: 115
<212> TYPE: PRT
<213> ORGANISM: Artificial Sequence
<220> FEATURE:
<223> OTHER INFORMATION: Synthetic Construct

<400> SEQUENCE: 104

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Phe Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115
```

<210> SEQ ID NO 105
<211> LENGTH: 108
<212> TYPE: PRT
<213> ORGANISM: Artificial Sequence
<220> FEATURE:
<223> OTHER INFORMATION: Synthetic Construct

```
<400> SEQUENCE: 105

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Gln
            20                  25                  30

Tyr Leu Ala Trp Tyr Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Ala Trp Pro
                85                  90                  95

Leu Thr Phe Gly Gln Gly Thr Lys Val Glu Ile Lys
            100                 105

<210> SEQ ID NO 106
<211> LENGTH: 115
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Thr Trp Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
    115

<210> SEQ ID NO 107
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
50                  55                  60
```

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Lys Trp Pro
                85                  90                  95

Leu Thr Phe Gly Gln Gly Thr Lys Val Glu Ile Lys
                100                 105

<210> SEQ ID NO 108
<211> LENGTH: 108
<212> TYPE: PRT
<213> ORGANISM: Artificial Sequence
<220> FEATURE:
<223> OTHER INFORMATION: Synthetic Construct

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Val
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Arg Ala Trp Pro
                85                  90                  95

Leu Thr Phe Gly Gln Gly Thr Lys Val Glu Ile Lys
                100                 105

<210> SEQ ID NO 109
<211> LENGTH: 108
<212> TYPE: PRT
<213> ORGANISM: Artificial Sequence
<220> FEATURE:
<223> OTHER INFORMATION: Synthetic Construct

<400> SEQUENCE: 109

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ile Ala Val Ser Ser Thr
                20                  25                  30

Tyr Leu Ala Trp Tyr Gln Gln Lys Pro Gly Gln Ala Pro Arg Leu Leu
            35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Val Trp Pro
                85                  90                  95

Leu Thr Phe Gly Gln Gly Thr Lys Val Glu Ile Lys
                100                 105

<210> SEQ ID NO 110
<211> LENGTH: 115
<212> TYPE: PRT
<213> ORGANISM: Artificial Sequence
<220> FEATURE:
<223> OTHER INFORMATION: Synthetic Construct -continued

<400> SEQUENCE: 110

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Leu Phe Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

<210> SEQ ID NO 111
<211> LENGTH: 108
<212> TYPE: PRT
<213> ORGANISM: Artificial Sequence
<220> FEATURE:
<223> OTHER INFORMATION: Synthetic Construct

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Pro Arg Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Asp Trp Pro
                85                  90                  95

Leu Thr Phe Gly Gln Gly Thr Lys Val Glu Ile Lys
            100                 105

<210> SEQ ID NO 112
<211> LENGTH: 115
<212> TYPE: PRT
<213> ORGANISM: Artificial Sequence
<220> FEATURE:
<223> OTHER INFORMATION: Synthetic Construct

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ile Gly Gly Ser Gly Gly Ser Leu Pro Tyr Ala Asp Ser Val
    50                  55                  60

-continued

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Asp Ile Trp Gly Gln Gly Thr Leu Val Thr
            100                 105                 110

Val Ser Ser
        115

<210> SEQ ID NO 113
<211> LENGTH: 108
<212> TYPE: PRT
<213> ORGANISM: Artificial Sequence
<220> FEATURE:
<223> OTHER INFORMATION: Synthetic Construct

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
 65                 70                  75                  80

Pro Glu Asp Phe Ala Val Tyr Tyr Cys Gln Gln Tyr Gln Glu Trp Pro
                85                  90                  95

Leu Thr Phe Gly Gln Gly Thr Lys Val Glu Ile Lys
            100                 105

<210> SEQ ID NO 114
<211> LENGTH: 114
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Pro Met Ser Trp Val Arg Gln Ala Pro Gly Lys Gly Leu Glu Trp Val
        35                  40                  45

Ser Ala Ala Leu Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser

<210> SEQ ID NO 115
<211> LENGTH: 108

```
<212> TYPE: PRT
<213> ORGANISM: Artificial Sequence
<220> FEATURE:
<223> OTHER INFORMATION: Synthetic Construct

<400> SEQUENCE: 115

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Met Ser Trp Pro
                85                  90                  95

Leu Thr Phe Gly Gln Gly Thr Lys Val Glu Ile Lys
            100                 105

<210> SEQ ID NO 116
<211> LENGTH: 108
<212> TYPE: PRT
<213> ORGANISM: Artificial Sequence
<220> FEATURE:
<223> OTHER INFORMATION: Synthetic Construct

<400> SEQUENCE: 116

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Tyr Leu Ala Trp Tyr Gln Gln Lys Pro Gly Gln Ala Pro Arg Leu Leu
        35                  40                  45

Ile Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Lys Ser Trp Pro
                85                  90                  95

Leu Thr Phe Gly Gln Gly Thr Lys Val Glu Ile Lys
            100                 105

<210> SEQ ID NO 117
<211> LENGTH: 108
<212> TYPE: PRT
<213> ORGANISM: Artificial Sequence
<220> FEATURE:
<223> OTHER INFORMATION: Synthetic Construct

<400> SEQUENCE: 117

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Leu
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
```

```
                    50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Tyr Gly Trp Pro
                     85                  90                  95

Leu Thr Phe Gly Gln Gly Thr Lys Val Glu Ile Lys
                100                 105

<210> SEQ ID NO 118
<211> LENGTH: 115
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Pro Met Ser Trp Val Arg Gln Ala Pro Gly Lys Gly Leu Glu Trp Val
             35                  40                  45

Ser Ala Ile Gly Gly Ser Gly Gly Ser Leu Pro Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ala Asp Trp Gly Gln Gly Thr Leu Val Thr
                100                 105                 110

Val Ser Ser
        115

<210> SEQ ID NO 119
<211> LENGTH: 108
<212> TYPE: PRT
<213> ORGANISM: Artificial Sequence
<220> FEATURE:
<223> OTHER INFORMATION: Synthetic Construct

<400> SEQUENCE: 119

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Pro Ile Ser Ser Ser
                 20                  25                  30

Tyr Leu Ala Trp Tyr Gln Gln Lys Pro Gly Gln Ala Pro Arg Leu Leu
             35                  40                  45

Met Tyr Asp Ala Ser Ile Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gln Gly Trp Pro
                 85                  90                  95

Leu Thr Phe Gly Gln Gly Thr Lys Val Glu Ile Lys
                100                 105

<210> SEQ ID NO 120
<211> LENGTH: 115
```

```
<212> TYPE: PRT
<213> ORGANISM: Artificial Sequence
<220> FEATURE:
<223> OTHER INFORMATION: Synthetic Construct

<400> SEQUENCE: 120
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asp Ser Gly Phe Val Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115

```
<210> SEQ ID NO 121
<211> LENGTH: 108
<212> TYPE: PRT
<213> ORGANISM: Artificial Sequence
<220> FEATURE:
<223> OTHER INFORMATION: Synthetic Construct

<400> SEQUENCE: 121
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Glu Phe Trp Pro
                85                  90                  95

Leu Thr Phe Gly Gln Gly Thr Lys Val Glu Ile Lys
            100                 105

```
<210> SEQ ID NO 122
<211> LENGTH: 115
<212> TYPE: PRT
<213> ORGANISM: Artificial Sequence
<220> FEATURE:
<223> OTHER INFORMATION: Synthetic Construct

<400> SEQUENCE: 122
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val

```
                   35                  40                  45

Ser Ala Ile Gly Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Trp Pro Met Ser Leu Trp Gly Gln Gly Thr Leu Val Thr
            100                 105                 110

Val Ser Ser
        115

<210> SEQ ID NO 123
<211> LENGTH: 108
<212> TYPE: PRT
<213> ORGANISM: Artificial Sequence
<220> FEATURE:
<223> OTHER INFORMATION: Synthetic Construct

<400> SEQUENCE: 123

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Thr
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Met Ser Trp Pro
                 85                  90                  95

Leu Thr Phe Gly Gln Gly Thr Lys Val Glu Ile Lys
            100                 105

<210> SEQ ID NO 124
<211> LENGTH: 108
<212> TYPE: PRT
<213> ORGANISM: Artificial Sequence
<220> FEATURE:
<223> OTHER INFORMATION: Synthetic Construct

<400> SEQUENCE: 124

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Ser Ser Thr
             20                  25                  30

Tyr Leu Ala Trp Tyr Gln Gln Lys Pro Gly Gln Ala Pro Arg Leu Leu
         35                  40                  45

Met Tyr Asp Ala Ser Ile Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Tyr Trp Pro
                 85                  90                  95

Leu Thr Phe Gly Gln Gly Thr Lys Val Glu Ile Lys
            100                 105
```

<210> SEQ ID NO 125
<211> LENGTH: 115
<212> TYPE: PRT
<213> ORGANISM: Artificial Sequence
<220> FEATURE:
<223> OTHER INFORMATION: Synthetic Construct

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Cys Leu Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Asp Ser Trp Gly Gln Gly Thr Leu Val Thr
            100                 105                 110

Val Ser Ser
        115
```

<210> SEQ ID NO 126
<211> LENGTH: 108
<212> TYPE: PRT
<213> ORGANISM: Artificial Sequence
<220> FEATURE:
<223> OTHER INFORMATION: Synthetic Construct

<400> SEQUENCE: 126

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gln Trp Pro
                85                  90                  95

Leu Thr Phe Gly Gln Gly Thr Lys Val Glu Ile Lys
            100                 105
```

<210> SEQ ID NO 127
<211> LENGTH: 115
<212> TYPE: PRT
<213> ORGANISM: Artificial Sequence
<220> FEATURE:
<223> OTHER INFORMATION: Synthetic Construct

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Pro Met Ser Trp Val Arg Gln Ala Pro Gly Lys Gly Leu Glu Trp Val
            35                  40                  45

Ser Ala Leu Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Ser Leu Trp Gly Gln Gly Thr Leu Val Thr
            100                 105                 110

Val Ser Ser
        115
```

<210> SEQ ID NO 128
<211> LENGTH: 108
<212> TYPE: PRT
<213> ORGANISM: Artificial Sequence
<220> FEATURE:
<223> OTHER INFORMATION: Synthetic Construct

<400> SEQUENCE: 128

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Val Arg
            20                  25                  30

Tyr Leu Ala Trp Tyr Gln Gln Lys Pro Gly Gln Ala Pro Arg Leu Leu
        35                  40                  45

Met Tyr Asp Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Trp Pro
                85                  90                  95

Ile Thr Phe Gly Gln Gly Thr Lys Val Glu Ile Lys
            100                 105
```

<210> SEQ ID NO 129
<211> LENGTH: 5
<212> TYPE: PRT
<213> ORGANISM: Artificial Sequence
<220> FEATURE:
<223> OTHER INFORMATION: Synthetic Construct

<400> SEQUENCE: 129

```
Ser Tyr Ala Met Thr
1               5
```

<210> SEQ ID NO 130
<211> LENGTH: 7
<212> TYPE: PRT
<213> ORGANISM: Artificial Sequence
<220> FEATURE:
<223> OTHER INFORMATION: Synthetic Construct

<400> SEQUENCE: 130

```
Gly Phe Thr Phe Gly Ser Tyr
1               5
```

<210> SEQ ID NO 131

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 131

Gly Phe Thr Phe Gly Ser Tyr Ala Met Thr
1               5                   10

<210> SEQ ID NO 132
<211> LENGTH: 17
<212> TYPE: PRT
<213> ORGANISM: Artificial Sequence
<220> FEATURE:
<223> OTHER INFORMATION: Synthetic Construct

<400> SEQUENCE: 132

Ala Ile Ser Gly Ser Gly Gly Asn Thr Phe Tyr Ala Asp Ser Val Lys
1               5                   10                  15

Gly

<210> SEQ ID NO 133
<211> LENGTH: 6
<212> TYPE: PRT
<213> ORGANISM: Artificial Sequence
<220> FEATURE:
<223> OTHER INFORMATION: Synthetic Construct

<400> SEQUENCE: 133

Ser Gly Ser Gly Gly Asn
1               5

<210> SEQ ID NO 134
<211> LENGTH: 10
<212> TYPE: PRT
<213> ORGANISM: Artificial Sequence
<220> FEATURE:
<223> OTHER INFORMATION: Synthetic Construct

<400> SEQUENCE: 134

Val Ser Pro Ile Ala Ser Gly Met Asp Tyr
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Val Ser Pro Ile Ala Ala Gln Met Asp Tyr
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Synthetic Construct

<400> SEQUENCE: 136

Val Ser Pro Ile Ala Ala Leu Met Asp Tyr
1               5                   10
```

```
<210> SEQ ID NO 137
<211> LENGTH: 10
<212> TYPE: PRT
<213> ORGANISM: Artificial Sequence
<220> FEATURE:
<223> OTHER INFORMATION: Synthetic Construct

<400> SEQUENCE: 137

Val Ser Pro Ile Ala Ala Pro Met Asp Tyr
1               5                   10

<210> SEQ ID NO 138
<211> LENGTH: 17
<212> TYPE: PRT
<213> ORGANISM: Artificial Sequence
<220> FEATURE:
<223> OTHER INFORMATION: Synthetic Construct

<400> SEQUENCE: 138

Ala Ile Ser Gly Ser Gly Gly Asn Thr Phe Tyr Ala Asp Gln Arg Lys
1               5                   10                  15

Gly

<210> SEQ ID NO 139
<211> LENGTH: 17
<212> TYPE: PRT
<213> ORGANISM: Artificial Sequence
<220> FEATURE:
<223> OTHER INFORMATION: Synthetic Construct

<400> SEQUENCE: 139

Ala Ile Asp Tyr Ser Gly Gly Asn Thr Phe Tyr Ala Asp Ser Val Lys
1               5                   10                  15

Gly

<210> SEQ ID NO 140
<211> LENGTH: 6
<212> TYPE: PRT
<213> ORGANISM: Artificial Sequence
<220> FEATURE:
<223> OTHER INFORMATION: Synthetic Construct

<400> SEQUENCE: 140

Asp Tyr Ser Ser Gly Asn
1               5

<210> SEQ ID NO 141
<211> LENGTH: 17
<212> TYPE: PRT
<213> ORGANISM: Artificial Sequence
<220> FEATURE:
<223> OTHER INFORMATION: Synthetic Construct

<400> SEQUENCE: 141

Ala Ile Ser Tyr Gln Gly Gly Asn Thr Phe Tyr Ala Asp Ser Val Lys
1               5                   10                  15

Gly

<210> SEQ ID NO 142
<211> LENGTH: 6
<212> TYPE: PRT
<213> ORGANISM: Artificial Sequence
<220> FEATURE:
<223> OTHER INFORMATION: Synthetic Construct

<400> SEQUENCE: 142
```

Ser Tyr Gln Gly Gly Asn
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Ala Ile Ser Leu Thr Gly Gly Asn Thr Phe Tyr Ala Asp Ser Val Lys
1               5                   10                  15

Gly

<210> SEQ ID NO 144
<211> LENGTH: 6
<212> TYPE: PRT
<213> ORGANISM: Artificial Sequence
<220> FEATURE:
<223> OTHER INFORMATION: Synthetic Construct

<400> SEQUENCE: 144

Ser Leu Thr Gly Gly Asn
1               5

<210> SEQ ID NO 145
<211> LENGTH: 17
<212> TYPE: PRT
<213> ORGANISM: Artificial Sequence
<220> FEATURE:
<223> OTHER INFORMATION: Synthetic Construct

<400> SEQUENCE: 145

Ala Ile Ser His Ala Gly Gly Asn Thr Phe Tyr Ala Asp Ser Val Lys
1               5                   10                  15

Gly

<210> SEQ ID NO 146
<211> LENGTH: 6
<212> TYPE: PRT
<213> ORGANISM: Artificial Sequence
<220> FEATURE:
<223> OTHER INFORMATION: Synthetic Construct

<400> SEQUENCE: 146

Ser His Ala Gly Gly Asn
1               5

<210> SEQ ID NO 147
<211> LENGTH: 17
<212> TYPE: PRT
<213> ORGANISM: Artificial Sequence
<220> FEATURE:
<223> OTHER INFORMATION: Synthetic Construct

<400> SEQUENCE: 147

Ala Ile Ser Gly Ser Gly Gly Asn Thr Phe Tyr Ala Asp Gln Leu Lys
1               5                   10                  15

Gly

<210> SEQ ID NO 148
<211> LENGTH: 10
<212> TYPE: PRT

<213> ORGANISM: Artificial Sequence
<220> FEATURE:
<223> OTHER INFORMATION: Synthetic Construct

<400> SEQUENCE: 148

Val Ser Pro Ile Tyr Ala Gly Met Asp Tyr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Val Ser Pro Ile Ala Ala Glu Met Asp Tyr
1               5                   10

<210> SEQ ID NO 150
<211> LENGTH: 5
<212> TYPE: PRT
<213> ORGANISM: Artificial Sequence
<220> FEATURE:
<223> OTHER INFORMATION: Synthetic Construct

<400> SEQUENCE: 150

Ser Tyr Ala Met Asn
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic Construct

<400> SEQUENCE: 151

Gly Phe Thr Phe Ser Ser Tyr
1               5

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct

<400> SEQUENCE: 152

Gly Phe Thr Phe Ser Ser Tyr Ala Met Asn
1               5                   10

<210> SEQ ID NO 153
<211> LENGTH: 17
<212> TYPE: PRT
<213> ORGANISM: Artificial Sequence
<220> FEATURE:
<223> OTHER INFORMATION: Synthetic Construct

<400> SEQUENCE: 153

Ala Ile Ser Asp Ser Gly Gly Ser Thr Tyr Tyr Ala Asp Ser Val Lys
1               5                   10                  15

Gly

<210> SEQ ID NO 154
<211> LENGTH: 6

```
<212> TYPE: PRT
<213> ORGANISM: Artificial Sequence
<220> FEATURE:
<223> OTHER INFORMATION: Synthetic Construct

<400> SEQUENCE: 154

Ser Asp Ser Gly Gly Ser
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic Construct

<400> SEQUENCE: 155

Tyr Trp Pro Met Asp Ile
1               5

<210> SEQ ID NO 156
<211> LENGTH: 5
<212> TYPE: PRT
<213> ORGANISM: Artificial Sequence
<220> FEATURE:
<223> OTHER INFORMATION: Synthetic Construct

<400> SEQUENCE: 156

Ser Tyr Pro Met Ser
1               5

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Gly Phe Thr Phe Ser Ser Tyr Pro Met Ser
1               5                   10

<210> SEQ ID NO 158
<211> LENGTH: 17
<212> TYPE: PRT
<213> ORGANISM: Artificial Sequence
<220> FEATURE:
<223> OTHER INFORMATION: Synthetic Construct

<400> SEQUENCE: 158

Ala Ile Gly Gly Ser Gly Gly Ser Leu Pro Tyr Ala Asp Ser Val Lys
1               5                   10                  15

Gly

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct

<400> SEQUENCE: 159

Gly Gly Ser Gly Gly Ser
1               5

<210> SEQ ID NO 160
```

```
<211> LENGTH: 17
<212> TYPE: PRT
<213> ORGANISM: Artificial Sequence
<220> FEATURE:
<223> OTHER INFORMATION: Synthetic Construct

<400> SEQUENCE: 160

Ala Ile Leu Asp Ser Gly Gly Ser Thr Tyr Tyr Ala Asp Ser Val Lys
1               5                   10                  15

Gly

<210> SEQ ID NO 161
<211> LENGTH: 6
<212> TYPE: PRT
<213> ORGANISM: Artificial Sequence
<220> FEATURE:
<223> OTHER INFORMATION: Synthetic Construct

<400> SEQUENCE: 161

Tyr Trp Pro Met Asp Ser
1               5

<210> SEQ ID NO 162
<211> LENGTH: 17
<212> TYPE: PRT
<213> ORGANISM: Artificial Sequence
<220> FEATURE:
<223> OTHER INFORMATION: Synthetic Construct

<400> SEQUENCE: 162

Ala Ile Gly Gly Ser Gly Gly Ser Thr Tyr Tyr Ala Asp Ser Val Lys
1               5                   10                  15

Gly

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct

<400> SEQUENCE: 163

Ala Ile Ser Asp Ser Gly Gly Ser Ala Trp Tyr Ala Asp Ser Val Lys
1               5                   10                  15

Gly

<210> SEQ ID NO 164
<211> LENGTH: 6
<212> TYPE: PRT
<213> ORGANISM: Artificial Sequence
<220> FEATURE:
<223> OTHER INFORMATION: Synthetic Construct

<400> SEQUENCE: 164

Tyr Trp Pro Met Ser Leu
1               5

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165
```

```
Ala Ile Ser Asp Phe Gly Gly Ser Thr Tyr Tyr Ala Asp Ser Val Lys
1               5                   10                  15

Gly

<210> SEQ ID NO 166
<211> LENGTH: 6
<212> TYPE: PRT
<213> ORGANISM: Artificial Sequence
<220> FEATURE:
<223> OTHER INFORMATION: Synthetic Construct

<400> SEQUENCE: 166

Ser Asp Phe Gly Gly Ser
1               5

<210> SEQ ID NO 167
<211> LENGTH: 17
<212> TYPE: PRT
<213> ORGANISM: Artificial Sequence
<220> FEATURE:
<223> OTHER INFORMATION: Synthetic Construct

<400> SEQUENCE: 167

Ala Ile Thr Ala Ser Gly Gly Ser Thr Tyr Tyr Ala Asp Ser Val Lys
1               5                   10                  15

Gly

<210> SEQ ID NO 168
<211> LENGTH: 9
<212> TYPE: PRT
<213> ORGANISM: Artificial Sequence
<220> FEATURE:
<223> OTHER INFORMATION: Synthetic Construct

<400> SEQUENCE: 168

Thr Ala Ser Gly Gly Ser Leu Thr Ser
1               5

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct

<400> SEQUENCE: 169

Ala Ile Ser Asp Ser Gly Gly Ser Arg Trp Tyr Ala Asp Ser Val Lys
1               5                   10                  15

Gly

<210> SEQ ID NO 170
<211> LENGTH: 6
<212> TYPE: PRT
<213> ORGANISM: Artificial Sequence
<220> FEATURE:
<223> OTHER INFORMATION: Synthetic Construct

<400> SEQUENCE: 170

Tyr Trp Pro Met Thr Pro
1               5

<210> SEQ ID NO 171
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 171

Ala Val Leu Asp Ser Gly Gly Ser Thr Tyr Tyr Ala Asp Ser Val Lys
1               5                   10                  15
Gly

<210> SEQ ID NO 172
<211> LENGTH: 6
<212> TYPE: PRT
<213> ORGANISM: Artificial Sequence
<220> FEATURE:
<223> OTHER INFORMATION: Synthetic Construct

<400> SEQUENCE: 172

Leu Asp Ser Gly Gly Ser
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic Construct

<400> SEQUENCE: 173

Tyr Trp Pro Met Ser Asp
1               5

<210> SEQ ID NO 174
<211> LENGTH: 17
<212> TYPE: PRT
<213> ORGANISM: Artificial Sequence
<220> FEATURE:
<223> OTHER INFORMATION: Synthetic Construct

<400> SEQUENCE: 174

Ala Ile Ser Asp Ser Gly Gly Ser Lys Trp Tyr Ala Asp Ser Val Lys
1               5                   10                  15
Gly

<210> SEQ ID NO 175
<211> LENGTH: 17
<212> TYPE: PRT
<213> ORGANISM: Artificial Sequence
<220> FEATURE:
<223> OTHER INFORMATION: Synthetic Construct

<400> SEQUENCE: 175

Ala Ile Ser Asp Ser Gly Gly Ser Gly Trp Tyr Ala Asp Ser Val Lys
1               5                   10                  15
Gly

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct

<400> SEQUENCE: 176

Ala Ile Ser Asp Ser Gly Gly Ser Cys Trp Tyr Ala Asp Ser Val Lys
1               5                   10                  15
```

```
<210> SEQ ID NO 177
<211> LENGTH: 17
<212> TYPE: PRT
<213> ORGANISM: Artificial Sequence
<220> FEATURE:
<223> OTHER INFORMATION: Synthetic Construct

<400> SEQUENCE: 177

Ala Ile Phe Ala Ser Gly Gly Ser Thr Tyr Tyr Ala Asp Ser Val Lys
1               5                   10                  15

Gly

<210> SEQ ID NO 178
<211> LENGTH: 6
<212> TYPE: PRT
<213> ORGANISM: Artificial Sequence
<220> FEATURE:
<223> OTHER INFORMATION: Synthetic Construct

<400> SEQUENCE: 178

Phe Ala Ser Gly Gly Ser
1               5

<210> SEQ ID NO 179
<211> LENGTH: 6
<212> TYPE: PRT
<213> ORGANISM: Artificial Sequence
<220> FEATURE:
<223> OTHER INFORMATION: Synthetic Construct

<400> SEQUENCE: 179

Ser Gly Trp Gly Gly Ser
1               5

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Ala Ile Met Ser Ser Gly Gly Pro Leu Tyr Tyr Ala Asp Ser Val Lys
1               5                   10                  15

Gly

<210> SEQ ID NO 181
<211> LENGTH: 6
<212> TYPE: PRT
<213> ORGANISM: Artificial Sequence
<220> FEATURE:
<223> OTHER INFORMATION: Synthetic Construct

<400> SEQUENCE: 181

Met Ser Ser Gly Gly Pro
1               5

<210> SEQ ID NO 182
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 182

Tyr Trp Pro Met Ala Leu
1               5

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Ala Ile Leu Met Ser Gly Gly Ser Thr Tyr Tyr Ala Asp Ser Val Lys
1               5                   10                  15

Gly

<210> SEQ ID NO 184
<211> LENGTH: 6
<212> TYPE: PRT
<213> ORGANISM: Artificial Sequence
<220> FEATURE:
<223> OTHER INFORMATION: Synthetic Construct

<400> SEQUENCE: 184

Leu Met Ser Gly Gly Ser
1               5

<210> SEQ ID NO 185
<211> LENGTH: 17
<212> TYPE: PRT
<213> ORGANISM: Artificial Sequence
<220> FEATURE:
<223> OTHER INFORMATION: Synthetic Construct

<400> SEQUENCE: 185

Ala Ile Ser Asp Ser Gly Gly Tyr Arg Tyr Tyr Ala Asp Ser Val Lys
1               5                   10                  15

Gly

<210> SEQ ID NO 186
<211> LENGTH: 6
<212> TYPE: PRT
<213> ORGANISM: Artificial Sequence
<220> FEATURE:
<223> OTHER INFORMATION: Synthetic Construct

<400> SEQUENCE: 186

Ser Asp Ser Gly Gly Tyr
1               5

<210> SEQ ID NO 187
<211> LENGTH: 17
<212> TYPE: PRT
<213> ORGANISM: Artificial Sequence
<220> FEATURE:
<223> OTHER INFORMATION: Synthetic Construct

<400> SEQUENCE: 187

Ala Ile Leu Ser Ser Gly Gly Ser Thr Tyr Tyr Ala Asp Ser Val Lys
1               5                   10                  15

Gly

<210> SEQ ID NO 188
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 188

Leu Ser Ser Gly Gly Ser
1               5

<210> SEQ ID NO 189
<211> LENGTH: 7
<212> TYPE: PRT
<213> ORGANISM: Artificial Sequence
<220> FEATURE:
<223> OTHER INFORMATION: Synthetic Construct

<400> SEQUENCE: 189

Ala Tyr Trp Pro Met Ser Pro
1               5

<210> SEQ ID NO 190
<211> LENGTH: 17
<212> TYPE: PRT
<213> ORGANISM: Artificial Sequence
<220> FEATURE:
<223> OTHER INFORMATION: Synthetic Construct

<400> SEQUENCE: 190

Ala Ile Gly Gly Ser Gly Gly Trp Ser Tyr Tyr Ala Asp Ser Val Lys
1               5                   10                  15
Gly

<210> SEQ ID NO 191
<211> LENGTH: 6
<212> TYPE: PRT
<213> ORGANISM: Artificial Sequence
<220> FEATURE:
<223> OTHER INFORMATION: Synthetic Construct

<400> SEQUENCE: 191

Gly Gly Ser Gly Gly Trp
1               5

<210> SEQ ID NO 192
<211> LENGTH: 17
<212> TYPE: PRT
<213> ORGANISM: Artificial Sequence
<220> FEATURE:
<223> OTHER INFORMATION: Synthetic Construct

<400> SEQUENCE: 192

Ala Thr Val Gly Ser Gly Gly Ser Ile Gly Tyr Ala Asp Ser Val Lys
1               5                   10                  15
Gly

<210> SEQ ID NO 193
<211> LENGTH: 6
<212> TYPE: PRT
<213> ORGANISM: Artificial Sequence
<220> FEATURE:
<223> OTHER INFORMATION: Synthetic Construct

<400> SEQUENCE: 193

Val Gly Ser Gly Gly Ser
1               5
```

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct

<400> SEQUENCE: 194

Ala Ile Gly Gly Ser Gly Gly Ser Ile His Tyr Ala Asp Ser Val Lys
1               5                   10                  15

Gly

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

Ala His Ile Gly Ser Gly Gly Ser Thr Tyr Tyr Ala Asp Ser Val Lys
1               5                   10                  15

Gly

<210> SEQ ID NO 196
<211> LENGTH: 6
<212> TYPE: PRT
<213> ORGANISM: Artificial Sequence
<220> FEATURE:
<223> OTHER INFORMATION: Synthetic Construct

<400> SEQUENCE: 196

Ile Gly Ser Gly Gly Ser
1               5

<210> SEQ ID NO 197
<211> LENGTH: 6
<212> TYPE: PRT
<213> ORGANISM: Artificial Sequence
<220> FEATURE:
<223> OTHER INFORMATION: Synthetic Construct

<400> SEQUENCE: 197

Tyr Trp Pro Met Asp Pro
1               5

<210> SEQ ID NO 198
<211> LENGTH: 17
<212> TYPE: PRT
<213> ORGANISM: Artificial Sequence
<220> FEATURE:
<223> OTHER INFORMATION: Synthetic Construct

<400> SEQUENCE: 198

Ala Ile Gly Gly Ser Gly Gly Ser Leu Gly Tyr Ala Asp Ser Val Lys
1               5                   10                  15

Gly

<210> SEQ ID NO 199
<211> LENGTH: 17
<212> TYPE: PRT
<213> ORGANISM: Artificial Sequence
<220> FEATURE:
<223> OTHER INFORMATION: Synthetic Construct -continued

```
<400> SEQUENCE: 199

Ala Ile Gly Gly Ser Gly Thr Trp Thr Tyr Tyr Ala Asp Ser Val Lys
1               5                   10                  15

Gly

<210> SEQ ID NO 200
<211> LENGTH: 6
<212> TYPE: PRT
<213> ORGANISM: Artificial Sequence
<220> FEATURE:
<223> OTHER INFORMATION: Synthetic Construct

<400> SEQUENCE: 200

Gly Gly Ser Gly Thr Trp
1               5

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct

<400> SEQUENCE: 201

Ala Leu Phe Gly Ser Gly Gly Ser Thr Tyr Tyr Ala Asp Ser Val Lys
1               5                   10                  15

Gly

<210> SEQ ID NO 202
<211> LENGTH: 6
<212> TYPE: PRT
<213> ORGANISM: Artificial Sequence
<220> FEATURE:
<223> OTHER INFORMATION: Synthetic Construct

<400> SEQUENCE: 202

Phe Gly Ser Gly Gly Ser
1               5

<210> SEQ ID NO 203
<211> LENGTH: 17
<212> TYPE: PRT
<213> ORGANISM: Artificial Sequence
<220> FEATURE:
<223> OTHER INFORMATION: Synthetic Constrict

<400> SEQUENCE: 203

Ala Ala Leu Gly Ser Gly Gly Ser Thr Tyr Tyr Ala Asp Ser Val Lys
1               5                   10                  15

Gly

<210> SEQ ID NO 204
<211> LENGTH: 6
<212> TYPE: PRT
<213> ORGANISM: Artificial Sequence
<220> FEATURE:
<223> OTHER INFORMATION: Synthetic Construct

<400> SEQUENCE: 204

Leu Gly Ser Gly Gly Ser
1               5

<210> SEQ ID NO 205
<211> LENGTH: 6
```

```
<212> TYPE: PRT
<213> ORGANISM: Artificial Sequence
<220> FEATURE:
<223> OTHER INFORMATION: Synthetic Construct

<400> SEQUENCE: 205

Tyr Trp Pro Met Ala Asp
1               5

<210> SEQ ID NO 206
<211> LENGTH: 17
<212> TYPE: PRT
<213> ORGANISM: Artificial Sequence
<220> FEATURE:
<223> OTHER INFORMATION: Synthetic Construct

<400> SEQUENCE: 206

Ala Ile Ser Asp Ser Gly Gly Phe Val Tyr Tyr Ala Asp Ser Val Lys
1               5                   10                  15

Gly

<210> SEQ ID NO 207
<211> LENGTH: 6
<212> TYPE: PRT
<213> ORGANISM: Artificial Sequence
<220> FEATURE:
<223> OTHER INFORMATION: Synthetic Construct

<400> SEQUENCE: 207

Ser Asp Ser Gly Gly Phe
1               5

<210> SEQ ID NO 208
<211> LENGTH: 17
<212> TYPE: PRT
<213> ORGANISM: Artificial Sequence
<220> FEATURE:
<223> OTHER INFORMATION: Synthetic Construct

<400> SEQUENCE: 208

Ala Cys Leu Asp Ser Gly Gly Ser Thr Tyr Tyr Ala Asp Ser Val Lys
1               5                   10                  15

Gly

<210> SEQ ID NO 209
<211> LENGTH: 12
<212> TYPE: PRT
<213> ORGANISM: Artificial Sequence
<220> FEATURE:
<223> OTHER INFORMATION: Synthetic Construct

<400> SEQUENCE: 209

Arg Ala Ser Gln Ser Val Ser Ser Ser Tyr Leu Ala
1               5                   10

<210> SEQ ID NO 210
<211> LENGTH: 7
<212> TYPE: PRT
<213> ORGANISM: Artificial Sequence
<220> FEATURE:
<223> OTHER INFORMATION: Synthetic Construct

<400> SEQUENCE: 210

Gly Ala Ser Ser Arg Ala Thr
1               5
```

<210> SEQ ID NO 211
<211> LENGTH: 10
<212> TYPE: PRT
<213> ORGANISM: Artificial Sequence
<220> FEATURE:
<223> OTHER INFORMATION: Synthetic Construct

<400> SEQUENCE: 211

Gln His Tyr Gly Ser Pro Pro Ser Phe Thr
1               5                   10

<210> SEQ ID NO 212
<211> LENGTH: 12
<212> TYPE: PRT
<213> ORGANISM: Artificial Sequence
<220> FEATURE:
<223> OTHER INFORMATION: Synthetic Construct

<400> SEQUENCE: 212

Arg Ala Ser Gln Ser Leu Gly Ser Phe Tyr Leu Ala
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic Construct

<400> SEQUENCE: 213

Lys His Tyr Gly Trp Pro Pro Ser Phe Thr
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic Construct

<400> SEQUENCE: 214

Gln His Tyr Asn Tyr Pro Pro Ser Phe Thr
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Synthetic Construct

<400> SEQUENCE: 215

Arg Ala Ser Gln Ser Val Gly Asp Phe Tyr Leu Ala
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Gln His Tyr Pro Tyr Pro Pro Ser Phe Thr
1               5                   10

```
<210> SEQ ID NO 217
<211> LENGTH: 12
<212> TYPE: PRT
<213> ORGANISM: Artificial Sequence
<220> FEATURE:
<223> OTHER INFORMATION: Synthetic Construct

<400> SEQUENCE: 217

Arg Ala Ser Gln Ser Val Ser Ser Tyr Pro Ser
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Synthetic Construct

<400> SEQUENCE: 218

Arg Ala Ser Gln Ser Val Ser Ala His Tyr Leu Ala
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Synthetic Construct

<400> SEQUENCE: 219

Arg Ala Ser Gln Ser Val Ser Ser Phe Phe Leu Ala
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Synthetic Construct

<400> SEQUENCE: 220

Lys Tyr Tyr Pro Tyr Pro Pro Ser Phe Thr
1               5                   10

<210> SEQ ID NO 221
<211> LENGTH: 7
<212> TYPE: PRT
<213> ORGANISM: Artificial Sequence
<220> FEATURE:
<223> OTHER INFORMATION: Synthetic Construct

<400> SEQUENCE: 221

Asp Ala Ser Ile Arg Ala Thr
1               5

<210> SEQ ID NO 222
<211> LENGTH: 9
<212> TYPE: PRT
<213> ORGANISM: Artificial Sequence
<220> FEATURE:
<223> OTHER INFORMATION: Synthetic Construct

<400> SEQUENCE: 222

Gln Gln Tyr Gly Ser Trp Pro Leu Thr
1               5

<210> SEQ ID NO 223
```

```
<211> LENGTH: 12
<212> TYPE: PRT
<213> ORGANISM: Artificial Sequence
<220> FEATURE:
<223> OTHER INFORMATION: Synthetic Construct

<400> SEQUENCE: 223

Arg Ala Ser Gln Ser Val Ser Val Leu Tyr Leu Ala
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Gln Gln Tyr Gln Arg Trp Pro Leu Thr
1               5

<210> SEQ ID NO 225
<211> LENGTH: 9
<212> TYPE: PRT
<213> ORGANISM: Artificial Sequence
<220> FEATURE:
<223> OTHER INFORMATION: Synthetic Construct

<400> SEQUENCE: 225

Gln Gln Tyr Gln Ser Trp Pro Leu Thr
1               5

<210> SEQ ID NO 226
<211> LENGTH: 12
<212> TYPE: PRT
<213> ORGANISM: Artificial Sequence
<220> FEATURE:
<223> OTHER INFORMATION: Synthetic Construct

<400> SEQUENCE: 226

Arg Ala Ser Gln Ser Val Ser Asp Leu Tyr Leu Ala
1               5                   10

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Gln Gln Tyr Gln Thr Trp Pro Leu Thr
1               5

<210> SEQ ID NO 228
<211> LENGTH: 12
<212> TYPE: PRT
<213> ORGANISM: Artificial Sequence
<220> FEATURE:
<223> OTHER INFORMATION: Synthetic Construct

<400> SEQUENCE: 228

Arg Ala Ser Gln Ser Val Ser Asn Leu Tyr Leu Ala
1               5                   10

<210> SEQ ID NO 229
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 229

Gln Gln Tyr Gln Gly Trp Pro Leu Thr
1               5

<210> SEQ ID NO 230
<211> LENGTH: 12
<212> TYPE: PRT
<213> ORGANISM: Artificial Sequence
<220> FEATURE:
<223> OTHER INFORMATION: Synthetic Construct

<400> SEQUENCE: 230

Arg Ala Ser Gln Ser Val Ser Ala Tyr Tyr Leu Ala
1               5                   10

<210> SEQ ID NO 231
<211> LENGTH: 9
<212> TYPE: PRT
<213> ORGANISM: Artificial Sequence
<220> FEATURE:
<223> OTHER INFORMATION: Synthetic Construct

<400> SEQUENCE: 231

Gln Gln Tyr Glu Arg Trp Pro Leu Thr
1               5

<210> SEQ ID NO 232
<211> LENGTH: 12
<212> TYPE: PRT
<213> ORGANISM: Artificial Sequence
<220> FEATURE:
<223> OTHER INFORMATION: Synthetic Construct

<400> SEQUENCE: 232

Arg Ala Ser Gln Ser Val Ser Ser Leu Tyr Leu Ala
1               5                   10

<210> SEQ ID NO 233
<211> LENGTH: 9
<212> TYPE: PRT
<213> ORGANISM: Artificial Sequence
<220> FEATURE:
<223> OTHER INFORMATION: Synthetic Construct

<400> SEQUENCE: 233

Gln Gln Tyr Gln Val Trp Pro Leu Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Construct

<400> SEQUENCE: 234

Gln Gln Tyr Leu Asp Trp Pro Leu Thr
1               5

<210> SEQ ID NO 235
<211> LENGTH: 12
<212> TYPE: PRT
```

```
<213> ORGANISM: Artificial Sequence
<220> FEATURE:
<223> OTHER INFORMATION: Synthetic Construct

<400> SEQUENCE: 235

Arg Ala Ser Gln Ser Val Ser Ala Leu Tyr Leu Ala
1               5                   10

<210> SEQ ID NO 236
<211> LENGTH: 9
<212> TYPE: PRT
<213> ORGANISM: Artificial Sequence
<220> FEATURE:
<223> OTHER INFORMATION: SEQ ID NO.: 237

<400> SEQUENCE: 236

Gln Gln Tyr Leu Ala Trp Pro Leu Thr
1               5

<210> SEQ ID NO 237
<211> LENGTH: 9
<212> TYPE: PRT
<213> ORGANISM: Artificial Sequence
<220> FEATURE:
<223> OTHER INFORMATION: Synthetic Construct

<400> SEQUENCE: 237

Gln Gln Tyr Phe Thr Trp Pro Leu Thr
1               5

<210> SEQ ID NO 238
<211> LENGTH: 12
<212> TYPE: PRT
<213> ORGANISM: Artificial Sequence
<220> FEATURE:
<223> OTHER INFORMATION: Synthetic Construct

<400> SEQUENCE: 238

Arg Ala Ser Gln Ser Val Ser Pro Tyr Tyr Leu Ala
1               5                   10

<210> SEQ ID NO 239
<211> LENGTH: 12
<212> TYPE: PRT
<213> ORGANISM: Artificial Sequence
<220> FEATURE:
<223> OTHER INFORMATION: Synthetic Construct

<400> SEQUENCE: 239

Arg Ala Ser Gln Ser Val Ser Val Glu Tyr Leu Ala
1               5                   10

<210> SEQ ID NO 240
<211> LENGTH: 9
<212> TYPE: PRT
<213> ORGANISM: Artificial Sequence
<220> FEATURE:
<223> OTHER INFORMATION: Synthetic Construct

<400> SEQUENCE: 240

Gln Gln Tyr Ala Arg Trp Pro Leu Thr
1               5

<210> SEQ ID NO 241
<211> LENGTH: 12
<212> TYPE: PRT
<213> ORGANISM: Artificial Sequence
```

```
<220> FEATURE:
<223> OTHER INFORMATION: Synthetic Construct

<400> SEQUENCE: 241

Arg Ala Ser Gln Ser Val Ser Glu Leu Tyr Leu Ala
1               5                   10

<210> SEQ ID NO 242
<211> LENGTH: 9
<212> TYPE: PRT
<213> ORGANISM: Artificial Sequence
<220> FEATURE:
<223> OTHER INFORMATION: Synthetic Construct

<400> SEQUENCE: 242

Gln Gln Tyr Phe Gly Trp Pro Leu Thr
1               5

<210> SEQ ID NO 243
<211> LENGTH: 12
<212> TYPE: PRT
<213> ORGANISM: Artificial Sequence
<220> FEATURE:
<223> OTHER INFORMATION: Synthetic Construct

<400> SEQUENCE: 243

Arg Ala Ser Gln Ser Val Glu Met Ser Tyr Leu Ala
1               5                   10

<210> SEQ ID NO 244
<211> LENGTH: 9
<212> TYPE: PRT
<213> ORGANISM: Artificial Sequence
<220> FEATURE:
<223> OTHER INFORMATION: Synthetic Construct

<400> SEQUENCE: 244

Gln Gln Tyr Ala His Trp Pro Leu Thr
1               5

<210> SEQ ID NO 245
<211> LENGTH: 12
<212> TYPE: PRT
<213> ORGANISM: Artificial Sequence
<220> FEATURE:
<223> OTHER INFORMATION: Synthetic Construct

<400> SEQUENCE: 245

Arg Ala Ser Gln Ser Val Ser Ala Gln Tyr Leu Ala
1               5                   10

<210> SEQ ID NO 246
<211> LENGTH: 12
<212> TYPE: PRT
<213> ORGANISM: Artificial Sequence
<220> FEATURE:
<223> OTHER INFORMATION: Synthetic Construct

<400> SEQUENCE: 246

Gly Pro Ser Gln Ser Val Ser Ser Ser Tyr Leu Ala
1               5                   10

<210> SEQ ID NO 247
<211> LENGTH: 12
<212> TYPE: PRT
<213> ORGANISM: Artificial Sequence
<220> FEATURE:
```

```
<223> OTHER INFORMATION: Synthetic Construct

<400> SEQUENCE: 247

Arg Ala Ser Gln Ser Val Ser Ser Ser Tyr Trp Ala
1               5                   10

<210> SEQ ID NO 248
<211> LENGTH: 9
<212> TYPE: PRT
<213> ORGANISM: Artificial Sequence
<220> FEATURE:
<223> OTHER INFORMATION: Synthetic Construct

<400> SEQUENCE: 248

Gln Gln Tyr Glu Ser Trp Pro Leu Thr
1               5

<210> SEQ ID NO 249
<211> LENGTH: 12
<212> TYPE: PRT
<213> ORGANISM: Artificial Sequence
<220> FEATURE:
<223> OTHER INFORMATION: Synthetic Construct

<400> SEQUENCE: 249

Arg Gly Gly Gln Ser Val Ser Ser Ser Tyr Leu Ala
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Synthetic Construct

<400> SEQUENCE: 250

Arg Ala Ser Gln Ser Val Ser Phe Leu Tyr Leu Ala
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Synthetic Construct

<400> SEQUENCE: 251

Arg Ala Ser Gln Ser Val Ser Ser Thr Tyr Leu Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: Synthetic Construct

<400> SEQUENCE: 252

Asp Ala Ser Ser Arg Ala Pro
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 253

Gln Gln Tyr Ser Thr Ser Pro Leu Thr
1               5

<210> SEQ ID NO 254
<211> LENGTH: 12
<212> TYPE: PRT
<213> ORGANISM: Artificial Sequence
<220> FEATURE:
<223> OTHER INFORMATION: Synthetic Construct

<400> SEQUENCE: 254

Arg Ala Ser Gln Ser Val Ser Pro Glu Tyr Leu Ala
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic Construct

<400> SEQUENCE: 255

Gln Gln Tyr Ser Val Trp Pro Leu Thr
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

Gln Gln Tyr Ser Ala Trp Pro Leu Thr
1               5

<210> SEQ ID NO 257
<211> LENGTH: 12
<212> TYPE: PRT
<213> ORGANISM: Artificial Sequence
<220> FEATURE:
<223> OTHER INFORMATION: Synthetic Construct

<400> SEQUENCE: 257

Arg Ala Ser Gln Ser Val Ser Ser Val Tyr Leu Ala
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Synthetic Construct

<400> SEQUENCE: 258

Gln Gln Tyr Ser Thr Trp Pro Leu Thr
1               5

<210> SEQ ID NO 259
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 259

Gln Gln Tyr Ser Arg Trp Pro Leu Thr
1               5

<210> SEQ ID NO 260
<211> LENGTH: 12
<212> TYPE: PRT
<213> ORGANISM: Artificial Sequence
<220> FEATURE:
<223> OTHER INFORMATION: Synthetic Construct

<400> SEQUENCE: 260

Arg Ala Ser Gln Ser Val Ser Pro Leu Tyr Leu Ala
1               5                   10

<210> SEQ ID NO 261
<211> LENGTH: 9
<212> TYPE: PRT
<213> ORGANISM: Artificial Sequence
<220> FEATURE:
<223> OTHER INFORMATION: Synthetic Construct

<400> SEQUENCE: 261

Gln Gln Tyr Ser Ala Phe Pro Leu Thr
1               5

<210> SEQ ID NO 262
<211> LENGTH: 12
<212> TYPE: PRT
<213> ORGANISM: Artificial Sequence
<220> FEATURE:
<223> OTHER INFORMATION: Synthetic Construct

<400> SEQUENCE: 262

Trp Leu Ser Gln Ser Val Ser Ser Thr Tyr Leu Ala
1               5                   10

<210> SEQ ID NO 263
<211> LENGTH: 9
<212> TYPE: PRT
<213> ORGANISM: Artificial Sequence
<220> FEATURE:
<223> OTHER INFORMATION: Synthetic Construct

<400> SEQUENCE: 263

Gln Gln Tyr Ser Glu Trp Pro Leu Thr
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic Construct

<400> SEQUENCE: 264

Gln Gln Tyr Ser Ser Trp Pro Leu Thr
1               5

<210> SEQ ID NO 265
<211> LENGTH: 12
<212> TYPE: PRT
<213> ORGANISM: Artificial Sequence
<220> FEATURE:
<223> OTHER INFORMATION: Synthetic Construct

<400> SEQUENCE: 265
```

Arg Ala Ser Gln Ser Val Ser Ser Leu Phe Leu Ala
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Synthetic Construct

<400> SEQUENCE: 266

Ala Cys Ser Gln Ser Val Ser Ser Thr Tyr Leu Ala
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Synthetic Construct

<400> SEQUENCE: 267

Arg Ala Ser Cys Asp Val Ser Ser Thr Tyr Leu Ala
1               5                   10

<210> SEQ ID NO 268
<211> LENGTH: 9
<212> TYPE: PRT
<213> ORGANISM: Artificial Sequence
<220> FEATURE:
<223> OTHER INFORMATION: Synthetic Construct

<400> SEQUENCE: 268

Gln Gln Tyr Met Arg Ser Pro Leu Thr
1               5

<210> SEQ ID NO 269
<211> LENGTH: 12
<212> TYPE: PRT
<213> ORGANISM: Artificial Sequence
<220> FEATURE:
<223> OTHER INFORMATION: Synthetic Construct

<400> SEQUENCE: 269

Arg Ala Ser Glu Ala Val Pro Ser Thr Tyr Leu Ala
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Synthetic Construct

<400> SEQUENCE: 270

Cys Ser Ser Gln Ser Val Ser Ser Thr Tyr Leu Ala
1               5                   10

<210> SEQ ID NO 271
<211> LENGTH: 12
<212> TYPE: PRT
<213> ORGANISM: Artificial Sequence
<220> FEATURE:
<223> OTHER INFORMATION: Synthetic Construct

<400> SEQUENCE: 271

```
Arg Ala Ser Val Arg Val Ser Ser Thr Tyr Leu Ala
1               5                   10

<210> SEQ ID NO 272
<211> LENGTH: 9
<212> TYPE: PRT
<213> ORGANISM: Artificial Sequence
<220> FEATURE:
<223> OTHER INFORMATION: Synthetic Construct

<400> SEQUENCE: 272

Gln Gln Tyr Met Lys Trp Pro Leu Thr
1               5

<210> SEQ ID NO 273
<211> LENGTH: 12
<212> TYPE: PRT
<213> ORGANISM: Artificial Sequence
<220> FEATURE:
<223> OTHER INFORMATION: Synthetic Construct

<400> SEQUENCE: 273

Arg Ala Ser Gln Ser Val Ser Ala Ala Tyr Leu Ala
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Synthetic Construct

<400> SEQUENCE: 274

Gln Gln Tyr Met Cys Trp Pro Leu Thr
1               5

<210> SEQ ID NO 275
<211> LENGTH: 12
<212> TYPE: PRT
<213> ORGANISM: Artificial Sequence
<220> FEATURE:
<223> OTHER INFORMATION: Synthetic Construct

<400> SEQUENCE: 275

Arg Ala Ser Gln Ser Val Ser Ser Ser Tyr Trp Gly
1               5                   10

<210> SEQ ID NO 276
<211> LENGTH: 9
<212> TYPE: PRT
<213> ORGANISM: Artificial Sequence
<220> FEATURE:
<223> OTHER INFORMATION: Synthetic Construct

<400> SEQUENCE: 276

Gln Gln Tyr Gln Cys Trp Pro Leu Thr
1               5

<210> SEQ ID NO 277
<211> LENGTH: 12
<212> TYPE: PRT
<213> ORGANISM: Artificial Sequence
<220> FEATURE:
<223> OTHER INFORMATION: Synthetic Construct

<400> SEQUENCE: 277

Arg Ala Ser Gln Ser Val Ser Ser Pro Tyr Leu Ala
```

```
<210> SEQ ID NO 278
<211> LENGTH: 9
<212> TYPE: PRT
<213> ORGANISM: Artificial Sequence
<220> FEATURE:
<223> OTHER INFORMATION: Synthetic Construct

<400> SEQUENCE: 278

Gln Gln Tyr Lys Ala Trp Pro Leu Thr
1               5

<210> SEQ ID NO 279
<211> LENGTH: 12
<212> TYPE: PRT
<213> ORGANISM: Artificial Sequence
<220> FEATURE:
<223> OTHER INFORMATION: Synthetic Construct

<400> SEQUENCE: 279

Arg Ala Ser Gln Ser Val Ser Tyr Leu Tyr Leu Ala
1               5                   10

<210> SEQ ID NO 280
<211> LENGTH: 9
<212> TYPE: PRT
<213> ORGANISM: Artificial Sequence
<220> FEATURE:
<223> OTHER INFORMATION: Synthetic Construct

<400> SEQUENCE: 280

Gln Gln Tyr Met Glu Trp Pro Leu Thr
1               5

<210> SEQ ID NO 281
<211> LENGTH: 9
<212> TYPE: PRT
<213> ORGANISM: Artificial Sequence
<220> FEATURE:
<223> OTHER INFORMATION: Synthetic Construct

<400> SEQUENCE: 281

Gln Gln Tyr Gln Ala Trp Pro Leu Thr
1               5

<210> SEQ ID NO 282
<211> LENGTH: 9
<212> TYPE: PRT
<213> ORGANISM: Artificial Sequence
<220> FEATURE:
<223> OTHER INFORMATION: Synthetic Construct

<400> SEQUENCE: 282

Gln Gln Tyr Gln Lys Trp Pro Leu Thr
1               5

<210> SEQ ID NO 283
<211> LENGTH: 12
<212> TYPE: PRT
<213> ORGANISM: Artificial Sequence
<220> FEATURE:
<223> OTHER INFORMATION: Synthetic Construct

<400> SEQUENCE: 283

Arg Ala Ser Gln Ser Val Ser Ala Val Tyr Leu Ala
1               5                   10
```

<210> SEQ ID NO 284
<211> LENGTH: 9
<212> TYPE: PRT
<213> ORGANISM: Artificial Sequence
<220> FEATURE:
<223> OTHER INFORMATION: Synthetic Construct

<400> SEQUENCE: 284

Gln Gln Tyr Arg Ala Trp Pro Leu Thr
1               5

<210> SEQ ID NO 285
<211> LENGTH: 12
<212> TYPE: PRT
<213> ORGANISM: Artificial Sequence
<220> FEATURE:
<223> OTHER INFORMATION: Synthetic Construct

<400> SEQUENCE: 285

Arg Ala Ser Ile Ala Val Ser Ser Thr Tyr Leu Ala
1               5                   10

<210> SEQ ID NO 286
<211> LENGTH: 9
<212> TYPE: PRT
<213> ORGANISM: Artificial Sequence
<220> FEATURE:
<223> OTHER INFORMATION: Synthetic Construct

<400> SEQUENCE: 286

Gln Gln Tyr Met Val Trp Pro Leu Thr
1               5

<210> SEQ ID NO 287
<211> LENGTH: 12
<212> TYPE: PRT
<213> ORGANISM: Artificial Sequence
<220> FEATURE:
<223> OTHER INFORMATION: Synthetic Construct

<400> SEQUENCE: 287

Arg Pro Arg Gln Ser Val Ser Ser Ser Tyr Leu Ala
1               5                   10

<210> SEQ ID NO 288
<211> LENGTH: 9
<212> TYPE: PRT
<213> ORGANISM: Artificial Sequence
<220> FEATURE:
<223> OTHER INFORMATION: Synthetic Construct

<400> SEQUENCE: 288

Gln Gln Tyr Gln Asp Trp Pro Leu Thr
1               5

<210> SEQ ID NO 289
<211> LENGTH: 9
<212> TYPE: PRT
<213> ORGANISM: Artificial Sequence
<220> FEATURE:
<223> OTHER INFORMATION: Synthetic Construct

<400> SEQUENCE: 289

Gln Gln Tyr Gln Glu Trp Pro Leu Thr
1               5

```
<210> SEQ ID NO 290
<211> LENGTH: 12
<212> TYPE: PRT
<213> ORGANISM: Artificial Sequence
<220> FEATURE:
<223> OTHER INFORMATION: Synthetic Construct

<400> SEQUENCE: 290

Arg Ala Ser Gln Ser Val Ser Ala Ser Tyr Leu Ala
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic Construct

<400> SEQUENCE: 291

Gln Gln Tyr Met Ser Trp Pro Leu Thr
1               5

<210> SEQ ID NO 292
<211> LENGTH: 12
<212> TYPE: PRT
<213> ORGANISM: Artificial Sequence
<220> FEATURE:
<223> OTHER INFORMATION: Synthetic Construct

<400> SEQUENCE: 292

Arg Ala Ser Gln Ser Val Ser Tyr Met Tyr Leu Ala
1               5                   10

<210> SEQ ID NO 293
<211> LENGTH: 9
<212> TYPE: PRT
<213> ORGANISM: Artificial Sequence
<220> FEATURE:
<223> OTHER INFORMATION: Synthetic Construct

<400> SEQUENCE: 293

Gln Gln Tyr Lys Ser Trp Pro Leu Thr
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic Construct

<400> SEQUENCE: 294

Gln Gln Tyr Tyr Gly Trp Pro Leu Thr
1               5

<210> SEQ ID NO 295
<211> LENGTH: 12
<212> TYPE: PRT
<213> ORGANISM: Artificial Sequence
<220> FEATURE:
<223> OTHER INFORMATION: Synthetic Construct

<400> SEQUENCE: 295

Arg Ala Ser Gln Pro Ile Ser Ser Ser Tyr Leu Ala
1               5                   10
```

```
<210> SEQ ID NO 296
<211> LENGTH: 9
<212> TYPE: PRT
<213> ORGANISM: Artificial Sequence
<220> FEATURE:
<223> OTHER INFORMATION: Synthetic Construct

<400> SEQUENCE: 296

Gln Gln Tyr Glu Phe Trp Pro Leu Thr
1               5

<210> SEQ ID NO 297
<211> LENGTH: 12
<212> TYPE: PRT
<213> ORGANISM: Artificial Sequence
<220> FEATURE:
<223> OTHER INFORMATION: Synthetic Construct

<400> SEQUENCE: 297

Arg Ala Ser Gln Gly Ile Ser Ser Thr Tyr Leu Ala
1               5                   10

<210> SEQ ID NO 298
<211> LENGTH: 9
<212> TYPE: PRT
<213> ORGANISM: Artificial Sequence
<220> FEATURE:
<223> OTHER INFORMATION: Synthetic Construct

<400> SEQUENCE: 298

Gln Gln Tyr Ala Tyr Trp Pro Leu Thr
1               5

<210> SEQ ID NO 299
<211> LENGTH: 12
<212> TYPE: PRT
<213> ORGANISM: Artificial Sequence
<220> FEATURE:
<223> OTHER INFORMATION: Synthetic Construct

<400> SEQUENCE: 299

Arg Ala Ser Gln Ser Val Ser Val Arg Tyr Leu Ala
1               5                   10

<210> SEQ ID NO 300
<211> LENGTH: 9
<212> TYPE: PRT
<213> ORGANISM: Artificial Sequence
<220> FEATURE:
<223> OTHER INFORMATION: Synthetic Construct

<400> SEQUENCE: 300

Gln Gln Tyr Gly Ser Trp Pro Ile Thr
1               5

<210> SEQ ID NO 301
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: wherein X is A or P
<220> FEATURE:
<221> NAME/KEY: VARIANT
<222> LOCATION: (5)..(5)
<223> OTHER INFORMATION: wherein  X is T, N, or S
```

```
<400> SEQUENCE: 301

Ser Tyr Xaa Met Xaa
1               5

<210> SEQ ID NO 302
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: wherein X is G or S

<400> SEQUENCE: 302

Gly Phe Thr Phe Xaa Ser Tyr
1               5

<210> SEQ ID NO 303
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: wherein X is G or S
<220> FEATURE:
<221> NAME/KEY: VARIANT
<222> LOCATION: (8)..(8)
<223> OTHER INFORMATION: wherein  X is A or P
<220> FEATURE:
<221> NAME/KEY: VARIANT
<222> LOCATION: (10)..(10)
<223> OTHER INFORMATION: wherein X is T, N, or S

<400> SEQUENCE: 303

Gly Phe Thr Phe Xaa Ser Tyr Xaa Met Xaa
1               5                   10

<210> SEQ ID NO 304
<211> LENGTH: 17
<212> TYPE: PRT
<213> ORGANISM: Artificial Sequence
<220> FEATURE:
<223> OTHER INFORMATION: Synthetic Construct

<400> SEQUENCE: 304

Ala Ile Ser Gly Trp Gly Gly Ser Leu Pro Tyr Ala Asp Ser Val Lys
1               5                   10                  15

Gly

<210> SEQ ID NO 305
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(2)
<223> OTHER INFORMATION: wherein X is I, V, T, H, L, A, or C
<220> FEATURE:
<221> NAME/KEY: VARIANT
<222> LOCATION: (3)..(3)
<223> OTHER INFORMATION: wherein X is S, D, G, T, I, L, F, M, or V
<220> FEATURE:
```

```
<221> NAME/KEY: VARIANT
<222> LOCATION: (4)..(4)
<223> OTHER INFORMATION: wherein X is G, Y, L, H, D, A, S, or M
<220> FEATURE:
<221> NAME/KEY: VARIANT
<222> LOCATION: (5)..(5)
<223> OTHER INFORMATION: wherein  X is S, Q, T, A, F, or W
<220> FEATURE:
<221> NAME/KEY: VARIANT
<222> LOCATION: (7)..(7)
<223> OTHER INFORMATION: wherein  X is G or T
<220> FEATURE:
<221> NAME/KEY: VARIANT
<222> LOCATION: (8)..(8)
<223> OTHER INFORMATION: wherein ;X is N, S, P, Y, W, or F
<220> FEATURE:
<221> NAME/KEY: VARIANT
<222> LOCATION: (9)..(9)
<223> OTHER INFORMATION: wherein ;X is S, T, I, L, T, A, R, V, K, G, or
      C
<220> FEATURE:
<221> NAME/KEY: VARIANT
<222> LOCATION: (10)..(10)
<223> OTHER INFORMATION: wherein  X is F, Y, P, W, H, or G
<220> FEATURE:
<221> NAME/KEY: VARIANT
<222> LOCATION: (14)..(14)
<223> OTHER INFORMATION: wherein X is V, R, or L
<220> FEATURE:
<221> NAME/KEY: VARIANT
<222> LOCATION: (15)..(15)
<223> OTHER INFORMATION: wherein X is G or T

<400> SEQUENCE: 305

Ala Xaa Xaa Xaa Xaa Gly Xaa Xaa Xaa Xaa Tyr Ala Asp Xaa Xaa Lys
1               5                   10                  15

Gly

<210> SEQ ID NO 306
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: wherein X is S, V, I, D, G, T, L, F, or M
<220> FEATURE:
<221> NAME/KEY: VARIANT
<222> LOCATION: (2)..(2)
<223> OTHER INFORMATION: wherein  X is G, Y, L, H, D, A, S, or M
<220> FEATURE:
<221> NAME/KEY: VARIANT
<222> LOCATION: (3)..(3)
<223> OTHER INFORMATION: wherein  X is S, G, F, or W
<220> FEATURE:
<221> NAME/KEY: VARIANT
<222> LOCATION: (4)..(4)
<223> OTHER INFORMATION: wherein  X is G or S
<220> FEATURE:
<221> NAME/KEY: VARIANT
<222> LOCATION: (5)..(5)
<223> OTHER INFORMATION: wherein  X is G or T
<220> FEATURE:
<221> NAME/KEY: VARIANT
<222> LOCATION: (6)..(6)
<223> OTHER INFORMATION: wherein X is N, S, P, Y, or W

<400> SEQUENCE: 306

Xaa Xaa Xaa Xaa Xaa Xaa
1               5

<210> SEQ ID NO 307
```

```
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: wherein X is A or Y
<220> FEATURE:
<221> NAME/KEY: VARIANT
<222> LOCATION: (6)..(6)
<223> OTHER INFORMATION: wherein  X is A or S
<220> FEATURE:
<221> NAME/KEY: VARIANT
<222> LOCATION: (7)..(7)
<223> OTHER INFORMATION: wherein  X is G, Q, L, P, or E

<400> SEQUENCE: 307

Val Ser Pro Ile Xaa Xaa Xaa Met Asp Tyr
1               5                   10

<210> SEQ ID NO 308
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (5)..(5)
<223> OTHER INFORMATION: wherein X is D, S, T, or A
<220> FEATURE:
<221> NAME/KEY: VARIANT
<222> LOCATION: (6)..(6)
<223> OTHER INFORMATION: wherein X is I, S, L, P, or D

<400> SEQUENCE: 308

Tyr Trp Pro Met Xaa Xaa
1               5

<210> SEQ ID NO 309
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: wherein X is R, G, W, A, or C
<220> FEATURE:
<221> NAME/KEY: VARIANT
<222> LOCATION: (2)..(2)
<223> OTHER INFORMATION: wherein X is A, P, G, L, C, or S
<220> FEATURE:
<221> NAME/KEY: VARIANT
<222> LOCATION: (3)..(3)
<223> OTHER INFORMATION: wherein  X is S, G, or R
<220> FEATURE:
<221> NAME/KEY: VARIANT
<222> LOCATION: (4)..(4)
<223> OTHER INFORMATION: wherein X is Q, C, E, V, or I
<220> FEATURE:
<221> NAME/KEY: VARIANT
<222> LOCATION: (5)..(5)
<223> OTHER INFORMATION: wherein X is S, P, G, A, R, or D
<220> FEATURE:
<221> NAME/KEY: VARIANT
<222> LOCATION: (6)..(6)
<223> OTHER INFORMATION: wherein X is V, G, I, or L
<220> FEATURE:
<221> NAME/KEY: VARIANT
<222> LOCATION: (7)..(7)
<223> OTHER INFORMATION: wherein X is S, E, D, P, or G
```

```
<220> FEATURE:
<221> NAME/KEY: VARIANT
<222> LOCATION: (8)..(8)
<223> OTHER INFORMATION: wherein X is S, P, F, A, M, E, V, N, D, or Y
<220> FEATURE:
<221> NAME/KEY: VARIANT
<222> LOCATION: (9)..(9)
<223> OTHER INFORMATION: wherein X is T, I, V, E, S, F, A, M, Q, Y, H,
      or R
<220> FEATURE:
<221> NAME/KEY: VARIANT
<222> LOCATION: (10)..(10)
<223> OTHER INFORMATION: wherein  X is Y or F
<220> FEATURE:
<221> NAME/KEY: VARIANT
<222> LOCATION: (11)..(11)
<223> OTHER INFORMATION: wherein  X is L, W, or P
<220> FEATURE:
<221> NAME/KEY: VARIANT
<222> LOCATION: (12)..(12)
<223> OTHER INFORMATION: wherein  X is A, S, or G

<400> SEQUENCE: 309

Xaa Xaa Xaa Xaa Xaa Xaa Xaa Xaa Xaa Xaa Xaa Xaa
1               5                   10

<210> SEQ ID NO 310
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: wherein X is G or D
<220> FEATURE:
<221> NAME/KEY: VARIANT
<222> LOCATION: (4)..(4)
<223> OTHER INFORMATION: wherein  X is S or I
<220> FEATURE:
<221> NAME/KEY: VARIANT
<222> LOCATION: (7)..(7)
<223> OTHER INFORMATION: wherein X is T or P

<400> SEQUENCE: 310

Xaa Ala Ser Xaa Arg Ala Xaa
1               5

<210> SEQ ID NO 311
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(1)
<223> OTHER INFORMATION: wherein X is Q or K
<220> FEATURE:
<221> NAME/KEY: VARIANT
<222> LOCATION: (2)..(2)
<223> OTHER INFORMATION: wherein  X is H or Y
<220> FEATURE:
<221> NAME/KEY: VARIANT
<222> LOCATION: (4)..(4)
<223> OTHER INFORMATION: wherein  X is G, N, or P
<220> FEATURE:
<221> NAME/KEY: VARIANT
<222> LOCATION: (5)..(5)
<223> OTHER INFORMATION: wherein  X is S, W, or Y

<400> SEQUENCE: 311

Xaa Xaa Tyr Xaa Xaa Pro Pro Ser Phe Thr
```

<210> SEQ ID NO 312
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: wherein X is G, Q, E, L, F, A, S, M, K, R, or Y
<220> FEATURE:
<221> NAME/KEY: VARIANT
<222> LOCATION: (5)..(5)
<223> OTHER INFORMATION: wherein X is S, R, T, G, V, F, Y, D, A, H, V, E, K, or C
<220> FEATURE:
<221> NAME/KEY: VARIANT
<222> LOCATION: (6)..(6)
<223> OTHER INFORMATION: wherein X is W, F, or S
<220> FEATURE:
<221> NAME/KEY: VARIANT
<222> LOCATION: (8)..(8)
<223> OTHER INFORMATION: wherein X is L or I

<400> SEQUENCE: 312

Gln Gln Tyr Xaa Xaa Xaa Pro Xaa Thr
1               5

<210> SEQ ID NO 313
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (30)..(30)
<223> OTHER INFORMATION: wherein X is G or S
<220> FEATURE:
<221> NAME/KEY: VARIANT
<222> LOCATION: (33)..(33)
<223> OTHER INFORMATION: wherein X is A or P
<220> FEATURE:
<221> NAME/KEY: VARIANT
<222> LOCATION: (35)..(35)
<223> OTHER INFORMATION: wherein X is T, N, or S
<220> FEATURE:
<221> NAME/KEY: VARIANT
<222> LOCATION: (51)..(51)
<223> OTHER INFORMATION: wherein X is I, V, T, H, L, A, or C
<220> FEATURE:
<221> NAME/KEY: VARIANT
<222> LOCATION: (52)..(52)
<223> OTHER INFORMATION: wherein X is S, D, G, T, I, L, F, M, or V
<220> FEATURE:
<221> NAME/KEY: VARIANT
<222> LOCATION: (53)..(53)
<223> OTHER INFORMATION: wherein X is G, Y, L, H, D, A, S, or M
<220> FEATURE:
<221> NAME/KEY: VARIANT
<222> LOCATION: (54)..(54)
<223> OTHER INFORMATION: wherein X is S, Q, T, A, F, or W
<220> FEATURE:
<221> NAME/KEY: VARIANT
<222> LOCATION: (56)..(56)
<223> OTHER INFORMATION: wherein X is G or T
<220> FEATURE:
<221> NAME/KEY: VARIANT
<222> LOCATION: (57)..(57)
<223> OTHER INFORMATION: wherein X is N, S, P, Y, W, or F
<220> FEATURE:
<221> NAME/KEY: VARIANT
<222> LOCATION: (58)..(58)
<223> OTHER INFORMATION: wherein X is S, T, I, L, T, A, R, V, K, G, or

```
                             C
<220> FEATURE:
<221> NAME/KEY: VARIANT
<222> LOCATION: (59)..(59)
<223> OTHER INFORMATION: wherein  X is F, Y, P, W, H, or G
<220> FEATURE:
<221> NAME/KEY: VARIANT
<222> LOCATION: (63)..(63)
<223> OTHER INFORMATION: wherein X is V, R, or L
<220> FEATURE:
<221> NAME/KEY: VARIANT
<222> LOCATION: (64)..(64)
<223> OTHER INFORMATION: wherein X is G or T
<220> FEATURE:
<221> NAME/KEY: VARIANT
<222> LOCATION: (103)..(103)
<223> OTHER INFORMATION: wherein X is A or Y
<220> FEATURE:
<221> NAME/KEY: VARIANT
<222> LOCATION: (104)..(104)
<223> OTHER INFORMATION: wherein  X is A or S
<220> FEATURE:
<221> NAME/KEY: VARIANT
<222> LOCATION: (105)..(105)
<223> OTHER INFORMATION: wherein  X is G, Q, L, P, or E

<400> SEQUENCE: 313

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Ser Tyr
            20                  25                  30

Xaa Met Xaa Trp Val Arg Gln Ala Pro Gly Lys Gly Leu Glu Trp Val
        35                  40                  45

Ser Ala Xaa Xaa Xaa Xaa Gly Xaa Xaa Xaa Xaa Tyr Ala Asp Xaa Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Pro Ile Xaa Xaa Xaa Met Asp Tyr Trp Gly Gln Gly
            100                 105                 110

Thr Leu Val Thr Val Ser Ser
            115

<210> SEQ ID NO 314
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (30)..(30)
<223> OTHER INFORMATION: wherein X is G or S
<220> FEATURE:
<221> NAME/KEY: VARIANT
<222> LOCATION: (33)..(33)
<223> OTHER INFORMATION: wherein X is A or P
<220> FEATURE:
<221> NAME/KEY: VARIANT
<222> LOCATION: (35)..(35)
<223> OTHER INFORMATION: wherein X is T, N, or S
<220> FEATURE:
<221> NAME/KEY: VARIANT
<222> LOCATION: (51)..(51)
<223> OTHER INFORMATION: wherein X is I, V, T, H, L, A, or C
<220> FEATURE:
<221> NAME/KEY: VARIANT
<222> LOCATION: (52)..(52)
<223> OTHER INFORMATION: wherein X is S, D, G, T, I, L, F, M, or V
```

```
<220> FEATURE:
<221> NAME/KEY: VARIANT
<222> LOCATION: (53)..(53)
<223> OTHER INFORMATION: wherein X is G, Y, L, H, D, A, S, or M
<220> FEATURE:
<221> NAME/KEY: VARIANT
<222> LOCATION: (54)..(54)
<223> OTHER INFORMATION: wherein  X is S, Q, T, A, F, or W
<220> FEATURE:
<221> NAME/KEY: VARIANT
<222> LOCATION: (56)..(56)
<223> OTHER INFORMATION: wherein  X is G or T
<220> FEATURE:
<221> NAME/KEY: VARIANT
<222> LOCATION: (57)..(57)
<223> OTHER INFORMATION: wherein  X is N, S, P, Y, W, or F
<220> FEATURE:
<221> NAME/KEY: VARIANT
<222> LOCATION: (58)..(58)
<223> OTHER INFORMATION: wherein  X is S, T, I, L, T, A, R, V, K, G, or
      C
<220> FEATURE:
<221> NAME/KEY: VARIANT
<222> LOCATION: (59)..(59)
<223> OTHER INFORMATION: wherein X is F, Y, P, W, H, or G
<220> FEATURE:
<221> NAME/KEY: VARIANT
<222> LOCATION: (63)..(63)
<223> OTHER INFORMATION: wherein  X is V, R, or L
<220> FEATURE:
<221> NAME/KEY: VARIANT
<222> LOCATION: (64)..(64)
<223> OTHER INFORMATION: wherein X13 is G or T
<220> FEATURE:
<221> NAME/KEY: VARIANT
<222> LOCATION: (103)..(103)
<223> OTHER INFORMATION: wherein  X is D, S, T, or A
<220> FEATURE:
<221> NAME/KEY: VARIANT
<222> LOCATION: (104)..(104)
<223> OTHER INFORMATION: wherein X is I, S, L, P, or D

<400> SEQUENCE: 314

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Xaa Ser Tyr
            20                  25                  30

Xaa Met Xaa Trp Val Arg Gln Ala Pro Gly Lys Gly Leu Glu Trp Val
        35                  40                  45

Ser Ala Xaa Xaa Xaa Xaa Gly Xaa Xaa Xaa Xaa Tyr Ala Asp Xaa Xaa
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Trp Pro Met Xaa Xaa Trp Gly Gln Gly Thr Leu Val Thr
            100                 105                 110

Val Ser Ser
        115

<210> SEQ ID NO 315
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (24)..(24)
<223> OTHER INFORMATION: wherein X is R, G, W, A, or C
```

```
<220> FEATURE:
<221> NAME/KEY: VARIANT
<222> LOCATION: (25)..(25)
<223> OTHER INFORMATION: wherein X is A, P, G, L, C, or S
<220> FEATURE:
<221> NAME/KEY: VARIANT
<222> LOCATION: (26)..(26)
<223> OTHER INFORMATION: wherein X is S, G, or R
<220> FEATURE:
<221> NAME/KEY: VARIANT
<222> LOCATION: (27)..(27)
<223> OTHER INFORMATION: wherein X is Q, C, E, V, or I
<220> FEATURE:
<221> NAME/KEY: VARIANT
<222> LOCATION: (28)..(28)
<223> OTHER INFORMATION: wherein X is S, L, P, G, A, R, or D
<220> FEATURE:
<221> NAME/KEY: VARIANT
<222> LOCATION: (29)..(29)
<223> OTHER INFORMATION: wherein X is V, G, I, or L
<220> FEATURE:
<221> NAME/KEY: VARIANT
<222> LOCATION: (30)..(30)
<223> OTHER INFORMATION: wherein X is S, E, D, P, or G
<220> FEATURE:
<221> NAME/KEY: VARIANT
<222> LOCATION: (31)..(31)
<223> OTHER INFORMATION: wherein X is S, P, F, A, M, E, V, N, D, or Y
<220> FEATURE:
<221> NAME/KEY: VARIANT
<222> LOCATION: (32)..(32)
<223> OTHER INFORMATION: wherein X is I, T, V, E, S, A, M, Q, Y, H, R,
      or F
<220> FEATURE:
<221> NAME/KEY: VARIANT
<222> LOCATION: (33)..(33)
<223> OTHER INFORMATION: wherein X is Y or F
<220> FEATURE:
<221> NAME/KEY: VARIANT
<222> LOCATION: (34)..(34)
<223> OTHER INFORMATION: wherein X is L, W, or P
<220> FEATURE:
<221> NAME/KEY: VARIANT
<222> LOCATION: (35)..(35)
<223> OTHER INFORMATION: wherein X is A, S, or G
<220> FEATURE:
<221> NAME/KEY: VARIANT
<222> LOCATION: (51)..(51)
<223> OTHER INFORMATION: wherein X is G or D
<220> FEATURE:
<221> NAME/KEY: VARIANT
<222> LOCATION: (54)..(54)
<223> OTHER INFORMATION: wherein X is S or I
<220> FEATURE:
<221> NAME/KEY: VARIANT
<222> LOCATION: (57)..(57)
<223> OTHER INFORMATION: wherein X is T or P
<220> FEATURE:
<221> NAME/KEY: VARIANT
<222> LOCATION: (90)..(90)
<223> OTHER INFORMATION: wherein X is Q or K
<220> FEATURE:
<221> NAME/KEY: VARIANT
<222> LOCATION: (91)..(91)
<223> OTHER INFORMATION: wherein X is H or Y
<220> FEATURE:
<221> NAME/KEY: VARIANT
<222> LOCATION: (93)..(93)
<223> OTHER INFORMATION: wherein X is G, N, or P
<220> FEATURE:
<221> NAME/KEY: VARIANT
<222> LOCATION: (94)..(94)
<223> OTHER INFORMATION: wherein X is S, W, or Y

<400> SEQUENCE: 315

Glu Ile Val Leu Thr Gln Ser Pro Gly Thr Leu Ser Leu Ser Pro Gly
1               5                   10                  15
```

```
Glu Arg Ala Thr Leu Ser Cys Xaa Xaa Xaa Xaa Xaa Xaa Xaa Xaa
                 20                  25                  30

Xaa Xaa Xaa Trp Tyr Gln Gln Lys Pro Gly Gln Ala Pro Arg Leu Leu
         35                  40                  45

Met Tyr Xaa Ala Ser Xaa Arg Ala Xaa Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Xaa Xaa Tyr Xaa Xaa Pro Pro
                 85                  90                  95

Ser Phe Thr Phe Gly Gln Gly Thr Lys Val Glu Ile Lys
                100                 105
```

<210> SEQ ID NO 316
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (24)..(24)
<223> OTHER INFORMATION: wherein X is R, G, W, A, or C
<220> FEATURE:
<221> NAME/KEY: VARIANT
<222> LOCATION: (25)..(25)
<223> OTHER INFORMATION: wherein X is A, P, G, L, C, or S
<220> FEATURE:
<221> NAME/KEY: VARIANT
<222> LOCATION: (26)..(26)
<223> OTHER INFORMATION: wherein X is S, G, or R
<220> FEATURE:
<221> NAME/KEY: VARIANT
<222> LOCATION: (27)..(27)
<223> OTHER INFORMATION: wherein X is Q, C, E, V, or I
<220> FEATURE:
<221> NAME/KEY: VARIANT
<222> LOCATION: (28)..(28)
<223> OTHER INFORMATION: wherein X is S, L, P, G, A, R, or D
<220> FEATURE:
<221> NAME/KEY: VARIANT
<222> LOCATION: (29)..(29)
<223> OTHER INFORMATION: wherein X is V, G, or I
<220> FEATURE:
<221> NAME/KEY: VARIANT
<222> LOCATION: (30)..(30)
<223> OTHER INFORMATION: wherein X is S, E, D, or P
<220> FEATURE:
<221> NAME/KEY: VARIANT
<222> LOCATION: (31)..(31)
<223> OTHER INFORMATION: wherein X is S, P, F, A, M, E, V, N, D, or Y
<220> FEATURE:
<221> NAME/KEY: VARIANT
<222> LOCATION: (32)..(32)
<223> OTHER INFORMATION: wherein X is I, T, V, E, S, A, M, Q, Y, H, or R
<220> FEATURE:
<221> NAME/KEY: VARIANT
<222> LOCATION: (33)..(33)
<223> OTHER INFORMATION: wherein X is Y or F
<220> FEATURE:
<221> NAME/KEY: VARIANT
<222> LOCATION: (34)..(34)
<223> OTHER INFORMATION: wherein X is L, W, or P
<220> FEATURE:
<221> NAME/KEY: VARIANT
<222> LOCATION: (35)..(35)
<223> OTHER INFORMATION: wherein X is A, S, or G
<220> FEATURE:
<221> NAME/KEY: VARIANT
<222> LOCATION: (51)..(51)
<223> OTHER INFORMATION: wherein X is G or D
<220> FEATURE:
<221> NAME/KEY: VARIANT

```
<222> LOCATION: (54)..(54)
<223> OTHER INFORMATION: wherein X is S or I
<220> FEATURE:
<221> NAME/KEY: VARIANT
<222> LOCATION: (57)..(57)
<223> OTHER INFORMATION: wherein X is T or P
<220> FEATURE:
<221> NAME/KEY: VARIANT
<222> LOCATION: (93)..(93)
<223> OTHER INFORMATION: wherein X is G, Q, E, L, F, A, S, M, R, K, or Y
<220> FEATURE:
<221> NAME/KEY: VARIANT
<222> LOCATION: (94)..(94)
<223> OTHER INFORMATION: wherein X is S, R, T, G, R, V, D, A, H, E, K,
      C, F, or Y
<220> FEATURE:
<221> NAME/KEY: VARIANT
<222> LOCATION: (95)..(95)
<223> OTHER INFORMATION: wherein  X is W, S, or F
<220> FEATURE:
<221> NAME/KEY: VARIANT
<222> LOCATION: (97)..(97)
<223> OTHER INFORMATION: wherein  X is L or I

<400> SEQUENCE: 316

Glu Ile Val Leu Thr Gln Ser Pro Gly Thr Leu Ser Leu Ser Pro Gly
1               5                   10                  15

Glu Arg Ala Thr Leu Ser Cys Xaa Xaa Xaa Xaa Xaa Xaa Xaa Xaa
            20                  25                  30

Xaa Xaa Xaa Trp Tyr Gln Gln Lys Pro Gly Gln Ala Pro Arg Leu Leu
        35                  40                  45

Met Tyr Xaa Ala Ser Xaa Arg Ala Xaa Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Xaa Xaa Xaa Pro
                85                  90                  95

Xaa Phe Gly Gln Gly Thr Lys Val Glu Ile Lys
            100                 105

<210> SEQ ID NO 317
<211> LENGTH: 108
<212> TYPE: PRT
<213> ORGANISM: Artificial Sequence
<220> FEATURE:
<223> OTHER INFORMATION: Synthetic Construct

<400> SEQUENCE: 317

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ala Leu
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ala Trp Pro
                85                  90                  95

Leu Thr Phe Gly Gln Gly Thr Lys Val Glu Ile Lys
            100                 105
```

```
<210> SEQ ID NO 318
<211> LENGTH: 21
<212> TYPE: PRT
<213> ORGANISM: Homo sapiens

<400> SEQUENCE: 318

Met Ala Leu Pro Val Thr Ala Leu Leu Leu Pro Leu Ala Leu Leu Leu
1               5                   10                  15

His Ala Ala Arg Pro
            20

<210> SEQ ID NO 319
<211> LENGTH: 16
<212> TYPE: PRT
<213> ORGANISM: Homo sapiens

<400> SEQUENCE: 319

Gly Leu Ala Val Ser Thr Ile Ser Ser Phe Phe Pro Pro Gly Tyr Gln
1               5                   10                  15

<210> SEQ ID NO 320
<211> LENGTH: 45
<212> TYPE: PRT
<213> ORGANISM: Homo sapiens

<400> SEQUENCE: 320

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 321
<211> LENGTH: 231
<212> TYPE: PRT
<213> ORGANISM: Homo sapiens

<400> SEQUENCE: 321

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160
```

Ile Ala Val Glu Trp Glu Ser Asn Gly Gln Pro Glu Asn Asn Tyr Lys
               165                 170                 175

Thr Thr Pro Pro Val Leu Asp Ser Asp Gly Ser Phe Phe Leu Tyr Ser
           180                 185                 190

Lys Leu Thr Val Asp Lys Ser Arg Trp Gln Gln Gly Asn Val Phe Ser
       195                 200                 205

Cys Ser Val Met His Glu Ala Leu His Asn His Tyr Thr Gln Lys Ser
   210                 215                 220

Leu Ser Leu Ser Pro Gly Lys
225                 230

<210> SEQ ID NO 322
<211> LENGTH: 24
<212> TYPE: PRT
<213> ORGANISM: Homo sapiens

<400> SEQUENCE: 322

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 323
<211> LENGTH: 42
<212> TYPE: PRT
<213> ORGANISM: Homo sapiens

<400> SEQUENCE: 323

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 324
<211> LENGTH: 112
<212> TYPE: PRT
<213> ORGANISM: Homo sapiens

<400> SEQUENCE: 324

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 325
<211> LENGTH: 52
<212> TYPE: PRT

<213> ORGANISM: Homo sapiens

<400> SEQUENCE: 325

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
            20                  25                  30

Arg Thr Arg Lys Gly Phe Arg Leu Leu Asn Pro His Pro Lys Pro Asn
        35                  40                  45

Pro Lys Asn Asn
    50

<210> SEQ ID NO 326
<211> LENGTH: 215
<212> TYPE: PRT
<213> ORGANISM: Homo sapiens

<400> SEQUENCE: 326

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu
    210                 215

<210> SEQ ID NO 327
<211> LENGTH: 42
<212> TYPE: PRT
<213> ORGANISM: Homo sapiens

<400> SEQUENCE: 327

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

```
Pro Glu Glu Glu Glu Gly Gly Cys Glu Leu
        35                  40

<210> SEQ ID NO 328
<211> LENGTH: 41
<212> TYPE: PRT
<213> ORGANISM: Homo sapiens

<400> SEQUENCE: 328

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 329
<211> LENGTH: 18
<212> TYPE: PRT
<213> ORGANISM: Homo sapiens

<400> SEQUENCE: 329

Met Ile Pro Ala Val Val Leu Leu Leu Leu Leu Val Glu Gln Ala
1               5                   10                  15

Ala Ala

<210> SEQ ID NO 330
<211> LENGTH: 43
<212> TYPE: PRT
<213> ORGANISM: Artificial Sequence
<220> FEATURE:
<223> OTHER INFORMATION: Synthetic Construct

<400> SEQUENCE: 330

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser
        35                  40

<210> SEQ ID NO 331
<211> LENGTH: 22
<212> TYPE: PRT
<213> ORGANISM: Homo sapiens

<400> SEQUENCE: 331

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 332
<211> LENGTH: 21
<212> TYPE: PRT
<213> ORGANISM: Homo sapiens

<400> SEQUENCE: 332

Gly Ser Gly Glu Gly Arg Gly Ser Leu Leu Thr Cys Gly Asp Val Glu
1               5                   10                  15

Glu Asn Pro Gly Pro
```

<210> SEQ ID NO 333
<211> LENGTH: 15
<212> TYPE: PRT
<213> ORGANISM: Artificial Sequence
<220> FEATURE:
<223> OTHER INFORMATION: Synthetic Construct

<400> SEQUENCE: 333

Gly Gly Gly Gly Ser Gly Gly Gly Ser Gly Gly Gly Gly Ser
1               5                   10                  15

<210> SEQ ID NO 334
<211> LENGTH: 530
<212> TYPE: PRT
<213> ORGANISM: Homo Sapiens

<400> SEQUENCE: 334

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
                100                 105                 110

Ser His Asp Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
        210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
                260                 265                 270

Leu Thr Pro Glu Gln Val Val Ala Ile Ala Ser Asn Ile Gly Gly Lys
            275                 280                 285

Gln Ala Leu Glu Thr Val Gln Ala Leu Leu Pro Val Leu Cys Gln Ala
        290                 295                 300

```
His Gly Leu Thr Pro Gln Gln Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Ala Ile Ala
370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 335
<211> LENGTH: 530
<212> TYPE: PRT
<213> ORGANISM: Artificial Sequence
<220> FEATURE:
<223> OTHER INFORMATION: Synthetic Construct

<400> SEQUENCE: 335

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Ala Ile Ala Ser Asn Gly Gly
            35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
            115                 120                 125
```

```
Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser His Asp Gly Gly Lys Gln Ala Leu Glu Thr Val
        180                 185                 190

Gln Arg Leu Leu Pro Val Leu Cys Gln Ala His Gly Leu Thr Pro Gln
    195                 200                 205

Gln Val Val Ala Ile Ala Ser Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 336
<211> LENGTH: 530
<212> TYPE: PRT
<213> ORGANISM: Artificial Sequence
<220> FEATURE:
<223> OTHER INFORMATION: Synthetic Construct

<400> SEQUENCE: 336

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365
```

```
Leu Cys Gln Ala His Gly Leu Thr Pro Glu Gln Val Val Ala Ile Ala
        370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 337
<211> LENGTH: 539
<212> TYPE: PRT
<213> ORGANISM: Artificial Sequence
<220> FEATURE:
<223> OTHER INFORMATION: Synthetic Construct

<400> SEQUENCE: 337

Asn Pro Gln Arg Ser Thr Val Trp Tyr Leu Thr Pro Gln Gln Val Val
1               5                   10                  15

Ala Ile Ala Ser Asn Asn Gly Gly Lys Gln Ala Leu Glu Thr Val Gln
            20                  25                  30

Arg Leu Leu Pro Val Leu Cys Gln Ala His Gly Leu Thr Pro Gln Gln
        35                  40                  45

Val Val Ala Ile Ala Ser Asn Gly Gly Gly Lys Gln Ala Leu Glu Thr
    50                  55                  60

Val Gln Arg Leu Leu Pro Val Leu Cys Gln Ala His Gly Leu Thr Pro
65                  70                  75                  80

Gln Gln Val Val Ala Ile Ala Ser Asn Gly Gly Lys Gln Ala Leu
                85                  90                  95

Glu Thr Val Gln Arg Leu Leu Pro Val Leu Cys Gln Ala His Gly Leu
            100                 105                 110

Thr Pro Gln Gln Val Val Ala Ile Ala Ser Asn Asn Gly Gly Lys Gln
        115                 120                 125

Ala Leu Glu Thr Val Gln Arg Leu Leu Pro Val Leu Cys Gln Ala His
    130                 135                 140

Gly Leu Thr Pro Glu Gln Val Val Ala Ile Ala Ser His Asp Gly Gly
145                 150                 155                 160

Lys Gln Ala Leu Glu Thr Val Gln Arg Leu Leu Pro Val Leu Cys Gln
                165                 170                 175

Ala His Gly Leu Thr Pro Glu Gln Val Val Ala Ile Ala Ser His Asp
            180                 185                 190
```

```
Gly Gly Lys Gln Ala Leu Glu Thr Val Gln Arg Leu Leu Pro Val Leu
            195                 200                 205

Cys Gln Ala His Gly Leu Thr Pro Gln Gln Val Val Ala Ile Ala Ser
            210                 215                 220

Asn Gly Gly Lys Gln Ala Leu Glu Thr Val Gln Arg Leu Leu Pro
225                 230                 235                 240

Val Leu Cys Gln Ala His Gly Leu Thr Pro Gln Gln Val Val Ala Ile
            245                 250                 255

Ala Ser Asn Gly Gly Lys Gln Ala Leu Glu Thr Val Gln Arg Leu
            260                 265                 270

Leu Pro Val Leu Cys Gln Ala His Gly Leu Thr Pro Gln Gln Val Val
            275                 280                 285

Ala Ile Ala Ser Asn Gly Gly Gly Lys Gln Ala Leu Glu Thr Val Gln
            290                 295                 300

Arg Leu Leu Pro Val Leu Cys Gln Ala His Gly Leu Thr Pro Gln Gln
305                 310                 315                 320

Val Val Ala Ile Ala Ser Asn Gly Gly Gly Lys Gln Ala Leu Glu Thr
            325                 330                 335

Val Gln Arg Leu Leu Pro Val Leu Cys Gln Ala His Gly Leu Thr Pro
            340                 345                 350

Gln Gln Val Val Ala Ile Ala Ser Asn Asn Gly Gly Lys Gln Ala Leu
            355                 360                 365

Glu Thr Val Gln Arg Leu Leu Pro Val Leu Cys Gln Ala His Gly Leu
            370                 375                 380

Thr Pro Gln Gln Val Val Ala Ile Ala Ser Asn Asn Gly Gly Lys Gln
385                 390                 395                 400

Ala Leu Glu Thr Val Gln Arg Leu Leu Pro Val Leu Cys Gln Ala His
            405                 410                 415

Gly Leu Thr Pro Gln Gln Val Val Ala Ile Ala Ser Asn Asn Gly Gly
            420                 425                 430

Lys Gln Ala Leu Glu Thr Val Gln Arg Leu Leu Pro Val Leu Cys Gln
            435                 440                 445

Ala His Gly Leu Thr Pro Gln Gln Val Val Ala Ile Ala Ser Asn Gly
            450                 455                 460

Gly Gly Lys Gln Ala Leu Glu Thr Val Gln Arg Leu Leu Pro Val Leu
465                 470                 475                 480

Cys Gln Ala His Gly Leu Thr Pro Gln Gln Val Val Ala Ile Ala Ser
            485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Gln Gln Val Val Ala Ile
            515                 520                 525

Ala Ser Asn Gly Gly Gly Arg Pro Ala Leu Glu
            530                 535

<210> SEQ ID NO 338
<211> LENGTH: 530
<212> TYPE: PRT
<213> ORGANISM: Artificial Sequence
<220> FEATURE:
<223> OTHER INFORMATION: Synthetic Construct

<400> SEQUENCE: 338

Leu Thr Pro Glu Gln Val Val Ala Ile Ala Ser His Asp Gly Gly Lys
1               5                   10                  15
```

-continued

```
Gln Ala Leu Glu Thr Val Gln Arg Leu Leu Pro Val Leu Cys Gln Ala
             20                  25                  30

His Gly Leu Thr Pro Glu Gln Val Val Ala Ile Ala Ser His Asp Gly
         35                  40                  45

Gly Lys Gln Ala Leu Glu Thr Val Gln Arg Leu Leu Pro Val Leu Cys
     50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
```

```
                435                 440                 445
Val Ala Ile Ala Ser Asn Asn Gly Gly Lys Gln Ala Leu Glu Thr Val
450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 339
<211> LENGTH: 530
<212> TYPE: PRT
<213> ORGANISM: Artificial Sequence
<220> FEATURE:
<223> OTHER INFORMATION: Synthetic Construct

<400> SEQUENCE: 339

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser Asn Ile Gly Gly Lys Gln Ala Leu Glu Thr Val
        180                 185                 190

Gln Ala Leu Leu Pro Val Leu Cys Gln Ala His Gly Leu Thr Pro Gln
    195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
```

```
                   260                 265                 270
Leu Thr Pro Gln Gln Val Val Ala Ile Ala Ser Asn Gly Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 340
<211> LENGTH: 530
<212> TYPE: PRT
<213> ORGANISM: Artificial Sequence
<220> FEATURE:
<223> OTHER INFORMATION: Synthetic Construct

<400> SEQUENCE: 340

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
```

```
                   85                  90                  95
Leu Cys Gln Ala His Gly Leu Thr Pro Gln Gln Val Ala Ile Ala
                100                 105                 110

Ser Asn Gly Gly Gly Lys Gln Ala Leu Glu Thr Val Gln Arg Leu Leu
                115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
                180                 185                 190

Gln Arg Leu Leu Pro Val Leu Cys Gln Ala His Gly Leu Thr Pro Gln
                195                 200                 205

Gln Val Val Ala Ile Ala Ser Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Glu Gln Val Val Ala Ile Ala Ser His Asp Gly Gly Lys
                275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
                340                 345                 350

Asp Gly Gly Lys Gln Ala Leu Glu Thr Val Gln Arg Leu Leu Pro Val
                355                 360                 365

Leu Cys Gln Ala His Gly Leu Thr Pro Glu Gln Val Val Ala Ile Ala
                370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
                435                 440                 445

Val Ala Ile Ala Ser His Asp Gly Gly Lys Gln Ala Leu Glu Thr Val
                450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
                500                 505                 510
```

```
Pro Gln Gln Val Val Ala Ile Ala Ser Asn Gly Gly Arg Pro Ala
        515                 520                 525

Leu Glu
    530

<210> SEQ ID NO 341
<211> LENGTH: 530
<212> TYPE: PRT
<213> ORGANISM: Artificial Sequence
<220> FEATURE:
<223> OTHER INFORMATION: Synthetic Construct

<400> SEQUENCE: 341

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65              70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335
```

-continued

Gln Ala His Gly Leu Thr Pro Gln Gln Val Val Ala Ile Ala Ser Asn
                340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530

<210> SEQ ID NO 342
<211> LENGTH: 136
<212> TYPE: PRT
<213> ORGANISM: Homo sapiens

<400> SEQUENCE: 342

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Ala Cys Pro Tyr Ser Asn Pro Ser Leu Cys
        35                  40                  45

Ser Gly Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
    130                 135

<210> SEQ ID NO 343
<211> LENGTH: 453
<212> TYPE: PRT

<213> ORGANISM: Artificial Sequence
<220> FEATURE:
<223> OTHER INFORMATION: Synthetic Construct

<400> SEQUENCE: 343

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gly Ser Trp Pro Leu Thr Phe Gly Gln Gly Thr Lys Val
                245                 250                 255

Glu Ile Lys Gly Leu Ala Val Ser Thr Ile Ser Ser Phe Phe Pro Pro
            260                 265                 270

Gly Tyr Gln Ile Tyr Ile Trp Ala Pro Leu Ala Gly Thr Cys Gly Val
        275                 280                 285

Leu Leu Leu Ser Leu Val Ile Thr Leu Tyr Cys Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
```

```
                385                 390                 395                 400
Asn Glu Leu Gln Lys Asp Lys Met Ala Glu Ala Tyr Ser Glu Ile Gly
                    405                 410                 415

Met Lys Gly Glu Arg Arg Gly Lys Gly His Asp Gly Leu Tyr Gln
                420                 425                 430

Gly Leu Ser Thr Ala Thr Lys Asp Thr Tyr Asp Ala Leu His Met Gln
                435                 440                 445

Ala Leu Pro Pro Arg
        450

<210> SEQ ID NO 344
<211> LENGTH: 482
<212> TYPE: PRT
<213> ORGANISM: Artificial Sequence
<220> FEATURE:
<223> OTHER INFORMATION: Synthetic Construct

<400> SEQUENCE: 344

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Tyr Trp Pro Met Asp Ile Trp Gly Gln
            115                 120                 125

Gly Thr Leu Val Thr Val Ser Ser Gly Gly Gly Gly Ser Gly Gly Gly
        130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Ser Ser Tyr Leu Ala Trp Tyr Gln Gln Lys Pro
                180                 185                 190

Gly Gln Ala Pro Arg Leu Leu Met Tyr Asp Ala Ser Ile Arg Ala Thr
            195                 200                 205

Gly Ile Pro Asp Arg Phe Ser Gly Ser Gly Ser Gly Thr Asp Phe Thr
        210                 215                 220

Leu Thr Ile Ser Arg Leu Glu Pro Glu Asp Phe Ala Val Tyr Tyr Cys
225                 230                 235                 240

Gln Gln Tyr Gly Ser Trp Pro Leu Thr Phe Gly Gln Gly Thr Lys Val
                245                 250                 255

Glu Ile Lys Thr Thr Thr Pro Ala Pro Arg Pro Pro Thr Pro Ala Pro
                260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
```

```
            290                 295                 300
Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
                340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Gln
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
                435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 345
<211> LENGTH: 668
<212> TYPE: PRT
<213> ORGANISM: Artificial Sequence
<220> FEATURE:
<223> OTHER INFORMATION: Synthetic Construct

<400> SEQUENCE: 345

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
        50                  55                  60

Gly Leu Glu Trp Val Ser Ala Ile Ser Asp Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Tyr Trp Pro Met Asp Ile Trp Gly Gln
            115                 120                 125

Gly Thr Leu Val Thr Val Ser Ser Gly Gly Gly Ser Gly Gly Gly
        130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175
```

-continued

```
Ser Gln Ser Val Ser Ser Tyr Leu Ala Trp Tyr Gln Gln Lys Pro
            180                 185                 190
Gly Gln Ala Pro Arg Leu Leu Met Tyr Asp Ala Ser Ile Arg Ala Thr
        195                 200                 205
Gly Ile Pro Asp Arg Phe Ser Gly Ser Gly Ser Gly Thr Asp Phe Thr
    210                 215                 220
Leu Thr Ile Ser Arg Leu Glu Pro Glu Asp Phe Ala Val Tyr Tyr Cys
225                 230                 235                 240
Gln Gln Tyr Gly Ser Trp Pro Leu Thr Phe Gly Gln Gly Thr Lys Val
                245                 250                 255
Glu Ile Lys Glu Pro Lys Ser Pro Asp Lys Thr His Thr Cys Pro Pro
            260                 265                 270
Cys Pro Ala Pro Pro Val Ala Gly Pro Ser Val Phe Leu Phe Pro Pro
        275                 280                 285
Lys Pro Lys Asp Thr Leu Met Ile Ala Arg Thr Pro Glu Val Thr Cys
    290                 295                 300
Val Val Val Asp Val Ser His Glu Asp Pro Glu Val Lys Phe Asn Trp
305                 310                 315                 320
Tyr Val Asp Gly Val Glu Val His Asn Ala Lys Thr Lys Pro Arg Glu
                325                 330                 335
Glu Gln Tyr Asn Ser Thr Tyr Arg Val Val Ser Val Leu Thr Val Leu
            340                 345                 350
His Gln Asp Trp Leu Asn Gly Lys Glu Tyr Lys Cys Lys Val Ser Asn
        355                 360                 365
Lys Ala Leu Pro Ala Pro Ile Glu Lys Thr Ile Ser Lys Ala Lys Gly
    370                 375                 380
Gln Pro Arg Glu Pro Gln Val Tyr Thr Leu Pro Pro Ser Arg Asp Glu
385                 390                 395                 400
Leu Thr Lys Asn Gln Val Ser Leu Thr Cys Leu Val Lys Gly Phe Tyr
                405                 410                 415
Pro Ser Asp Ile Ala Val Glu Trp Glu Ser Asn Gly Gln Pro Glu Asn
            420                 425                 430
Asn Tyr Lys Thr Thr Pro Pro Val Leu Asp Ser Asp Gly Ser Phe Phe
        435                 440                 445
Leu Tyr Ser Lys Leu Thr Val Asp Lys Ser Arg Trp Gln Gln Gly Asn
    450                 455                 460
Val Phe Ser Cys Ser Val Met His Glu Ala Leu His Asn His Tyr Thr
465                 470                 475                 480
Gln Lys Ser Leu Ser Leu Ser Pro Gly Lys Ile Tyr Ile Trp Ala Pro
                485                 490                 495
Leu Ala Gly Thr Cys Gly Val Leu Leu Leu Ser Leu Val Ile Thr Leu
            500                 505                 510
Tyr Cys Lys Arg Gly Arg Lys Lys Leu Leu Tyr Ile Phe Lys Gln Pro
        515                 520                 525
Phe Met Arg Pro Val Gln Thr Thr Gln Glu Glu Asp Gly Cys Ser Cys
    530                 535                 540
Arg Phe Pro Glu Glu Glu Glu Gly Gly Cys Glu Leu Arg Val Lys Phe
545                 550                 555                 560
Ser Arg Ser Ala Asp Ala Pro Ala Tyr Gln Gln Gly Gln Asn Gln Leu
                565                 570                 575
Tyr Asn Glu Leu Asn Leu Gly Arg Arg Glu Glu Tyr Asp Val Leu Asp
            580                 585                 590
```

Lys Arg Arg Gly Arg Asp Pro Glu Met Gly Gly Lys Pro Arg Arg Lys
            595                 600                 605

Asn Pro Gln Glu Gly Leu Tyr Asn Glu Leu Gln Lys Asp Lys Met Ala
610                 615                 620

Glu Ala Tyr Ser Glu Ile Gly Met Lys Gly Glu Arg Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665

<210> SEQ ID NO 346
<211> LENGTH: 453
<212> TYPE: PRT
<213> ORGANISM: Artificial Sequence
<220> FEATURE:
<223> OTHER INFORMATION: Synthetic Construct

<400> SEQUENCE: 346

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Leu Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Gly
                165                 170                 175

Gly Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gln Ser Trp Pro Leu Thr Phe Gly Gln Gly Thr Lys Val
                245                 250                 255

Glu Ile Lys Gly Leu Ala Val Ser Thr Ile Ser Ser Phe Phe Pro Pro
            260                 265                 270

Gly Tyr Gln Ile Tyr Ile Trp Ala Pro Leu Ala Gly Thr Cys Gly Val
        275                 280                 285

```
Leu Leu Leu Ser Leu Val Ile Thr Leu Tyr Cys Lys Arg Gly Arg Lys
        290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu
                325                 330                 335

Gly Gly Cys Glu Leu Arg Val Lys Phe Ser Arg Ser Ala Asp Ala Pro
                340                 345                 350

Ala Tyr Gln Gln Gly Gln Asn Gln Leu Tyr Asn Glu Leu Asn Leu Gly
                355                 360                 365

Arg Arg Glu Glu Tyr Asp Val Leu Asp Lys Arg Gly Arg Asp Pro
370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
                420                 425                 430

Gly Leu Ser Thr Ala Thr Lys Asp Thr Tyr Asp Ala Leu His Met Gln
                435                 440                 445

Ala Leu Pro Pro Arg
                450

<210> SEQ ID NO 347
<211> LENGTH: 482
<212> TYPE: PRT
<213> ORGANISM: Artificial Sequence
<220> FEATURE:
<223> OTHER INFORMATION: Synthetic Construct

<400> SEQUENCE: 347

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
    50                  55                  60

Gly Leu Glu Trp Val Ser Ala Ile Leu Ser Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Tyr Trp Pro Met Asp Ile Trp Gly Gln
            115                 120                 125

Gly Thr Leu Val Thr Val Ser Ser Gly Gly Gly Ser Gly Gly Gly
    130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Gly
                165                 170                 175

Gly Gln Ser Val Ser Ser Ser Tyr Leu Ala Trp Tyr Gln Gln Lys Pro
                180                 185                 190
```

Gly Gln Ala Pro Arg Leu Leu Met Tyr Asp Ala Ser Ile Arg Ala Thr
            195                 200                 205

Gly Ile Pro Asp Arg Phe Ser Gly Ser Gly Ser Gly Thr Asp Phe Thr
            210                 215                 220

Leu Thr Ile Ser Arg Leu Glu Pro Glu Asp Phe Ala Val Tyr Tyr Cys
225                 230                 235                 240

Gln Gln Tyr Gln Ser Trp Pro Leu Thr Phe Gly Gln Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
            275                 280                 285

Ala Ala Gly Gly Ala Val His Thr Arg Gly Leu Asp Phe Ala Cys Asp
290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 348
<211> LENGTH: 668
<212> TYPE: PRT
<213> ORGANISM: Artificial Sequence
<220> FEATURE:
<223> OTHER INFORMATION: Synthetic Construct

<400> SEQUENCE: 348

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Leu Ser Ser Gly Gly Ser Thr Tyr

```
            65                  70                  75                  80
Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
            115                 120                 125

Gly Thr Leu Val Thr Val Ser Ser Gly Gly Gly Ser Gly Gly Gly
130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Gly
                165                 170                 175

Gly Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
            195                 200                 205

Gly Ile Pro Asp Arg Phe Ser Gly Ser Gly Ser Gly Thr Asp Phe Thr
            210                 215                 220

Leu Thr Ile Ser Arg Leu Glu Pro Glu Asp Phe Ala Val Tyr Tyr Cys
225                 230                 235                 240

Gln Gln Tyr Gln Ser Trp Pro Leu Thr Phe Gly Gln Gly Thr Lys Val
                245                 250                 255

Glu Ile Lys Glu Pro Lys Ser Pro Asp Lys Thr His Thr Cys Pro Pro
            260                 265                 270

Cys Pro Ala Pro Pro Val Ala Gly Pro Ser Val Phe Leu Phe Pro Pro
            275                 280                 285

Lys Pro Lys Asp Thr Leu Met Ile Ala Arg Thr Pro Glu Val Thr Cys
            290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
            370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
            435                 440                 445

Leu Tyr Ser Lys Leu Thr Val Asp Lys Ser Arg Trp Gln Gln Gly Asn
            450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ile Tyr Ile Trp Ala Pro
            485                 490                 495
```

```
Leu Ala Gly Thr Cys Gly Val Leu Leu Leu Ser Leu Val Ile Thr Leu
                500                 505                 510

Tyr Cys Lys Arg Gly Arg Lys Lys Leu Leu Tyr Ile Phe Lys Gln Pro
            515                 520                 525

Phe Met Arg Pro Val Gln Thr Thr Gln Glu Glu Asp Gly Cys Ser Cys
530                 535                 540

Arg Phe Pro Glu Glu Glu Gly Gly Cys Glu Leu Arg Val Lys Phe
545                 550                 555                 560

Ser Arg Ser Ala Asp Ala Pro Ala Tyr Gln Gln Gly Gln Asn Gln Leu
                565                 570                 575

Tyr Asn Glu Leu Asn Leu Gly Arg Arg Glu Glu Tyr Asp Val Leu Asp
            580                 585                 590

Lys Arg Arg Gly Arg Asp Pro Glu Met Gly Gly Lys Pro Arg Arg Lys
            595                 600                 605

Asn Pro Gln Glu Gly Leu Tyr Asn Glu Leu Gln Lys Asp Lys Met Ala
        610                 615                 620

Glu Ala Tyr Ser Glu Ile Gly Met Lys Gly Glu Arg Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665

<210> SEQ ID NO 349
<211> LENGTH: 453
<212> TYPE: PRT
<213> ORGANISM: Artificial Sequence
<220> FEATURE:
<223> OTHER INFORMATION: Synthetic Construct

<400> SEQUENCE: 349

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Phe Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Asp Leu Tyr Leu Ala Trp Tyr Gln Gln Lys Pro
            180                 185                 190
```

Gly Gln Ala Pro Arg Leu Leu Met Tyr Asp Ala Ser Ile Arg Ala Thr
            195                 200                 205

Gly Ile Pro Asp Arg Phe Ser Gly Ser Gly Ser Gly Thr Asp Phe Thr
            210                 215                 220

Leu Thr Ile Ser Arg Leu Glu Pro Glu Asp Phe Ala Val Tyr Tyr Cys
225                 230                 235                 240

Gln Gln Tyr Gln Thr Trp Pro Leu Thr Phe Gly Gln Gly Thr Lys Val
            245                 250                 255

Glu Ile Lys Gly Leu Ala Val Ser Thr Ile Ser Ser Phe Phe Pro Pro
            260                 265                 270

Gly Tyr Gln Ile Tyr Ile Trp Ala Pro Leu Ala Gly Thr Cys Gly Val
            275                 280                 285

Leu Leu Leu Ser Leu Val Ile Thr Leu Tyr Cys Lys Arg Gly Arg Lys
            290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
            325                 330                 335

Gly Gly Cys Glu Leu Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
            355                 360                 365

Arg Arg Glu Glu Tyr Asp Val Leu Asp Lys Arg Arg Gly Arg Asp Pro
            370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
            405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
            435                 440                 445

Ala Leu Pro Pro Arg
    450

<210> SEQ ID NO 350
<211> LENGTH: 482
<212> TYPE: PRT
<213> ORGANISM: Artificial Sequence
<220> FEATURE:
<223> OTHER INFORMATION: Synthetic Construct

<400> SEQUENCE: 350

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
            50                  55                  60

Gly Leu Glu Trp Val Ser Ala Ile Ser Asp Phe Gly Ser Thr Tyr Tyr
65                  70                  75                  80

Tyr Ala Asp Ser Val Lys Gly Arg Phe Thr Ile Ser Arg Asp Asn Ser
            85                  90                  95

```
Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Ser Gly Gly Gly
    130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Asp Leu Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gln Thr Trp Pro Leu Thr Phe Gly Gln Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 351
<211> LENGTH: 668
<212> TYPE: PRT
```

<213> ORGANISM: Artificial Sequence
<220> FEATURE:
<223> OTHER INFORMATION: Synthetic Construct

<400> SEQUENCE: 351

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Phe Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Asp Leu Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gln Thr Trp Pro Leu Thr Phe Gly Gln Gly Thr Lys Val
                245                 250                 255

Glu Ile Lys Glu Pro Lys Ser Pro Asp Lys Thr His Thr Cys Pro Pro
            260                 265                 270

Cys Pro Ala Pro Pro Val Ala Gly Pro Ser Val Phe Leu Phe Pro Pro
        275                 280                 285

Lys Pro Lys Asp Thr Leu Met Ile Ala Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
```

```
                385                 390                 395                 400
Leu Thr Lys Asn Gln Val Ser Leu Thr Cys Leu Val Lys Gly Phe Tyr
                    405                 410                 415
Pro Ser Asp Ile Ala Val Glu Trp Glu Ser Asn Gly Gln Pro Glu Asn
                420                 425                 430
Asn Tyr Lys Thr Thr Pro Pro Val Leu Asp Ser Asp Gly Ser Phe Phe
            435                 440                 445
Leu Tyr Ser Lys Leu Thr Val Asp Lys Ser Arg Trp Gln Gln Gly Asn
        450                 455                 460
Val Phe Ser Cys Ser Val Met His Glu Ala Leu His Asn His Tyr Thr
465                 470                 475                 480
Gln Lys Ser Leu Ser Leu Ser Pro Gly Lys Ile Tyr Ile Trp Ala Pro
                    485                 490                 495
Leu Ala Gly Thr Cys Gly Val Leu Leu Leu Ser Leu Val Ile Thr Leu
                500                 505                 510
Tyr Cys Lys Arg Gly Arg Lys Lys Leu Leu Tyr Ile Phe Lys Gln Pro
            515                 520                 525
Phe Met Arg Pro Val Gln Thr Thr Gln Glu Glu Asp Gly Cys Ser Cys
        530                 535                 540
Arg Phe Pro Glu Glu Glu Glu Gly Gly Cys Glu Leu Arg Val Lys Phe
545                 550                 555                 560
Ser Arg Ser Ala Asp Ala Pro Ala Tyr Gln Gln Gly Gln Asn Gln Leu
                    565                 570                 575
Tyr Asn Glu Leu Asn Leu Gly Arg Arg Glu Glu Tyr Asp Val Leu Asp
                580                 585                 590
Lys Arg Arg Gly Arg Asp Pro Glu Met Gly Gly Lys Pro Arg Arg Lys
            595                 600                 605
Asn Pro Gln Glu Gly Leu Tyr Asn Glu Leu Gln Lys Asp Lys Met Ala
        610                 615                 620
Glu Ala Tyr Ser Glu Ile Gly Met Lys Gly Glu Arg Arg Arg Gly Lys
625                 630                 635                 640
Gly His Asp Gly Leu Tyr Gln Gly Leu Ser Thr Ala Thr Lys Asp Thr
                    645                 650                 655
Tyr Asp Ala Leu His Met Gln Ala Leu Pro Pro Arg
                660                 665

<210> SEQ ID NO 352
<211> LENGTH: 453
<212> TYPE: PRT
<213> ORGANISM: Artificial Sequence
<220> FEATURE:
<223> OTHER INFORMATION: Synthetic Construct

<400> SEQUENCE: 352

Met Ala Leu Pro Val Thr Ala Leu Leu Leu Pro Leu Ala Leu Leu Leu
1               5                   10                  15
His Ala Ala Arg Pro Glu Val Gln Leu Leu Glu Ser Gly Gly Gly Leu
                20                  25                  30
Val Gln Pro Gly Gly Ser Leu Arg Leu Ser Cys Ala Ala Ser Gly Phe
            35                  40                  45
Thr Phe Ser Ser Tyr Pro Met Ser Trp Val Arg Gln Ala Pro Gly Lys
        50                  55                  60
Gly Leu Glu Trp Val Ser Ala Ile Gly Gly Ser Gly Gly Ser Thr Tyr
65                  70                  75                  80
Tyr Ala Asp Ser Val Lys Gly Arg Phe Thr Ile Ser Arg Asp Asn Ser
```

85                  90                  95
Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ser Trp Gly Gln
            115                 120                 125

Gly Thr Leu Val Thr Val Ser Ser Gly Gly Gly Ser Gly Gly Gly
        130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
            165                 170                 175

Ser Gln Ser Val Ser Ser Thr Tyr Leu Ala Trp Tyr Gln Gln Lys Pro
            180                 185                 190

Gly Gln Ala Pro Arg Leu Leu Ile Tyr Asp Ala Ser Ser Arg Ala Pro
            195                 200                 205

Gly Ile Pro Asp Arg Phe Ser Gly Ser Gly Ser Gly Thr Asp Phe Thr
            210                 215                 220

Leu Thr Ile Ser Arg Leu Glu Pro Glu Asp Phe Ala Val Tyr Tyr Cys
225                 230                 235                 240

Gln Gln Tyr Ser Thr Ser Pro Leu Thr Phe Gly Gln Gly Thr Lys Val
            245                 250                 255

Glu Ile Lys Gly Leu Ala Val Ser Thr Ile Ser Ser Phe Phe Pro Pro
            260                 265                 270

Gly Tyr Gln Ile Tyr Ile Trp Ala Pro Leu Ala Gly Thr Cys Gly Val
            275                 280                 285

Leu Leu Leu Ser Leu Val Ile Thr Leu Tyr Cys Lys Arg Gly Arg Lys
            290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu
            325                 330                 335

Gly Gly Cys Glu Leu Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
            355                 360                 365

Arg Arg Glu Glu Tyr Asp Val Leu Asp Lys Arg Gly Arg Asp Pro
            370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
            405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
            435                 440                 445

Ala Leu Pro Pro Arg
        450

<210> SEQ ID NO 353
<211> LENGTH: 482
<212> TYPE: PRT
<213> ORGANISM: Artificial Sequence
<220> FEATURE:
<223> OTHER INFORMATION: Synthetic Construct

```
<400> SEQUENCE: 353

Met Ala Leu Pro Val Thr Ala Leu Leu Leu Pro Leu Ala Leu Leu Leu
1               5                   10                  15
His Ala Ala Arg Pro Glu Val Gln Leu Leu Glu Ser Gly Gly Gly Leu
            20                  25                  30
Val Gln Pro Gly Gly Ser Leu Arg Leu Ser Cys Ala Ala Ser Gly Phe
        35                  40                  45
Thr Phe Ser Ser Tyr Pro Met Ser Trp Val Arg Gln Ala Pro Gly Lys
    50                  55                  60
Gly Leu Glu Trp Val Ser Ala Ile Gly Gly Ser Gly Gly Ser Thr Tyr
65                  70                  75                  80
Tyr Ala Asp Ser Val Lys Gly Arg Phe Thr Ile Ser Arg Asp Asn Ser
                85                  90                  95
Lys Asn Thr Leu Tyr Leu Gln Met Asn Ser Leu Arg Ala Glu Asp Thr
            100                 105                 110
Ala Val Tyr Tyr Cys Ala Arg Tyr Trp Pro Met Asp Ser Trp Gly Gln
        115                 120                 125
Gly Thr Leu Val Thr Val Ser Ser Gly Gly Gly Ser Gly Gly Gly Gly
    130                 135                 140
Gly Ser Gly Gly Gly Gly Ser Glu Ile Val Leu Thr Gln Ser Pro Gly
145                 150                 155                 160
Thr Leu Ser Leu Ser Pro Gly Glu Arg Ala Thr Leu Ser Cys Arg Ala
                165                 170                 175
Ser Gln Ser Val Ser Ser Thr Tyr Leu Ala Trp Tyr Gln Gln Lys Pro
            180                 185                 190
Gly Gln Ala Pro Arg Leu Leu Ile Tyr Asp Ala Ser Ser Arg Ala Pro
        195                 200                 205
Gly Ile Pro Asp Arg Phe Ser Gly Ser Gly Ser Gly Thr Asp Phe Thr
    210                 215                 220
Leu Thr Ile Ser Arg Leu Glu Pro Glu Asp Phe Ala Val Tyr Tyr Cys
225                 230                 235                 240
Gln Gln Tyr Ser Thr Ser Pro Leu Thr Phe Gly Gln Gly Thr Lys Val
                245                 250                 255
Glu Ile Lys Thr Thr Thr Pro Ala Pro Arg Pro Pro Thr Pro Ala Pro
            260                 265                 270
Thr Ile Ala Ser Gln Pro Leu Ser Leu Arg Pro Glu Ala Cys Arg Pro
        275                 280                 285
Ala Ala Gly Gly Ala Val His Thr Arg Gly Leu Asp Phe Ala Cys Asp
    290                 295                 300
Ile Tyr Ile Trp Ala Pro Leu Ala Gly Thr Cys Gly Val Leu Leu Leu
305                 310                 315                 320
Ser Leu Val Ile Thr Leu Tyr Cys Lys Arg Gly Arg Lys Lys Leu Leu
                325                 330                 335
Tyr Ile Phe Lys Gln Pro Phe Met Arg Pro Val Gln Thr Thr Gln Glu
            340                 345                 350
Glu Asp Gly Cys Ser Cys Arg Phe Pro Glu Glu Glu Glu Gly Gly Cys
        355                 360                 365
Glu Leu Arg Val Lys Phe Ser Arg Ser Ala Asp Ala Pro Ala Tyr Gln
    370                 375                 380
Gln Gly Gln Asn Gln Leu Tyr Asn Glu Leu Asn Leu Gly Arg Arg Glu
385                 390                 395                 400
Glu Tyr Asp Val Leu Asp Lys Arg Arg Gly Arg Asp Pro Glu Met Gly
                405                 410                 415
```

```
Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 354
<211> LENGTH: 668
<212> TYPE: PRT
<213> ORGANISM: Artificial Sequence
<220> FEATURE:
<223> OTHER INFORMATION: Synthetic Construct

<400> SEQUENCE: 354

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Pro Met Ser Trp Val Arg Gln Ala Pro Gly Lys
    50                  55                  60

Gly Leu Glu Trp Val Ser Ala Ile Gly Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ser Trp Gly Gln
        115                 120                 125

Gly Thr Leu Val Thr Val Ser Ser Gly Gly Gly Ser Gly Gly Gly Gly
    130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Gln Ser Val Ser Ser Thr Tyr Leu Ala Trp Tyr Gln Gln Lys Pro
            180                 185                 190

Gly Gln Ala Pro Arg Leu Leu Ile Tyr Asp Ala Ser Ser Arg Ala Pro
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Ser Thr Ser Pro Leu Thr Phe Gly Gln Gly Thr Lys Val
                245                 250                 255

Glu Ile Lys Glu Pro Lys Ser Pro Asp Lys Thr His Thr Cys Pro Pro
            260                 265                 270

Cys Pro Ala Pro Pro Val Ala Gly Pro Ser Val Phe Leu Phe Pro Pro
        275                 280                 285
```

```
Lys Pro Lys Asp Thr Leu Met Ile Ala Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ile Tyr Ile Trp Ala Pro
                485                 490                 495

Leu Ala Gly Thr Cys Gly Val Leu Leu Leu Ser Leu Val Ile Thr Leu
            500                 505                 510

Tyr Cys Lys Arg Gly Arg Lys Lys Leu Leu Tyr Ile Phe Lys Gln Pro
        515                 520                 525

Phe Met Arg Pro Val Gln Thr Thr Gln Glu Glu Asp Gly Cys Ser Cys
530                 535                 540

Arg Phe Pro Glu Glu Glu Glu Gly Gly Cys Glu Leu Arg Val Lys Phe
545                 550                 555                 560

Ser Arg Ser Ala Asp Ala Pro Ala Tyr Gln Gln Gly Gln Asn Gln Leu
                565                 570                 575

Tyr Asn Glu Leu Asn Leu Gly Arg Arg Glu Glu Tyr Asp Val Leu Asp
            580                 585                 590

Lys Arg Arg Gly Arg Asp Pro Glu Met Gly Gly Lys Pro Arg Arg Lys
        595                 600                 605

Asn Pro Gln Glu Gly Leu Tyr Asn Glu Leu Gln Lys Asp Lys Met Ala
610                 615                 620

Glu Ala Tyr Ser Glu Ile Gly Met Lys Gly Glu Arg Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665

<210> SEQ ID NO 355
<211> LENGTH: 453
<212> TYPE: PRT
<213> ORGANISM: Artificial Sequence
<220> FEATURE:
<223> OTHER INFORMATION: Synthetic Construct
```

-continued

<400> SEQUENCE: 355

Met Ala Leu Pro Val Thr Ala Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Pro Met Ser Trp Val Arg Gln Ala Pro Gly Lys
    50                  55                  60

Gly Leu Glu Trp Val Ser Ala Ile Gly Gly Ser Gly Gly Trp Ser Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Tyr Trp Pro Met Asp Ser Trp Gly Gln
            115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Trp Leu
                165                 170                 175

Ser Gln Ser Val Ser Ser Thr Tyr Leu Ala Trp Tyr Gln Gln Lys Pro
                180                 185                 190

Gly Gln Ala Pro Arg Leu Leu Ile Tyr Asp Ala Ser Ser Arg Ala Pro
            195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Ser Glu Trp Pro Leu Thr Phe Gly Gln Gly Thr Lys Val
                245                 250                 255

Glu Ile Lys Gly Leu Ala Val Ser Thr Ile Ser Ser Phe Phe Pro Pro
                260                 265                 270

Gly Tyr Gln Ile Tyr Ile Trp Ala Pro Leu Ala Gly Thr Cys Gly Val
            275                 280                 285

Leu Leu Leu Ser Leu Val Ile Thr Leu Tyr Cys Lys Arg Gly Arg Lys
    290                 295                 300

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
                325                 330                 335

Gly Gly Cys Glu Leu Arg Val Lys Phe Ser Arg Ser Ala Asp Ala Pro
                340                 345                 350

Ala Tyr Gln Gln Gly Gln Asn Gln Leu Tyr Asn Glu Leu Asn Leu Gly
            355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly

```
                        405                 410                 415
Met Lys Gly Glu Arg Arg Gly Lys Gly His Asp Gly Leu Tyr Gln
                420                 425                 430

Gly Leu Ser Thr Ala Thr Lys Asp Thr Tyr Asp Ala Leu His Met Gln
            435                 440                 445

Ala Leu Pro Pro Arg
    450

<210> SEQ ID NO 356
<211> LENGTH: 482
<212> TYPE: PRT
<213> ORGANISM: Artificial Sequence
<220> FEATURE:
<223> OTHER INFORMATION: Synthetic Construct

<400> SEQUENCE: 356

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Pro Met Ser Trp Val Arg Gln Ala Pro Gly Lys
    50                  55                  60

Gly Leu Glu Trp Val Ser Ala Ile Gly Gly Ser Gly Gly Trp Ser Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ser Trp Gly Gln
        115                 120                 125

Gly Thr Leu Val Thr Val Ser Ser Gly Gly Gly Ser Gly Gly Gly Gly
    130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Trp Leu
                165                 170                 175

Ser Gln Ser Val Ser Ser Thr Tyr Leu Ala Trp Tyr Gln Gln Lys Pro
            180                 185                 190

Gly Gln Ala Pro Arg Leu Leu Ile Tyr Asp Ala Ser Ser Arg Ala Pro
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Ser Glu Trp Pro Leu Thr Phe Gly Gln Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
```

```
305                 310                 315                 320
Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
                340                 345                 350

Glu Asp Gly Cys Ser Cys Arg Phe Pro Glu Glu Glu Glu Gly Gly Cys
                355                 360                 365

Glu Leu Arg Val Lys Phe Ser Arg Ser Ala Asp Ala Pro Ala Tyr Gln
            370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
                435                 440                 445

Glu Arg Arg Arg Gly Lys Gly His Asp Gly Leu Tyr Gln Gly Leu Ser
            450                 455                 460

Thr Ala Thr Lys Asp Thr Tyr Asp Ala Leu His Met Gln Ala Leu Pro
465                 470                 475                 480

Pro Arg

<210> SEQ ID NO 357
<211> LENGTH: 668
<212> TYPE: PRT
<213> ORGANISM: Artificial Sequence
<220> FEATURE:
<223> OTHER INFORMATION: Synthetic Construct

<400> SEQUENCE: 357

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Pro Met Ser Trp Val Arg Gln Ala Pro Gly Lys
        50                  55                  60

Gly Leu Glu Trp Val Ser Ala Ile Gly Gly Ser Gly Gly Trp Ser Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Tyr Trp Pro Met Asp Ser Trp Gly Gln
            115                 120                 125

Gly Thr Leu Val Thr Val Ser Ser Gly Gly Gly Gly Ser Gly Gly Gly
        130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Trp Leu
                165                 170                 175

Ser Gln Ser Val Ser Ser Thr Tyr Leu Ala Trp Tyr Gln Gln Lys Pro
                180                 185                 190
```

```
Gly Gln Ala Pro Arg Leu Leu Ile Tyr Asp Ala Ser Ser Arg Ala Pro
        195                 200                 205

Gly Ile Pro Asp Arg Phe Ser Gly Ser Gly Ser Gly Thr Asp Phe Thr
210                 215                 220

Leu Thr Ile Ser Arg Leu Glu Pro Glu Asp Phe Ala Val Tyr Tyr Cys
225                 230                 235                 240

Gln Gln Tyr Ser Glu Trp Pro Leu Thr Phe Gly Gln Gly Thr Lys Val
            245                 250                 255

Glu Ile Lys Glu Pro Lys Ser Pro Asp Lys Thr His Thr Cys Pro Pro
            260                 265                 270

Cys Pro Ala Pro Pro Val Ala Gly Pro Ser Val Phe Leu Phe Pro Pro
            275                 280                 285

Lys Pro Lys Asp Thr Leu Met Ile Ala Arg Thr Pro Glu Val Thr Cys
290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
            435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ile Tyr Ile Trp Ala Pro
                485                 490                 495

Leu Ala Gly Thr Cys Gly Val Leu Leu Leu Ser Leu Val Ile Thr Leu
            500                 505                 510

Tyr Cys Lys Arg Gly Arg Lys Lys Leu Leu Tyr Ile Phe Lys Gln Pro
    515                 520                 525

Phe Met Arg Pro Val Gln Thr Thr Gln Glu Glu Asp Gly Cys Ser Cys
530                 535                 540

Arg Phe Pro Glu Glu Glu Glu Gly Gly Cys Glu Leu Arg Val Lys Phe
545                 550                 555                 560

Ser Arg Ser Ala Asp Ala Pro Ala Tyr Gln Gln Gly Gln Asn Gln Leu
                565                 570                 575

Tyr Asn Glu Leu Asn Leu Gly Arg Arg Glu Glu Tyr Asp Val Leu Asp
            580                 585                 590

Lys Arg Arg Gly Arg Asp Pro Glu Met Gly Gly Lys Pro Arg Arg Lys
    595                 600                 605
```

```
Asn Pro Gln Glu Gly Leu Tyr Asn Glu Leu Gln Lys Asp Lys Met Ala
    610                 615                 620

Glu Ala Tyr Ser Glu Ile Gly Met Lys Gly Glu Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665

<210> SEQ ID NO 358
<211> LENGTH: 453
<212> TYPE: PRT
<213> ORGANISM: Artificial Sequence
<220> FEATURE:
<223> OTHER INFORMATION: Synthetic Construct

<400> SEQUENCE: 358

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Arg Trp
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Thr Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Val Arg Val Ser Ser Thr Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Met Lys Trp Pro Leu Thr Phe Gly Gln Gly Thr Lys Val
                245                 250                 255

Glu Ile Lys Gly Leu Ala Val Ser Thr Ile Ser Ser Phe Phe Pro Pro
            260                 265                 270

Gly Tyr Gln Ile Tyr Ile Trp Ala Pro Leu Ala Gly Thr Cys Gly Val
        275                 280                 285

Leu Leu Leu Ser Leu Val Ile Thr Leu Tyr Cys Lys Arg Gly Arg Lys
    290                 295                 300
```

Lys Leu Leu Tyr Ile Phe Lys Gln Pro Phe Met Arg Pro Val Gln Thr
305                 310                 315                 320

Thr Gln Glu Glu Asp Gly Cys Ser Cys Arg Phe Pro Glu Glu Glu Glu
            325                 330                 335

Gly Gly Cys Glu Leu Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
            355                 360                 365

Arg Arg Glu Glu Tyr Asp Val Leu Asp Lys Arg Gly Arg Asp Pro
370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
            405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
            435                 440                 445

Ala Leu Pro Pro Arg
      450

<210> SEQ ID NO 359
<211> LENGTH: 482
<212> TYPE: PRT
<213> ORGANISM: Artificial Sequence
<220> FEATURE:
<223> OTHER INFORMATION: Synthetic Construct

<400> SEQUENCE: 359

Met Ala Leu Pro Val Thr Ala Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Arg Trp
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Thr Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Val Arg Val Ser Ser Thr Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
210                 215                 220

Leu Thr Ile Ser Arg Leu Glu Pro Glu Asp Phe Ala Val Tyr Tyr Cys
225                 230                 235                 240

Gln Gln Tyr Met Lys Trp Pro Leu Thr Phe Gly Gln Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 360
<211> LENGTH: 668
<212> TYPE: PRT
<213> ORGANISM: Artificial Sequence
<220> FEATURE:
<223> OTHER INFORMATION: Synthetic Construct

<400> SEQUENCE: 360

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Ser Asp Ser Gly Gly Ser Arg Trp
65                  70                  75                  80

Tyr Ala Asp Ser Val Lys Gly Arg Phe Thr Ile Ser Arg Asp Asn Ser

-continued

```
                85                  90                  95
Lys Asn Thr Leu Tyr Leu Gln Met Asn Ser Leu Arg Ala Glu Asp Thr
                    100                 105                 110

Ala Val Tyr Tyr Cys Thr Arg Tyr Trp Pro Met Asp Ile Trp Gly Gln
            115                 120                 125

Gly Thr Leu Val Thr Val Ser Ser Gly Gly Gly Ser Gly Gly Gly
        130                 135                 140

Gly Ser Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Ala
                165                 170                 175

Ser Val Arg Val Ser Ser Thr Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Met Lys Trp Pro Leu Thr Phe Gly Gln Gly Thr Lys Val
                245                 250                 255

Glu Ile Lys Glu Pro Lys Ser Pro Asp Lys Thr His Thr Cys Pro Pro
            260                 265                 270

Cys Pro Ala Pro Pro Val Ala Gly Pro Ser Val Phe Leu Phe Pro Pro
        275                 280                 285

Lys Pro Lys Asp Thr Leu Met Ile Ala Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Ile Tyr Ile Trp Ala Pro
                485                 490                 495

Leu Ala Gly Thr Cys Gly Val Leu Leu Leu Ser Leu Val Ile Thr Leu
            500                 505                 510
```

Tyr Cys Lys Arg Gly Arg Lys Lys Leu Leu Tyr Ile Phe Lys Gln Pro
            515                 520                 525

Phe Met Arg Pro Val Gln Thr Thr Gln Glu Glu Asp Gly Cys Ser Cys
        530                 535                 540

Arg Phe Pro Glu Glu Glu Gly Gly Cys Glu Leu Arg Val Lys Phe
545                 550                 555                 560

Ser Arg Ser Ala Asp Ala Pro Ala Tyr Gln Gln Gly Gln Asn Gln Leu
                565                 570                 575

Tyr Asn Glu Leu Asn Leu Gly Arg Arg Glu Glu Tyr Asp Val Leu Asp
            580                 585                 590

Lys Arg Arg Gly Arg Asp Pro Glu Met Gly Gly Lys Pro Arg Arg Lys
        595                 600                 605

Asn Pro Gln Glu Gly Leu Tyr Asn Glu Leu Gln Lys Asp Lys Met Ala
    610                 615                 620

Glu Ala Tyr Ser Glu Ile Gly Met Lys Gly Glu Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665

<210> SEQ ID NO 361
<211> LENGTH: 453
<212> TYPE: PRT
<213> ORGANISM: Artificial Sequence
<220> FEATURE:
<223> OTHER INFORMATION: Synthetic Construct

<400> SEQUENCE: 361

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Gly Ser Tyr Ala Met Thr Trp Val Arg Gln Ala Pro Gly Lys
    50                  55                  60

Gly Leu Glu Trp Val Ser Ala Ile Asp Tyr Ser Gly Asn Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Ser Pro Ile Ala Ser Gly Met Asp
        115                 120                 125

Tyr Trp Gly Gln Gly Thr Leu Val Thr Val Ser Ser Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Ser Val Ser Ser Ser Tyr Pro Ser Trp Tyr
            180                 185                 190

Gln Gln Lys Pro Gly Gln Ala Pro Arg Leu Leu Ile Tyr Gly Ala Ser
        195                 200                 205

```
Ser Arg Ala Thr Gly Ile Pro Asp Arg Phe Ser Gly Ser Gly
    210                 215                 220

Thr Asp Phe Thr Leu Thr Ile Ser Arg Leu Glu Pro Glu Asp Phe Ala
225                 230                 235                 240

Val Tyr Tyr Cys Gln His Tyr Pro Tyr Pro Ser Phe Thr Phe Gly
                245                 250                 255

Gln Gly Thr Lys Val Glu Ile Lys Gly Leu Ala Val Ser Thr Ile Ser
                260                 265                 270

Ser Phe Phe Pro Pro Gly Tyr Gln Ile Tyr Ile Trp Ala Pro Leu Ala
                275                 280                 285

Gly Thr Cys Gly Val Leu Leu Leu Ser Leu Val Ile Thr Leu Tyr Cys
            290                 295                 300

Lys Arg Gly Arg Lys Lys Leu Leu Tyr Ile Phe Lys Gln Pro Phe Met
305                 310                 315                 320

Arg Pro Val Gln Thr Thr Gln Glu Glu Asp Gly Cys Ser Cys Arg Phe
                325                 330                 335

Pro Glu Glu Glu Glu Gly Gly Cys Glu Leu Arg Val Lys Phe Ser Arg
                340                 345                 350

Ser Ala Asp Ala Pro Ala Tyr Gln Gln Gly Gln Asn Gln Leu Tyr Asn
                355                 360                 365

Glu Leu Asn Leu Gly Arg Arg Glu Glu Tyr Asp Val Leu Asp Lys Arg
            370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
            435                 440                 445

Ala Leu His Met Gln
        450

<210> SEQ ID NO 362
<211> LENGTH: 487
<212> TYPE: PRT
<213> ORGANISM: Artificial Sequence
<220> FEATURE:
<223> OTHER INFORMATION: Synthetic Construct

<400> SEQUENCE: 362

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Gly Ser Tyr Ala Met Thr Trp Val Arg Gln Ala Pro Gly Lys
        50                  55                  60

Gly Leu Glu Trp Val Ser Ala Ile Asp Tyr Ser Gly Asn Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110
```

Ala Val Tyr Tyr Cys Ala Arg Val Ser Pro Ile Ala Ser Gly Met Asp
            115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Ser Val Ser Ser Ser Tyr Pro Ser Trp Tyr
            180                 185                 190

Gln Gln Lys Pro Gly Gln Ala Pro Arg Leu Leu Ile Tyr Gly Ala Ser
            195                 200                 205

Ser Arg Ala Thr Gly Ile Pro Asp Arg Phe Ser Gly Ser Gly Ser Gly
    210                 215                 220

Thr Asp Phe Thr Leu Thr Ile Ser Arg Leu Glu Pro Glu Asp Phe Ala
225                 230                 235                 240

Val Tyr Tyr Cys Gln His Tyr Pro Tyr Pro Ser Phe Thr Phe Gly
                245                 250                 255

Gln Gly Thr Lys Val Glu Ile Lys Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 363
<211> LENGTH: 673
<212> TYPE: PRT
<213> ORGANISM: Artificial Sequence
<220> FEATURE:

<223> OTHER INFORMATION: Synthetic Construct

<400> SEQUENCE: 363

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Gly Ser Tyr Ala Met Thr Trp Val Arg Gln Ala Pro Gly Lys
    50                  55                  60

Gly Leu Glu Trp Val Ser Ala Ile Asp Tyr Ser Gly Gly Asn Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Ser Pro Ile Ala Ser Gly Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Ser Val Ser Ser Ser Tyr Pro Ser Trp Tyr
            180                 185                 190

Gln Gln Lys Pro Gly Gln Ala Pro Arg Leu Leu Ile Tyr Gly Ala Ser
        195                 200                 205

Ser Arg Ala Thr Gly Ile Pro Asp Arg Phe Ser Gly Ser Gly Ser Gly
    210                 215                 220

Thr Asp Phe Thr Leu Thr Ile Ser Arg Leu Glu Pro Glu Asp Phe Ala
225                 230                 235                 240

Val Tyr Tyr Cys Gln His Tyr Pro Tyr Pro Ser Phe Thr Phe Gly
                245                 250                 255

Gln Gly Thr Lys Val Glu Ile Lys Glu Pro Lys Ser Pro Asp Lys Thr
            260                 265                 270

His Thr Cys Pro Pro Cys Pro Ala Pro Val Ala Gly Pro Ser Val
        275                 280                 285

Phe Leu Phe Pro Pro Lys Pro Lys Asp Thr Leu Met Ile Ala Arg Thr
290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400
```

```
Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
            515                 520                 525

Ile Phe Lys Gln Pro Phe Met Arg Pro Val Gln Thr Thr Gln Glu Glu
        530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Gln Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 364
<211> LENGTH: 453
<212> TYPE: PRT
<213> ORGANISM: Artificial Sequence
<220> FEATURE:
<223> OTHER INFORMATION: Synthetic Construct

<400> SEQUENCE: 364

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Gly Ser Tyr Ala Met Thr Trp Val Arg Gln Ala Pro Gly Lys
        50                  55                  60

Gly Leu Glu Trp Val Ser Ala Ile Ser Gly Ser Gly Gly Asn Thr Phe
65                  70                  75                  80

Tyr Ala Asp Ser Val Lys Gly Arg Phe Thr Ile Ser Arg Asp Asn Ser
```

```
                85                  90                  95
Lys Asn Thr Leu Tyr Leu Gln Met Asn Ser Leu Arg Ala Glu Asp Thr
            100                 105                 110

Ala Val Tyr Tyr Cys Ala Arg Val Ser Pro Ile Ala Ala Pro Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Leu Gly Ser Phe Tyr Leu Ala Trp Tyr Gln
            180                 185                 190

Gln Lys Pro Gly Gln Ala Pro Arg Leu Leu Ile Tyr Gly Ala Ser Ser
        195                 200                 205

Arg Ala Thr Gly Ile Pro Asp Arg Phe Ser Gly Ser Gly Ser Gly Thr
    210                 215                 220

Asp Phe Thr Leu Thr Ile Ser Arg Leu Glu Pro Glu Asp Phe Ala Val
225                 230                 235                 240

Tyr Tyr Cys Gln His Tyr Asn Tyr Pro Pro Ser Phe Thr Phe Gly Gln
                245                 250                 255

Gly Thr Lys Val Glu Ile Lys Gly Leu Ala Val Ser Thr Ile Ser Ser
            260                 265                 270

Phe Phe Pro Pro Gly Tyr Gln Ile Tyr Ile Trp Ala Pro Leu Ala Gly
        275                 280                 285

Thr Cys Gly Val Leu Leu Leu Ser Leu Val Ile Thr Leu Tyr Cys Lys
    290                 295                 300

Arg Gly Arg Lys Lys Leu Leu Tyr Ile Phe Lys Gln Pro Phe Met Arg
305                 310                 315                 320

Pro Val Gln Thr Thr Gln Glu Glu Asp Gly Cys Ser Cys Arg Phe Pro
                325                 330                 335

Glu Glu Glu Glu Gly Gly Cys Glu Leu Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala
    450

<210> SEQ ID NO 365
<211> LENGTH: 486
<212> TYPE: PRT
<213> ORGANISM: Artificial Sequence
<220> FEATURE:
<223> OTHER INFORMATION: Synthetic Construct
```

```
<400> SEQUENCE: 365

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Gly Ser Tyr Ala Met Thr Trp Val Arg Gln Ala Pro Gly Lys
    50                  55                  60

Gly Leu Glu Trp Val Ser Ala Ile Ser Gly Ser Gly Gly Asn Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Ser Pro Ile Ala Ala Pro Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Leu Gly Ser Phe Tyr Leu Ala Trp Tyr Gln
            180                 185                 190

Gln Lys Pro Gly Gln Ala Pro Arg Leu Leu Ile Tyr Gly Ala Ser Ser
        195                 200                 205

Arg Ala Thr Gly Ile Pro Asp Arg Phe Ser Gly Ser Gly Ser Gly Thr
    210                 215                 220

Asp Phe Thr Leu Thr Ile Ser Arg Leu Glu Pro Glu Asp Phe Ala Val
225                 230                 235                 240

Tyr Tyr Cys Gln His Tyr Asn Tyr Pro Pro Ser Phe Thr Phe Gly Gln
                245                 250                 255

Gly Thr Lys Val Glu Ile Lys Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415
```

```
Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 366
<211> LENGTH: 672
<212> TYPE: PRT
<213> ORGANISM: Artificial Sequence
<220> FEATURE:
<223> OTHER INFORMATION: Synthetic Construct

<400> SEQUENCE: 366

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Gly Ser Tyr Ala Met Thr Trp Val Arg Gln Ala Pro Gly Lys
    50                  55                  60

Gly Leu Glu Trp Val Ser Ala Ile Ser Gly Ser Gly Gly Asn Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Ser Pro Ile Ala Ala Pro Met Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Glu Ile Val Leu Thr
145                 150                 155                 160

Gln Ser Pro Gly Thr Leu Ser Leu Ser Pro Gly Glu Arg Ala Thr Leu
                165                 170                 175

Ser Cys Arg Ala Ser Gln Leu Gly Ser Phe Tyr Leu Ala Trp Tyr Gln
            180                 185                 190

Gln Lys Pro Gly Gln Ala Pro Arg Leu Leu Ile Tyr Gly Ala Ser Ser
        195                 200                 205

Arg Ala Thr Gly Ile Pro Asp Arg Phe Ser Gly Ser Gly Ser Gly Thr
    210                 215                 220

Asp Phe Thr Leu Thr Ile Ser Arg Leu Glu Pro Glu Asp Phe Ala Val
225                 230                 235                 240

Tyr Tyr Cys Gln His Tyr Asn Tyr Pro Pro Ser Phe Thr Phe Gly Gln
                245                 250                 255

Gly Thr Lys Val Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285
```

Leu Phe Pro Pro Lys Pro Lys Asp Thr Leu Met Ile Ala Arg Thr Pro
290                 295                 300

Glu Val Thr Cys Val Val Asp Val Ser His Glu Asp Pro Glu Val
305                 310                 315                 320

Lys Phe Asn Trp Tyr Val Asp Gly Val Glu Val His Asn Ala Lys Thr
            325                 330                 335

Lys Pro Arg Glu Glu Gln Tyr Asn Ser Thr Tyr Arg Val Val Ser Val
        340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
            405                 410                 415

Lys Gly Phe Tyr Pro Ser Asp Ile Ala Val Glu Trp Glu Ser Asn Gly
        420                 425                 430

Gln Pro Glu Asn Asn Tyr Lys Thr Thr Pro Pro Val Leu Asp Ser Asp
            435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Ile Tyr
            485                 490                 495

Ile Trp Ala Pro Leu Ala Gly Thr Cys Gly Val Leu Leu Leu Ser Leu
        500                 505                 510

Val Ile Thr Leu Tyr Cys Lys Arg Gly Arg Lys Lys Leu Leu Tyr Ile
            515                 520                 525

Phe Lys Gln Pro Phe Met Arg Pro Val Gln Thr Thr Gln Glu Glu Asp
530                 535                 540

Gly Cys Ser Cys Arg Phe Pro Glu Glu Glu Glu Gly Gly Cys Glu Leu
545                 550                 555                 560

Arg Val Lys Phe Ser Arg Ser Ala Asp Ala Pro Ala Tyr Gln Gln Gly
            565                 570                 575

Gln Asn Gln Leu Tyr Asn Glu Leu Asn Leu Gly Arg Arg Glu Glu Tyr
        580                 585                 590

Asp Val Leu Asp Lys Arg Arg Gly Arg Asp Pro Glu Met Gly Gly Lys
            595                 600                 605

Pro Arg Arg Lys Asn Pro Gln Glu Gly Leu Tyr Asn Glu Leu Gln Lys
610                 615                 620

Asp Lys Met Ala Glu Ala Tyr Ser Glu Ile Gly Met Lys Gly Glu Arg
625                 630                 635                 640

Arg Arg Gly Lys Gly His Asp Gly Leu Tyr Gln Gly Leu Ser Thr Ala
            645                 650                 655

Thr Lys Asp Thr Tyr Asp Ala Leu His Met Gln Ala Leu Pro Pro Arg
        660                 665                 670

<210> SEQ ID NO 367
<211> LENGTH: 345
<212> TYPE: DNA
<213> ORGANISM: Artificial Sequence
<220> FEATURE:

<223> OTHER INFORMATION: Synthetic Construct
<220> FEATURE:
<221> NAME/KEY: misc_feature
<222> LOCATION: (293)..(293)
<223> OTHER INFORMATION: n is a, c, g, or t

<400> SEQUENCE: 367

| | | | | | | |
|---|---|---|---|---|---|---|
| gaggtgcagc | tgctggaatc | tggcggagga | ctggtgcagc | ctggcggctc | tctgagactg | 60 |
| tcttgtgccg | ccagcggctt | caccttcagc | agctacgcca | tgaactgggt | gcgccaggcc | 120 |
| cctggcaaag | gcctggaatg | ggtgtccgcc | atcagcgata | gcggcggcag | cacctactac | 180 |
| gccgatagcg | tgaagggccg | gttcaccatc | agcggggaca | acagcaagaa | cacccctgtac | 240 |
| ctgcagatga | acagcctgcg | ggccgaggac | accgccgtgt | actactgtgc | canatactgg | 300 |
| cccatggaca | tctggggcca | gggaaccttg | gtcaccgtct | cctca | | 345 |

<210> SEQ ID NO 368
<211> LENGTH: 324
<212> TYPE: DNA
<213> ORGANISM: Artificial Sequence
<220> FEATURE:
<223> OTHER INFORMATION: Synthetic Construct

<400> SEQUENCE: 368

| | | | | | | |
|---|---|---|---|---|---|---|
| gagatcgtgc | tgacacagag | ccctggcacc | ctgagcctgt | ctccaggcga | aagagccacc | 60 |
| ctgtcctgca | aagccagcca | gagcgtgtcc | agcagctacc | tggcctggta | tcagcaaaag | 120 |
| cccggccagg | ctcccccggct | gctgatgtac | gatgccagca | tcagagccac | cggcatcccc | 180 |
| gacagatttt | ccggctctgg | cagcggcacc | gacttcaccc | tgaccatcag | cagactggaa | 240 |
| cccgaggact | tcgccgtgta | ctactgccag | cagtacggca | gctggcccct | gacatttggc | 300 |
| cagggcacaa | aggtggagat | caaa | | | | 324 |

<210> SEQ ID NO 369
<211> LENGTH: 345
<212> TYPE: DNA
<213> ORGANISM: Artificial Sequence
<220> FEATURE:
<223> OTHER INFORMATION: Synthetic Construct

<400> SEQUENCE: 369

| | | | | | | |
|---|---|---|---|---|---|---|
| gaggtgcagc | tgctggaatc | tggcggagga | ctggtgcagc | ctggcggctc | tctgagactg | 60 |
| tcttgtgccg | ccagcggctt | caccttcagc | agctacgcca | tgaactgggt | gcgccaggcc | 120 |
| cctggtaaag | gtttggaatg | ggtttctgct | attctgtcgt | ctggtggttc | tacttactat | 180 |
| gccgattctg | ttaagggtag | attcaccatt | tctagagaca | actctaagaa | cacccttgtac | 240 |
| ttgcaaatga | actccttgag | agctgaagat | actgctgttt | attactgtgc | tagatactgg | 300 |
| ccaatggata | tttggggtca | aggtactctg | gtcaccgtct | cctca | | 345 |

<210> SEQ ID NO 370
<211> LENGTH: 324
<212> TYPE: DNA
<213> ORGANISM: Artificial Sequence
<220> FEATURE:
<223> OTHER INFORMATION: Synthetic Construct

<400> SEQUENCE: 370

| | | | | | | |
|---|---|---|---|---|---|---|
| gagatcgtgc | tgacacagag | ccctggcacc | ctgagcctgt | ctcctggtga | aagagctact | 60 |
| ttgtcttgta | aggggggtca | atccgtttcc | tcttcttatt | tggcttggta | tcaacaaaaa | 120 |
| ccaggtcaag | ctccaagatt | attgatgtac | gatgcttcta | ttagagccac | cggtattcca | 180 |

```
gatagatttt ctggttctgg ttccggtact gatttcactt tgactatctc tagattggaa      240
ccagaagatt tcgctgttta ctactgtcaa caatatcagt cttggccatt gacttttggt      300
caaggtacaa aggttgaaat caaa                                              324
```

<210> SEQ ID NO 371
<211> LENGTH: 345
<212> TYPE: DNA
<213> ORGANISM: Artificial Sequence
<220> FEATURE:
<223> OTHER INFORMATION: Synthetic Construct

<400> SEQUENCE: 371

```
gaggtgcagc tgctggaatc tggcggagga ctggtgcagc ctggcggctc tctgagactg       60
tcttgtgccg ccagcggctt caccttcagc agctacccta tgagctgggt cgcccaggcc      120
cctggcaaag gactggaatg ggtgtccgcc atcggaggct ctggcggcag cacctactac      180
gccgatagcg tgaagggccg gttcaccatc agccgggaca cagcaagaa cacccctgtac     240 ctgcaaatga acagcctgcg ggccgaggac accgccgtgt actactgtgc cagatactgg      300
cccatggaca gctggggcca gggaactttg gtcaccgtct cctca                     345
```

<210> SEQ ID NO 372
<211> LENGTH: 324
<212> TYPE: DNA
<213> ORGANISM: Artificial Sequence
<220> FEATURE:
<223> OTHER INFORMATION: Synthetic Construct

<400> SEQUENCE: 372

```
gagatcgtgc tgacacagag ccctggcacc ctgagcctgt ctccaggcga aagagccacc       60
ctgtcctgca agccagcca gagcgtgtcc agcacatacc tggcctggta tcagcaaaag      120
cccggccagg ctcccccggct gctgatctac gatgcctctt ctagagcccc tggcatcccc      180
gacagattca gcggctctgg cagcggcacc gacttcaccc tgaccatcag cagactggaa      240
cccgaggact cgccgtgta ctactgccag cagtacagca ccagccccct gacctttggc      300
cagggcacaa aggtggagat caaa                                              324
```

<210> SEQ ID NO 373
<211> LENGTH: 345
<212> TYPE: DNA
<213> ORGANISM: Artificial Sequence
<220> FEATURE:
<223> OTHER INFORMATION: Synthetic Construct

<400> SEQUENCE: 373

```
gaggtgcagc tgctggaatc tggcggagga ctggtgcagc ctggcggctc tctgagactg       60
tcttgtgccg ccagcggctt caccttcagc agctacccta tgagctgggt cgccaggcc      120 cctggtaaag gtttggaatg ggtttctgct attggtggtt caggtggttg gagttattat      180
gccgattctg ttaagggtag attcaccatt tctagagaca actctaagaa caccttgtac      240
ttgcaaatga actccttgag agctgaagat actgctgttt attactgtgc tagatactgg      300
ccaatggatt cttggggtca aggtactctg gtcaccgtct cctca                     345
```

<210> SEQ ID NO 374
<211> LENGTH: 324
<212> TYPE: DNA
<213> ORGANISM: Artificial Sequence
<220> FEATURE:

<223> OTHER INFORMATION: Synthetic Construct

<400> SEQUENCE: 374

```
gagatcgtgc tgacacagag ccctggcacc ctgagcctgt ctcctggtga aagagctact    60
ttgtcttgtt ggttgtctca atctgttttcc tctacttact tggcttggta tcaacaaaaa   120
ccaggtcaag ctccaagatt attgatctac gatgcttctt ctagagcacc aggtattcca   180
gatagatttt ctggttctgg ttccggtact gatttcactt tgactatctc tagattggaa   240
ccagaagatt tcgctgttta ctactgccaa caatactctg agtggccatt gacttttggt   300
caaggtacaa aggttgaaat caaa                                           324
```

<210> SEQ ID NO 375
<211> LENGTH: 345
<212> TYPE: DNA
<213> ORGANISM: Artificial Sequence
<220> FEATURE:
<223> OTHER INFORMATION: Synthetic Construct

<400> SEQUENCE: 375

```
gaggtgcagc tgctggaatc tggcggagga ctggtgcagc ctggcggctc tctgagactg    60
tcttgtgccg ccagcggctt caccttcagc agctacgcca tgaactgggt gcgccaggcc   120
cctggtaaag gtttggaatg ggtttctgct atttctgatt ctggtggttc taggtggtat   180
gccgattctg ttaagggtag attcaccatt tctagagaca actctaagaa cacccttgtac  240
ttgcaaatga actccttgag agctgaagat actgctgttt attactgtac gcggtactgg   300
ccaatggata tttggggtca aggtactctg gtcaccgtct cctca                   345
```

<210> SEQ ID NO 376
<211> LENGTH: 324
<212> TYPE: DNA
<213> ORGANISM: Artificial Sequence
<220> FEATURE:
<223> OTHER INFORMATION: Synthetic Construct

<400> SEQUENCE: 376

```
gagatcgtgc tgacacagag ccctggcacc ctgagcctgt ctcctggtga aagagctact    60
ttgtcttgtt ggttgtctca atctgttttcc tctacttact tggcttggta tcaacaaaaa   120
ccaggtcaag ctccaagatt attgatctac gatgcttctt ctagagcacc aggtattcca   180
gatagatttt ctggttctgg ttccggtact gatttcactt tgactatctc tagattggaa   240
ccagaagatt tcgctgttta ctactgccaa caatactctg agtggccatt gacttttggt   300
caaggtacaa aggttgaaat caaa                                           324
```

<210> SEQ ID NO 377
<211> LENGTH: 11
<212> TYPE: PRT
<213> ORGANISM: Artificial Sequence
<220> FEATURE:
<223> OTHER INFORMATION: Synthetic Construct

<400> SEQUENCE: 377

Arg Ala Ser Gln Leu Gly Ser Phe Tyr Leu Ala
1               5                   10

<210> SEQ ID NO 378
<211> LENGTH: 118
<212> TYPE: PRT
<213> ORGANISM: Artificial Sequence
<220> FEATURE:

<223> OTHER INFORMATION: Synthetic Construct

<400> SEQUENCE: 378

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ser Trp Ser Gly Ala Phe Asp Asn Trp Gly Gln Gly Thr
            100                 105                 110

Leu Val Thr Val Ser Ser
            115

<210> SEQ ID NO 379
<211> LENGTH: 109
<212> TYPE: PRT
<213> ORGANISM: Artificial Sequence
<220> FEATURE:
<223> OTHER INFORMATION: Synthetic Construct

<400> SEQUENCE: 379

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Tyr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Pro Pro
                85                  90                  95

Ser Phe Thr Phe Gly Gln Gly Thr Lys Val Glu Ile Lys
            100                 105

<210> SEQ ID NO 380
<211> LENGTH: 118
<212> TYPE: PRT
<213> ORGANISM: Artificial Sequence
<220> FEATURE:
<223> OTHER INFORMATION: Synthetic Construct

<400> SEQUENCE: 380

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Phe Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Val Gly Thr Ser Gly Ala Phe Gly Ile Trp Gly Gln Gly Thr
            100                 105                 110

Leu Val Thr Val Ser Ser
        115

<210> SEQ ID NO 381
<211> LENGTH: 5
<212> TYPE: PRT
<213> ORGANISM: Artificial Sequence
<220> FEATURE:
<223> OTHER INFORMATION: Synthetic Construct

<400> SEQUENCE: 381

Ser Tyr Ala Met Ser
1               5

<210> SEQ ID NO 382
<211> LENGTH: 10
<212> TYPE: PRT
<213> ORGANISM: Artificial Sequence
<220> FEATURE:
<223> OTHER INFORMATION: Synthetic Construct

<400> SEQUENCE: 382

Gly Phe Thr Phe Ser Ser Tyr Ala Met Ser
1               5                   10

<210> SEQ ID NO 383
<211> LENGTH: 6
<212> TYPE: PRT
<213> ORGANISM: Artificial Sequence
<220> FEATURE:
<223> OTHER INFORMATION: Synthetic Construct

<400> SEQUENCE: 383

Ser Ala Ser Gly Gly Ser
1               5

<210> SEQ ID NO 384
<211> LENGTH: 17
<212> TYPE: PRT
<213> ORGANISM: Artificial Sequence
<220> FEATURE:
<223> OTHER INFORMATION: Synthetic Construct

<400> SEQUENCE: 384

Ala Ile Ser Ala Ser Gly Gly Ser Thr Tyr Tyr Ala Asp Ser Val Lys
1               5                   10                  15

Gly

<210> SEQ ID NO 385
<211> LENGTH: 9
<212> TYPE: PRT
<213> ORGANISM: Artificial Sequence
<220> FEATURE:
<223> OTHER INFORMATION: Synthetic Construct

<400> SEQUENCE: 385

Leu Ser Trp Ser Gly Ala Phe Asp Asn
```

```
<210> SEQ ID NO 386
<211> LENGTH: 5
<212> TYPE: PRT
<213> ORGANISM: Artificial Sequence
<220> FEATURE:
<223> OTHER INFORMATION: Synthetic Construct

<400> SEQUENCE: 386

Ser Tyr Ala Met Ser
1               5

<210> SEQ ID NO 387
<211> LENGTH: 7
<212> TYPE: PRT
<213> ORGANISM: Artificial Sequence
<220> FEATURE:
<223> OTHER INFORMATION: Synthetic Construct

<400> SEQUENCE: 387

Gly Phe Thr Phe Arg Ser Tyr
1               5

<210> SEQ ID NO 388
<211> LENGTH: 10
<212> TYPE: PRT
<213> ORGANISM: Artificial Sequence
<220> FEATURE:
<223> OTHER INFORMATION: Synthetic Construct

<400> SEQUENCE: 388

Gly Phe Thr Phe Arg Ser Tyr Ala Met Ser
1               5                   10

<210> SEQ ID NO 389
<211> LENGTH: 6
<212> TYPE: PRT
<213> ORGANISM: Artificial Sequence
<220> FEATURE:
<223> OTHER INFORMATION: Synthetic Construct

<400> SEQUENCE: 389

Ser Gly Ser Gly Gly Ser
1               5

<210> SEQ ID NO 390
<211> LENGTH: 17
<212> TYPE: PRT
<213> ORGANISM: Artificial Sequence
<220> FEATURE:
<223> OTHER INFORMATION: Synthetic Construct

<400> SEQUENCE: 390

Ala Ile Ser Gly Ser Gly Gly Ser Thr Phe Tyr Ala Asp Ser Val Lys
1               5                   10                  15

Gly

<210> SEQ ID NO 391
<211> LENGTH: 9
<212> TYPE: PRT
<213> ORGANISM: Artificial Sequence
<220> FEATURE:
<223> OTHER INFORMATION: Synthetic Construct

<400> SEQUENCE: 391
```

-continued

Val Gly Thr Ser Gly Ala Phe Gly Ile
1               5

<210> SEQ ID NO 392
<211> LENGTH: 7
<212> TYPE: PRT
<213> ORGANISM: Artificial Sequence
<220> FEATURE:
<223> OTHER INFORMATION: Synthetic Construct

<400> SEQUENCE: 392

Gly Ala Ser Ser Arg Ala Tyr
1               5

<210> SEQ ID NO 393
<211> LENGTH: 10
<212> TYPE: PRT
<213> ORGANISM: Artificial Sequence
<220> FEATURE:
<223> OTHER INFORMATION: Synthetic Construct

<400> SEQUENCE: 393

Gln His Tyr Gly Ser Pro Pro Leu Phe Thr
1               5                   10

<210> SEQ ID NO 394
<211> LENGTH: 12
<212> TYPE: PRT
<213> ORGANISM: Artificial Sequence
<220> FEATURE:
<223> OTHER INFORMATION: Synthetic Construct

<400> SEQUENCE: 394

Arg Ala Ser Gln Asn Val Ser Ser Ser Tyr Leu Ala
1               5                   10

<210> SEQ ID NO 395
<211> LENGTH: 7
<212> TYPE: PRT
<213> ORGANISM: Artificial Sequence
<220> FEATURE:
<223> OTHER INFORMATION: Synthetic Construct

<400> SEQUENCE: 395

Gly Ala Ser Tyr Arg Ala Thr
1               5

<210> SEQ ID NO 396
<211> LENGTH: 519
<212> TYPE: PRT
<213> ORGANISM: Artificial Sequence
<220> FEATURE:
<223> OTHER INFORMATION: P5AC1-A2 BCMA CAR construct with R2 epitope

<400> SEQUENCE: 396

Met Ala Leu Pro Val Thr Ala Leu Leu Leu Pro Leu Ala Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Asn Trp Val Arg Gln Ala Pro Gly Lys
    50                  55                  60

Gly Leu Glu Trp Val Ser Ala Ile Leu Ser Ser Gly Gly Ser Thr Tyr
65                  70                  75                  80

-continued

```
Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Tyr Trp Pro Met Asp Ile Trp Gly Gln
        115                 120                 125

Gly Thr Leu Val Thr Val Ser Ser Gly Gly Gly Gly Ser Gly Gly Gly
    130                 135                 140

Gly Ser Gly Gly Gly Gly Ser Glu Ile Val Leu Thr Gln Ser Pro Gly
145                 150                 155                 160

Thr Leu Ser Leu Ser Pro Gly Glu Arg Ala Thr Leu Ser Cys Arg Gly
                165                 170                 175

Gly Gln Ser Val Ser Ser Ser Tyr Leu Ala Trp Tyr Gln Gln Lys Pro
            180                 185                 190

Gly Gln Ala Pro Arg Leu Leu Met Tyr Asp Ala Ser Ile Arg Ala Thr
        195                 200                 205

Gly Ile Pro Asp Arg Phe Ser Gly Ser Gly Ser Gly Thr Asp Phe Thr
    210                 215                 220

Leu Thr Ile Ser Arg Leu Glu Pro Glu Asp Phe Ala Val Tyr Tyr Cys
225                 230                 235                 240

Gln Gln Tyr Gln Ser Trp Pro Leu Thr Phe Gly Gln Gly Thr Lys Val
                245                 250                 255

Glu Ile Lys Gly Ser Gly Gly Gly Ser Cys Pro Tyr Ser Asn Pro
            260                 265                 270

Ser Leu Cys Ser Gly Gly Gly Gly Ser Cys Pro Tyr Ser Asn Pro Ser
        275                 280                 285

Leu Cys Ser Gly Gly Gly Gly Ser Thr Thr Thr Pro Ala Pro Arg Pro
    290                 295                 300

Pro Thr Pro Ala Pro Thr Ile Ala Ser Gln Pro Leu Ser Leu Arg Pro
305                 310                 315                 320

Glu Ala Cys Arg Pro Ala Ala Gly Gly Ala Val His Thr Arg Gly Leu
                325                 330                 335

Asp Phe Ala Cys Asp Ile Tyr Ile Trp Ala Pro Leu Ala Gly Thr Cys
            340                 345                 350

Gly Val Leu Leu Leu Ser Leu Val Ile Thr Leu Tyr Cys Lys Arg Gly
        355                 360                 365

Arg Lys Lys Leu Leu Tyr Ile Phe Lys Gln Pro Phe Met Arg Pro Val
    370                 375                 380

Gln Thr Thr Gln Glu Glu Asp Gly Cys Ser Cys Arg Phe Pro Glu Glu
385                 390                 395                 400

Glu Glu Gly Gly Cys Glu Leu Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
        435                 440                 445

Asp Pro Glu Met Gly Gly Lys Pro Arg Arg Lys Asn Pro Gln Glu Gly
    450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495
```

-continued

```
Tyr Gln Gly Leu Ser Thr Ala Thr Lys Asp Thr Tyr Asp Ala Leu His
            500                 505                 510

Met Gln Ala Leu Pro Pro Arg
        515
```

<210> SEQ ID NO 397
<211> LENGTH: 9
<212> TYPE: PRT
<213> ORGANISM: Homo sapiens

<400> SEQUENCE: 397

```
Cys Pro Tyr Ser Asn Pro Ser Leu Cys
1               5
```

<210> SEQ ID NO 398
<211> LENGTH: 37
<212> TYPE: PRT
<213> ORGANISM: Artificial Sequence
<220> FEATURE:
<223> OTHER INFORMATION: R2 epitope

<400> SEQUENCE: 398

```
Gly Ser Gly Gly Gly Gly Ser Cys Pro Tyr Ser Asn Pro Ser Leu Cys
1               5                   10                  15

Ser Gly Gly Gly Gly Ser Cys Pro Tyr Ser Asn Pro Ser Leu Cys Ser
            20                  25                  30

Gly Gly Gly Gly Ser
        35
```

<210> SEQ ID NO 399
<211> LENGTH: 1497
<212> TYPE: DNA
<213> ORGANISM: Artificial Sequence
<220> FEATURE:
<223> OTHER INFORMATION: nucleic acid sequence encoding P5AC1-V2.1

<400> SEQUENCE: 399

```
atggcactgc ctgtgaccgc cctgctgctg ccactggccc tgctgctgca cgccgcccgg      60
ccagaggtgc agctgctgga gagcggagga ggactggtgc agccaggagg aagcctgaga     120
ctgtcctgcg ccgcctctgg cttcaccttc agctcctacg ccatgaactg ggtgaggcag     180
gcaccaggca agggactgga gtgggtgtct gccatcctgt ctagcggcgg cagcacctac     240
tatgccgatt ccgtgaaggg ccgcttcaca atcagccggg acaactccaa gaataccctg     300
tacctgcaga tgaacagcct gagagccgag gatacagccg tgtactattg cgccaggtat     360
tggcccatgg acatctgggg ccagggcaca ctggtgaccg tgtcctctgg aggaggagga     420
tccggcggag gaggctctgg cggcggcggc agcgagatcg tgctgacaca gagcccaggc     480
accctgagcc tgtcccctgg agagagagcc accctgtctt gtaggggcgg ccagagcgtg     540
agctcctctt acctggcctg gtatcagcag aagccaggcc aggcccccag actgctgatg     600
tacgacgcct ccatcagggc aacaggcatc cccgatcggt tctctggaag cggatccgga     660
accgacttta cactgaccat ctccaggctg gagcctgagg atttcgccgt gtactattgc     720
cagcagtacc agtcttggcc actgacattt ggccagggca ccaaggtgga gatcaaggga     780
tccggaggag gaggatcttg cccttattcc aacccatctc tgtgcaccac aacccctgca     840
ccaaggccac ctacaccagc acctaccatc gcctctcagc cactgagcct gagacccgag     900
gcctgtaggc ctgcagcagg aggagcagtg cacacacggg gactggactt tgcctgcgat     960
atctacatct gggcacctct ggcaggaaca tgtggcgtgc tgctgctgag cctggtcatc    1020
```

```
acc ctgtact gcaagagagg caggaagaag ctgctgtata tcttcaagca gccctttatg    1080
cgccctgtgc agacaaccca ggaggaggat ggctgctcct gtaggttccc agaagaggag    1140
gagggaggat gtgagctgcg cgtgaagttt tctcggagcg ccgacgcacc tgcataccag    1200
cagggacaga atcagctgta taacgagctg aatctgggcc ggagagagga gtatgacgtg    1260
ctggataaga ggaggggaag ggacccagag atgggaggca agccacggag aaagaacccc    1320
caggagggcc tgtacaatga gctgcagaag gataagatgg ccgaggccta tagcgagatc    1380
ggcatgaagg gagagaggcg ccggggcaag ggacacgacg gactgtacca gggactgtcc    1440
acagccacca aggacaccta tgatgccctg cacatgcagg ccctgccacc aaggtga      1497
```

<210> SEQ ID NO 400
<211> LENGTH: 157
<212> TYPE: PRT
<213> ORGANISM: Artificial Sequence
<220> FEATURE:
<223> OTHER INFORMATION: Synthetic construct RQR8 with signal sequence

<400> SEQUENCE: 400

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155
```

<210> SEQ ID NO 401
<211> LENGTH: 109
<212> TYPE: PRT
<213> ORGANISM: Artificial Sequence
<220> FEATURE:
<223> OTHER INFORMATION: Synthetic Construct

<400> SEQUENCE: 401

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Tyr Gly Ile Pro Asp Arg Phe Ser
    50                  55                  60
```

-continued

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln His Tyr Gly Ser Pro Pro
                 85                  90                  95

Leu Phe Thr Phe Gly Gln Gly Thr Lys Val Glu Ile Lys
                100                 105
```

CHIMERIC ANTIGEN RECEPTORS TARGETING B-CELL MATURATION ANTIGEN

CROSS-REFERENCE TO RELATED APPLICATIONS

This application is a divisional of U.S. application Ser. No. 16/384,719, filed on Apr. 15, 2019, which is a divisional of U.S. application Ser. No. 15/085,317, filed on Mar. 30, 2016, now issued as U.S. Pat. No. 10,294,304 on May 21, 2019, which claims the benefit of U.S. Provisional Application No. 62/146,825 filed Apr. 13, 2015, U.S. Provisional Application No. 62/286,473 filed Jan. 25, 2016, and U.S. Provisional Application No. 62/301,177 filed Feb. 29, 2016, all of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "ALGN_003_04US_SeqList_ST25.txt" created on Jan. 29, 2019, and having a size of ~372,605 bytes. The sequence listing contained in this .txt file is part of the specification and is incorporated herein by reference in its entirety.

FIELD

The invention relates to chimeric antigen receptors (CAR). CARs are able to redirect immune cell specificity and reactivity toward a selected target exploiting the ligand-binding domain properties. In particular, the invention relates to CARs that specifically bind to B-Cell Maturation Antigen (BCMA specific CARs). The invention further relates to polynucleotides encoding BCMA specific CAR and isolated cells expressing BCMA specific CARs at their surface. The invention further relates to methods for engineering immune cells expressing BCMA specific CARs at their surface. The invention is particularly useful for the treatment of B-cell lymphomas and leukemia. The invention further relates to immune cells comprising the BCMA specific CARs (BCMA specific CAR-T cells), compositions comprising the BCMA specific CAR-T cells, and methods of using the BCMA specific CAR-T cells for treating conditions associated with malignant cells expressing BCMA (e.g., cancer).

BACKGROUND

Multiple myeloma is a malignancy characterized by an accumulation of clonal plasma cells (see, e.g., Lonial et al., Clinical Cancer Res., 77(6): 1264-1277 (2011)). Current therapies for MM often cause remissions, but nearly all patients eventually relapse and die (see, e.g., Rajkumar, Nature Rev. Clinical Oncol, 5(8): 479-491 (2011)).

Adoptive transfer of T cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). T cells can be genetically modified to express chimeric antigen receptors (CARs), which are fusion proteins comprised of an antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)).

B-cell maturation antigen (BCMA, CD269, or TNFRSF17) is a member of the tumor necrosis factor receptor (TNFR) superfamily. BCMA was identified in a malignant human T cell lymphoma containing a t(4;16) translocation. The gene is selectively expressed in the B-cell lineage with the highest expression in plasmablasts and plasma cells, antibody secreting cells. BCMA binds two ligands, B-cell activation factor (BAFF) (also called B-lymphoctye stimulator (BLyS) and APOL-related leukocyte expressed ligand (TALL-1)) and a proliferation-inducing ligand (APRIL) with affinity of 1 uM and 16 nM, respectively. Binding of APRIL or BAFF to BCMA promotes a signaling cascade involving NF-kappa B, Elk-1, c-Jun N-terminal kinase and the p38 mitogen-activated protein kinase, which produce signals for cell survival and proliferation. BCMA is also expressed on malignant B cells and several cancers that involve B lymphocytes including multiple myeloma, plasmacytoma, Hodgkin's Lymphoma, and chronic lymphocytic leukemia. In autoimmune diseases where plasmablasts are involved such as systemic lupus erythematosus (SLE) and rheumatoid arthritis, BCMA expressing antibody-producing cells secrete autoantibodies that attack self.

In the case of multiple myeloma, about 24,000 new cases are newly diagnosed in the United States each year, and this number represents about 15% of the newly diagnosed hematological cancers in the United States. An average of 11,000 deaths result from multiple myeloma each year, and the average 5-year survival rate is about 44%, with median survival of 50-55 months. Current treatment for multiple myeloma is focused on plasma cells apoptosis and/or decreasing osteoclast activity (e.g., chemotherapy, thalidomide, lenalidomide, bisphosphonates, and/or proteasome inhibitors such as bortezomib (VELCADE®) or carfilzomib). However, multiple myeloma remains an incurable disease, and almost all patients have developed resistance to these agents and eventually relapse. Accordingly, an alternative treatment to multiple myeloma, such as using an anti-BCMA antagonist including BCMA specific CARs and BCMA specific CAR-T cells, would make a superior therapeutic agent.

SUMMARY

Chimeric antigen receptors (CARs) that bind to BCMA are provided. It is demonstrated that certain BCMA specific CARs are effective when expressed in T cells to activate T cells upon contact with BCMA. Advantageously, the BCMA specific CARs provided herein bind human and cynomolgous monkey BCMA. Also advantageously, the BCMA specific CAR-T cells provided herein exhibit degranulation activity, increased interferon gamma production, and/or cytotoxic activity upon contact with BCMA-expressing cells.

In one aspect, the invention provides a BCMA specific CAR comprising an extracellular ligand-binding domain, a first transmembrane domain, and an intracellular signaling domain, wherein the extracellular ligand-binding domain domain comprises (a) a heavy chain variable (VH) region comprising (i) a VH complementarity determining region one (CDR1) comprising the sequence $SYX_1MX_2$, wherein $X_1$ is A or P; and $X_2$ is T, N, or S (SEQ ID NO: 301), $GFTFX_1SY$, wherein $X_1$ is G or S (SEQ ID NO: 302), or $GFTFX_1SYX_2MX_3$, wherein $X_1$ is G or S, $X_2$ is A or P; and $X_3$ is T, N, or S (SEQ ID NO: 303); (ii) a VH CDR2 comprising the sequence AX₁X₂X₃X₄GX₅X₆X₇X₈YADX₉X₁₀KG, wherein X₁ is I, V, T, H, L, A, or C; X₂ is S, D, G, T, I, L, F, M, or V; X₃ is G, Y, L, H, D, A, S, or M; X₄ is S, Q, T, A, F, or W; X₅ is G or T; X₆ is N, S, P, Y, W, or F; X₇ is S, T, I, L, T, A, R, V, K, G, or C; X₈ is F, Y, P, W, H, or G; X₉ is V, R, or L; and X₁₀ is G or T (SEQ ID NO: 305), or X₁X₂X₃X₄X₅X₆, wherein X₁ is S, V, I, D, G, T, L, F, or M; X₂ is G, Y, L, H, D, A, S, or M; X₃ is S, G, F, or W; X₄ is G or S; X₅ is G or T; and X₆ is N, S, P, Y, or W (SEQ ID NO: 306); and iii) a VH CDR3 comprising the sequence VSPIX₁X₂X₃X₄, wherein X₁ is A or Y; X₂ is A or S; and X₃ is G, Q, L, P, or E (SEQ ID NO: 307), or YWPMX₁X₂, wherein X₁ is D, S, T, or A; and X₂ is I, S, L, P, or D (SEQ ID NO: 308); and/or (b) a light chain variable (VL) region comprising (i) a VL CDR1 comprising the sequence X₁X₂X₃X₄X₅X₆X₇X₈X₉X₁₀X₁₁X₁₂, wherein X₁ is R, G, W, A, or C; X₂ is A, P, G, L, C, or S; X₃ is S, G, or R; X₄ is Q, C, E, V, or I; X₅ is S, L, P, G, A, R, or D; X₆ is V, G, or I; X₇ is S, E, D, or P; X₈ is S, P, F, A, M, E, V, N, D, or Y; X₉ is I, T, V, E, S, A, M, Q, Y, H, or R; X₁₀ is Y or F; X₁₁ is L, W, or P; and X₁₂ is A, S, or G (SEQ ID NO: 309); (ii) a VL CDR2 comprising the sequence X₁ASX₂RAX₃, wherein X₁ is G or D; X₂ is S or I; and X₃ is T or P (SEQ ID NO: 310); and (iii) a VL CDR3 comprising the sequence QQYX₁X₂X₃PX₄T, wherein X₁ is G, Q, E, L, F, A, S, M, K, R, or Y; X₂ is S, R, T, G, V, F, Y, D, A, H, V, E, K, or C; X₃ is W, F, or S; and X₄ is L or I (SEQ ID NO: 311), or QQYX₁X₂X₃PX₄, wherein X₁ is G, Q, E, L, F, A, S, M, R, K, or Y; X₂ is S, R, T, G, R, V, D, A, H, E, K, C, F, or Y; X₃ is W, S, or F; and X₄ is L or I (SEQ ID NO: 312).

In another aspect, the invention provides a BCMA specific CAR comprising an extracellular ligand-binding domain, a first transmembrane domain, and an intracellular signaling domain, wherein the extracellular domain comprises a single chain Fv fragment (scFv) comprising a heavy chain variable (VH) region comprising three CDRs from the VH region comprising the sequence shown in SEQ ID NO: 33, 72, 39, 76, 83, 92, 25, or 8; and a light chain variable (VL) region comprising three CDRs from the VL region shown in SEQ ID NO: 34, 73, 40, 77, 84, 93, 18, or 80. In some embodiments, the VH region can comprise the sequence shown in SEQ ID NO: 33, 72, 39, 76, 83, 92, 25, or 8, or a variant thereof with one or several conservative amino acid substitutions in residues that are not within a CDR and/or the VL region can comprise the amino acid sequence shown in SEQ ID NO: 34, 73, 40, 77, 84, 93, 18, or 80, or a variant thereof with one or several amino acid substitutions in amino acids that are not within a CDR.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 150, 151, 152, 156, 157, 129, 130, or 131; (ii) a VH CDR2 comprising the sequence shown in 153, 154, 187, 188, 165, 166, 162, 159, 190, 191, 169, 154, 139, 140, 132, or 133; and (iii) a VH CD3 comprising the sequence shown in 155, 161, 134, or 137; and/or (b) a light chain variable region (VL) comprising (i) a VL CDR1 comprising the sequence shown in SEQ ID NO: 209, 249, 226, 251, 262, 271, 217, or 377; (ii) a VL CDR2 comprising the sequence shown in SEQ ID NO: 221, 252, or 210; and (iii) a VL CDR3 comprising the sequence shown in SEQ ID NO: 222, 225, 227, 253, 263, 272, 216, or 214.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 150, 151, or 152; (ii) a VH CDR2 comprising the sequence shown in 153 or 154; and (iii) a VH CD3 comprising the sequence shown in 155; and/or (b) a light chain variable region (VL) comprising (i) a VL CDR1 comprising the sequence shown in SEQ ID NO: 209; (ii) a VL CDR2 comprising the sequence shown in SEQ ID NO: 221, and (iii) a VL CDR2 comprising the sequence shown in SEQ ID NO: 222.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 150, 151, or 152; (ii) a VH CDR2 comprising the sequence shown in 187 or 188; and (iii) a VH CD3 comprising the sequence shown in 155; and/or (b) a light chain variable region (VL) comprising (i) a VL CDR1 comprising the sequence shown in SEQ ID NO: 249; (ii) a VL CDR2 comprising the sequence shown in SEQ ID NO: 221, and (iii) a VL CDR3 comprising the sequence shown in SEQ ID NO: 225.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 150, 151, or 152; (ii) a VH CDR2 comprising the sequence shown in 165 or 166; and (iii) a VH CD3 comprising the sequence shown in 155; and/or (b) a light chain variable region (VL) comprising (i) a VL CDR1 comprising the sequence shown in SEQ ID NO: 226; (ii) a VL CDR2 comprising the sequence shown in SEQ ID NO: 221, and (iii) a VL CDR3 comprising the sequence shown in SEQ ID NO: 227.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 156, 151, or 157; (ii) a VH CDR2 comprising the sequence shown in 162 or 159; and (iii) a VH CD3 comprising the sequence shown in 161; and/or (b) a light chain variable region (VL) comprising (i) a VL CDR1 comprising the sequence shown in SEQ ID NO: 251; (ii) a VL CDR2 comprising the sequence shown in SEQ ID NO: 252, and (iii) a VL CDR3 comprising the sequence shown in SEQ ID NO: 253.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 156, 151, or 157; (ii) a VH CDR2 comprising the sequence shown in 190 or 191; and (iii) a VH CD3 comprising the sequence shown in 161; and/or (b) a light chain variable region (VL) comprising (i) a VL CDR1 comprising the sequence shown in SEQ ID NO: 262; (ii) a VL CDR2 comprising the sequence shown in SEQ ID NO: 252, and (iii) a VL CDR3 comprising the sequence shown in SEQ ID NO: 263.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 150, 151, or 152; (ii) a VH CDR2 comprising the sequence shown in 169 or 154; and (iii) a VH CD3 comprising the sequence shown in 155; and/or (b) a light chain variable region (VL) comprising (i) a VL CDR1 comprising the sequence shown in SEQ ID NO: 271; (ii) a VL CDR2 comprising the sequence shown in SEQ ID NO: 221, and (iii) a VL CDR3 comprising the sequence shown in SEQ ID NO: 272.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 129, 130, or 131; (ii) a VH CDR2 comprising the sequence shown in 139 or 140; and (iii) a VH CD3 comprising the sequence shown in 134; and/or (b) a light chain variable region (VL) comprising (i) a VL CDR1 comprising the sequence shown in SEQ ID NO: 217; (ii) a VL CDR2 comprising the sequence shown in SEQ ID NO: 210, and (iii) a VL CDR3 comprising the sequence shown in SEQ ID NO: 216.

In some embodiments, the extracellular ligand-binding domain domain of a BCMA specific CAR provided herein comprises (a) a heavy chain variable (VH) region comprising (i) a VH complementarity determining region one (CDR1) comprising the sequence shown in SEQ ID NO: 129, 130, or 131; (ii) a VH CDR2 comprising the sequence shown in 132 or 133; and (iii) a VH CD3 comprising the sequence shown in 137; and/or (b) a light chain variable region (VL) comprising (i) a VL CDR1 comprising the sequence shown in SEQ ID NO: 377; (ii) a VL CDR2 comprising the sequence shown in SEQ ID NO: 210, and (iii) a VL CDR3 comprising the sequence shown in SEQ ID NO: 214.

In some embodiments, the intracellular signaling domain comprises a CD3ζ signaling domain. In some embodiments, the intracellular signaling domain comprises a 4-1BB domain. In some embodiments, the CAR can further comprise another intracellular signaling domain. In some embodiments, the additional intracellular signaling domain can comprise a 4-1 BB domain.

In some embodiments, the CAR can comprise a stalk domain between the extracellular ligand-binding domain and the first transmembrane domain. In some embodiments, the stalk domain can be selected from the group consisting of: a human CD8α hinge, an IgG1 hinge, and an FcγRIIIα hinge.

In some embodiments, the first transmembrane domain can comprise a CD8α chain transmembrane domain.

In some embodiments, the CAR can comprise a CD20 epitope.

In some embodiments, the CAR can comprise another extracellular ligand-binding domain which is not specific for BCMA.

In some embodiments, the BCMA specific CAR can comprise the amino acid sequence shown in SEQ ID NO: 396.

In some embodiments of a CAR, the extracellular ligand-binding domain(s), the first transmembrane domain, and intracellular signaling domain(s) are on a single polypeptide.

In some embodiments, the CAR can comprise a second transmembrane domain, wherein the first transmembrane domain and the extracellular ligand-binding domain(s) are on a first polypeptide, and wherein the second transmembrane domain and the intracellular signaling domain(s) are on a second polypeptide, wherein the first transmembrane domain comprises a transmembrane domain from the α chain of the high-affinity IgE receptor (FcεRI) and the second transmembrane domain comprises a transmembrane domain from the γ or β chain of FcεRI. In some embodiments, the CAR can comprise a third polypeptide comprising a third transmembrane domain fused to an intracellular signaling domain from a co-stimulatory molecule, wherein the third transmembrane domain comprises a transmembrane domain from the γ or β chain of FcεRI.

In another aspect, the invention provides an isolated polynucleotide comprising a nucleic acid sequence encoding a BCMA specific CAR as described herein.

In another aspect, the invention provides an expression vector comprising a nucleic acid sequence encoding a BCMA specific CAR antibody as described herein.

In another aspect, the invention provides engineered immune cell expressing at its cell surface membrane a BCMA specific CAR as described herein. In some embodiments, the engineered immunce cell can comprise another CAR which is not specific for BCMA. In some embodiments, the engineered immunce cell can comprise a polynucleotide encoding a suicide polypeptide. In some embodiments, the suicide polypeptide is RQR8.

In some embodiments, the immune cell can be derived from an inflammatory T-lymphocyte, a cytotoxic T-lymphocyte, a regulatory T-lymphocyte, or a helper T-lymphocyte.

In some embodiments, the engineered immune cell can comprise a disruption one or more endogenous genes, wherein the endogenous gene encodes TCRα, TCRβ, CD52, glucocorticoid receptor (GR), deoxycytidine kinase (DCK), or an immune checkpoint protein such as for example programmed death-1 (PD-1).

In some embodiments, immune cell is obtained from a healthy donor. In some embodiments, the immune cell is obtained from a patient.

In another aspect, the invention provides an engineered immune cell expressing at its cell surface membrane a BCMA specific CAR as described herein for use as a medicament. In some embodiments, the medicament is for use in treatment of a B-cell related cancer selecting from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma.

In another aspect, the invention provides a method of engineering an immune cell comprising: providing an immune cell; and expressing at the surface of the cell at least one BCMA specific CAR as described herein.

In some embodiments, the method comprises: providing an immune cell; introducing into the cell at least one polynucleotide encoding said BCMA specific CAR; and expressing said polynucleotide into the cell.

In some embodiments, the method comprises providing an immune cell; introducing into the cell at least one polynucleotide encoding said BCMA specific CAR; and introducing at least one other CAR which is not specific for BCMA.

In another aspect, the invention provides a method of treating a subject suffering from a condition associated with malignant cells, the method comprising: providing a immune cell expressing at the surface a BCMA specific CAR as described herein; and administering said immune cells to said patient.

In another aspect, the invention provides a pharmaceutical composition comprising an engineered immune cell as described herein.

In another aspect, the invention provides a method of treating a condition associated with malignant cells expressing BCMA in a subject comprising administering to a subject in need thereof an effective amount of a pharmaceutical composition of claim comprising an engineered immune cell as described herein. In some embodiments, the condition is a cancer. In some embodiments, the cancer is a B-cell related cancer selecting from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other B-cell related lymphoma.

In another aspect, the invention provides a method of inhibiting tumor growth or progression in a subject who has malignant cells expressing BCMA, comprising administering to the subject in need thereof an effective amount of a pharmaceutical composition comprising an engineered immune cell as described herein.

In another aspect, the invention provides a method inhibiting metastasis of malignant cells expressing BCMA in a subject, comprising administering to the subject in need thereof an effective amount of the pharmaceutical composition comprising an engineered immune cell as described herein.

In another aspect, the invention provides a method inducing tumor regression in a subject who has malignant cells expressing BCMA, comprising administering to the subject in need thereof an effective amount of the pharmaceutical composition of a pharmaceutical composition comprising an engineered immune cell as described herein.

In some embodiments, any of the above methods further comprises administering one or more additional therapies, such as for example, a monoclonal antibody and/or a chemotherapeutic. In some embodiments, the monoclonal antibody can be, for example, an antibody that binds to a checkpoint inhibitor such as, for example, an anti-PD-1 antibody or an anti-PD-L1 antibody. In some embodiments, any of the above methods further comprises administering a nucleoside analog therapy, such as for example fludarabine or clofarabine, to the subject.

DETAILED DESCRIPTION

Figure 1:
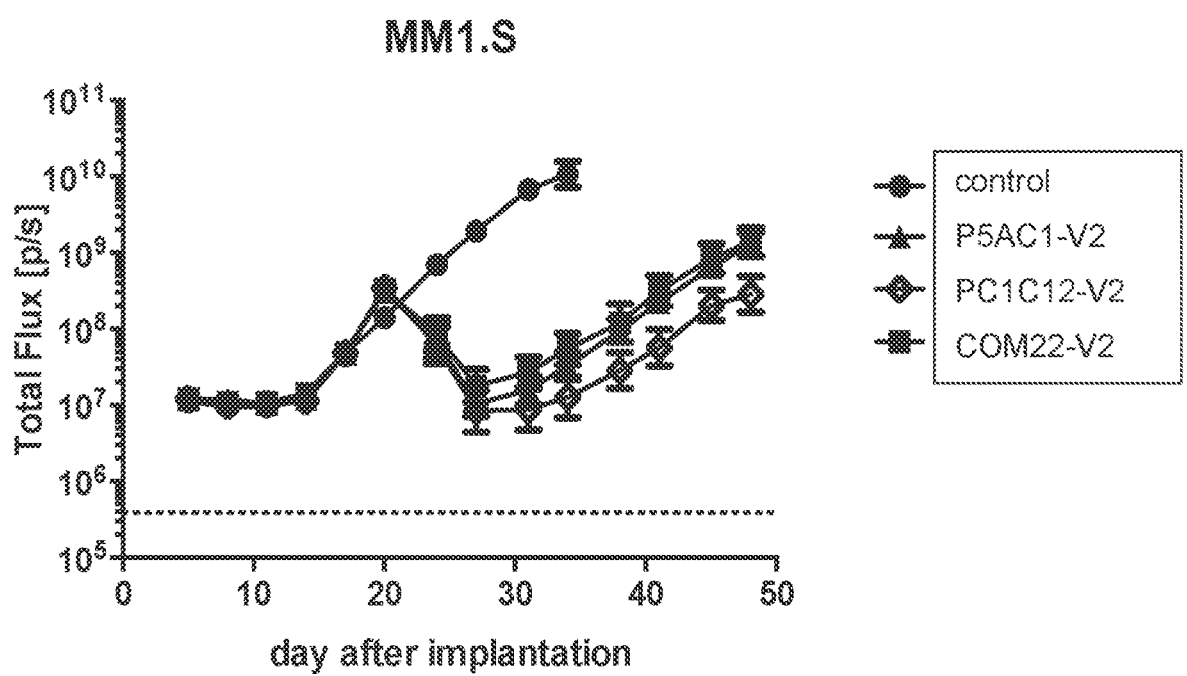
FIG. 1 depicts a graph summarizing the results of treatment with BCMA specific CAR-T cells in the MM1.S tumor model.

The invention disclosed herein provides chimeric antigen receptors (CARs) and immune cells comprising CARs (CAR-T cells) that specifically bind to BCMA (e.g., human BCMA). The invention also provides polynucleotides encoding these CARs, compositions comprising these CAR-T cells, and methods of making and using these CARs and CAR-T cells. The invention also provides methods for treating a condition associated with malignant BCMA expression in a subject, such as cancer.

General Techniques

The practice of the invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The term "extracellular ligand-binding domain" as used herein refers to an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

The term "stalk domain" or "hinge domain" are used interchangeably herein to refer to any oligo- or polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on a T cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1 BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1 BBL, OX40L, inducible costimulatory ligand (ICOS-L), intercellular adhesion molecule (ICAM, CD30L, CD40, CD70, CD83, HLA-G, MICA, M1CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., BCMA). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antibody conjugate, or a polypeptide that "preferentially binds" or "specifically binds" (used interchangeably herein) to a target (e.g., BCMA protein) is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a BCMA epitope is an antibody that binds this epitope with greater affinity, avidity, more readily, and/or with greater duration than it binds to other BCMA epitopes or non-BCMA epitopes. It is also understood that by reading this definition, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')$_2$ or other antigen binding subsequences of antibodies) that contain minimal sequence derived from non-human immunoglobulin. Preferably, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569, 825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

A "monovalent antibody" comprises one antigen binding site per molecule (e.g., IgG or Fab). In some instances, a monovalent antibody can have more than one antigen binding sites, but the binding sites are from different antigens.

A "bivalent antibody" comprises two antigen binding sites per molecule (e.g., IgG). In some instances, the two binding sites have the same antigen specificities. However, bivalent antibodies may be bispecific.

A "bispecific," "dual-specific" or "bifunctional" antibody is a hybrid antibody having two different antigen binding sites. The two antigen binding sites of a bispecific antibody bind to two different epitopes, which may reside on the same or different protein targets.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art a "constant region" of an antibody refers to the constant region of the antibody light chain or the constant region of the antibody heavy chain, either alone or in combination.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "immune cell" refers to a cell of hematopoietic origin functionally involved in the initiation and/or execution of innate and/or adaptative immune response.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "autologous" means that cells, a cell line, or population of cells used for treating patients are originating from said patient or from a Human Leucocyte Antigen (HLA) compatible donor.

As used herein "allogeneic" means that cells or population of cells used for treating patients are not originating from said patient but from a donor.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of BCMA expressing tumor, remission of a BCMA associated disease (e.g., cancer), decreasing symptoms resulting from a BCMA associated disease (e.g., cancer), increasing the quality of life of those suffering from a BCMA associated disease (e.g., cancer), decreasing the dose of other medications required to treat a BCMA associated disease (e.g., cancer), delaying the progression of a BCMA associated disease (e.g., cancer), curing a BCMA associated disease (e.g., cancer), and/or prolong survival of patients having a BCMA associated disease (e.g., cancer).

"Ameliorating" means a lessening or improvement of one or more symptoms as compared to not administering a BCMA antibody or a BCMA antibody conjugate. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various BCMA associated diseases or conditions (such as for example multiple myeloma), decreasing the dose of other medications required to treat the disease, enhancing the effect of another medication, and/or delaying the progression of the BCMA associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, horses, dogs, cats, mice and rats.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

The term "$k_{on}$", as used herein, refers to the rate constant for association of an antibody to an antigen.

The term "$k_{off}$", as used herein, refers to the rate constant for dissociation of an antibody from the antibody/antigen complex.

The term "$K_D$", as used herein, refers to the equilibrium dissociation constant of an antibody-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the invention encompasses not only the entire group listed as a whole, but each member of the group individually and all possible subgroups of the main group, but also the main group absent one or more of the group members. The invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the invention. The materials, methods, and examples are illustrative only and not intended to be limiting.

BCMA Specific CARs and Methods of Making Thereof

The invention provides CARs that bind to BCMA (e.g., human BCMA (e.g., SEQ ID NO: 354 or accession number: Q02223-2). BCMA specific CARs provided herein include single chain CARS and multichain CARs. The CARs have the ability to redirect T cell specificity and reactivity toward BCMA in a non-MHC-restricted manner, exploiting the antigen-binding properties of monoclonal antibodies. The non-MHC-restricted antigen recognition gives T cells expressing CARs the ability to recognize an antigen independent of antigen processing, thus bypassing a major mechanism of tumor escape.

In some embodiments, CARs provided herein comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

In some embodiments, a BCMA specific multichain CAR is based on the high affinity receptor for IgE (FcεRI). The FcεRI expressed on mast cells and basophiles triggers allergic reactions. FcεRI is a tetrameric complex composed of a single α subunit, a single β subunit, and two disulfide-linked γ subunits. The a subunit contains the IgE-binding domain. The β and γ subunits contain ITAMs that mediate signal transduction. In some embodiments, the extracellular domain of the FcRα chain is deleted and replaced by a BCMA specific extracellular ligand-binding domain. In some embodiments, the multichain BCMA specific CAR comprises an scFv that binds specifically to BCMA, the CD8α hinge, and the ITAM of the FcRβ chain. In some embodiments, the CAR may or may not comprise the FcRγ chain.

In some embodiments, the extracellular ligand-binding domain comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence $(GGGGS)_3$ (SEQ ID NO: 333), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

In some embodiments, the extracellular ligand-binding domain comprises (a) a VH region comprising (i) a VH complementarity determining region one (CDR1) comprising the sequence $SYX_1MX_2$, wherein $X_1$ is A or P; and $X_2$ is T, N, or S (SEQ ID NO: 301), $GFTFX_1SY$, wherein $X_1$ is G or S (SEQ ID NO: 302), or $GFTFX_1SYX_2MX_3$, wherein $X_1$ is G or S, $X_2$ is A or P; and $X_3$ is T, N, or S (SEQ ID NO: 303); (ii) a VH CDR2 comprising the sequence $AX_1X_2X_3X_4GX_5X_6X_7X_8YADX_9X_{19}KG$, wherein $X_1$ is I, V, T, H, L, A, or C; $X_2$ is S, D, G, T, I, L, F, M, or V; $X_3$ is G, Y, L, H, D, A, S, or M; $X_4$ is S, Q, T, A, F, or W; $X_5$ is G or T; $X_6$ is N, S, P, Y, W, or F; $X_7$ is S, T, I, L, T, A, R, V, K, G, or C; X$_8$ is F, Y, P, W, H, or G; X$_9$ is V, R, or L; and X$_{10}$ is G or T (SEQ ID NO: 305), or X$_1$X$_2$X$_3$X$_4$X$_5$X$_6$, wherein X$_1$ is S, V, I, D, G, T, L, F, or M; X$_2$ is G, Y, L, H, D, A, S, or M; X$_3$ is S, G, F, or W; X$_4$ is G or S; X$_5$ is G or T; and X$_6$ is N, S, P, Y, or W (SEQ ID NO: 306); and iii) a VH CDR3 comprising the sequence VSPIX$_1$X$_2$X$_3$X$_4$, wherein X$_1$ is A or Y; X$_2$ is A or S; and X$_3$ is G, Q, L, P, or E (SEQ ID NO: 307), or YWPMX$_1$X$_2$, wherein X$_1$ is D, S, T, or A; and X$_2$ is I, S, L, P, or D (SEQ ID NO: 308); and a VL region comprising (i) a VL CDR1 comprising the sequence X$_1$X$_2$X$_3$X$_4$X$_5$X$_6$X$_7$X$_8$X$_9$X$_{10}$X$_{11}$X$_{12}$, wherein X$_1$ is R, G, W, A, or C; X$_2$ is A, P, G, L, C, or S; X$_3$ is S, G, or R; X$_4$ is Q, C, E, V, or I; X$_5$ is S, L, P, G, A, R, or D; X$_6$ is V, G, or I; X$_7$ is S, E, D, or P; X$_8$ is S, P, F, A, M, E, V, N, D, or Y; X$_9$ is I, T, V, E, S, A, M, Q, Y, H, or R; X$_{10}$ is Y or F; X$_{11}$ is L, W, or P; and X$_{12}$ is A, S, or G (SEQ ID NO: 309); (ii) a VL CDR2 comprising the sequence X$_1$ASX$_2$RAX$_3$, wherein X$_1$ is G or D; X$_2$ is S or I; and X$_3$ is T or P (SEQ ID NO: 310); and (iii) a VL CDR3 comprising the sequence QQYX$_1$X$_2$X$_3$PX$_4$T, wherein X$_1$ is G, Q, E, L, F, A, S, M, K, R, or Y; X$_2$ is S, R, T, G, V, F, Y, D, A, H, V, E, K, or C; X$_3$ is W, F, or S; and X$_4$ is L or I (SEQ ID NO: 311), or QQYX$_1$X$_2$X$_3$PX$_4$, wherein X$_1$ is G, Q, E, L, F, A, S, M, R, K, or Y; X$_2$ is S, R, T, G, R, V, D, A, H, E, K, C, F, or Y; X$_3$ is W, S, or F; and X$_4$ is L or I (SEQ ID NO: 312). In some embodiments, the VH and VL are linked together by a flexible linker. In some embodiments a flexible linker comprises the amino acid sequence shown in SEQ ID NO: 333.

In another aspect, provided is CAR, which specifically binds to BCMA, wherein the CAR comprises an extracellular ligand-binding domain comprising: a VH region comprising a VH CDR1, VH CDR2, and VH CDR3 of the VH sequence shown in SEQ ID NO: 2, 3, 7, 8, 24, 25, 26, 27, 28, 29, 30, 31, 32, 33, 35, 37, 39, 42, 44, 46, 48, 50, 52, 54, 56, 58, 60, 62, 64, 66, 68, 70, 72, 74, 76, 78, 83, 87, 92, 78, 95, 97, 99, 101, 104, 106, 110, 112, 114, 76, 118, 120, 122, 112, 125, 127, 313, or 314; and/or a VL region comprising VL CDR1, VL CDR2, and VL CDR3 of the VL sequence shown in SEQ ID NO: 1, 4, 5, 6, 9, 10, 11, 12, 13, 15, 16, 17, 18, 19, 20, 21, 22, 23, 34, 36, 38, 40, 41, 43, 45, 47, 49, 51, 53, 57, 59, 61, 63, 65, 67, 69, 71, 73, 75, 77, 79, 317, 81, 82, 84, 85, 86, 88, 89, 90, 91, 93, 94, 96, 98, 100, 102, 103, 105, 107, 108, 109, 111, 113, 115, 116, 117, 119, 121, 123, 124, 126, 128, 315, or 316. In some embodiments, the VH and VL are linked together by a flexible linker. In some embodiments a flexible linker comprises the amino acid sequence shown in SEQ ID NO: 333.

In some embodiments, a CAR of the invention comprises an extracellular ligand-binding domain having any one of partial light chain sequence as listed in Table 1 and/or any one of partial heavy chain sequence as listed in Table 1. In Table 1, the underlined sequences are CDR sequences according to Kabat and in bold according to Chothia, except for the following heavy chain CDR2 sequences, in which the Chothia CDR sequences are underlined and the Kabat CDR sequences are in bold: P5A2_VHVL, A02_Rd4_0.6 nM_C06, A02_Rd4_0.6 nM_C09 A02_Rd4_6 nM_C16, A02_Rd4_6 nM_C03, A02_Rd4_6 nM_C01, A02_Rd4_6 nM_C26 A02_Rd4_6 nM_C25, A02_Rd4_6 nM_C22, A02_Rd4_6 nM_C19, A02_Rd4_0.6 nM_C03 A02_Rd4_6 nM_C07, A02_Rd4_6 nM_C23, A02_Rd4_0.6 nM_C18, A02_Rd4_6 nM_C10, A02_Rd4_6 nM_C05, A02_Rd4_0.6 nM_C10, A02_Rd4_6 nM_C04, A02_Rd4_0.6 nM_C26, A02_Rd4_0.6 nM_C13, A02_Rd4_0.6 nM_C01, A02_Rd4_6 nM_C08, P5C1_VHVL, C01_Rd4_6 nM_C24, C01_Rd4_6 nM_C26, C01_Rd4_6 nM_C10, C01_Rd4_0.6 nM_C27 C01_Rd4_6 nM_C20, C01_Rd4_6 nM_C12, C01_Rd4_0.6 nM_C16, C01_Rd4_0.6 nM_C09, C01_Rd4_6 nM_C09, C01_Rd4_0.6 nM_C03, C01_Rd4_0.6 nM_C06, C01_Rd4_6 nM_C04, COMBO_Rd4_0.6 nM_C22, COMBO_Rd4_6 nM_C21, COMBO_Rd4_6 nM_C10, COMBO_Rd4_0.6 nM_C04, COMBO_Rd4_6 nM_C25, COMBO_Rd4_0.6 nM_C21, COMBO_Rd4_6 nM_C11, COMBO_Rd4_0.6 nM_C20, COMBO_Rd4_6 nM_C09, COMBO_Rd4_6 nM_C08, COMBO_Rd4_0.6 nM_C19, COMBO_Rd4_0.6 nM_C02, COMBO_Rd4_0.6 nM_C23, COMBO_Rd4_0.6 nM_C29, COMBO_Rd4_0.6 nM_C09, COMBO_Rd4_6 nM_C12, COMBO_Rd4_0.6 nM_C30, COMBO_Rd4_6 nM_C14, COMBO_Rd4_6 nM_C07, COMBO_Rd4_6 nM_C02, COMBO_Rd4_0.6 nM_C05, COMBO_Rd4_0.6 nM_C17, COMBO_Rd4_6 nM_C22, and COMBO_Rd4_0.6 nM_C11.

TABLE 1

| mAb | Light Chain | Heavy Chain |
| --- | --- | --- |
| P6E01/<br>P6E01 | EIVLTQSPGTLSLSPGERATLSCRASQSVSSSYLAWY<br>QQKPGQAPRLLIYGASSRATGIPDRFSGSGSGTDFTL<br>TISRLEPEDFAVYYCQHYGSPPSFTFGQGTKVEIK<br>(SEQ ID NO: 1) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIASGMDYWGQGTLVTVSS<br>(SEQ ID NO: 2) |
| P6E01/<br>H3.AQ | EIVLTQSPGTLSLSPGERATLSCRASQSVSSSYLAWY<br>QQKPGQAPRLLIYGASSRATGIPDRFSGSGSGTDFTL<br>TISRLEPEDFAVYYCQHYGSPPSFTFGQGTKVEIK<br>(SEQ ID NO: 1) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.LGF/<br>L3.KW/<br>P6E01 | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 4) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIASGMDYWGQGTLVTVSS<br>(SEQ ID NO: 2) |
| L1.LGF/<br>L3.NY/<br>P6E01 | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 5) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIASGMDYWGQGTLVTVSS<br>(SEQ ID NO: 2) |
| L1.GDF/<br>L3.NY/<br>P6E01 | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 6) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIASGMDYWGQGTLVTVSS<br>(SEQ ID NO: 2) |

TABLE 1-continued

| mAb | Light Chain | Heavy Chain |
|---|---|---|
| L1.LGF/<br>L3.KW/<br>H3.AL | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 4) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARARVSPIAALMDYWGQGTLVTVS<br>S (SEQ ID NO: 7) |
| L1.LGF/<br>L3.KW/<br>H3.AP | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 4) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAPMDYWGQGTLVTVSS<br>(SEQ ID NO: 8) |
| L1.LGF/<br>L3.KW/<br>H3.AQ | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 4) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.LGF/<br>L3.PY/<br>H3.AP | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYPYPPSFTFGQGTKVEIK<br>(SEQ ID NO: 9) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAPMDYWGQGTLVTVSS<br>(SEQ ID NO: 8) |
| L1.LGF/<br>L3.PY/<br>H3.AQ | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYPYPPSFTFGQGTKVEIK<br>(SEQ ID NO: 9) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.LGF/<br>L3.NY/<br>H3.AL | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 10) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARARVSPIAALMDYWGQGTLVTVS<br>S (SEQ ID NO: 7) |
| L1.LGF/<br>L3.NY/<br>H3.AP | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 10) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAPMDYWGQGTLVTVSS<br>(SEQ ID NO: 8) |
| L1.LGF/<br>L3.NY/<br>H3.AQ | EIVLTQSPGTLSLSPGERATLSCRASQSLGSFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 10) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.GDF/<br>L3.KW/<br>H3.AL | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 11) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARARVSPIAALMDYWGQGTLVTVS<br>S (SEQ ID NO: 7) |
| L1.GDF/<br>L3.KW/<br>H3.AP | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 11) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAPMDYWGQGTLVTVSS<br>(SEQ ID NO: 8) |
| L1.GDF/<br>L3.KW/<br>H3.AQ | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCKHYGWPPSFTFGQGTKVEIK<br>(SEQ ID NO: 11) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.GDF/<br>L3.PY/<br>H3.AQ | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCQHYPYPPSFTFGQGTKVEIK<br>(SEQ ID NO: 12) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |
| L1.GDF/<br>L3.NY/<br>H3.AL | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 13) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARARVSPIAALMDYWGQGTLVTVS<br>S (SEQ ID NO: 7) |
| L1.GDF/<br>L3.NY/<br>H3.AP | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 13) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAPMDYWGQGTLVTVSS<br>(SEQ ID NO: 8) |
| L1.GDF/<br>L3.NY/<br>H3.AQ | EIVLTQSPGTLSLSPGERATLSCRASQSVGDFYLAWY<br>QQKPGQAPRLLIYGASSRATGIPDRFSGSGSGTDFTL<br>TISRLEPEDFAVYYCQHYNYPPSFTFGQGTKVEIK<br>(SEQ ID NO: 14) | EVQLLESGGGLVQPGGSLRLSCAASGFTFGSYAMTWVRQA<br>PGKGLEWVSAISGSGGNTFYADSVKGRFTISRDNSKNTLY<br>LQMNSLRAEDTAVYYCARVSPIAAQMDYWGQGTLVTVSS<br>(SEQ ID NO: 3) |

TABLE 1-continued

| mAb | Light Chain | Heavy Chain |
|---|---|---|
| L3.KW/ P6E01 | EIVLTQSPGTLSLSPGERATLSCRASQSVSSSYLAWYQQKPGQAPRLLIYGASSRATGIPDRFSGSGSGTDFTLTISRLEPEDFAVYYCKHYGWPPSFTFGQGTKVEIK (SEQ ID NO: 15) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ P6E01 | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.NY/ P6E01 | EIVLTQSPGTLSLSPGERATLSCRASQSVSSSYLAWYQQKPGQAPRLLIYGASSRATGIPDRFSGSGSGTDFTLTISRLEPEDFAVYYCQHYNYPPSFTFGQGTKVEIK (SEQ ID NO: 17) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L1.PS/ P6E01 | EIVLTQSPGTLSLSPGERATLSCRASQSVSSSYPSWYQQKPGQAPRLLIYGASSRATGIPDRFSGSGSGTDFTLTISRLEPEDFAVYYCQHYPYPPSFTFGQGTKVEIK (SEQ ID NO: 18) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L1.AH/ P6E01 | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L1.FF/ P6E01 | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L1.PH/ P6E01 | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L3.KY/ P6E01 | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ L3.KF/ P6E01 | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIASGMDYWGQGTLVTVSS (SEQ ID NO: 2) |
| L3.PY/ H2.QR | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISGSGGNTFYADQRKGRFTISRDNSKNTLYLQMNSLRAEDTAVYYCARVSPIASGMDYWGQGTLVTVSS (SEQ ID NO: 24) |
| L3.PY/ H2.DY | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAID YSGGNTFYADSVKGRFTISRDNSKNTLYLQMNSLRAEDTAVYYCARVSPIASGMDYWGQGTLVTVSS (SEQ ID NO: 25) |
| L3.PY/ H2.YQ | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISYQGGNTFYADSVKGRFTISRDNSKNTLYLQMNSLRAEDTAVYYCARVSPIASGMDYWGQGTLVTVSS (SEQ ID NO: 26) |
| L3.PY/ H2.LT | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISLTGGNTFYADSVKGRFTISRDNSKNTLYLQMNSLRAEDTAVYYCARVSPIASGMDYWGQGTLVTVSS (SEQ ID NO: 27) |
| L3.PY/ H2.HA | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISHAGGNTFYADSVKGRFTISRDNSKNTLYLQMNSLRAEDTAVYYCARVSPIASGMDYWGQGTLVTVSS (SEQ ID NO: 28) |
| L3.PY/ H2.QL | EIVLTQSPGTLSLSPGERATLSCRASQSVSSSYLAWYQQKPGQAPRLLIYGASSRATGIPDRFSGSGSGTDFTLTISRLEPEDFAVYYCQHYPYPPSFTFGQGTKVEIK (SEQ ID NO: 16) | EVQLLESGGGLVQPGGSLRLSCAASGFTFGSYAMTWVRQAPGKGLEWVSAISGSGGNTFYADQLKGRFTISRDNSKNTLYLQMNSLRAEDTAVYYCARVSPIASGMDYWGQGTLVTVSS (SEQ ID NO: 29) |

TABLE 1-continued

| mAb | Light Chain | Heavy Chain |
|---|---|---|
| L3.PY/ H3.YA | EIVLTQSPGTLSLSPGERATLSCRASQSVSSSYLAWY QQKPGQAPRLLIYGASSRATGIPDRFSGSGSGTDFTL TISRLEPEDFAVYYCQHYPYPPSFTFGQGTKVEIK (SEQ ID NO: 16) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIYAGMDYWGQGTLVTVSS (SEQ ID NO: 30) |
| L3.PY/ H3.AE | EIVLTQSPGTLSLSPGERATLSCRASQSVSSSYLAWY QQKPGQAPRLLIYGASSRATGIPDRFSGSGSGTDFTL TISRLEPEDFAVYYCQHYPYPPSFTFGQGTKVEIK (SEQ ID NO: 16) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIAAEMDYWGQGTLVTVSS (SEQ ID NO: 31) |
| L3.PY/ H3.AQ | EIVLTQSPGTLSLSPGERATLSCRASQSVSSSYLAWY QQKPGQAPRLLIYGASSRATGIPDRFSGSGSGTDFTL TISRLEPEDFAVYYCQHYPYPPSFTFGQGTKVEIK (SEQ ID NO: 16) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIAAQMDYWGQGTLVTVSS (SEQ ID NO: 3) |
| L3.PY/ H3.TAQ | EIVLTQSPGTLSLSPGERATLSCRASQSVSSSYLAWY QQKPGQAPRLLIYGASSRATGIPDRFSGSGSGTDFTL TISRLEPEDFAVYYCQHYPYPPSFTFGQGTKVEIK (SEQ ID NO: 16) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCTRVSPIAAQMDYWGQGTLVTVSS (SEQ ID NO: 32) |
| L3.PY/ P6E01 | EIVLTQSPGTLSLSPGERATLSCRASQSVSSSYLAWY QQKPGQAPRLLIYGASSRATGIPDRFSGSGSGTDFTL TISRLEPEDFAVYYCQHYPYPPSFTFGQGTKVEIK (SEQ ID NO: 16) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIASGMDYWGQGTLVTVSS (SEQ ID NO: 2) |
| L3.PY/ L1.PS/ H2.QR | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISGSGGNTFYADQRKGRFTISRDNSKNTLY LQMNSLRAEDTAVYYCARVSPIASGMDYWGQGTLVTVSS (SEQ ID NO: 24) |
| L3.PY/ L1.PS/ H2.DY | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAID YSGGNTFYADSVKGRFTISRDNSKNTLY LQMNSLRAEDTAVYYCARVSPIASGMDYWGQGTLVTVSS (SEQ ID NO: 25) |
| L3.PY/ L1.PS/ H2.YQ | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISYQGGNTFYADSVKGRFTISRDNSKNTLY LQMNSLRAEDTAVYYCARVSPIASGMDYWGQGTLVTVSS (SEQ ID NO: 26) |
| L3.PY/ L1.PS/ H2.LT | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISLTGGNTFYADSVKGRFTISRDNSKNTLY LQMNSLRAEDTAVYYCARVSPIASGMDYWGQGTLVTVSS (SEQ ID NO: 27) |
| L3.PY/ L1.PS/ H2.HA | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISHAGGNTFYADSVKGRFTISRDNSKNTLY LQMNSLRAEDTAVYYCARVSPIASGMDYWGQGTLVTVSS (SEQ ID NO: 28) |
| L3.PY/ L1.PS/ H2.QL | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISGSGGNTFYADQLKGRFTISRDNSKNTLY LQMNSLRAEDTAVYYCARVSPIASGMDYWGQGTLVTVSS (SEQ ID NO: 29) |
| L3.PY/ L1.PS/ H3.YA | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIYAGMDYWGQGTLVTVSS (SEQ ID NO: 30) |
| L3.PY/ L1.PS/ H3.AE | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIAAEMDYWGQGTLVTVSS (SEQ ID NO: 31) |
| L3.PY/ L1.PS/ H3.AQ | EIVLTQSPGTLSLSPGERATLSCRASQSVSSSYPSWY QQKPGQAPRLLIYGASSRATGIPDRFSGSGSGTDFTL TISRLEPEDFAVYYCQHYPYPPSFTFGQGTKVEIK (SEQ ID NO: 18) | EVQLLESGGGLVQPGGSLRLSCAASGFTFGSYAMTWVRQA PGKGLEWVSAISGSGGNTFYADSVKGRFTISRDNSKNTLY LQMNSLRAEDTAVYYCARVSPIAAQMDYWGQGTLVTVSS (SEQ ID NO: 3) |

TABLE 1-continued

| mAb | Light Chain | Heavy Chain |
| --- | --- | --- |
| L3.PY/ L1.PS/ H3.TAQ | EIVLTQSPGTLSLSPGERATLSCRASQSVSSSYPSWYQQKPGQAPRLLIYGASSRATGIPDRFSGSGSGTDFTLTISRLEPEDFAVYYCQHYPYPPSFTFGQGTKVEIK (SEQ ID NO: 18) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| L3.PY/ L1.AH/ H2.QR | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADQRKGRFTISRDNSKNTLYLQMNSLRAEDTAVYYCARVSPIASGMDYWGQGTLVTVSS (SEQ ID NO: 24) |
| L3.PY/ L1.AH/ H2.DY | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAID YSGGNTFYADSVKGRFTISRDNSKNTLYLQMNSLRAEDTAVYYCARVSPIASGMDYWGQGTLVTVSS (SEQ ID NO: 25) |
| L3.PY/ L1.AH/ H2.YQ | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISYQGGNTFYADSVKGRFTISRDNSKNTLYLQMNSLRAEDTAVYYCARVSPIASGMDYWGQGTLVTVSS (SEQ ID NO: 26) |
| L3.PY/ L1.AH/ H2.LT | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISLTGGNTFYADSVKGRFTISRDNSKNTLYLQMNSLRAEDTAVYYCARVSPIASGMDYWGQGTLVTVSS (SEQ ID NO: 27) |
| L3.PY/ L1.AH/ H2.HA | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISHAGGNTFYADSVKGRFTISRDNSKNTLYLQMNSLRAEDTAVYYCARVSPIASGMDYWGQGTLVTVSS (SEQ ID NO: 28) |
| L3.PY/ L1.AH/ H2.QL | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADQLKGRFTISRDNSKNTLYLQMNSLRAEDTAVYYCARVSPIASGMDYWGQGTLVTVSS (SEQ ID NO: 29) |
| L3.PY/ L1.AH/ H3.YA | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIYAGMDYWGQGTLVTVSS (SEQ ID NO: 30) |
| L3.PY/ L1.AH/ H3.AE | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAEMDYWGQGTLVTVSS (SEQ ID NO: 31) |
| L3.PY/ L1.AH/ H3.AQ | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAQMDYWGQGTLVTVSS (SEQ ID NO: 3) |
| L3.PY/ L1.AH/ H3.TAQ | EIVLTQSPGTLSLSPGERATLSCRASQSVSAHYLAWYQQKPGQAPRLLIYGASSRATGIPDRFSGSGSGTDFTLTISRLEPEDFAVYYCQHYPYPPSFTFGQGTKVEIK (SEQ ID NO: 19) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| L3.PY/ L1.FF/ H2.QR | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADQRKGRFTISRDNSKNTLYLQMNSLRAEDTAVYYCARVSPIASGMDYWGQGTLVTVSS (SEQ ID NO: 24) |
| L3.PY/ L1.FF/ H2.DY | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAIDYSGGNTFYADSVKGRFTISRDNSKNTLYLQMNSLRAEDTAVYYCARVSPIASGMDYWGQGTLVTVSS (SEQ ID NO: 25) |
| L3.PY/ L1.FF/ H2.YQ | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISYQGGNTFYADSVKGRFTISRDNSKNTLYLQMNSLRAEDTAVYYCARVSPIASGMDYWGQGTLVTVSS (SEQ ID NO: 26) |
| L3.PY/ L1.FF/ H2.LT | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISLTGGNTFYADSVKGRFTISRDNSKNTLYLQMNSLRAEDTAVYYCARVSPIASGMDYWGQGTLVTVSS (SEQ ID NO: 27) |

TABLE 1-continued

| mAb | Light Chain | Heavy Chain |
|---|---|---|
| L3.PY/ L1.FF/ H2.HA | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISHAGGNTFYADSVKGRFTISRDNSKNTLYLQMNSLRAEDTAVYYCARVSPIASGMDYWGQGTLVTVSS (SEQ ID NO: 28) |
| L3.PY/ L1.FF/ H2.QL | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADQLKGRFTISRDNSKNTLYLQMNSLRAEDTAVYYCARVSPIASGMDYWGQGTLVTVSS (SEQ ID NO: 29) |
| L3.PY/ L1.FF/ H3.YA | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIYAGMDYWGQGTLVTVSS (SEQ ID NO: 30) |
| L3.PY/ L1.FF/ H3.AE | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAEMDYWGQGTLVTVSS (SEQ ID NO: 31) |
| L3.PY/ L1.FF/ H3.AQ | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAQMDYWGQGTLVTVSS (SEQ ID NO: 3) |
| L3.PY/ L1.FF/ H3.TAQ | EIVLTQSPGTLSLSPGERATLSCRASQSVSSFFLAWYQQKPGQAPRLLIYGASSRATGIPDRFSGSGSGTDFTLTISRLEPEDFAVYYCQHYPYPPSFTFGQGTKVEIK (SEQ ID NO: 20) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| L3.PY/ L1.PH/ H2.QR | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISGSGGNTFYADQRKGRFTISRDNSKNTLYLQMNSLRAEDTAVYYCARVSPIASGMDYWGQGTLVTVSS (SEQ ID NO: 24) |
| L3.PY/ L1.PH/ H2.HA | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISHAGGNTFYADSVKGRFTISRDNSKNTLYLQMNSLRAEDTAVYYCARVSPIASGMDYWGQGTLVTVSS (SEQ ID NO: 28) |
| L3.PY/ L1.PH/ H3.AE | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAEMDYWGQGTLVTVSS (SEQ ID NO: 31) |
| L3.PY/ L1.PH/ H3.AQ | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAQMDYWGQGTLVTVSS (SEQ ID NO: 3) |
| L3.PY/ L1.PH/ H3.TAQ | EIVLTQSPGTLSLSPGERATLSCRASQSVSPHYLAWYQQKPGQAPRLLIYGASSRATGIPDRFSGSGSGTDFTLTISRLEPEDFAVYYCQHYPYPPSFTFGQGTKVEIK (SEQ ID NO: 21) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| L3.PY/ L3.KY/ H2.QR | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISGSGGNTFYADQRKGRFTISRDNSKNTLYLQMNSLRAEDTAVYYCARVSPIASGMDYWGQGTLVTVSS (SEQ ID NO: 24) |
| L3.PY/ L3.KY/ H2.DY | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAID YSGGNTFYADSVKGRFTISRDNSKNTLYLQMNSLRAEDTAVYYCARVSPIASGMDYWGQGTLVTVSS (SEQ ID NO: 25) |
| L3.PY/ L3.KY/ H2.YQ | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISYQGGNTFYADSVKGRFTISRDNSKNTLYLQMNSLRAEDTAVYYCARVSPIASGMDYWGQGTLVTVSS (SEQ ID NO: 26) |
| L3.PY/ L3.KY/ H2.LT | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISLTGGNTFYADSVKGRFTISRDNSKNTLYLQMNSLRAEDTAVYYCARVSPIASGMDYWGQGTLVTVSS (SEQ ID NO: 27) |

TABLE 1-continued

| mAb | Light Chain | Heavy Chain |
| --- | --- | --- |
| L3.PY/ L3.KY/ H2.HA | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISHAGGNTFYADSVKGRFTISRDNSKNTLYLQMNSLRAEDTAVYYCARVSPIASGMDYWGQGTLVTVSS (SEQ ID NO: 28) |
| L3.PY/ L3.KY/ H2.QL | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISGSGGNTFYADQLKGRFTISRDNSKNTLYLQMNSLRAEDTAVYYCARVSPIASGMDYWGQGTLVTVSS (SEQ ID NO: 29) |
| L3.PY/ L3.KY/ H3.YA | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIYAGMDYWGQGTLVTVSS (SEQ ID NO: 30) |
| L3.PY/ L3.KY/ H3.TAQ | EIVLTQSPGTLSLSPGERATLSCRASQSVSSSYLAWYQQKPGQAPRLLIYGASSRATGIPDRFSGSGSGTDFTLTISRLEPEDFAVYYCKYYPYPPSFTFGQGTKVEIK (SEQ ID NO: 22) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| L3.PY/ L3.KF/ H2.DY | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAID YSGGNTFYADSVKGRFTISRDNSKNTLYLQMNSLRAEDTAVYYCARVSPIASGMDYWGQGTLVTVSS (SEQ ID NO: 25) |
| L3.PY/ L3.KF/ H2.YQ | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISYQGGNTFYADSVKGRFTISRDNSKNTLYLQMNSLRAEDTAVYYCARVSPIASGMDYWGQGTLVTVSS (SEQ ID NO: 26) |
| L3.PY/ L3.KF/ H2.LT | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISLTGGNTFYADSVKGRFTISRDNSKNTLYLQMNSLRAEDTAVYYCARVSPIASGMDYWGQGTLVTVSS (SEQ ID NO: 27) |
| L3.PY/ L3.KF/ H2.QL | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADQLKGRFTISRDNSKNTLYLQMNSLRAEDTAVYYCARVSPIASGMDYWGQGTLVTVSS (SEQ ID NO: 29) |
| L3.PY/ L3.KF/ H3.YA | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIYAGMDYWGQGTLVTVSS (SEQ ID NO: 30) |
| L3.PY/ L3.KF/ H3.AE | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAEMDYWGQGTLVTVSS (SEQ ID NO: 31) |
| L3.PY/ L3.KF/ H3.AQ | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAQMDYWGQGTLVTVSS (SEQ ID NO: 3) |
| L3.PY/ L3.KF/ H3.TAQ | EIVLTQSPGTLSLSPGERATLSCRASQSVSSSYLAWYQQKPGQAPRLLIYGASSRATGIPDRFSGSGSGTDFTLTISRLEPEDFAVYYCKFYPYPPSFTFGQGTKVEIK (SEQ ID NO: 23) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCTRVSPIAAQMDYWGQGTLVTVSS (SEQ ID NO: 32) |
| P5A2_VHVL | EIVLTQSPGTLSLSPGERATLSCRASQSVSSSYLAWYQQKPGQAPRLLMYDASIRATGIPDRFSGSGSGTDFTLTISRLEPEDFAVYYCQQYGSWPLTFGQGTKVEIK (SEQ ID NO: 34) | EVQLLESGGGLVQPGGSLRLSCAASGFTFSSYAMNWVRQAPGKGLEWVSAISDSGGSTYYADSVKGRFTISRDNSKNTLYLQMNSLRAEDTAVYYCARYWPMDIWGQGTLVTVSS (SEQ ID NO: 33) |
| A02_Rd4_ 0.6nM_C06 | EIVLTQSPGTLSLSPGERATLSCRASQSVSVIYLAWYQQKPGQAPRLLMYDASIRATGIPDRFSGSGSGTDFTLTISRLEPEDFAVYYCQQYQRWPLTFGQGTKVEIK (SEQ ID NO: 36) | EVQLLESGGGLVQPGGSLRLSCAASGFTFSSYAMNWVRQAPGKGLEWVSAISDSGGSAWYADSVKGRFTISRDNSKNTLYLQMNSLRAEDTAVYYCARYWPMSLWGQGTLVTVSS (SEQ ID NO: 35) |
| A02_Rd4_ 0.6nM_C09 | EIVLTQSPGTLSLSPGERATLSCRASQSVSSSYLAWYQQKPGQAPRLLMYDASIRATGIPDRFSGSGSGTDFTLTISRLEPEDFAVYYCQQYQSWPLTFGQGTKVEIK (SEQ ID NO: 38) | EVQLLESGGGLVQPGGSLRLSCAASGFTFSSYAMNWVRQAPGKGLEWVSAISDSGGSMWYADSVKGRFTISRDNSKNTLYLQMNSLRAEDTAVYYCARYWPMSLWGQGTLVTVSS (SEQ ID NO: 37) |

TABLE 1-continued

| mAb | Light Chain | Heavy Chain |
|---|---|---|
| A02_Rd4_6nM_C16 (P5AC16) | EIVLTQSPGTLSLSPGERATLSCRASQSVSDIYLAWYQQKPGQAPRLLMYDASIRATGIPDRFSGSGSGTDFTLTISRLEPEDFAVYYCQQYQTWPLTFGQGTKVEIK (SEQ ID NO: 40) | EVQLLESGGGLVQPGGSLRLSCAASGFTFSSYAMNWVRQAPGKGLEWVSAISdFGGSTYYADSVKGRFTISRDNSKNTLYLQMNSLRAEDTAVYYCARYWPMDIWGQGTLVTSS (SEQ ID NO: 39) |
| A02_Rd4_6nM_C03 | EIVLTQSPGTLSLSPGERATLSCRASQSVSNLYLAWYQQKPGQAPRLLMYDASIRATGIPDRFSGSGSGTDFTLTISRLEPEDFAVYYCQQYQGWPLTFGQGTKVEIK (SEQ ID NO: 41) | EVQLLESGGGLVQPGGSLRLSCAASGFTFSSYAMNWVRQAPGKGLEWVSAISDSGGSTYYADSVKGRFTISRDNSKNTLYLQMNSLRAEDTAVYYCARYWPMDIWGQGTLVTSS (SEQ ID NO: 33) |
| A02_Rd4_6nM_C01 | EIVLTQSPGTLSLSPGERATLSCRASQSVSAYYLAWYQQKPGQAPRLLMYDASIRATGIPDRFSGSGSGTDFTLTISRLEPEDFAVYYCQQYERWPLTFGQGTKVEIK (SEQ ID NO: 43) | EVQLLESGGGLVQPGGSLRLSCAASGFTFSSYAMNWVRQAPGKGLEWVSAITASGGSTYYADSVKGRFTISRDNSKNTLYLQMNSLRAEDTAVYYCARYWPMSLWGQGTLVTSS (SEQ ID NO: 42) |
| A02_Rd4_6nM_C26 | EIVLTQSPGTLSLSPGERATLSCRASQSVSSLYLAWYQQKPGQAPRLLMYDASIRATGIPDRFSGSGSGTDFTLTISRLEPEDFAVYYCQQYQVWPLTFGQGTKVEIK (SEQ ID NO: 45) | EVQLLESGGGLVQPGGSLRLSCAASGFTFSSYAMNWVRQAPGKGLEWVSAISDSGGSTYYADSVKGRFTISRDNSKNTLYLQMNSLRAEDTAVYYCARYWPMSLWGQGTLVTSS (SEQ ID NO: 44) |
| A02_Rd4_6nM_C25 | EIVLTQSPGTLSLSPGERATLSCRASQSVSSSYLAWYQQKPGQAPRLLMYDASIRATGIPDRFSGSGSGTDFTLTISRLEPEDFAVYYCQQYLDWPLTFGQGTKVEIK (SEQ ID NO: 47) | EVQLLESGGGLVQPGGSLRLSCAASGFTFSSYAMNWVRQAPGKGLEWVSAISdSGGSRWYADSVKGRFTISRDNSKNTLYLQMNSLRAEDTAVYYCARYWPMTPWGQGTLVTSS (SEQ ID NO: 46) |
| A02_Rd4_6nM_C22 | EIVLTQSPGTLSLSPGERATLSCRASQSVSSSYLAWYQQKPGQAPRLLMYDASIRATGIPDRFSGSGSGTDFTLTISRLEPEDFAVYYCQQYQVWPLTFGQGTKVEIK (SEQ ID NO: 49) | EVQLLESGGGLVQPGGSLRLSCAASGFTFSSYAMNWVRQAPGKGLEWVSAVLdSGGSTYYADSVKGRFTISRDNSKNTLYLQMNSLRAEDTAVYYCARYWPMTPWGQGTLVTSS (SEQ ID NO: 48) |
| A02_Rd4_6nM_C19 | EIVLTQSPGTLSLSPGERATLSCRASQSVSVIYLAWYQQKPGQAPRLLMYDASIRATGIPDRFSGSGSGTDFTLTISRLEPEDFAVYYCQQYLAWPLTFGQGTKVEIK (SEQ ID NO: 51) | EVQLLESGGGLVQPGGSLRLSCAASGFTFSSYAMNWVRQAPGKGLEWVSAISdSGGSRWYADSVKGRFTISRDNSKNTLYLQMNSLRAEDTAVYYCARYWPMSDWGQGTLVTSS (SEQ ID NO: 50) |
| A02_Rd4_0.6nM_C03 | EIVLTQSPGTLSLSPGERATLSCRASQSVSSSYLAWYQQKPGQAPRLLMYDASIRATGIPDRFSGSGSGTDFTLTISRLEPEDFAVYYCQQYFTWPLTFGQGTKVEIK (SEQ ID NO: 53) | EVQLLESGGGLVQPGGSLRLSCAASGFTFSSYAMNWVRQAPGKGLEWVSAISdSGGSKWYADSVKGRFTISRDNSKNTLYLQMNSLRAEDTAVYYCARYWPMSLWGQGTLVTSS (SEQ ID NO: 52) |
| A02_Rd4_6nM_C07 | EIVLTQSPGTLSLSPGERATLSCRASQSVSPyYLAWYQQKPGQAPRLLMYDASIRATGIPDRFSGSGSGTDFTLTISRLEPEDFAVYYCQQYERWPLTFGQGTKVEIK (SEQ ID NO: 55) | EVQLLESGGGLVQPGGSLRLSCAASGFTFSSYAMNWVRQAPGKGLEWVSAIGGSGGSLPYADSVKGRFTISRDNSKNTLYLQMNSLRAEDTAVYYCARYWPMSDWGQGTLVTSS (SEQ ID NO: 54) |
| A02_Rd4_6nM_C23 | EIVLTQSPGTLSLSPGERATLSCRASQSVSVEYLAWYQQKPGQAPRLLMYDASIRATGIPDRFSGSGSGTDFTLTISRLEPEDFAVYYCQQYARWPLTFGQGTKVEIK (SEQ ID NO: 57) | EVQLLESGGGLVQPGGSLRLSCAASGFTFSSYAMNWVRQAPGKGLEWVSAISdSGGSGWYADSVKGRFTISRDNSKNTLYLQMNSLRAEDTAVYYCARYWPMSLWGQGTLVTSS (SEQ ID NO: 56) |
| A02_Rd4_0.6nM_C18 | EIVLTQSPGTLSLSPGERATLSCRASQSVSEIYLAWYQQKPGQAPRLLMYDASIRATGIPDRFSGSGSGTDFTLTISRLEPEDFAVYYCQQYFGWPLTFGQGTKVEIK (SEQ ID NO: 59) | EVQLLESGGGLVQPGGSLRLSCAASGFTFSSYAMNWVRQAPGKGLEWVSAVLdSGGSTYYADSVKGRFTISRDNSKNTLYLQMNSLRAEDTAVYYCARYWPMSLWGQGTLVTSS (SEQ ID NO: 58) |
| A02_Rd4_6nM_C10 | EIVLTQSPGTLSLSPGERATLSCRASQSVEMSYLAWYQQKPGQAPRLLMYDASIRATGIPDRFSGSGSGTDFTLTISRLEPEDFAVYYCQQYAHWPLTFGQGTKVEIK (SEQ ID NO: 61) | EVQLLESGGGLVQPGGSLRLSCAASGFTFSSYAMNWVRQAPGKGLEWVSAISdSGGSGWYADSVKGRFTISRDNSKNTLYLQMNSLRAEDTAVYYCARYWPMTPWGQGTLVTSS (SEQ ID NO: 60) |
| A02_Rd4_6nM_C05 | EIVLTQSPGTLSLSPGERATLSCRASQSVSSSYLAWYQQKPGQAPRLLMYDASIRATGIPDRFSGSGSGTDFTLTISRLEPEDFAVYYCQQYQRWPLTFGQGTKVEIK (SEQ ID NO: 63) | EVQLLESGGGLVQPGGSLRLSCAASGFTFSSYAMNWVRQAPGKGLEWVSAIFaSGGSTYYADSVKGRFTISRDNSKNTLYLQMNSLRAEDTAVYYCARYWPMTPWGQGTLVTSS (SEQ ID NO: 62) |
| A02_Rd4_0.6nM_C10 | EIVLTQSPGTLSLSPGERATLSCRASQSVSAQYLAWYQQKPGQAPRLLMYDASIRATGIPDRFSGSGSGTDFTLTISRLEPEDFAVYYCQQYQRWPLTFGQGTKVEIK (SEQ ID NO: 65) | EVQLLESGGGLVQPGGSLRLSCAASGFTFSSYAMNWVRQAPGKGLEWVSAISgWGGSLPYADSVKGRFTISRDNSKNTLYLQMNSLRAEDTAVYYCARYWPMDSWGQGTLVTSS (SEQ ID NO: 64) |
| A02_Rd4_6nM_C04 | EIVLTQSPGTLSLSPGERATLSCRASQSVSAIYLAWYQQKPGQAPRLLMYDASIRATGIPDRFSGSGSGTDFTLTISRLEPEDFAVYYCQQYQVWPLTFGQGTKVEIK (SEQ ID NO: 67) | EVQLLESGGGLVQPGGSLRLSCAASGFTFSSYAMNWVRQAPGKGLEWVSAIMsSGGPLYADSVKGRFTISRDNSKNTLYLQMNSLRAEDTAVYYCARYWPMALWGQGTLVTSS (SEQ ID NO: 66) |

TABLE 1-continued

| mAb | Light Chain | Heavy Chain |
|---|---|---|
| A02_Rd4_ 0.6nM_C26 | EIVLTQSPGTLSLSPGERATLSCGPSQSVSSSYLAWYQQKPGQAPRLLMYDASIRATGIPDRFSGSGSGTDFTLTISRLEPEDFAVYYCQQYQSWPLTFGQGTKVEIK (SEQ ID NO: 69) | EVQLLESGGGLVQPGGSLRLSCAASGFTFSSYAMNWVRQAPGKGLEWVSAILmSGGSTYYADSVKGRFTISRDNSKNTLYLQMNSLRAEDTAVYYCARYWPMSLWGQGTLVTVSS (SEQ ID NO: 68) |
| A02_Rd4_ 0.6nM_C13 | EIVLTQSPGTLSLSPGERATLSCRASQSVSSSYWAWYQQKPGQAPRLLMYDASIRATGIPDRFSGSGSGTDFTLTISRLEPEDFAVYYCQQYESWPLTFGQGTKVEIK (SEQ ID NO: 71) | EVQLLESGGGLVQPGGSLRLSCAASGFTFSSYAMNWVRQAPGKGLEWVSAISdSGGYRYYADSVKGRFTISRDNSKNTLYLQMNSLRAEDTAVYYCARYWPMSLWGQGTLVTVSS (SEQ ID NO: 70) |
| A02_Rd4_ 0.6nM_C01 (P5AC1) | EIVLTQSPGTLSLSPGERATLSCRGGQSVSSSYLAWYQQKPGQAPRLLMYDASIRATGIPDRFSGSGSGTDFTLTISRLEPEDFAVYYCQQYQSWPLTFGQGTKVEIK (SEQ ID NO: 73) | EVQLLESGGGLVQPGGSLRLSCAASGFTFSSYAMNWVRQAPGKGLEWVSAILsSGGSTYYADSVKGRFTISRDNSKNTLYLQMNSLRAEDTAVYYCARYWPMDIWGQGTLVTVSS (SEQ ID NO: 72) |
| A02_Rd4_ 6nM_C08 | EIVLTQSPGTLSLSPGERATLSCRASQSVSFIYLAWYQQKPGQAPRLLMYDASIRATGIPDRFSGSGSGTDFTLTISRLEPEDFAVYYCQQYGSWPLTFGQGTKVEIK (SEQ ID NO: 75) | EVQLLESGGGLVQPGGSLRLSCAASGFTFSSYAMNWVRQAPGKGLEWVSAILdSGGSTYYADSVKGRFTISRDNSKNTLYLQMNSLRAEDTAVYYCARYWPMSPWGQGTLVTVSS (SEQ ID NO: 74) |
| P5C1_VHVL (PC1) | EIVLTQSPGTLSLSPGERATLSCRASQSVSSTYLAWYQQKPGQAPRLLIYDASSRAPGIPDRFSGSGSGTDFTLTISRLEPEDFAVYYCQQYSTSPLTFGQGTKVEIK (SEQ ID NO: 77) | EVQLLESGGGLVQPGGSLRLSCAASGFTFSSYPMSWVRQAPGKGLEWVSAIGGSGGSTYYADSVKGRFTISRDNSKNTLYLQMNSLRAEDTAVYYCARYWPMDSWGQGTLVTVSS (SEQ ID NO: 76) |
| C01_Rd4_ 6nM_C24 | EIVLTQSPGTLSLSPGERATLSCRASQSVSPEYLAWYQQKPGQAPRLLIYDASSRAPGIPDRFSGSGSGTDFTLTISRLEPEDFAVYYCQQYSVWPLTFGQGTKVEIK (SEQ ID NO: 79) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 6nM_C26 | EIVLTQSPGTLSLSPGERATLSCRASQSVSAIYLAWYQQKPGQAPRLLIYDASSRAPGIPDRFSGSGSGTDFTLTISRLEPEDFAVYYCQQYSAWPLTFGQGTKVEIK (SEQ ID NO: 317) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 6nM_C10 | EIVLTQSPGTLSLSPGERATLSCRASQSVSSvYLAWYQQKPGQAPRLLIYDASSRAPGIPDRFSGSGSGTDFTLTISRLEPEDFAVYYCQQYSTWPLTFGQGTKVEIK (SEQ ID NO: 79) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 0.6nM_C27 | EIVLTQSPGTLSLSPGERATLSCRASQSVSSTYLAWYQQKPGQAPRLLIYDASSRAPGIPDRFSGSGSGTDFTLTISRLEPEDFAVYYCQQYSRWPLTFGQGTKVEIK (SEQ ID NO: 81) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 6nM_C20 | EIVLTQSPGTLSLSPGERATLSCRASQSVSPIYLAWYQQKPGQAPRLLIYDASSRAPGIPDRFSGSGSGTDFTLTISRLEPEDFAVYYCQQYSAFPLTFGQGTKVEIK (SEQ ID NO: 82) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 6nM_C12 (PC1C12) | EIVLTQSPGTLSLSPGERATLSCWLSQSVSSTYLAWYQQKPGQAPRLLIYDASSRAPGIPDRFSGSGSGTDFTLTISRLEPEDFAVYYCQQYSEWPLTFGQGTKVEIK (SEQ ID NO: 84) | EVQLLESGGGLVQPGGSLRLSCAASGFTFSSYPMSWVRQAPGKGLEWVSAIGgSGGWSYYADSVKGRFTISRDNSKNTLYLQMNSLRAEDTAVYYCARYWPMDSWGQGTLVTVSS (SEQ ID NO: 83) |
| C01_Rd4_ 0.6nM_C16 | EIVLTQSPGTLSLSPGERATLSCRASQSVSSTYLAWYQQKPGQAPRLLIYDASSRAPGIPDRFSGSGSGTDFTLTISRLEPEDFAVYYCQQYSSWPLTFGQGTKVEIK (SEQ ID NO: 85) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 0.6nM_C09 | EIVLTQSPGTLSLSPGERATLSCRASQSVSSIFLAWYQQKPGQAPRLLIYDASSRAPGIPDRFSGSGSGTDFTLTISRLEPEDFAVYYCQQYSAWPLTFGQGTKVEIK (SEQ ID NO: 86) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDSWGQGTLVTVSS (SEQ ID NO: 78) |
| C01_Rd4_ 6nM_C09 | EIVLTQSPGTLSLSPGERATLSCACSQSVSSTYLAWYQQKPGQAPRLLIYDASSRAPGIPDRFSGSGSGTDFTLTISRLEPEDFAVYYCQQYSAWPLTFGQGTKVEIK (SEQ ID NO: 88) | EVQLLESGGGLVQPGGSLRLSCAASGFTFSSYPMSWVRQAPGKGLEWVSATVgSGGSIGYADSVKGRFTISRDNSKNTLYLQMNSLRAEDTAVYYCARYWPMDSWGQGTLVTVSS (SEQ ID NO: 87) |
| C01_Rd4_ 0.6nM_C03 | EIVLTQSPGTLSLSPGERATLSCRASCDVSSTYLAWYQQKPGQAPRLLIYDASSRAPGIPDRFSGSGSGTDFTLTISRLEPEDFAVYYCQQYMRSPLTFGQGTKVEIK (SEQ ID NO: 89) | EVQLLESGGGLVQPGGSLRLSCAASGFTFSSYPMSWVRQAPGKGLEWVSAIGgSGGSLPYADSVKGRFTISRDNSKNTLYLQMNSLRAEDTAVYYCARYWPMDSWGQGTLVTVSS (SEQ ID NO: 78) |

TABLE 1-continued

| mAb | Light Chain | Heavy Chain |
|---|---|---|
| C01_Rd4_ 0.6nM_C06 | EIVLTQSPGTLSLSPGERATLSCRASEAVPSTYLAWY QQKPGQAPRLLIYDASSRAPGIPDRFSGSGSGTDFTL TISRLEPEDFAVYYCQQYSAFPLTFGQGTKVEIK (SEQ ID NO: 90) | EVQLLESGGGLVQPGGSLRLSCAASGFTFSSYPMSWVRQA PGKGLEWVSAIGgSGGGSLPYADSVKGTISRDNSKNTLYLQM NSLRAEDTAVYYCARYWPMDSWGQGTLVTSS (SEQ ID NO: 78) |
| C01_Rd4_ 6nM_C04 | EIVLTQSPGTLSLSPGERATLSCCSSQSVSSTYLAWY QQKPGQAPRLLIYDASSRAPGIPDRFSGSGSGTDFTL TISRLEPEDFAVYYCQQYSAFPLTFGQGTKVEIK (SEQ ID NO: 91) | EVQLLESGGGLVQPGGSLRLSCAASGFTFSSYPMSWVRQA PGKGLEWVSAIGgSGGGSLPYADSVKGRFTISRDNSKNTLY LQMNSLRAEDTAVYYCARYWPMDSWGQGTLVTSS (SEQ ID NO: 78) |
| COMBO_ Rd4_0.6nM_ C22 (COM22) | EIVLTQSPGTLSLSPGERATLSCRASVRVSSTYLAWY QQKPGQAPRLLMYDASIRATGIPDRFSGSGSGTDFTL TISRLEPEDFAVYYCQQYMKWPLTFGQGTKVEIK (SEQ ID NO: 93) | EVQLLESGGGLVQPGGSLRLSCAASGFTFSSYAMNWVRQA PGKGLEWVSAISdSGGGSRWYADSVKGRFTISRDNSKNTLY LQMNSLRAEDTAVYYCTRYWPMDIWGQGTLVTSS (SEQ ID NO: 92) |
| COMBO_ Rd4_ 6nM_C21 | EIVLTQSPGTLSLSPGERATLSCRASQSVSAAYLAWY QQKPGQAPRLLMYDASIRATGIPDRFSGSGSGTDFTL TISRLEPEDFAVYYCQQYMCWPLTFGQGTKVEIK (SEQ ID NO: 94) | EVQLLESGGGLVQPGGSLRLSCAASGFTFSSYPMSWVRQA PGKGLEWVSAIGgSGGGSLPYADSVKGRFTISRDNSKNTLY LQMNSLRAEDTAVYYCARYWPMDSWGQGTLVTSS (SEQ ID NO: 78) |
| COMBO_ Rd4_ 6nM_C10 | EIVLTQSPGTLSLSPGERATLSCRASQSVSSSYWGWY QQKPGQAPRLLMYDASIRATGIPDRFSGSGSGTDFTL TISRLEPEDFAVYYCQQYQCWPLTFGQGTKVEIK (SEQ ID NO: 96) | EVQLLESGGGLVQPGGSLRLSCAASGFTFSSYPMSWVRQA PGKGLEWVSAIGgSGGGSIHYADSVKGRFTISRDNSKNTLY LQMNSLRAEDTAVYYCARYWPMDSWGQGTLVTSS (SEQ ID NO: 95) |
| COMBO_ Rd4_ 0.6nM_C04 | EIVLTQSPGTLSLSPGERATLSCRASQSVSSTYLAWY QQKPGQAPRLLMYDASIRATGIPDRFSGSGSGTDFTL TISRLEPEDFAVYYCQQYQSWPLTFGQGTKVEIK (SEQ ID NO: 98) | EVQLLESGGGLVQPGGSLRLSCAASGFTFSSYPMSWVRQA PGKGLEWVSAHIgSGGSTYYADSVKGRFTISRDNSKNTLY LQMNSLRAEDTAVYYCARYWPMDSWGQGTLVTSS (SEQ ID NO: 97) |
| COMBO_ Rd4_ 6nM_C25 | EIVLTQSPGTLSLSPGERATLSCRASQSVSSpYLAWY QQKPGQAPRLLMYDASIRATGIPDRFSGSGSGTDFTL TISRLEPEDFAVYYCQQYQSWPLTFGQGTKVEIK (SEQ ID NO: 100) | EVQLLESGGGLVQPGGSLRLSCAASGFTFSSYPMSWVRQA PGKGLEWVSAIGgSGGGSTYYADSVKGRFTISRDNSKNTLY LQMNSLRAEDTAVYYCARYWPMDPWGQGTLVTSS (SEQ ID NO: 99) |
| COMBO_ Rd4_ 0.6nM_C21 | EIVLTQSPGTLSLSPGERATLSCRASQSVSSSYLAWY QQKPGQAPRLLMYDASIRATGIPDRFSGSGSGTDFTL TISRLEPEDFAVYYCQQYQSWPLTFGQGTKVEIK (SEQ ID NO: 38) | EVQLLESGGGLVQPGGSLRLSCAASGFTFSSYPMSWVRQA PGKGLEWVSAIGgSGGGSLPYADSVKGRFTISRDNSKNTLY LQMNSLRAEDTAVYYCARYWPMDSWGQGTLVTSS (SEQ ID NO: 78) |
| COMBO_ Rd4_ 6nM_C11 | EIVLTQSPGTLSLSPGERATLSCRASQSVSPIYLAWY QQKPGQAPRLLMYDASIRATGIPDRFSGSGSGTDFTL TISRLEPEDFAVYYCQQYKAWPLTFGQGTKVEIK (SEQ ID NO: 102) | EVQLLESGGGLVQPGGSLRLSCAASGFTFSSYPMSWVRQA PGKGLEWVSAIGGSGGSLGYADSVKGRFTISRDNSKNTLY LQMNSLRAEDTAVYYCARYWPMDSWGQGTLVTSS (SEQ ID NO: 101) |
| COMBO_ Rd4_ 0.6nM_C20 | EIVLTQSPGTLSLSPGERATLSCRASQSVSYLYLAWY QQKPGQAPRLLMYDASIRATGIPDRFSGSGSGTDFTL TISRLEPEDFAVYYCQQYMEWPLTFGQGTKVEIK (SEQ ID NO: 103) | EVQLLESGGGLVQPGGSLRLSCAASGFTFSSYPMSWVRQA PGKGLEWVSAIGGSGGSLPYADSVKGRFTISRDNSKNTLY LQMNSLRAEDTAVYYCARYWPMDSWGQGTLVTSS (SEQ ID NO: 78) |
| COMBO_ Rd4_ 6nM_C09 | EIVLTQSPGTLSLSPGERATLSCRASQSVSAQYLAWY QQKPGQAPRLLMYDASIRATGIPDRFSGSGSGTDFTL TISRLEPEDFAVYYCQQYQAWPLTFGQGTKVEIK (SEQ ID NO: 105) | EVQLLESGGGLVQPGGSLRLSCAASGFTFSSYPMSWVRQA PGKGLEWVSAIFASGGSTYYADSVKGRFTISRDNSKNTLY LQMNSLRAEDTAVYYCARYWPMDSWGQGTLVTSS (SEQ ID NO: 104) |
| COMBO_ Rd4_ 6nM_C08 | EIVLTQSPGTLSLSPGERATLSCRASQSVSSSYLAWY QQKPGQAPRLLMYDASIRATGIPDRFSGSGSGTDFTL TISRLEPEDFAVYYCQQYQKWPLTFGQGTKVEIK (SEQ ID NO: 107) | EVQLLESGGGLVQPGGSLRLSCAASGFTFSSYPMSWVRQA PGKGLEWVSAIGGSGTWTYYADSVKGRFTISRDNSKNTLY LQMNSLRAEDTAVYYCARYWPMDSWGQGTLVTSS (SEQ ID NO: 106) |
| COMBO_ Rd4_ 0.6nM_C19 | EIVLTQSPGTLSLSPGERATLSCRASQSVSAVYLAWY QQKPGQAPRLLMYDASIRATGIPDRFSGSGSGTDFTL TISRLEPEDFAVYYCQQYRAWPLTFGQGTKVEIK (SEQ ID NO: 108) | EVQLLESGGGLVQPGGSLRLSCAASGFTFSSYPMSWVRQA PGKGLEWVSAIGGSGGSLPYADSVKGRFTISRDNSKNTLY LQMNSLRAEDTAVYYCARYWPMDSWGQGTLVTSS (SEQ ID NO: 78) |
| COMBO_ Rd4_ 0.6nM_C02 | EIVLTQSPGTLSLSPGERATLSCRASIAVSSTYLAWY QQKPGQAPRLLMYDASIRATGIPDRFSGSGSGTDFTL TISRLEPEDFAVYYCQQYMVWPLTFGQGTKVEIK (SEQ ID NO: 109) | EVQLLESGGGLVQPGGSLRLSCAASGFTFSSYPMSWVRQA PGKGLEWVSAIGGSGGSLPYADSVKGRFTISRDNSKNTLY LQMNSLRAEDTAVYYCARYWPMDSWGQGTLVTSS (SEQ ID NO: 78) |
| COMBO_ Rd4_ 0.6nM_C23 | EIVLTQSPGTLSLSPGERATLSCRPRQSVSSSYLAWY QQKPGQAPRLLMYDASIRATGIPDRFSGSGSGTDFTL TISRLEPEDFAVYYCQQYQDWPLTFGQGTKVEIK (SEQ ID NO: 111) | EVQLLESGGGLVQPGGSLRLSCAASGFTFSSYPMSWVRQA PGKGLEWVSALFGSGGSTYYADSVKGRFTISRDNSKNTLY LQMNSLRAEDTAVYYCARYWPMDSWGQGTLVTSS (SEQ ID NO: 110) |

TABLE 1-continued

| mAb | Light Chain | Heavy Chain |
|---|---|---|
| COMBO_Rd4_0.6nM_C29 | EIVLTQSPGTLSLSPGERATLSCRASQSVSSSYLAWYQQKPGQAPRLLMYDASIRATGIPDRFSGSGSGTDFTLTISRLEPEDFAVYYCQQYQSWPLTFGQGTKVEIK (SEQ ID NO: 38) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDIWGQGTLVTVSS (SEQ ID NO: 112) |
| COMBO_Rd4_0.6nM_C09 | EIVLTQSPGTLSLSPGERATLSCRASQSVSSTYLAWYQQKPGQAPRLLMYDASIRATGIPDRFSGSGSGTDFTLTISRLEPEDFAVYYCQQYQEWPLTFGQGTKVEIK (SEQ ID NO: 113) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDIWGQGTLVTVSS (SEQ ID NO: 112) |
| COMBO_Rd4_6nM_C12 | EIVLTQSPGTLSLSPGERATLSCRASQSVSASYLAWYQQKPGQAPRLLMYDASIRATGIPDRFSGSGSGTDFTLTISRLEPEDFAVYYCQQYMSWPLTFGQGTKVEIK (SEQ ID NO: 115) | EVQLLESGGGLVQPGGSLRLSCAASGFTFSSYPMSWVRQAPGKGLEWVSAALGSGGSTYYADSVKGRFTISRDNSKNTLYLQMNSLRAEDTAVYYCARYWPMDSWGQGTLVTVSS (SEQ ID NO: 114) |
| COMBO_Rd4_0.6nM_C30 | EIVLTQSPGTLSLSPGERATLSCRASQSVSYMYLAWYQQKPGQAPRLLIYDASIRATGIPDRFSGSGSGTDFTLTISRLEPEDFAVYYCQQYKSWPLTFGQGTKVEIK (SEQ ID NO: 116) | EVQLLESGGGLVQPGGSLRLSCAASGFTFSSYPMSWVRQAPGKGLEWVSAIGGSGGSTYYADSVKGRFTISRDNSKNTLYLQMNSLRAEDTAVYYCARYWPMDSWGQGTLVTVSS (SEQ ID NO: 76) |
| COMBO_Rd4_0.6nM_C14 | EIVLTQSPGTLSLSPGERATLSCRASQSVSALYLAWYQQKPGQAPRLLMYDASIRATGIPDRFSGSGSGTDFTLTISRLEPEDFAVYYCQQYYGWPLTFGQGTKVEIK (SEQ ID NO: 117) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDIWGQGTLVTVSS (SEQ ID NO: 112) |
| COMBO_Rd4_6nM_C07 | EIVLTQSPGTLSLSPGERATLSCRASQPISSSYLAWYQQKPGQAPRLLMYDASIRATGIPDRFSGSGSGTDFTLTISRLEPEDFAVYYCQQYQGWPLTFGQGTKVEIK (SEQ ID NO: 119) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMADWGQGTLVTVSS (SEQ ID NO: 118) |
| COMBO_Rd4_6nM_C02 | EIVLTQSPGTLSLSPGERATLSCRASQSVSSSYLAWYQQKPGQAPRLLMYDASIRATGIPDRFSGSGSGTDFTLTISRLEPEDFAVYYCQQYEFWPLTFGQGTKVEIK (SEQ ID NO: 121) | EVQLLESGGGLVQPGGSLRLSCAASGFTFSSYAMNWVRQAPGKGLEWVSAISDSGGFVYYADSVKGRFTISRDNSKNTLYLQMNSLRAEDTAVYYCARYWPMDSWGQGTLVTVSS (SEQ ID NO: 120) |
| COMBO_Rd4_0.6nM_C05 | EIVLTQSPGTLSLSPGERATLSCRASQSVSSTYLAWYQQKPGQAPRLLMYDASIRATGIPDRFSGSGSGTDFTLTISRLEPEDFAVYYCQQYMSWPLTFGQGTKVEIK (SEQ ID NO: 123) | EVQLLESGGGLVQPGGSLRLSCAASGFTFSSYAMNWVRQAPGKGLEWVSAIGGSGGSTYYADSVKGRFTISRDNSKNTLYLQMNSLRAEDTAVYYCARYWPMSLWGQGTLVTVSS (SEQ ID NO: 122) |
| COMBO_Rd4_0.6nM_C17 | EIVLTQSPGTLSLSPGERATLSCRASQGISSTYLAWYQQKPGQAPRLLMYDASIRATGIPDRFSGSGSGTDFTLTISRLEPEDFAVYYCQQYAYWPLTFGQGTKVEIK (SEQ ID NO: 124) | EVQLLESGGGLVQPGGSLRLSCAASGFTFSSYPMSWVRQAPGKGLEWVSAIGGSGGSLPYADSVKGRFTISRDNSKNTLYLQMNSLRAEDTAVYYCARYWPMDIWGQGTLVTVSS (SEQ ID NO: 112) |
| COMBO_Rd4_6nM_C22 | EIVLTQSPGTLSLSPGERATLSCRASQSVSSSYLAWYQQKPGQAPRLLMYDASIRATGIPDRFSGSGSGTDFTLTISRLEPEDFAVYYCQQYQGWPLTFGQGTKVEIK (SEQ ID NO: 126) | EVQLLESGGGLVQPGGSLRLSCAASGFTFSSYAMNWVRQAPGKGLEWVSACLDSGGSTYYADSVKGRFTISRDNSKNTLYLQMNSLRAEDTAVYYCARYWPMDSWGQGTLVTVSS (SEQ ID NO: 125) |
| COMBO_Rd4_0.6nM_C11 | EIVLTQSPGTLSLSPGERATLSCRASQSVSVRYLAWYQQKPGQAPRLLMYDASIRATGIPDRFSGSGSGTDFTLTISRLEPEDFAVYYCQQYGSWPITFGQGTKVEIK (SEQ ID NO: 128) | EVQLLESGGGLVQPGGSLRLSCAASGFTFSSYPMSWVRQAPGKGLEWVSAALGSGGSTYYADSVKGRFTISRDNSKNTLYLQMNSLRAEDTAVYYCARYWPMSLWGQGTLVTVSS (SEQ ID NO: 127) |
| P6DY | EIVLTQSPGTLSLSPGERATLSCRASQSVSSSYPSWYQQKPGQAPRLLIYGASSRATGIPDRFSGSGSGTDFTLTISRLEPEDFAVYYCQHYPYPPSFTFGQGTKVEIK (SEQ ID NO: 18) | EVQLLESGGGLVQPGGSLRLSCAASGFTFGSYAMTWVRQAPGKGLEWVSAIDYSGGNTFYADSVKGRFTISRDNSKNTLYLQMNSLRAEDTAVYYCARVSPIASGMDYWGQGTLVTVSS (SEQ ID NO: 25) |
| P6AP | EIVLTQSPGTLSLSPGERATLSCRASQLGSFYLAWYQQKPGQAPRLLIYGASSRATGIPDRFSGSGSGTDFTLTISRLEPEDFAVYYCQHYNYPPSFTFGQGTKVEIK (SEQ ID NO: 80) | EVQLLESGGGLVQPGGSLRLSCAASGFTFGSYAMTWVRQAPGKGLEWVSAISGSGGNTFYADSVKGRFTISRDNSKNTLYLQMNSLRAEDTAVYYCARVSPIAAPMDYWGQGTLVTVSS (SEQ ID NO: 8) |
| Consensus | EIVLTQSPGTLSLSPGERATLSCX$_1$X$_2$X$_3$X$_4$X$_5$X$_6$X$_7$X$_8$X$_9$X$_{10}$X$_{11}$X$_{12}$WYQQKPGQAPRLLMYX$_{13}$ASX$_{14}$RAX$_{15}$GIPDRFSGSGSGTDFTLTISRLEPEDFAVYYCX$_{16}$X$_{17}$YX$_{18}$X$_{19}$PPSFTFGQGTKVEIK, wherein X$_1$ is R, G, W, A, or C; X$_2$ is A, P, G, L, C, or S; X$_3$ is S, G, or R; X$_4$ is Q, C, E, V, or I; X$_5$ is S, P, G, A, R, or D; X$_6$ is V, G, I, or L; X$_7$ is S, E, D, P, or G; X$_8$ is S, P, F, A, M, E, V, N, D, or Y; X$_9$ is I, T, V, E, S, A, M, Q, Y, H, R, or F; X$_{10}$ is Y or F; X$_{11}$ is L, W, or P; X$_{12}$ is A, S, or G, X$_{13}$ is G or | EVQLLESGGGLVQPGGSLRLSCAASGFTFX$_1$SYX$_2$MX$_3$WVRQAPGKGLEWVSAX$_4$X$_5$X$_6$X$_7$GX$_8$X$_9$X$_{10}$X$_{11}$YADX$_{12}$X$_{13}$KGRFTISRDNSKNTLYLQMNSLRAEDTAVYYCARVSPIX$_{14}$X$_{15}$X$_{16}$MDYWGQGTLVTVSS, wherein X$_1$ is G or S, X$_2$ is A or P; X$_3$ is T, N, or S; X$_4$ is I, V, T, H, L, A, or C; X$_5$ is D, G, T, I, L, F, M, or V; X$_6$ is G, Y, S, L, H, D, A, S, or M; X$_7$ is S, Q, T, A, F, or W; X$_8$ is G or T; X$_9$ is N, S, P, Y, W, or F; X$_{10}$ is S, T, I, L, T, A, R, V, K, G, or C; X$_{11}$ is F, Y, P, W, H, or G; X$_{12}$ is V, R, or L; X$_{13}$ is G or T; X$_{14}$ is A or Y; X$_{15}$ is A or S; |

TABLE 1-continued

| mAb | Light Chain | Heavy Chain |
|---|---|---|
| | D; $X_{14}$ is S or I; $X_{15}$ is T or P; $X_{16}$ is Q or K; $X_{17}$ is H or Y; $X_{18}$ is G, N, or P; and $X_{19}$ is S, W, or Y (SEQ ID NO: 315); or EIVLTQSPGTLSLSPGERATLSCX$_1$X$_2$X$_3$X$_4$X$_5$X$_6$X$_7$X$_8$X$_9$X$_{10}$X$_{11}$X$_{12}$WYQQKPGQAPRLLMYX$_{13}$ASX$_{14}$RAX$_{15}$GIPDRFSGSGSGTDFTLTISRLEPEDFAVYYCQQYX$_{16}$X$_{17}$X$_{18}$PX$_{19}$FGQGTKVEIK, wherein $X_1$ is R, G, W, A, or C; $X_2$ is A, P, G, L, C, or S; $X_3$ is G, or R; $X_4$ is Q, C, E, V, or I; $X_5$ is S, L, P, G, A, R, or D; $X_6$ is V, G, or I; $X_7$ is S, E, D, or P; $X_8$ is S, P, F, A, M, E, V, N, D, or Y; $X_9$ is I, T, V, E, S, A, M, Q, Y, H, or R; $X_{10}$ is Y or F; $X_{11}$ is L, W, or P; $X_{12}$ is A, S, or G; $X_{13}$ is G or D; $X_{14}$ is S or I; $X_{15}$ is T or P; $X_{16}$ is G, Q, E, L, F, A, S, M, R, K, or Y; $X_{17}$ is S, R, T, G, R, V, D, A, H, E, K, C, F, or Y; $X_{18}$ is W, S, or F; and $X_{19}$ is L or I (SEQ ID NO: 316) | and $X_{16}$ is G, Q, L, P, or E (SEQ ID NO: 313); or EVQLLESGGGLVQPGGSLRLSCAASGFTFX$_1$SYX$_2$MX$_3$WVRQAPGKGLEWVSAX$_4$X$_5$X$_6$X$_7$GX$_8$X$_9$X$_{10}$X$_{11}$YADX$_{12}$X$_{13}$KGRFTISRDNSKNTLYLQMNSLRAEDTAVYYCARYWPMX$_{14}$X$_{15}$WGQGTLVTVSS, wherein $X_1$ is G or S, $X_2$ is A or P; $X_3$ is T, N, or S; $X_4$ is I, V, T, H, L, A, or C; $X_5$ is S, D, G, T, I, L, F, M, or V; $X_6$ is G, Y, L, H, D, A, S, or M; $X_7$ is S, Q, T, A, F, or W; $X_8$ is G or T; $X_9$ is N, S, P, Y, W, or F; $X_{10}$ is S, T, I, L, T, A, R, V, K, G, or C; $X_{11}$ is F, Y, P, W, H, or G; $X_{12}$ is V, R, or L; $X_{13}$ is G or T; $X_{14}$ is D, S, T, or A; and $X_{15}$ is I, S, L, P, or D (SEQ ID NO: 314) |
| P4G4 | EIVLTQSPGTLSLSPGERATLSCRASQSVSSSYLAWYQQKPGQAPRLLIYGASSRAYGIPDRFSGSGSGTDFTLTISRLEPEDFAVYYCQHYGSPPLFTFGQGTKVEIK (SEQ ID NO: 401) | EVQLLESGGGLVQPGGSLRLSCAASGFTFSSYAMSWVRQAPGKGLEWVSAISASGGSTYYADSVKGRFTISRDNSKNTLYLQMNSLRAEDTAVYYCARLSWSGAFDNWGQGTLVTVSS (SEQ ID NO: 378) |
| P1A11 | EIVLTQSPGTLSLSPGERATLSCRASQNVSSSYLAWYQQKPGQAPRLLIYGASYRATGIPDRFSGSGSGTDFTLTISRLEPEDFAVYYCQHYGSPPSFTFGQGTKVEIK (SEQ ID NO: 379) | EVQLLESGGGLVQPGGSLRLSCAASGFTFRSYAMSWVRQAPGKGLEWVSAISGSGGSTFYADSVKGRFTISRDNSKNTLYLQMNSLRAEDTAVYYCATVGTSGAFGIWGQGTLVTVSS (SEQ ID NO: 380) |

Also provided herein are CDR portions of extracellular ligand-binding domains of CARs to BCMA (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 2 provides examples of CDR sequences provided herein.

TABLE 2

| | Heavy Chain | | |
|---|---|---|---|
| mAb | CDRH1 | CDRH2 | CDRH3 |
| P6E01 For the following mAbs: P6E01/P6E01; L1.LGF/L3.KW/P6E01; L1.LGF/L3.NY/P6E01; L1.GDF/L3.NY/P6E01; L3.KW/P6E01; L3.PY/P6E01; L3.NY/P6E01; L3.PY/L1.PS/P6E01; L3.PY/L1.AH/P6E01; L3.PY/L1.FF/P6E01; L3.PY/L1.PH/P6E01; L3.PY/L3.KY/P6E01; L3.PY/L3.KF/P6E01; and L3.PY/P6E01. | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat) SGSGGN (SEQ ID NO: 133) (Chothia) | VSPIASGMDY (SEQ ID NO: 134) |
| H3.AQ For the following mAbs: P6E01/H3.AQ; L1.LGF/L3.KW/H3.AQ; L1.LGF/L3.PY/H3.AQ | SYAMT (SEQ ID NO: 129) (Kabat); GFTFGSY (SEQ ID NO: 130) (Chothia); GFTFGSYAMT (SEQ ID NO: 131) (extended) | AISGSGGNTFYADSVKG (SEQ ID NO: 132) (Kabat) SGSGGN (SEQ ID NO: 133) (Chothia) | VSPIAAQMDY (SEQ ID NO: 135) |

TABLE 2-continued

| | | | |
|---|---|---|---|
| H3.AL<br>For the following mAbs:<br>L1.LGF/L3.KW/H3.AL;<br>L1.LGF/L3.NY/H3.AL;<br>and<br>L1.GDF/L3.NY/H3.AL. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYA DSVKG (SEQ ID NO: 132) (Kabat)<br>SGSGGN (SEQ ID NO: 133) (Chothia) | VSPIAALMD Y (SEQ ID NO: 136) |
| H3.AP<br>For the following mAbs:<br>L1.LGF/L3.KW/H3.AP;<br>L1.LGF/L3.PY/H3.AP;<br>L1.LGF/L3NY/H3.AP;<br>L1.GDF/L3.KW/H3.AP;<br>L1.GDF/L3NY/H3.AP;<br>P6AP. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYA DSVKG (SEQ ID NO: 132) (Kabat)<br>SGSGGN (SEQ ID NO: 133) (Chothia) | VSPIAAPMD Y (SEQ ID NO: 137) |
| H2.QR<br>For the following mAbs:<br>L3.PY/H2.QR;<br>L3.PY/L1.PS/H2.QR;<br>L3.PY/L1.AH/H2.QR;<br>L3.PY/L1.FF/H2.QR;<br>L3.PY/L1.PH/H2.QR;<br>and<br>L3.PY/L3.KY/H2.QR. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYA DQRKG (SEQ ID NO: 138) (Kabat)<br>SGSGGN (SEQ ID NO: 133) (Chothia) | VSPIASGMD Y (SEQ ID NO: 134) |
| H2.DY<br>For the following mAbs:<br>L3.PY/H2.DY; P6DY;<br>L3.PY/L1.PS/H2.DY;<br>L3.PY/L1.AH/H2.DY;<br>L3.PY/L1.FF/H2.DY;<br>L3.PY/L3.KY/H2.DY;<br>and<br>L3.PY/L3.KF/H2.DY. | SYAMT (SEQ ID NO: 129) (Kabat);<br>GFTFGSY (SEQ ID NO: 130) (Chothia);<br>GFTFGSYAMT (SEQ ID NO: 131) (extended) | AIDYSGGNTFYA DSVKG (SEQ ID NO: 139) (Kabat)<br>DYSSGN (SEQ ID NO: 140) (Chothia) | VSPIASGMD Y (SEQ ID NO: 134) |
| H2.YQ<br>For the following mAbs:<br>L3.PY/H2.YQ;<br>L3.PY/L1.PS/H2.YQ;<br>L3.PY/L1.AH/H2.YQ;<br>L3.PY/L1.FF/H2.YQ;<br>L3.PY/L3.KY/H2.YQ;<br>and<br>L3.PY/L3.KF/H2.YQ. | SYAMT (SEQ ID NO: 129) (Kabat);<br>GFTFGSY (SEQ ID NO: 130) (Chothia);<br>GFTFGSYAMT (SEQ ID NO: 131) (extended) | AISYQGGNTFYA DSVKG (SEQ ID NO: 141) (Kabat)<br>SYQGGN (SEQ ID NO: 142) (Chothia) | VSPIASGMD Y (SEQ ID NO: 134) |
| H2.LT<br>For the following mAbs:<br>L3.PY/H2.LT;<br>L3.PY/L1.PS/H2.LT;<br>L3.PY/L1.AH/H2.LT;<br>L3.PY/L1.FF/H2.LT;<br>L3.PY/L3.KY/H2.LT;<br>and<br>L3.PY/L3.KF/H2.LT. | SYAMT (SEQ ID NO: 129) (Kabat);<br>GFTFGSY (SEQ ID NO: 130) (Chothia);<br>GFTFGSYAMT (SEQ ID NO: 131) (extended) | AISLTGGNTFYA DSVKG (SEQ ID NO: 143) (Kabat)<br>SLTGGN (SEQ ID NO: 144) (Chothia) | VSPIASGMD Y (SEQ ID NO: 134) |
| H2.HA<br>For the following mAbs:<br>L3.PY/H2.HA;<br>L3.PY/L1.AH/H2.HA;<br>L3.PY/L1.FF/H2.HA;<br>L3.PY/L1.PH/H2.HA;<br>and<br>L3.PY/L3.KY/H2.HA. | SYAMT (SEQ ID NO: 129) (Kabat);<br>GFTFGSY (SEQ ID NO: 130) (Chothia);<br>GFTFGSYAMT (SEQ ID NO: 131) (extended) | AISHAGGNTFYA DSVKG (SEQ ID NO: 145) (Kabat)<br>SHAGGN (SEQ ID NO: 146) (Chothia) | VSPIASGMD Y (SEQ ID NO: 134) |
| H2.QL<br>For the following mAbs:<br>L3.PY/H2.QL;<br>L3.PY/L1.PS/H2.QL;<br>L3.PY/L1.AH/H2.QL;<br>L3.PY/L1.FF/H2.QL;<br>L3.PY/L3.KY/H2.QL;<br>and<br>L3.PY/L3.KF/H2.QL. | SYAMT (SEQ ID NO: 129) (Kabat);<br>GFTFGSY (SEQ ID NO: 130) (Chothia);<br>GFTFGSYAMT (SEQ ID NO: 131) (extended) | AISGSGGNTFYA DQLKG (SEQ ID NO: 147) (Kabat)<br>SGSGGN (SEQ ID NO: 133) (Chothia) | VSPIASGMD Y (SEQ ID NO: 134) |
| H3.YA<br>For the following mAbs:<br>L3.PY/H3.YA; | SYAMT (SEQ ID NO: 129) (Kabat);<br>GFTFGSY (SEQ ID | AISGSGGNTFYA DSVKG (SEQ ID NO: 132) (Kabat) | VSPIYAGMD Y (SEQ ID NO: 148) |

TABLE 2-continued

| | | | |
|---|---|---|---|
| L3.PY/L1.PS/H3.YA;<br>L3.PY/L1.AH/H3.YA;<br>L3.PY/L1.FF/H3.YA;<br>L3.PY/L3.KY/H3.YA;<br>and<br>L3.PY/L3.KF/H3.YA. | NO: 130) (Chothia);<br>GFTFGSYAMT (SEQ<br>ID NO: 131)<br>(extended) | SGSGGN (SEQ<br>ID NO: 133)<br>(Chothia) | |
| H3.AE<br>For the following mAbs:<br>L3.PY/H3.AE;<br>L3.PY/L1.AH/H3.AE;<br>L3.PY/L1.FF/H3.AE;<br>L3.PY/L1.PH/H3.AE;<br>and<br>L3.PY/L3.KF/H3.AE. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AISGSGGNTFYA<br>DSVKG (SEQ ID<br>NO: 132) (Kabat)<br>SGSGGN (SEQ<br>ID NO: 133)<br>(Chothia) | VSPIAAEMD<br>Y (SEQ ID<br>NO: 149) |
| H3.TAQ<br>For the following mAbs:<br>L3.PY/H3.TAQ;<br>L3.PY/L1.PS/H3.TAQ;<br>L3.PY/L1.AH/H3.TAQ;<br>L3.PY/L1.FF/H3.TAQ;<br>L3.PY/L1.PH/H3.TAQ;<br>and<br>L3.PY/L3.KF/H3.TAQ. | SYAMT (SEQ ID NO:<br>129) (Kabat);<br>GFTFGSY (SEQ ID<br>NO: 130) (Chothia);<br>GFTFGSYAMT (SEQ<br>ID NO: 131)<br>(extended) | AISGSGGNTFYA<br>DSVKG (SEQ ID<br>NO: 132) (Kabat)<br>SGSGGN (SEQ<br>ID NO: 133)<br>(Chothia) | VSPIAAQMD<br>Y (SEQ ID<br>NO: 135) |
| P5A2_VHVL and<br>A02_Rd4_6nM_C03 | SYAMN (SEQ ID NO:<br>150) (Kabat);<br>GFTFSSY (SEQ ID<br>NO: 151) (Chothia);<br>GFTFSSYAMN (SEQ<br>ID NO: 152)<br>(extended) | AISDSGGSTYYA<br>DSVKG<br>(SEQ ID NO: 153)<br>(Kabat)<br>SDSGGS (SEQ<br>ID NO: 154)<br>(Chothia) | YWPMDI<br>(SEQ ID NO:<br>155) |
| COMBO_Rd4_0.6nM_C17;<br>COMBO_Rd4_0.6nM_C14;<br>COMBO_Rd4_0.6nM_C29;<br>and<br>COMBO_Rd4_0.6nM_C09 | SYPMS (SEQ ID NO:<br>156) (Kabat);<br>GFTFSSY (SEQ ID<br>NO: 151) (Chothia);<br>GFTFSSYPMS (SEQ<br>ID NO: 157)<br>(extended) | AIGGSGGSLPYA<br>DSVKG<br>(SEQ ID NO: 158)<br>(Kabat)<br>GGSGGS (SEQ<br>ID NO: 159)<br>(Chothia) | YWPMDI<br>(SEQ ID NO:<br>155) |
| C01_Rd4_6nM_C04;<br>C01_Rd4_0.6nM_C03;<br>C01_Rd4_0.6nM_C06;<br>COMBO_Rd4_0.6nM_C02;<br>COMBO_Rd4_6nM_C21;<br>C01_Rd4_6nM_C26;<br>COMBO_Rd4_0.6nM_C19;<br>C01_Rd4_6nM_C24;<br>C01_Rd4_6nM_C20;<br>C01_Rd4_0.6nM_C09;<br>COMBO_Rd4_0.6nM_C21;<br>C01_Rd4_0.6nM_C04_C27;<br>C01_Rd4_0.6nM_C16;<br>C01_Rd4_6nM_C10;<br>COMBO_Rd4_0.6nM_C20 | SYPMS (SEQ ID NO:<br>156) (Kabat);<br>GFTFSSY (SEQ ID<br>NO: 151) (Chothia);<br>GFTFSSYPMS (SEQ<br>ID NO: 157)<br>(extended) | AIGGSGGSLPYA<br>DSVKG<br>(SEQ ID NO: 158)<br>(Kabat)<br>GGSGGS (SEQ<br>ID NO: 159)<br>(Chothia) | YWPMDS<br>(SEQ ID NO:<br>161) |
| P5C1_VHVL (PC1) and<br>COMBO_Rd4_0.6nM_C30 | SYPMS (SEQ ID NO:<br>156) (Kabat);<br>GFTFSSY (SEQ ID<br>NO: 151) (Chothia);<br>GFTFSSYPMS (SEQ<br>ID NO: 157)<br>(extended) | AIGGSGGSTYYA<br>DSVKG<br>(SEQ ID NO: 162)<br>(Kabat)<br>GGSGGS (SEQ<br>ID NO: 159)<br>(Chothia) | YWPMDS<br>(SEQ ID NO:<br>161) |
| A02_Rd4_0.6nM_C06 | SYAMN (SEQ ID NO:<br>150) (Kabat);<br>GFTFSSY (SEQ ID<br>NO: 151) (Chothia);<br>GFTFSSYAMN (SEQ<br>ID NO: 152)<br>(extended) | AISDSGGSAWY<br>ADSVKG<br>(SEQ ID NO: 163)<br>(Kabat)<br>SDSGGS (SEQ<br>ID NO: 154)<br>(Chothia) | YWPMSL<br>(SEQ ID NO:<br>164) |

TABLE 2-continued

| | | | |
|---|---|---|---|
| A02_Rd4_0.6nM_C09 | SYAMN (SEQ ID NO: 150) (Kabat); GFTFSSY (SEQ ID NO: 151) (Chothia); GFTFSSYAMN (SEQ ID NO: 152) (extended) | AISDSGGSAWY ADSVKG (SEQ ID NO: 163) (Kabat) SDSGGS (SEQ ID NO: 154) (Chothia) | YWPMSL (SEQ ID NO: 164) |
| A02_Rd4_0.6nM_C16; A02_Rd4_6nM_C16 (P5A16) | SYAMN (SEQ ID NO: 150) (Kabat); GFTFSSY (SEQ ID NO: 151) (Chothia); GFTFSSYAMN (SEQ ID NO: 152) (extended) | AISDFGGSTYYA DSVKG (SEQ ID NO: 165) (Kabat) SDFGGS (SEQ ID NO: 166) (Chothia) | YWPMDI (SEQ ID NO: 155) |
| A02_Rd4_6nM_C01 | SYAMN (SEQ ID NO: 150) (Kabat); GFTFSSY (SEQ ID NO: 151) (Chothia); GFTFSSYAMN (SEQ ID NO: 152) (extended) | AITASGGSTYYA DSVKG (SEQ ID NO: 167) (Kabat) TASGGS (SEQ ID NO: 168) (Chothia) | YWPMSL (SEQ ID NO: 164) |
| A02_Rd4_6nM_C26 | SYAMN (SEQ ID NO: 150) (Kabat); GFTFSSY (SEQ ID NO: 151) (Chothia); GFTFSSYAMN (SEQ ID NO: 152) (extended) | AISDSGGSTYYA DSVKG (SEQ ID NO: 153) (Kabat) SDSGGS (SEQ ID NO: 154) (Chothia) | YWPMSL (SEQ ID NO: 164) |
| A02_Rd4_6nM_C25 | SYAMN (SEQ ID NO: 150) (Kabat); GFTFSSY (SEQ ID NO: 151) (Chothia); GFTFSSYAMN (SEQ ID NO: 152) (extended) | AISDSGGSRWY ADSVKG (SEQ ID NO: 169) (Kabat) SDSGGS (SEQ ID NO: 154) (Chothia) | YWPMTP (SEQ ID NO: 170) |
| A02_Rd4_6nM_C22 | SYAMN (SEQ ID NO: 150) (Kabat); GFTFSSY (SEQ ID NO: 151) (Chothia); GFTFSSYAMN (SEQ ID NO: 152) (extended) | AVLDSGGSTYY ADSVKG (SEQ ID NO: 171) (Kabat) LDSGGS (SEQ ID NO: 172) (Chothia) | YWPMTP (SEQ ID NO: 170) |
| A02_Rd4_6nM_C19 | SYAMN (SEQ ID NO: 150) (Kabat); GFTFSSY (SEQ ID NO: 151) (Chothia); GFTFSSYAMN (SEQ ID NO: 152) (extended) | AISDSGGSRWY ADSVKG (SEQ ID NO: 169) (Kabat) SDSGGS (SEQ ID NO: 154) (Chothia) | YWPMSD (SEQ ID NO: 173) |
| A02_Rd4_0.6nM_C03 | SYAMN (SEQ ID NO: 150) (Kabat); GFTFSSY (SEQ ID NO: 151) (Chothia); GFTFSSYAMN (SEQ ID NO: 152) (extended) | AISDSGGSKWY ADSVKG (SEQ ID NO: 174) (Kabat) SDSGGS (SEQ ID NO: 154) (Chothia) | YWPMSL (SEQ ID NO: 164) |
| A02_Rd4_6nM_C07 | SYAMN (SEQ ID NO: 150) (Kabat); GFTFSSY (SEQ ID NO: 151) (Chothia); GFTFSSYAMN (SEQ ID NO: 152) (extended) | AIGGSGGSLPYA DSVKG (SEQ ID NO: 158) (Kabat) GGSGGS (SEQ ID NO: 159) (Chothia) | YWPMDS (SEQ ID NO: 161) |
| A02_Rd4_6nM_C23 | SYAMN (SEQ ID NO: 150) (Kabat); GFTFSSY (SEQ ID NO: 151) (Chothia); GFTFSSYAMN (SEQ ID NO: 152) (extended) | AISDSGGSGWY ADSVKG (SEQ ID NO: 175) (Kabat) SDSGGS (SEQ ID NO: 154) (Chothia) | YWPMSL (SEQ ID NO: 164) |

TABLE 2-continued

| | | | |
|---|---|---|---|
| A02_Rd4_0.6nM_C18 | SYAMN (SEQ ID NO: 150) (Kabat); GFTFSSY (SEQ ID NO: 151) (Chothia); GFTFSSYAMN (SEQ ID NO: 152) (extended) | AVLDSGGSTYY ADSVKG (SEQ ID NO: 171) (Kabat) LDSGGS (SEQ ID NO: 172) (Chothia) | YWPMSL (SEQ ID NO: 164) |
| A02_Rd4_6nM_C10 | SYAMN (SEQ ID NO: 150) (Kabat); GFTFSSY (SEQ ID NO: 151) (Chothia); GFTFSSYAMN (SEQ ID NO: 152) (extended) | AISDSGGSCWY ADSVKG (SEQ ID NO: 176) (Kabat) SDSGGS (SEQ ID NO: 154) (Chothia) | YWPMTP (SEQ ID NO: 170) |
| A02_Rd4_6nM_C05 | SYAMN (SEQ ID NO: 150) (Kabat); GFTFSSY (SEQ ID NO: 151) (Chothia); GFTFSSYAMN (SEQ ID NO: 152) (extended) | AIFASGGSTYYA DSVKG (SEQ ID NO: 177) (Kabat) FASGGS (SEQ ID NO: 178) (Chothia) | YWPMTP (SEQ ID NO: 170) |
| A02_Rd4_0.6nM_C10 | SYAMN (SEQ ID NO: 150) (Kabat); GFTFSSY (SEQ ID NO: 151) (Chothia); GFTFSSYAMN (SEQ ID NO: 152) (extended) | AISGWGGSLPY ADSVKG (SEQ ID NO: 304) (Kabat) SGWGGS (SEQ ID NO: 179) (Chothia) | YWPMDS (SEQ ID NO: 161) |
| A02_Rd4_6nM_C04 | SYAMN (SEQ ID NO: 150) (Kabat); GFTFSSY (SEQ ID NO: 151) (Chothia); GFTFSSYAMN (SEQ ID NO: 152) (extended) | AIMSSGGPLYYA DSVKG (SEQ ID NO: 180) (Kabat) MSSGGP (SEQ ID NO: 181) (Chothia) | YWPMAL (SEQ ID NO: 182) |
| A02_Rd4_0.6nM_C26 | SYAMN (SEQ ID NO: 150) (Kabat); GFTFSSY (SEQ ID NO: 151) (Chothia); GFTFSSYAMN (SEQ ID NO: 152) (extended) | AILMSGGSTYYA DSVKG (SEQ ID NO: 183) (Kabat) LMSGGS (SEQ ID NO: 184) (Chothia) | YWPMSL (SEQ ID NO: 164) |
| A02_Rd4_0.6nM_C13 | SYAMN (SEQ ID NO: 150) (Kabat); GFTFSSY (SEQ ID NO: 151) (Chothia); GFTFSSYAMN (SEQ ID NO: 152) (extended) | AISDSGGYRYYA DSVKG (SEQ ID NO: 185) (Kabat) SDSGGY (SEQ ID NO: 186) (Chothia) | YWPMSL (SEQ ID NO: 164) |
| A02_Rd4_0.6nM_C01 (P5AC1) | SYAMN (SEQ ID NO: 150) (Kabat); GFTFSSY (SEQ ID NO: 151) (Chothia); GFTFSSYAMN (SEQ ID NO: 152) (extended) | AILSSGGSTYYA DSVKG (SEQ ID NO: 187) (Kabat) LSSGGS (SEQ ID NO: 188) (Chothia) | YWPMDI (SEQ ID NO: 155) |
| A02_Rd4_6nM_C08 | SYAMN (SEQ ID NO: 150) (Kabat); GFTFSSY (SEQ ID NO: 151) (Chothia); GFTFSSYAMN (SEQ ID NO: 152) (extended) | AILDSGGSTYYA DSVKG (SEQ ID NO: 160) (Kabat) LDSGGS (SEQ ID NO: 172) (Chothia) | YWPMSP (SEQ ID NO: 189) |
| C01_Rd4_6nM_C12 (PC1C12) | SYPMS (SEQ ID NO: 156) (Kabat); GFTFSSY (SEQ ID NO: 151) (Chothia); GFTFSSYPMS (SEQ ID NO: 157) (extended) | AIGGSGGWSYY ADSVKG (SEQ ID NO: 190) (Kabat) GGSGGW (SEQ ID NO: 191) (Chothia) | YWPMDS (SEQ ID NO: 161) |

TABLE 2-continued

| | | | |
|---|---|---|---|
| C01_Rd4_6nM_C09 | SYPMS (SEQ ID NO: 156) (Kabat); GFTFSSY (SEQ ID NO: 151) (Chothia); GFTFSSYPMS (SEQ ID NO: 157) (extended) | ATVGSGGSIGYA DSVKG (SEQ ID NO: 192) (Kabat) VGSGGS (SEQ ID NO: 193) (Chothia) | YWPMDS (SEQ ID NO: 161) |
| COMBO_Rd4_0.6nM_C22 (COM22) | SYAMN (SEQ ID NO: 150) (Kabat); GFTFSSY (SEQ ID NO: 151) (Chothia); GFTFSSYAMN (SEQ ID NO: 152) (extended) | AISDSGGSRWY ADSVKG (SEQ ID NO: 169) (Kabat) SDSGGS (SEQ ID NO: 154) (Chothia) | YWPMDI (SEQ ID NO: 155) |
| COMBO_Rd4_0.6nM_C10 | SYPMS (SEQ ID NO: 156) (Kabat); GFTFSSY (SEQ ID NO: 151) (Chothia); GFTFSSYPMS (SEQ ID NO: 157) (extended) | AIGGSGGSIHYA DSVKG (SEQ ID NO: 194) (Kabat) GGSGGS (SEQ ID NO: 159) (Chothia) | YWPMDS (SEQ ID NO: 161) |
| COMBO_Rd4_0.6nM_C04 | SYPMS (SEQ ID NO: 156) (Kabat); GFTFSSY (SEQ ID NO: 151) (Chothia); GFTFSSYPMS (SEQ ID NO: 157) (extended) | AHIGSGGSTYYA DSVKG (SEQ ID NO: 195) (Kabat) IGSGGS (SEQ ID NO: 196) (Chothia) | YWPMDS (SEQ ID NO: 161) |
| COMBO_Rd4_0.6nM_C25 | SYPMS (SEQ ID NO: 156) (Kabat); GFTFSSY (SEQ ID NO: 151) (Chothia); GFTFSSYPMS (SEQ ID NO: 157) (extended) | AIGGSGGSTYYA DSVKG (SEQ ID NO: 162) (Kabat) GGSGGS (SEQ ID NO: 159) (Chothia) | YWPMDP (SEQ ID NO: 197) |
| COMBO_Rd4_6nM_C21 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYA DSVKG (SEQ ID NO: 158) (Kabat) GGSGGS (SEQ ID NO: 159) (Chothia) | YWPMDS (SEQ ID NO: 161) |
| COMBO_Rd4_6nM_C11 | SYPMS (SEQ ID NO: 156) (Kabat); GFTFSSY (SEQ ID NO: 151) (Chothia); GFTFSSYPMS (SEQ ID NO: 157) (extended) | AIGGSGGSLGYA DSVKG (SEQ ID NO: 198) (Kabat) GGSGGS (SEQ ID NO: 159) (Chothia) | YWPMDS (SEQ ID NO: 161) |
| COMBO_Rd4_6nM_C09 | SYPMS (SEQ ID NO: 156) (Kabat); GFTFSSY (SEQ ID NO: 151) (Chothia); GFTFSSYPMS (SEQ ID NO: 157) (extended) | AIFASGGSTYYA DSVKG (SEQ ID NO: 177) (Kabat) FASGGS (SEQ ID NO: 178) (Chothia) | YWPMDS (SEQ ID NO: 161) |
| COMBO_Rd4_6nM_C08 | SYPMS (SEQ ID NO: 156) (Kabat); GFTFSSY (SEQ ID NO: 151) (Chothia); GFTFSSYPMS (SEQ ID NO: 157) (extended) | AIGGSGTWTYY ADSVKG (SEQ ID NO: 199) (Kabat) GGSGTW (SEQ ID NO: 200) (Chothia) | YWPMDS (SEQ ID NO: 161) |
| COMBO_Rd4_0.6nM_C23 | SYPMS (SEQ ID NO: 156) (Kabat); GFTFSSY (SEQ ID NO: 151) (Chothia); GFTFSSYPMS (SEQ ID NO: 157) (extended) | ALFGSGGSTYY ADSVKG (SEQ ID NO: 201) (Kabat) FGSGGS (SEQ ID NO: 202) (Chothia) | YWPMDS (SEQ ID NO: 161) |

TABLE 2-continued

| | | | |
|---|---|---|---|
| COMBO_Rd4_0.6nM_C12 | SYPMS (SEQ ID NO: 156) (Kabat); GFTFSSY (SEQ ID NO: 151) (Chothia); GFTFSSYPMS (SEQ ID NO: 157) (extended) | AALGSGGSTYY ADSVKG (SEQ ID NO: 203) (Kabat) LGSGGS (SEQ ID NO: 204) (Chothia) | YWPMDS (SEQ ID NO: 161) |
| COMBO_Rd4_6nM_C07 | SYPMS (SEQ ID NO: 156) (Kabat); GFTFSSY (SEQ ID NO: 151) (Chothia); GFTFSSYPMS (SEQ ID NO: 157) (extended) | AIGGSGGSLPYA DSVKG (SEQ ID NO: 158) (Kabat) GGSGGS (SEQ ID NO: 159) (Chothia) | YWPMAD (SEQ ID NO: 205) |
| COMBO_Rd4_6nM_C02 | SYAMN (SEQ ID NO: 150) (Kabat); GFTFSSY (SEQ ID NO: 151) (Chothia); GFTFSSYAMN (SEQ ID NO: 152) (extended) | AISDSGGFVYYA DSVKG (SEQ ID NO: 206) (Kabat) SDSGGF (SEQ ID NO: 207) (Chothia) | YWPMDS (SEQ ID NO: 161) |
| COMBO_Rd4_6nM_C05 | SYAMN (SEQ ID NO: 150) (Kabat); GFTFSSY (SEQ ID NO: 151) (Chothia); GFTFSSYAMN (SEQ ID NO: 152) (extended) | AIGGSGGSTYYA DSVKG (SEQ ID NO: 162) (Kabat) GGSGGS (SEQ ID NO: 159) (Chothia) | YWPMSL (SEQ ID NO: 164) |
| COMBO_Rd4_6nM_C22 | SYAMN (SEQ ID NO: 150) (Kabat); GFTFSSY (SEQ ID NO: 151) (Chothia); GFTFSSYAMN (SEQ ID NO: 152) (extended) | ACLDSGGSTYY ADSVKG (SEQ ID NO: 208) (Kabat) LDSGGS (SEQ ID NO: 172) (Chothia) | YWPMDS (SEQ ID NO: 161) |
| COMBO_Rd4_6nM_C11 | SYPMS (SEQ ID NO: 156) (Kabat); GFTFSSY (SEQ ID NO: 151) (Chothia); GFTFSSYPMS (SEQ ID NO: 157) (extended) | AALGSGGSTYY ADSVKG (SEQ ID NO: 203) (Kabat) LGSGGS (SEQ ID NO: 204) (Chothia) | YWPMSL (SEQ ID NO: 164) |
| Heavy chain consensus | SYX$_1$MX$_2$, wherein X$_1$ is A or P; and X$_2$ is T, N, or S (Kabat) (SEQ ID NO: 301) GFTFX$_1$SY, wherein X$_1$ is G or S (Chothia) (SEQ ID NO: 302) GFTFX$_1$SYX$_2$MX$_3$, wherein X$_1$ is G or S, X$_2$ is A or P; and X$_3$ is T, N, or S (SEQ ID NO: 303) (extended) | AX$_1$X$_2$X$_3$X$_4$GX$_5$X$_6$ X$_7$X$_8$YADX$_9$X$_{10}$KG, wherein X$_1$ is I, V, T, H, L, A, or C; X$_2$ is S, D, G, T, I, L, F, M, or V; X$_3$ is G, Y, L, H, D, A, S, or M; X$_4$ is S, Q, T, A, F, or W; X$_5$ is G or T; X$_6$ is N, S, P, Y, W, or F; X$_7$ is S, T, I, L, T, A, R, V, K, G, or C; X$_8$ is F, Y, P, W, H, or G; X$_9$ is V, R, or L; and X$_{10}$ is G or T (Kabat) (SEQ ID NO: 305) X$_1$X$_2$X$_3$X$_4$X$_5$X$_6$, wherein X$_1$ is S, V, I, D, G, T, L, F, or M; X$_2$ is G, Y, L, H, D, A, S, or M; X$_3$ is S, G, F, or W; X$_4$ is G or S; X$_5$ is G or T; | VSPIX$_1$X$_2$X$_3$ MDY, wherein X$_1$ is A or Y; X$_2$ is A or S; and X$_3$ is G, Q, L, P, or E (SEQ ID NO: 307) YWPMX$_1$X$_2$, wherein X$_1$ is D, S, T, or A; and X$_2$ is I, S, L, P, or D (SEQ ID NO: 308) |

TABLE 2-continued

|  |  | and $X_6$ is N, S, P, Y, or W (Chothia) (SEQ ID NO: 306) |  |
|---|---|---|---|
| P4G4 | SYAMS (SEQ ID NO: 381) (Kabat); GFTFSSY (SEQ ID NO: 151) (Chothia); GFTFSSYAMS (SEQ ID NO: 382) (extended) | SASGGS (SEQ ID NO: 383) (Chothia) AISASGGSTYYA DSVKG (SEQ ID NO: 384) (Kabat) | LSWSGAFD N (SEQ ID NO: 385) |
| P1A11 | SYAMS (SEQ ID NO: 386) (Kabat); GFTFRSY (SEQ ID NO: 387) GFTFRSYAMS (SEQ ID NO: 388) | SGSGGS (SEQ ID NO: 389) (Chothia) AISGSGGSTFYA DSVKG (SEQ ID NO: 390) (Kabat) | VGTSGAFGI (SEQ ID NO: 391) |

Light Chain

| mAb | CDRL1 | CDRL2 | CDRL3 |
|---|---|---|---|
| P6E01 For the following mAbs: P6E01/P6E01; and P6E01/H3.AQ. | RASQSVSSSYLA (SEQ ID NO: 209) | GASSRAT (SEQ ID NO: 210) | QHYGSPPSF T (SEQ ID NO: 211) |
| L1.LGF/L3.KW For the following mAbs: L1.LGF/L3.KW/P6E01; L1.LGF/L3.KW/H3.AL; L1.LGF/L3.KW/H3.AP; and L1.LGF/L3.KW/H3.AQ | RASQSLGSFYLA (SEQ ID NO: 212) | GASSRAT (SEQ ID NO: 210) | KHYGWPPS FT (SEQ ID NO: 213) |
| L1.LGF/L3.NY For the following mAbs: L1.LGF/L3.NY/P6E01; L1.LGF/L3.NY/H3.AL; L1.LGF/L3.NY/H3.AP; and L1.LGF/L3.NY/H3AQ | RASQSLGSFYLA (SEQ ID NO: 212) | GASSRAT (SEQ ID NO: 210) | QHYNYPPSF T (SEQ ID NO: 214) |
| L1.GDF/L3.NY For the following mAbs: L1.GDF/L3.NY/P6E01; L1.GDF/L3.NY/H3.AL; L1.GDF/L3.NY/H3.AP; and L1.GDF/L3.NY/H3.AQ | RASQSVGDFYLA (SEQ ID NO: 215) | GASSRAT (SEQ ID NO: 210) | QHYNYPPSF T (SEQ ID NO: 214) |
| L1.LGF/L3.PY For the following mAbs: L1.LGF/L3.PY/H3.AP; and L1.LGF/L3.PY/H3.AQ | RASQSLGSFYLA (SEQ ID NO: 212) | GASSRAT (SEQ ID NO: 210) | QHYPYPPSFT (SEQ ID NO: 216) |
| L1.GDF/L3.KW For the following mAbs: L1.GDF/L3.KW/H3.AL; L1.GDF/L3.KW/H3.AP; and L1.GDF/L3.KW/H3.AQ | RASQSVGDFYLA (SEQ ID NO: 215) | GASSRAT (SEQ ID NO: 210) | KHYGWPPS FT (SEQ ID NO: 213) |
| L1.GDF/L3.PY/H3.AQ | RASQSVGDFYLA (SEQ ID NO: 215) | GASSRAT (SEQ ID NO: 210) | QHYPYPPSF T (SEQ ID NO: 216) |
| L3.KW/P6E01 | RASQSVSSSYLA (SEQ ID NO: 209) | GASSRAT (SEQ ID NO: 210) | KHYGWPPS FT (SEQ ID NO: 213) |
| L3.PY For the following mAbs: L3.PY/P6E01; L3.PY/H2.QR; L3.PY/H2.DY; L3.PY/H2.YQ; | RASQSVSSSYLA (SEQ ID NO: 209) | GASSRAT (SEQ ID NO: 210) | QHYPYPPSF T (SEQ ID NO: 216) |

TABLE 2-continued

L3.PY/H2.LT;
L3.PY/H2.HA;
L3.PY/H2.QL;
L3.PY/H3.YA;
L3.PY/H3.AE;
L3.PY/H3.AQ;
L3.PY/H3.TAQ

| | | | |
|---|---|---|---|
| L3.NY/P6E01 | RASQSVSSSYLA (SEQ ID NO: 209) | GASSRAT (SEQ ID NO: 210) | QHYNYPPSFT (SEQ ID NO: 214) |
| L3.PY/L1.PS<br>For the following mAbs:<br>L3.PY/L1.PS/P6E01;<br>P6DY;<br>L3.PY/L1.PS/H2.QR;<br>L3.PY/L1.PS/H2.DY;<br>L3.PY/L1.PS/H2.YQ;<br>L3.PY/L1.PS/H2.LT;<br>L3.PY/L1.PS/H2.HA;<br>L3.PY/L1.PS/H2.QL;<br>L3.PY/L1.PS/H3.YA;<br>L3.PY/L1.PS/H3.AE;<br>L3.PY/L1.PS/H3.AQ;<br>L3.PY/L1.PS/H3.TAQ; | RASQSVSSSYPS (SEQ ID NO: 217) | GASSRAT (SEQ ID NO: 210) | QHYPYPPSFT (SEQ ID NO: 216) |
| L3.PY/L1.AH<br>For the following mAbs:<br>L3.PY/L1.AH/P6E01;<br>L3.PY/L1.AH/H2.QR;<br>L3.PY/L1.AH/H2.DY;<br>L3.PY/L1.AH/H2.YQ;<br>L3.PY/L1.AH/H2.LT;<br>L3.PY/L1.AH/H2.HA;<br>L3.PY/L1.AH/H2.QL;<br>L3.PY/L1.AH/H3.YA;<br>L3.PY/L1.AH/H3.AE;<br>L3.PY/L1.AH/H3.AQ;<br>L3.PY/L1.AH/H3.TAQ | RASQSVSAHYLA (SEQ ID NO: 218) | GASSRAT (SEQ ID NO: 210) | QHYPYPPSFT (SEQ ID NO: 216) |
| L3.PY/L1.FF<br>For the following mAbs:<br>L3.PY/L1.FF/P6E01;<br>L3.PY/L1.FF/H2.QR;<br>L3.PY/L1.FF/H2.DY;<br>L3.PY/L1.FF/H2.YQ;<br>L3.PY/L1.FF/H2.LT;<br>L3.PY/L1.FF/H2.HA;<br>L3.PY/L1.FF/H2.QL;<br>L3.PY/L1.FF/H3.YA;<br>L3.PY/L1.FF/H3.AE;<br>L3.PY/L1.FF/H3.AQ;<br>and<br>L3.PY/L1.FF/H3.TAQ | RASQSVSSFFLA (SEQ ID NO: 219) | GASSRAT (SEQ ID NO: 210) | QHYPYPPSFT (SEQ ID NO: 216) |
| L3.PY/L1.PH<br>For the following mAbs:<br>L3.PY/L1.PH/P6E01;<br>L3.PY/L1.PH/H2.QR;<br>L3.PY/L1.PH/H2.HA;<br>L3.PY/L1.PH/H3.AE;<br>L3.PY/L1.PH/H3.AQ;<br>and<br>L3.PY/L1.PH/H3.TAQ | RASQSVSPHYLA (SEQ ID NO: 219) | GASSRAT (SEQ ID NO: 210) | QHYPYPPSFT (SEQ ID NO: 216) |
| L3.PY/L3.KY<br>For the following mAbs:<br>L3.PY/L3.KY/P6E01;<br>L3.PY/L3.KY/H2.QR;<br>L3.PY/L3.KY/H2.DY;<br>L3.PY/L3.KY/H2.YQ;<br>L3.PY/L3.KY/H2.LT; | RASQSVSSSYLA (SEQ ID NO: 209) | GASSRAT (SEQ ID NO: 210) | KYYPYPPSFT (SEQ ID NO: 220) |

TABLE 2-continued

| | | | |
|---|---|---|---|
| L3.PY/L3.KY/H2.HA;<br>L3.PY/L3.KY/H2.QL;<br>L3.PY/L3.KY/H3.YA;<br>and<br>L3.PY/L3.KY/H3.TAQ | | | |
| L3.PY/L3.KF<br>For the following mAbs:<br>L3.PY/L3.KF/H2.DY;<br>L3.PY/L3.KF/H2.YQ;<br>L3.PY/L3.KF/H2.LT;<br>L3.PY/L3.KF/H2.QL;<br>L3.PY/L3.KF/H3.YA;<br>L3.PY/L3.KF/H3.AE;<br>L3.PY/L3.KF/H3.AQ;<br>and<br>L3.PY/L3.KF/H3.TAQ | RASQSVSSSYLA<br>(SEQ ID NO: 209) | GASSRAT (SEQ ID NO: 210) | KFYPYPPSFT (SEQ ID NO: 220) |
| P5A2_VHVL (P5A) | RASQSVSSSYLA (SEQ ID NO: 209) | DASIRAT (SEQ ID NO: 221) | QQYGSWPLT (SEQ ID NO: 222) |
| A02_Rd4_0.6nM_C06 | RASQSVSVIYLA (SEQ ID NO: 223) | DASIRAT (SEQ ID NO: 221) | QQYQRWPLT (SEQ ID NO: 224) |
| A02_Rd4_0.6nM_C09;<br>COMBO_Rd_0.6nM_C29;<br>and<br>COMBO_Rd4_0.6nM_C21 | RASQSVSSSYLA (SEQ ID NO: 209) | DASIRAT (SEQ ID NO: 221) | QQYQSWPLT (SEQ ID NO: 225) |
| A02_Rd4_6nM_C16 (P5AC16) | RASQSVSDIYLA (SEQ ID NO: 226) | DASIRAT (SEQ ID NO: 221) | QQYQTWPLT (SEQ ID NO: 227) |
| A02_Rd4_6nM_C03 | RASQSVSNIYLA (SEQ ID NO: 228) | DASIRAT (SEQ ID NO: 221) | QQYGWPLT (SEQ ID NO: 229) |
| A02_Rd4_6nM_C01 | RASQSVSAYYLA (SEQ ID NO: 230) | DASIRAT (SEQ ID NO: 221) | QQYERWPLT (SEQ ID NO: 231) |
| A02_Rd4_6nM_C26 | RASQSVSSIYLA (SEQ ID NO: 232) | DASIRAT (SEQ ID NO: 221) | QQYQVWPLT (SEQ ID NO: 233) |
| A02_Rd4_6nM_C25 | RASQSVSSSYLA (SEQ ID NO: 209) | DASIRAT (SEQ ID NO: 221) | QQYLDWPLT (SEQ ID NO: 234) |
| A02_Rd4_6nM_C22 | RASQSVSSSYLA (SEQ ID NO: 209) | DASIRAT (SEQ ID NO: 221) | QQYQVWPLT (SEQ ID NO: 233) |
| A02_Rd4_6nM_C19 | RASQSVSVIYLA (SEQ ID NO: 223) | DASIRAT (SEQ ID NO: 221) | QQYLAWPLT (SEQ ID NO: 236) |
| A02_Rd4_0.6nM_C03 | RASQSVSSSYLA (SEQ ID NO: 209) | DASIRAT (SEQ ID NO: 221) | QQYFTWPLT (SEQ ID NO: 237) |
| A02_Rd4_6nM_C07 | RASQSVSPYYLA (SEQ ID NO: 238) | DASIRAT (SEQ ID NO: 221) | QQYERWPLT (SEQ ID NO: 231) |
| A02_Rd4_6nM_C23 | RASQSVSVEYLA (SEQ ID NO: 239) | DASIRAT (SEQ ID NO: 221) | QQYARWPLT (SEQ ID NO: 240) |

TABLE 2-continued

| | | | |
|---|---|---|---|
| A02_Rd4_0.6nM_C18 | RASQSVSEIYLA (SEQ ID NO: 241) | DASIRAT (SEQ ID NO: 221) | QQYFGWPLT (SEQ ID NO: 242) |
| A02_Rd4_6nM_C10 | RASQSVEMSYLA (SEQ ID NO: 243) | DASIRAT (SEQ ID NO: 221) | QQYAHWPLT (SEQ ID NO: 244) |
| A02_Rd4_6nM_C05 | RASQSVSSSYLA (SEQ ID NO: 209) | DASIRAT (SEQ ID NO: 221) | QQYQRWPLT (SEQ ID NO: 224) |
| A02_Rd4_0.6nM_C10 | RASQSVSAQYLA (SEQ ID NO: 245) | DASIRAT (SEQ ID NO: 221) | QQYQRWPLT (SEQ ID NO: 224) |
| A02_Rd4_6nM_C04 | RASQSVSAIYLA (SEQ ID NO: 235) | DASIRAT (SEQ ID NO: 221) | QQYQVWPLT (SEQ ID NO: 233) |
| A02_Rd4_0.6nM_C26 | GPSQSVSSSYLA (SEQ ID NO: 246) | DASIRAT (SEQ ID NO: 221) | QQYQSWPLT (SEQ ID NO: 225) |
| A02_Rd4_0.6nM_C13 | RASQSVSSSYWA (SEQ ID NO: 247) | DASIRAT (SEQ ID NO: 221) | QQYESWPLT (SEQ ID NO: 248) |
| A02_Rd4_0.6nM_C01 (P5AC1) | RGGQSVSSSYLA (SEQ ID NO: 249) | DASIRAT (SEQ ID NO: 221) | QQYQSWPLT (SEQ ID NO: 225) |
| A02_Rd4_6nM_C08 | RASQSVSFIYLA (SEQ ID NO: 250) | DASIRAT (SEQ ID NO: 221) | QQYGSWPLT (SEQ ID NO: 222) |
| P5C1_VHVL (PC1) | RASQSVSSTYLA (SEQ ID NO: 251) | DASSRAP (SEQ ID NO: 252) | QQYSTSPLT (SEQ ID NO: 253) |
| C01_Rd4_6nM_C24 | RASQSVSPEYLA (SEQ ID NO: 254) | DASSRAP (SEQ ID NO: 252) | QQYSVWPLT (SEQ ID NO: 255) |
| C01_Rd4_6nM_C26 | RASQSVSAIYLA (SEQ ID NO: 235) | DASSRAP (SEQ ID NO: 252) | QQYSAWPLT (SEQ ID NO: 256) |
| C01_Rd4_6nM_C10 | RASQSVSSVYLA (SEQ ID NO: 257) | DASSRAP (SEQ ID NO: 252) | QQYSTWPLT (SEQ ID NO: 258) |
| C01_Rd4_0.6nM_C27 | RASQSVSSTYLA (SEQ ID NO: 251) | DASSRAP (SEQ ID NO: 252) | QQYSRWPLT (SEQ ID NO: 259) |
| C01_Rd4_6nM_C20 | RASQSVSPIYLA (SEQ ID NO: 260) | DASSRAP (SEQ ID NO: 252) | QQYSAFPLT (SEQ ID NO: 261) |
| C01_Rd4_6nM_C12 (PC1C12) | WLSQSVSSTYLA (SEQ ID NO: 262) | DASSRAP (SEQ ID NO: 252) | QQYSEWPLT (SEQ ID NO: 263) |

TABLE 2-continued

| | | | |
|---|---|---|---|
| C01_Rd4_0.6nM_C16 | RASQSVSSTYLA (SEQ ID NO: 251) | DASSRAP (SEQ ID NO: 252) | QQYSSWPLT (SEQ ID NO: 264) |
| C01_Rd4_0.6nM_C09 | RASQSVSSIFLA (SEQ ID NO: 265) | DASSRAP (SEQ ID NO: 252) | QQYSAWPLT (SEQ ID NO: 256) |
| C01_Rd4_6nM_C09 | ACSQSVSSTYLA (SEQ ID NO: 266) | DASSRAP (SEQ ID NO: 252) | QQYSAWPLT (SEQ ID NO: 256) |
| C01_Rd4_0.6nM_C03 | RASCDVSSTYLA (SEQ ID NO: 267) | DASSRAP (SEQ ID NO: 252) | QQYMRSPLT (SEQ ID NO: 268) |
| C01_Rd4_0.6nM_C06 | RASEAVPSTYLA (SEQ ID NO: 269) | DASSRAP (SEQ ID NO: 252) | QQYSAFPLT (SEQ ID NO: 261) |
| C01_Rd4_0.6nM_C04 | CSSQSVSSTYLA (SEQ ID NO: 270) | DASSRAP (SEQ ID NO: 252) | QQYSAFPLT (SEQ ID NO: 261) |
| COMBO_Rd4_0.6nM_C22 (COM22) | RASVRVSSTYLA (SEQ ID NO: 271) | DASIRAT (SEQ ID NO: 221) | QQYMKWPLT (SEQ ID NO: 272) |
| COMBO_Rd4_6nM_C21 | RASQSVSAAYLA (SEQ ID NO: 273) | DASIRAT (SEQ ID NO: 221) | QQYMCWPLT (SEQ ID NO: 274) |
| COMBO_Rd4_6nM_C10 | RASQSVSSSYWG (SEQ ID NO: 275) | DASIRAT (SEQ ID NO: 221) | QQYQCWPLT (SEQ ID NO: 276) |
| COMBO_Rd4_0.6nM_C04 | RASQSVSSTYLA (SEQ ID NO: 251) | DASIRAT (SEQ ID NO: 221) | QQYQSWPLT (SEQ ID NO: 225) |
| COMBO_Rd4_6nM_C25 | RASQSVSSPYLA (SEQ ID NO: 277) | DASIRAT (SEQ ID NO: 221) | QQYQSWPLT (SEQ ID NO: 225) |
| COMBO_Rd4_6nM_C11 | RASQSVSPIYLA (SEQ ID NO: 260) | DASIRAT (SEQ ID NO: 221) | QQYKAWPLT (SEQ ID NO: 278) |
| COMBO_Rd4_0.6nM_C20 | RASQSVSYLYLA (SEQ ID NO: 279) | DASIRAT (SEQ ID NO: 221) | QQYMEWPLT (SEQ ID NO: 280) |
| COMBO_Rd4_6nM_C09 | RASQSVSAQYLA (SEQ ID NO: 245) | DASIRAT (SEQ ID NO: 221) | QQYQAWPLT (SEQ ID NO: 281) |
| COMBO_Rd4_6nM_C08 | RASQSVSSSYLA (SEQ ID NO: 209) | DASIRAT (SEQ ID NO: 221) | QQYQKWPLT (SEQ ID NO: 282) |
| COMBO_Rd4_0.6nM_C19 | RASQSVSAVYLA (SEQ ID NO: 283) | DASIRAT (SEQ ID NO: 221) | QQYRAWPLT (SEQ ID NO: 284) |

TABLE 2-continued

| | | | |
|---|---|---|---|
| COMBO_Rd4_0.6nM_C02 | RASIAVSSTYLA (SEQ ID NO: 285) | DASIRAT (SEQ ID NO: 221) | QQYMVWPLT (SEQ ID NO: 286) |
| COMBO_Rd4_0.6nM_C23 | RPRQSVSSSYLA (SEQ ID NO: 287) | DASIRAT (SEQ ID NO: 221) | QQYQDWPLT (SEQ ID NO: 288) |
| COMBO_Rd4_0.6nM_C09 | RASQSVSSTYLA (SEQ ID NO: 251) | DASIRAT (SEQ ID NO: 221) | QQYQEWPLT (SEQ ID NO: 289) |
| COMBO_Rd4_6nM_C12 | RASQSVSASYLA (SEQ ID NO: 290) | DASIRAT (SEQ ID NO: 221) | QQYMSWPLT (SEQ ID NO: 291) |
| COMBO_Rd4_0.6nM_C30 | RASQSVSYMYLA (SEQ ID NO: 292) | DASIRAT (SEQ ID NO: 221) | QQYKSWPLT (SEQ ID NO: 293) |
| COMBO_Rd4_0.6nM_C14 | RASQSVSAIYLA (SEQ ID NO: 235) | DASIRAT (SEQ ID NO: 221) | QQYYGWPLT (SEQ ID NO: 294) |
| COMBO_Rd4_6nM_C07 | RASQPISSSYLA (SEQ ID NO: 295) | DASIRAT (SEQ ID NO: 221) | QQYQGWPLT (SEQ ID NO: 229) |
| COMBO_Rd4_6nM_C02 | RASQSVSSSYLA (SEQ ID NO: 209) | DASIRAT (SEQ ID NO: 221) | QQYEFWPLT (SEQ ID NO: 296) |
| COMBO_Rd4_0.6nM_C05 | RASQSVSSTYLA (SEQ ID NO: 251) | DASIRAT (SEQ ID NO: 221) | QQYMSWPLT (SEQ ID NO: 291) |
| COMBO_Rd4_0.6nM_C17 | RASQGISSTYLA (SEQ ID NO: 297) | DASIRAT (SEQ ID NO: 221) | QQYAYWPLT (SEQ ID NO: 298) |
| COMBO_Rd4_6nM_C22 | RASQSVSSSYLA (SEQ ID NO: 209) | DASIRAT (SEQ ID NO: 221) | QQYQGWPLT (SEQ ID NO: 229) |
| COMBO_Rd4_0.6nM_C11 | RASQSVSVRYLA (SEQ ID NO: 299) | DASIRAT (SEQ ID NO: 221) | QQYGSWPIT (SEQ ID NO: 300) |
| Light chain consensus | $X_1X_2X_3X_4X_5X_6X_7X_8X_9X_{10}X_{11}X_{12}$, wherein $X_1$ is R, G, W, A, or C; $X_2$ is A, P, G, L, C, or S; $X_3$ is S, G, or R; $X_4$ is Q, C, E, V, or I; $X_5$ is S, P, G, A, R, or D; $X_6$ is V, G, I, or L; $X_7$ is S, E, D, P, or G; $X_8$ is S, P, F, A, M, E, V, N, D, or Y; $X_9$ is I, T, V, E, F S, A, M, Q, Y, H, or R; $X_{10}$ is Y or F; $X_{11}$ is L, | $X_1ASX_2RAX_3$, wherein $X_1$ is G or D; $X_2$ is S or I; and $X_3$ is T or P (SEQ ID NO: 310) | $X_1X_2YX_3X_4PPSFT$, wherein $X_1$ is Q or K; $X_2$ is H or Y; $X_3$ is G, N, or P; and $X_4$ is S, W, or Y (SEQ ID NO: 311) $QQYX_1X_2X_3PX_4T$, wherein $X_1$ is G, Q, E, L, F, A, S, M, |

TABLE 2-continued

| | W, or P; and X₁₂ is A, S, or G (SEQ ID NO: 309) | | K, R, or Y; X₂ is S, R, T, G, V, F, Y, D, A, H, V, E, K, or C; X₃ is W, F, or S; and X₄ is L or I (SEQ ID NO: 312) |
|---|---|---|---|
| P4G4 | RASQSVSSSYLA (SEQ ID NO: 209) | GASSRAY (SEQ ID NO: 392) | QHYGSPPLFT (SEQ ID NO: 393) |
| P1A11 | RASQNVSSSYLA (SEQ ID NO: 379) | GASYRAT (SEQ ID NO: 395) | QHYGSPPSFT (SEQ ID NO: 211) |
| P6AP | RASQLGSFYLA (SEQ ID NO: 377) | GASSRAT (SEQ ID NO: 210) | QHYNYPPSFT (SEQ ID NO: 214) |

The invention encompasses modifications to the CARs and polypeptides of the invention variants shown in Table 1, including functionally equivalent CARs having modifications which do not significantly affect their properties and variants which have enhanced or decreased activity and/or affinity. For example, the amino acid sequence may be mutated to obtain an antibody with the desired binding affinity to BCMA. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 2.1 under the heading of "conservative substitutions." If such substitutions result in a change in biological activity, then more substantial changes, denominated "exemplary substitutions" in Table 2.1, or as further described below in reference to amino acid classes, may be introduced and the products screened.

TABLE 2.1

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

In some embodiments, the invention provides a CAR comprising an extracellular ligand-binding domain that binds to BCMA and competes for binding to BCMA with a CAR described herein, including P6E01/P6E01, P6E01/H3.AQ, L1.LGF/L3.KW/P6E01; L1.LGF/L3.NY/P6E01, L1.GDF/L3.NY/P6E01, L1.LG F/L3.KW/H3.AL, L1.LGF/L3.KW/H3.AP, L1.LG F/L3.KW/H3.AQ, L1.LG F/L3.PY/H3.AP, L1.LGF/L3.PY/H3.AQ, L1.LG F/L3.NY/H3.AL, L1.LG F/L3.NY/H3.AP, L1.LG F/L3.NY/H3.AQ, L1.GDF/L3.KW/H3.AL, L1.GDF/L3.KW/H3.AP, L1.GDF/L3.KW/H3.AQ, L1.GDF/L3.PY/H3.AQ, L1.GDF/L3.NY/H3.AL, L1.GDF/L3.NY/H3.AP, L1.GDF/L3.NY/H3.AQ, L3.KW/P6E01, L3.PY/P6E01, L3.NY/P6E01, L3.PY/L1.PS/P6E01, L3.PY/L1.AH/P6E01, L3.PY/L1.FF/P6E01, L3.PY/L1.PH/P6E01, L3.PY/L3.KY/P6E01, L3.PY/L3.KF/P6E01, L3.PY/H2.QR, L3.PY/H2.DY, L3.PY/H2.YQ, L3.PY/H2.LT, L3.PY/H2.HA, L3.PY/H2.QL, L3.PY/H3.YA, L3.PY/H3.AE, L3.PY/H3.AQ, L3.PY/H3.TAQ, L3.PY/P6E01, L3.PY/L1.PS/H2.QR, L3.PY/L1.PS/H2.DY, L3.PY/L1.PS/H2.YQ, L3.PY/L1.PS/H2.LT, L3.PY/L1.PS/H2.HA, L3.PY/L1.PS/H2.QL, L3.PY/L1.PS/H3.YA, L3.PY/L1.PS/ H3.AE, L3.PY/L1.PS/H3.AQ, L3.PY/L1.PS/H3.TAQ, L3.PY/L1.AH/H2.QR, L3.PY/L1.AH/H2.DY, L3.PY/ L1.AH/H2.YQ, L3.PY/L1.AH/H2.LT, L3.PY/L1.AH/ H2.HA, L3.PY/L1.AH/H2.QL, L3.PY/L1.AH/H3.YA, L3.PY/L1.AH/H3.AE, L3.PY/L1.AH/H3.AQ, L3.PY/ L1.AH/H3.TAQ, L3.PY/L1.FF/H2.QR, L3.PY/L1.FF/ H2.DY, L3.PY/L1.FF/H2.YQ, L3.PY/L1.FF/H2.LT, L3.PY/ L1.FF/H2.HA, L3.PY/L1.FF/H2.QL, L3.PY/L1.FF/H3.YA, L3.PY/L1.FF/H3.AE, L3.PY/L1.FF/H3.AQ, L3.PY/L1.FF/ H3.TAQ, L3.PY/L1.PH/H2.QR, L3.PY/L1.PH/H2.HA, L3.PY/L1.PH/H3.AE, L3.PY/L1.PH/H3.AQ, L3.PY/ L1.PH/H3.TAQ, L3.PY/L3.KY/H2.QR, L3.PY/L3.KY/ H2.DY, L3.PY/L3.KY/H2.YQ L3.PY/L3.KY/H2.LT, L3.PY/L3.KY/H2.HA, L3.PY/L3.KY/H2.QL, L3.PY/ L3.KY/H3.YA L3.PY/L3.KY/H3.TAQ, L3.PY/L3.KF/ H2.DY, L3.PY/L3.KF/H2.YQ, L3.PY/L3.KF/H2.LT L3.PY/ L3.KF/H2.QL, L3.PY/L3.KF/H3.YA, L3.PY/L3.KF/ H3.AE, L3.PY/L3.KF/H3.AQ L3.PY/L3.KF/H3.TAQ, P5A2_VHVL, A02_Rd4_0.6 nM_C06, A02_Rd4_0.6 nM_C09 A02_Rd4_6 nM_C16, A02_Rd4_6 nM_C03, A02_Rd4_6 nM_C01, A02_Rd4_6 nM_C26 A02_Rd4_6 nM_C25, A02_Rd4_6 nM_C22, A02_Rd4_6 nM_C19, A02_Rd4_0.6 nM_C03 A02_Rd4_6 nM_C07, A02_Rd4_6 nM_C23, A02_Rd4_06 nM_C18, A02_Rd4_6 nM_C10 A02_Rd4_6 nM_C05, A02_Rd4_0.6 nM_C10, A02_Rd4_6 nM_C04, A02_Rd4_0.6 nM_C26 A02_Rd4_0.6 nM_C13, A02_Rd4_0.6 nM_C01, A02_Rd4_6 nM_C08, P5C1_VHVL, C01_Rd4_6 nM_C24, C01_Rd4_6 nM_C26, C01_Rd4_6 nM_C10, C01_Rd4_0.6 nM_C27 C01_Rd4_6 nM_C20, C01_Rd4_6 nM_C12, C01_Rd4_0.6 nM_C16, C01_Rd4_0.6 nM_C09 C01_Rd4_6 nM_C09, C01_Rd4_0.6 nM_C03, C01_Rd4_0.6 nM_C06, C01_Rd4_6 nM_C04 COMBO_Rd4_0.6 nM_C22, COMBO_Rd4_6 nM_C21, COMBO_Rd4_6 nM_C10, COMBO_Rd4_0.6 nM_C04, COMBO_Rd4_6 nM_C25, COMBO_Rd4_0.6 nM_C21, COMBO_Rd4_6 nM_C11, COMBO_Rd4_0.6 nM_C20, COMBO_Rd4_6 nM_C09, COMBO_Rd4_6 nM_C08, COMBO_Rd4_0.6 nM_C19, COMBO_Rd4_0.6 nM_C02, COMBO_Rd4_0.6 nM_C23, COMBO_Rd4_0.6 nM_C29, COMBO_Rd4_0.6 nM_C09, COMBO_Rd4_6 nM_C12, COMBO_Rd4_0.6 nM_C30, COMBO_Rd4_0.6 nM_C14, COMBO_Rd4_6 nM_C07, COMBO_Rd4_6 nM_C02, COMBO_Rd4_0.6 nM_C05, COMBO_Rd4_0.6 nM_C17, COMBO_Rd4_6 nM_C22, COMBO_Rd4_0.6 nM_C11, or COMBO_Rd4_0.6 nM_C29.

In some embodiments, the invention provides a CAR, which specifically binds to BCMA, wherein the CAR comprises a VH region comprising a sequence shown in SEQ ID NO: 33; and/or a VL region comprising a sequence shown in SEQ ID NO: 34. In some embodiments, the invention provides a CAR, which specifically binds to BCMA, wherein the CAR comprises a VH region comprising a sequence shown in SEQ ID NO: 33, 72, 39, 76, 83, 92, 25, or 8; and/or a VL region comprising a sequence shown in SEQ ID NO: 34, 73, 40, 77, 84, 93, 18, or 80. In some embodiments, the invention also provides CARs comprising CDR portions of antibodies to BCMA antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the BCMA specific CAR as described herein to BCMA (such as human BCMA (e.g., (SEQ ID NO: 354) can be about 0.002 to about 6500 nM. In some embodiments, the binding affinity is about any of 6500 nm, 6000 nm, 5986 nm, 5567 nm, 5500 nm, 4500 nm, 4000 nm, 3500 nm, 3000 nm, 2500 nm, 2134 nm, 2000 nm, 1500 nm, 1000 nm, 750 nm, 500 nm, 400 nm, 300 nm, 250 nm, 200 nM, 193 nM, 100 nM, 90 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM, 0.1 nM, 0.01 nM, or 0.002 nM. In some embodiments, the binding affinity is less than about any of 6500 nm, 6000 nm, 5500 nm, 5000 nm, 4000 nm, 3000 nm, 2000 nm, 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM, 4.5 nM, 4 nM, 3.5 nM, 3 nM, 2.5 nM, 2 nM, 1.5 nM, 1 nM, or 0.5 nM.

The intracellular signaling domain of a CAR according to the invention is responsible for intracellular signaling following the binding of extracellular ligand-binding domain to the target resulting in the activation of the immune cell and immune response. The intracellular signaling domain has the ability to activate of at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRζ, FcRγ, FcRβ, FcRε, CD3γ, CD3δ, CD3ε, CD5, CD22, CD79a, CD79b and CD66d. In some embodiments, the intracellular signaling domain of the CAR can comprise the CD3ζ signaling domain which has amino acid sequence with at least about 70%, preferably at least 80%, more preferably at least 90%, 95%, 97%, or 99% sequence identity with an amino acid sequence shown in SEQ. ID NO: 324. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP_006130.1). In some embodiments, the intracellular signaling domain of the CAR of the invention comprises amino acid sequence which comprises at least 70%, preferably at least 80%, more preferably at least 90%, 95%, 97%, or 99% sequence identity with an amino acid sequence shown in SEQ. ID NO: 323 and SEQ. ID NO: 327.

CARs are expressed on the surface membrane of the cell. Thus, the CAR can comprise a transmembrane domain. Suitable transmembrane domains for a CAR disclosed herein have the ability to (a) be expressed at the surface of a cell, preferably an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (a chain), p75 (β chain) or γ chain, subunit chain of Fc receptors, in particular Fcγ receptor III or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1). The transmembrane domain can further comprise a stalk domain between the extracellular ligand-binding domain and said transmembrane domain. A stalk domain may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, said transmembrane and hinge domains comprise a part of human CD8α chain, preferably which comprises at least 70%, preferably at least 80%, more preferably at least 90%, 95% 97%, or 99% sequence identity with amino acid sequence selected from the group consisting of SEQ ID NO: 318. In some embodiments, CARs disclosed herein can comprise an extracellular ligand-binding domain that specifically binds BCMA, CD8α human hinge and transmembrane domains, the CD3ζ signaling domain, and 4-1BB signaling domain.

Table 3 provides exemplary sequences of domains which can be used in the CARs disclosed herein.

TABLE 3

Exemplary sequences of CAR Components

| Domain | Amino Acid Sequence | SEQ ID NO: |
|---|---|---|
| CD8α signal peptide | MALPVTALLLPLALLLHAARP | 318 |
| FcγRIIIα hinge | GLAVSTISSFFPPGYQ | 319 |
| CD8α hinge | TTTPAPRPPTPAPTIASQPLSLRPE ACRPAAGGAVHTRGLDFACD | 320 |
| IgG1 hinge | EPKSPDKTHTCPPCPAPPVAGPSVF LFPPKPKDTLMIARTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | 321 |
| CD8α transmembrane (TM) domain | IYIWAPLAGTCGVLLLSLVITLYC | 322 |
| 41BB intracellular signaling domain (ISD) | KRGRKKLLYIFKQPFMRPVQTTQEE DGCSCRFPEEEEGGCEL | 323 |
| CD3ζ intracellular signaling domain (ISD) | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR | 324 |
| FcεRIα-TM-IC (FcεRIα chain transmembrane and intracellular domain) | FFIPLLVVILFAVDTGLFISTQQQV TFLLKIKRTRKGFRLLNPHPKPNPK NN | 325 |
| FcεRIβ-ΔITAM (FcεRIβ chain without ITAM) | MDTESNRRANLALPQEPSSVPAFEV LEISPQEVSSGRLLKSASSPPLHTW LTVLKKEQEFLGVTQILTAMICLCF GTVVCSVLDISHIEGDIFSSFKAGY PFWGAIFFSISGMLSIISERRNATY LVRGSLGANTASSIAGGTGITILII NLKKSLAYIHIHSCQKFFETKCFMA SFSTEIVVMMLFLTILGLGSAVSLT ICGAGEELKGNKVPE | 326 |
| 41BB-IC (41BB co-stimulatory domain) | KRGRKKLLYIFKQPFMRPVQTTQEE DGCSCRFPEEEEGGCEL | 327 |
| CD28-IC (CD28 co-stimulatory domain) | RSKRSRGGHSDYMNMTPRRPGPTRK HYQPYAPPRDFAAYRS | 328 |
| FcεRIγ-SP (signal peptide) | MIPAVVLLLLLLVEQAAA | 329 |
| FcεRI γ-ΔITAM (FcεRIγ chain without ITAM) | LGEPQLCYILDAILFLYGIVLTLLY CRLKIQVRKAAITSYEKS | 330 |
| GSG-P2A (GSG-P2A ribosomal skip polypeptide) | GSGATNFSLLKQAGDVEENPGP | 331 |
| GSG-T2A (GSG-T2A ribosomal skip polypeptide) | GSGEGRGSLLTCGDVEENPGP | 332 |

Downregulation or mutation of target antigens is commonly observed in cancer cells, creating antigen-loss escape variants. Thus, to offset tumor escape and render immune cell more specific to target, the BCMA specific CAR can comprise one or more additional extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In some embodiments, said different extracellular ligand-binding domains can be placed on different transmembrane polypeptides composing the CAR. In some embodiments, the invention relates to a population of CARs, each CAR comprising a different extracellular ligand-binding domain. In a particular, the invention relates to a method of engineering immune cells comprising providing an immune cell and expressing at the surface of the cell a population of CARs, each CAR comprising different extracellular ligand-binding domains. In another particular embodiment, the invention relates to a method of engineering an immune cell comprising providing an immune cell and introducing into the cell polynucleotides encoding polypeptides composing a population of CAR each one comprising different extracellular ligand-binding domains. By population of CARs, it is meant at least two, three, four, five, six or more CARs each one comprising different extracellular ligand-binding domains. The different extracellular ligand-binding domains according to the invention can preferably simultaneously bind different elements in target thereby augmenting immune cell activation and function. The invention also relates to an isolated immune cell which comprises a population of CARs each one comprising different extracellular ligand-binding domains.

In another aspect, the invention provides polynucleotides encoding any of the CARs and polypeptides described herein. Polynucleotides can be made and expressed by procedures known in the art.

In another aspect, the invention provides compositions (such as a pharmaceutical compositions) comprising any of the cells of the invention. In some embodiments, the composition comprises a cell comprising a polynucleotide encoding any of the CARs described herein. In still other embodiments, the composition comprises either or both of the polynucleotides shown in SEQ ID NO: 367 and SEQ ID NO:368 below:

```
P5A heavy chain variable region
                              (SEQ ID NO: 367)
GAGGTGCAGCTGCTGGAATCTGGCGGAGGACTGGT

GCAGCCTGGCGGCTCTCTGAGACTGTCTTGTGCCG

CCAGCGGCTTCACCTTCAGCAGCTACGCCATGAAC

TGGGTGCGCCAGGCCCCTGGCAAAGGCCTGGAATG

GGTGTCCGCCATCAGCGATAGCGGCGGCAGCACCT

ACTACGCCGATAGCGTGAAGGGCCGGTTCACCATC

AGCCGGGACAACAGCAAGAACACCCTGTACCTGCA

GATGAACAGCCTGCGGGCCGAGGACACCGCCGTGT

ACTACTGTGCCANATACTGGCCCATGGACATCTGG

GGCCAGGGAACCTTGGTCACCGTCTCCTCA

P5A light chain variable region
                              (SEQ ID NO: 368)
GAGATCGTGCTGACACAGAGCCCTGGCACCCTGAG

CCTGTCTCCAGGCGAAAGAGCCACCCTGTCCTGCA

AAGCCAGCCAGAGCGTGTCCAGCAGCTACCTGGCC

TGGTATCAGCAAAAGCCCGGCCAGGCTCCCCGGCT
```

```
-continued
GCTGATGTACGATGCCAGCATCAGAGCCACCGGCA

TCCCCGACAGATTTTCCGGCTCTGGCAGCGGCACC

GACTTCACCCTGACCATCAGCAGACTGGAACCCGA

GGACTTCGCCGTGTACTACTGCCAGCAGTACGGCA

GCTGGCCCCTGACATTTGGCCAGGGCACAAAGGT

GGAGATCAAA
```

In other embodiments, the composition comprises either or both of the polynucleotides shown in SEQ ID NO: 369 and SEQ ID NO: 370 below:

```
P5AC1 heavy chain variable region
                              (SEQ ID NO: 369)
GAGGTGCAGCTGCTGGAATCTGGCGGAGGACTGGT

GCAGCCTGGCGGCTCTCTGAGACTGTCTTGTGCCG

CCAGCGGCTTCACCTTCAGCAGCTACGCCATGAAC

TGGGTGCGCCAGGCCCCTGGTAAAGGTTTGGAATG

GGTTTCTGCTATTCTGTCGTCTGGTGGTTCTACTT

ACTATGCCGATTCTGTTAAGGGTAGATTCACCATT

TCTAGAGACAACTCTAAGAACACCTTGTACTTGCA

AATGAACTCCTTGAGAGCTGAAGATACTGCTGTTT

ATTACTGTGCTAGATACTGGCCAATGGATATTTGG

GGTCAAGGTACTCTGGTCACCGTCTCCTCA

P5AC1 light chain variable region
                              (SEQ ID NO: 370)
GAGATCGTGCTGACACAGAGCCCTGGCACCCTGAG

CCTGTCTCCTGGTGAAAGAGCTACTTTGTCTTGTA

GAGGGGGTCAATCCGTTTCCTCTTCTTATTTGGCT

TGGTATCAACAAAAACCAGGTCAAGCTCCAAGATT

ATTGATGTACGATGCTTCTATTAGAGCCACCGGTA

TTCCAGATAGATTTTCTGGTTCTGGTTCCGGTACT

GATTTCACTTTGACTATCTCTAGATTGGAACCAGA

AGATTTCGCTGTTTACTACTGTCAACAATATCAGT

CTTGGCCATTGACTTTTGGTCAAGGTACAAAGGTT

GAAATCAAA
```

In other embodiments, the composition comprises either or both of the polynucleotides shown in SEQ ID NO: 371 and SEQ ID NO: 372 below:

```
PC1 heavy chain variable region
                              (SEQ ID NO: 371)
GAGGTGCAGCTGCTGGAATCTGGCGGAGGACTGGT

GCAGCCTGGCGGCTCTCTGAGACTGTCTTGTGCCG

CCAGCGGCTTCACCTTCAGCAGCTACCCTATGAGC

TGGGTGCGCCAGGCCCCTGGCAAAGGACTGGAATG

GGTGTCCGCCATCGGAGGCTCTGGCGGCAGCACCT

ACTACGCCGATAGCGTGAAGGGCCGGTTCACCATC
```

-continued

AGCCGGGACAACAGCAAGAACACCCTGTACCTGCA

AATGAACAGCCTGCGGGCCGAGGACACCGCCGTGT

ACTACTGTGCCAGATACTGGCCCATGGACAGCTGG

GGCCAGGGAACTTTGGTCACCGTCTCCTCA

PC1 light chain variable region
(SEQ ID NO: 372)
GAGATCGTGCTGACACAGAGCCCTGGCACCCTGAG

CCTGTCTCCAGGCGAAAGAGCCACCCTGTCCTGCA

AAGCCAGCCAGAGCGTGTCCAGCACATACCTGGCC

TGGTATCA GCAAAAGCCCGGCCAGGCTCCCCGGC

TGCTGATCTACGATGCCTCTTCTAGAGCCCCTGG

CATCCCCGACAGATTCAGCGGCTCTGGCAGCGGCA

CCGACTTCACCCTGACCATCAGCAGACTGGAACC

CGAGGACTTCGCCGTGTACTACTGCCAGCAGTACA

GCACCAGCCCCCTGACCTTTGGCCAGGGCACAAA

GGTGGAGATCAAA.

In other embodiments, the composition comprises either or both of the polynucleotides shown in SEQ ID NO: 373 and SEQ ID NO: 374 below:

PC1C12 heavy chain variable region
(SEQ ID NO: 373)
GAGGTGCAGCTGCTGGAATCTGGCGGAGGACTGGT

GCAGCCTGGCGGCTCTCTGAGACTGTCTTGTGCCG

CCAGCGGCTTCACCTTCAGCAGCTACCCTATGAGC

TGGGTGCGCCAGGCCCCTGGTAAAGGTTTGGAATG

GGTTTCTGCTATTGGTGGTTCAGGTGGTTGGAGTT

ATTATGCCGATTCTGTTAAGGGTAGATTCACCATT

TCTAGAGACAACTCTAAGAACACCTTGTACTTGCA

AATGAACTCCTTGAGAGCTGAAGATACTGCTGTTT

ATTACTGTGCTAGATACTGGCCAATGGATTCTTGG

GGTCAAGGTACTCTGGTCACCGTCTCCTCA

PC1C12 light chain variable region
(SEQ ID NO: 374)
GAGATCGTGCTGACACAGAGCCCTGGCACCCTGAG

CCTGTCTCCTGGTGAAAGAGCTACTTTGTCTTGTT

GGTTGTCTCAATCTGTTTCCTCTACTTACTTGGCT

TGGTATCAACAAAAACCAGGTCAAGCTCCAAGATT

ATTGATCTACGATGCTTCTTCTAGAGCACCAGGTA

TTCCAGATAGATTTTCTGGTTCTGGTTCCGGTACT

GATTTCACTTTGACTATCTCTAGATTGGAACCAGA

AGATTTCGCTGTTTACTACTGCCAACAATACTCTG

AGTGGCCATTGACTTTTGGTCAAGGTACAAAGGTT

GAAATCAAA.

In other embodiments, the composition comprises either or both of the polynucleotides shown in SEQ ID NO: 375 and SEQ ID NO: 376 below:

COM22 heavy chain variable region
(SEQ ID NO: 375)
GAGGTGCAGCTGCTGGAATCTGGCGGAGGACTGGT

GCAGCCTGGCGGCTCTCTGAGACTGTCTTGTGCCG

CCAGCGGCTTCACCTTCAGCAGCTACGCCATGAAC

TGGGTGCGCCAGGCCCCTGGTAAAGGTTTGGAATG

GGTTTCTGCTATTTCTGATTCTGGTGGTTCTAGGT

GGTATGCCGATTCTGTTAAGGGTAGATTCACCATT

TCTAGAGACAACTCTAAGAACACCTTGTACTTGCA

AATGAACTCCTTGAGAGCTGAAGATACTGCTGTTT

ATTACTGTACGCGGTACTGGCCAATGGATATTTGG

GGTCAAGGTACTCTGGTCACCGTCTCCTCA

COM22 light chain variable region
(SEQ ID NO: 376)
GAGATCGTGCTGACACAGAGCCCTGGCACCCTGAG

CCTGTCTCCTGGTGAAAGAGCTACTTTGTCTTGTT

GGTTGTCTCAATCTGTTTCCTCTACTTACTTGGCT

TGGTATCAACAAAAACCAGGTCAAGCTCCAAGATT

ATTGATCTACGATGCTTCTTCTAGAGCACCAGGTA

TTCCAGATAGATTTTCTGGTTCTGGTTCCGGTACT

GATTTCACTTTGACTATCTCTAGATTGGAACCAGA

AGATTTCGCTGTTTACTACTGCCAACAATACTCTG

AGTGGCCATTGACTTTTGGTCAAGGTACAAAGGTT

GAAATCAAA.

Expression vectors, and administration of polynucleotide compositions are further described herein.

In another aspect, the invention provides a method of making any of the polynucleotides described herein.

Polynucleotides complementary to any such sequences are also encompassed by the invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the invention. Further, alleles of the genes comprising the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a BCMA specific CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In some embodiments the signal peptide comprises the amino acid sequence shown in SEQ ID NO: 318 or 329. Those skilled in the art will recognize that, in view of the degeneracy of the genetic code, considerable sequence variation is possible among these polynucleotide molecules. In some embodiments, nucleic acid sequences of the invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

In some embodiments, a polynucleotide according to the invention comprises the nucleic acid sequence selected from the group consisting of: SEQ. ID NO: 1397. The invention relates to polynucleotides comprising a nucleic acid sequence that has at least 70%, preferably at least 80%, more preferably at least 90%, 95%, 97%, or 99% sequence identity with nucleic acid sequence selected from the group consisting of SEQ ID NO: 1397.

Methods of Engineering an Immune Cell

Methods of preparing immune cells for use in immunotherapy are provided herein. In some embodiments, the methods comprise introducing a CAR according to the invention into immune cells, and expanding the cells. In some embodiments, the invention relates to a method of engineering an immune cell comprising: providing a cell and expressing at the surface of the cell at least one CAR as described above. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the method comprises: transfecting the cell with at least one polynucleotide encoding CAR as described above, and expressing the polynucleotides in the cell.

In some embodiments, the polynucleotides are present in lentiviral vectors for stable expression in the cells.

In some embodiments, the method can further comprise a step of genetically modifying a cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, CD52, GR, PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or Cas9 endonuclease.

In some embodiments, an additional catalytic domain is used with a rare-cutting endonuclease to enhance its capacity to inactivate targeted genes. For example, an additional catalytic domain can be a DNA end-processing enzyme. Non-limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non-limiting examples of such catalytic domain comprise of a protein domain or catalytically active derivate of the protein domain selected from the group consisting of hExoI (EXO1_HUMAN), Yeast ExoI (EXO1_YEAST), *E. coli* ExoI, Human TREX2, Mouse TREX1, Human $TREX_1$, Bovine TREX1, Rat TREX1, TdT (terminal deoxynucleotidyl transferase) Human DNA2, Yeast DNA2 (DNA2_YEAST). In some embodiments, an additional catalytic domain can have a 3'-5'-exonuclease activity, and In some embodiments, said additional catalytic domain is TREX, more preferably TREX2 catalytic domain (WO2012/058458). In some embodiments, said catalytic domain is encoded by a single chain TREX polypeptide. The additional catalytic domain may be fused to a nuclease fusion protein or chimeric protein. In some embodiments, the additional catalytic domain is fused using, for example, a peptide linker.

In some embodiments, the method further comprises a step of introducing into cells an exogeneous nucleic acid comprising at least a sequence homologous to a portion of the target nucleic acid sequence, such that homologous recombination occurs between the target nucleic acid sequence and the exogeneous nucleic acid. In some embodiments, said exogenous nucleic acid comprises first and second portions which are homologous to region 5' and 3' of the target nucleic acid sequence, respectively. The exogenous nucleic acid may also comprise a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogeneous nucleic acid. In some embodiments, homologous sequences of at least about 50 bp, greater than about 100 bp, or greater than about 200 bp can be used within the donor matrix. The exogenous nucleic acid can be, for example without limitation, from about 200 bp to about 6000 bp, more preferably from about 1000 bp to about 2000 bp. Shared nucleic acid homologies are located in regions flanking upstream and downstream the site of the break, and the nucleic acid sequence to be introduced is located between the two arms.

In some embodiments, a nucleic acid successively comprises a first region of homology to sequences upstream of said cleavage; a sequence to inactivate a targeted gene selected from the group consisting of TCRα, TCRβ, CD52, glucocorticoid receptor (GR), deoxycytidine kinase (DCK), and an immune checkpoint protein such as for example programmed death-1 (PD-1); and a second region of homology to sequences downstream of the cleavage. The polynucleotide introduction step can be simultaneous, before or after the introduction or expression of the rare-cutting endonuclease. Depending on the location of the target nucleic acid sequence wherein break event has occurred, such exogenous nucleic acid can be used to knock-out a gene, e.g. when exogenous nucleic acid is located within the open reading frame of the gene, or to introduce new sequences or genes of interest. Sequence insertions by using such exogenous nucleic acid can be used to modify a targeted existing gene, by correction or replacement of the gene (allele swap as a non-limiting example), or to up- or down-regulate the expression of the targeted gene (promoter swap as non-limiting example), the targeted gene correction or replacement. In some embodiments, inactivation of a genes selected from the group consisting of TCRα, TCRβ, CD52, GR, DCK, and immune checkpoint proteins, can be done at a precise genomic location targeted by a specific TALE-nuclease, wherein said specific TALE-nuclease catalyzes a cleavage and wherein the exogenous nucleic acid successively comprising at least a region of homology and a sequence to inactivate one targeted gene selected from the group consisting of TCRα, TCRβ, CD52, GR, DCK, immune checkpoint proteins which is integrated by homologous recombination. In some embodiments, several genes can be, successively or at the same time, inactivated by using several TALE-nucleases respectively and specifically targeting one defined gene and several specific polynucleotides for specific gene inactivation.

In some embodiments, the method comprises inactivation of one or more additional genes selected from the group consisting of TCRα, TCRβ, CD52, GR, DCK, and immune checkpoint proteins. In some embodiments, inactivation of a gene can be accomplished by introducing into the cells at least one rare-cutting endonuclease such that the rare-cutting endonuclease specifically catalyzes cleavage in a targeted sequence of the cell genome; and optionally, introducing into the cells an exogenous nucleic acid successively comprising a first region of homology to sequences upstream of the cleavage, a sequence to be inserted in the genome of the cell, and a second region of homology to sequences downstream of the cleavage; wherein the introduced exogenous nucleic acid inactivates a gene and integrates at least one exogenous polynucleotide sequence encoding at least one recombinant protein of interest. In some embodiments, the exogenous polynucleotide sequence is integrated within a gene encoding a protein selected from the group consisting of TCRα, TCRβ, CD52, GR, DCK, and immune checkpoint protein.

In another aspect, a step of genetically modifying cells can comprise: modifying T cells by inactivating at least one gene expressing a target for an immunosuppressive agent, and; expanding the cells, optionally in presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others may act through activation of T cells or by inhibiting the activation of helper cells. The methods according to the invention allow conferring immunosuppressive resistance to T cells for immunotherapy by inactivating the target of the immunosuppressive agent in T cells. As non-limiting examples, targets for immunosuppressive agent can be a receptor for an immunosuppressive agent such as for example without limitation CD52, glucocorticoid receptor (GR), FKBP family gene members, and cyclophilin family gene members.

In some embodiments, the genetic modification of the method involves expression, in provided cells to engineer, of one rare-cutting endonuclease such that the rare-cutting endonuclease specifically catalyzes cleavage in one targeted gene, thereby inactivating the targeted gene. In some embodiments, a method of engineering cells comprises at least one of the following steps: providing a T cell, such as from a cell culture or from a blood sample; selecting a gene in the T cell expressing a target for an immunosuppressive agent; introducing into the T cell a rare-cutting endonuclease able to selectively inactivate by DNA cleavage, preferably by double-strand break the gene encoding a target for the immunosuppressive agent, and expanding the cells, optionally in presence of the immunosuppressive agent.

In some embodiments, the method comprises: providing a T cell, such as from a cell culture or from a blood sample; selecting a gene in the T cell wherein the gene expresses a target for an immunosuppressive agent; transfecting the T cell with nucleic acid encoding a rare-cutting endonuclease able to selectively inactivate by DNA cleavage, preferably by double-strand break the gene encoding a target for the immunosuppressive agent, and expressing the rare-cutting endonucleases into the T cells; and expanding the cells, optionally in presence of the immunosuppressive agent.

In some embodiments, the rare-cutting endonuclease specifically targets CD52 or GR. In some embodiments, the gene selected for inactivation encodes CD52, and the immunosuppressive treatment comprises a humanized antibody targeting CD52 antigen. In some embodiments, the gene selected for inactivation encodes GR, and the immunosuppressive treatment comprises a corticosteroid such as dexamethasone. In some embodiments, the gene selected for inactivation is a FKBP family gene member or a variant thereof and the immunosuppressive treatment comprises FK506, also known as Tacrolimus or fujimycin. In some embodiments, the FKBP family gene member is FKBP12 or a variant thereof. In some embodiments, gene selected for inactivation is a cyclophilin family gene member or a variant thereof and the immunosuppressive treatment comprises cyclosporine.

In some embodiments, the rare-cutting endonuclease can be, for example, a meganuclease, a zinc finger nuclease, or a TALE-nuclease (TALEN). In some embodiments, the rare-cutting endonuclease is a TALE-nuclease.

Also provided herein are methods of engineering T cells, suitable for immunotherapy, wherein the methods comprise: genetically modifying T cells by inactivating at least immune checkpoint protein. In some embodiments the immune checkpoint protein is, for example, PD-1 and/or CTLA-4.In some embodiments, methods of genetically modifying a cell comprises: modifying T cells by inactivating at least one immune checkpoint protein; and expanding the cells. Immune checkpoint proteins include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), B7H5 (also known as C10orf54, homolog of mouse vista gene, accession number: NM_022153.1), LAIR1 (also known as CD305, GenBank accession number: CR542051.1), SIGLEC10 (GeneBank accession number: AY358337.1), 2B4 (also known as CD244, accession number: NM_001166664.1), which directly inhibit immune cells. For example, CTLA-4 is a cell-surface protein expressed on certain CD4 and CD8 T cells; when engaged by its ligands (B7-1 and B7-2) on antigen presenting cells, T cell activation and effector function are inhibited.

In some embodiments, said method to engineer cells comprises at least one of the following steps: providing a T cell, such as from a cell culture or from a blood sample; introducing into the T cell a rare-cutting endonuclease able to selectively inactivate by DNA cleavage, preferably by double-strand break one gene encoding a immune checkpoint protein; and expanding the cells. In some embodiments, the method comprises: providing a T cell, such as from a cell culture or from a blood sample; transfecting said T cell with nucleic acid encoding a rare-cutting endonuclease able to selectively inactivate by DNA cleavage, preferably by double-strand break a gene encoding a immune checkpoint protein; expressing the rare-cutting endonucleases into the T cells; expanding the cells. In some embodiments, the rare-cutting endonuclease specifically targets a gene selected from the group consisting of: PD-1, CTLA-4, LAG3, Tim3, BTLA, BY55, TIGIT, B7H5, LAIR1, SIGLEC10, 2B4, TCRα, and TCRβ. In some embodiments, the rare-cutting endonuclease can be a meganuclease, a zinc finger nuclease or a TALE-nuclease. In some embodiments, the rare-cutting endonuclease is a TALE-nuclease.

In some embodiments, the present invention can be particularly suitable for allogeneic immunotherapy. In such embodiments, cells may be modified by a method comprising: inactivating at least one gene encoding a component of the T cell receptor (TCR) in T cells; and expanding the T cells. In some embodiments, the genetic modification of the method relies on the expression, in provided cells to engineer, of one rare-cutting endonuclease such that the rare-cutting endonuclease specifically catalyzes cleavage in one targeted gene thereby inactivating the targeted gene. In some embodiments, said method to engineer cells comprises at least one of the following steps: providing a T cell, such as from a cell culture or from a blood sample; introducing into the T cell a rare-cutting endonuclease able to selectively inactivate by DNA cleavage, preferably by double-strand break at least one gene encoding a component of the T cell receptor (TCR), and expanding the cells.

In some embodiments, the method comprises: providing a T cell, such as from a cell culture or from a blood sample; transfecting said T cell with nucleic acid encoding a rare-cutting endonuclease able to selectively inactivate by DNA cleavage, preferably by double-strand break at least one gene encoding a component of the T cell receptor (TCR); expressing the rare-cutting endonucleases into the T cells; sorting the transformed T cells, which do not express TCR on their cell surface; and expanding the cells.

In some embodiments, the rare-cutting endonuclease can be a meganuclease, a zinc finger nuclease or a TALE-nuclease. In some embodiments, the rare-cutting endonuclease is a TALE-nuclease. In some embodiments the TALE-nucleases recognize and cleave a sequence encoding TCRα or TCRβ. In some embodiments a TALE-nuclease comprises a polypeptide sequence selected from the amino acid sequence shown in SEQ ID NO: 334, 335, 336, 337, 338, 339, 340, or 341

TALE-Nuclease Polypeptide Sequences:

```
Repeat TRAC T01-L
                                    (SEQ ID NO: 334)
LTPQQVVAIASNGGGKQALETVQRLLPVLCQAHGL

TPQQVVAIASNNGGKQALETVQRLLPVLCQAHGLT
```

PQQVVAIASNGGGKQALETVQRLLPVLCQAHGLTP

EQVVAIASHDGGKQALETVQRLLPVLCQAHGLTPE

QVVAIASHDGGKQALETVQRLLPVLCQAHGLTPEQ

VVAIASHDGGKQALETVQRLLPVLCQAHGLTPEQV

VAIASNIGGKQALETVQALLPVLCQAHGLTPEQVV

AIASHDGGKQALETVQRLLPVLCQAHGLTPEQVVA

IASNIGGKQALETVQALLPVLCQAHGLTPQQVVAI

ASNNGGKQALETVQRLLPVLCQAHGLTPEQVVAIA

SNIGGKQALETVQALLPVLCQAHGLTPQQVVAIAS

NGGGKQALETVQRLLPVLCQAHGLTPEQVVAIASN

IGGKQALETVQALLPVLCQAHGLTPQQVVAIASNG

GGKQALETVQRLLPVLCQAHGLTPEQVVAIASHDG

GKQALETVQRLLPVLCQAHGLTPQQVVAIASNGGG

RPALE

Repeat TRAC T01-R
                    (SEQ ID NO: 335)
LTPEQVVAIASHDGGKQALETVQRLLPVLCQAHGL

TPQQVVAIASNGGGKQALETVQRLLPVLCQAHGLT

PEQVVAIASHDGGKQALETVQRLLPVLCQAHGLTP

EQVVAIASNIGGKQALETVQALLPVLCQAHGLTPQ

QVVAIASNNGGKQALETVQRLLPVLCQAHGLTPEQ

VVAIASHDGGKQALETVQRLLPVLCQAHGLTPQQV

VAIASNGGGKQALETVQRLLPVLCQAHGLTPQQVV

AIASNNGGKQALETVQRLLPVLCQAHGLTPQQVVA

IASNNGGKQALETVQRLLPVLCQAHGLTPQQVVAI

ASNGGGKQALETVQRLLPVLCQAHGLTPEQVVAIA

SNIGGKQALETVQALLPVLCQAHGLTPEQVVAIAS

HDGGKQALETVQRLLPVLCQAHGLTPEQVVAIASN

IGGKQALETVQALLPVLCQAHGLTPEQVVAIASHD

GGKQALETVQRLLPVLCQAHGLTPQQVVAIASNNG

GKQALETVQRLLPVLCQAHGLTPQQVVAIASNGGG

RPALE

Repeat TRBC T01-L
                    (SEQ ID NO: 336)
LTPQQVVAIASNNGGKQALETVQRLLPVLCQAHGL

TPQQVVAIASNGGGKQALETVQRLLPVLCQAHGLT

PQQVVAIASNNGGKQALETVQRLLPVLCQAHGLTP

QQVVAIASNGGGKQALETVQRLLPVLCQAHGLTPQ

QVVAIASNGGGKQALETVQRLLPVLCQAHGLTPQQ

VVAIASNGGGKQALETVQRLLPVLCQAHGLTPQQV

VAIASNNGGKQALETVQRLLPVLCQAHGLTPEQVV

AIASNIGGKQALETVQALLPVLCQAHGLTPQQVVA

IASNNGGKQALETVQRLLPVLCQAHGLTPEQVVAI

ASHDGGKQALETVQRLLPVLCQAHGLTPEQVVAIA

SHDGGKQALETVQRLLPVLCQAHGLTPEQVVAIAS

NIGGKQALETVQALLPVLCQAHGLTPQQVVAIASN

GGGKQALETVQRLLPVLCQAHGLTPEQVVAIASHD

GGKQALETVQRLLPVLCQAHGLTPEQVVAIASNIG

GKQALETVQALLPVLCQAHGLTPQQVVAIASNGGG

RPALE

Repeat TRBC T01-R
                    (SEQ ID NO: 337)
NPQRSTVWYLTPQQVVAIASNNGGKQALETVQRLL

PVLCQAHGLTPQQVVAIASNGGGKQALETVQRLLP

VLCQAHGLTPQQVVAIASNNGGKQALETVQRLLPV

LCQAHGLTPQQVVAIASNNGGKQALETVQRLLPVL

CQAHGLTPEQVVAIASHDGGKQALETVQRLLPVLC

QAHGLTPEQVVAIASHDGGKQALETVQRLLPVLCQ

AHGLTPQQVVAIASNGGGKQALETVQRLLPVLCQA

HGLTPQQVVAIASNGGGKQALETVQRLLPVLCQAH

GLTPQQVVAIASNGGGKQALETVQRLLPVLCQAHG

LTPQQVVAIASNGGGKQALETVQRLLPVLCQAHGL

TPQQVVAIASNNGGKQALETVQRLLPVLCQAHGLT

PQQVVAIASNNGGKQALETVQRLLPVLCQAHGLTP

QQVVAIASNNGGKQALETVQRLLPVLCQAHGLTPQ

QVVAIASNGGGKQALETVQRLLPVLCQAHGLTPQQ

VVAIASNNGGKQALETVQRLLPVLCQAHGLTPQQV

VAIASNGGGRPALE

Repeat TRBC T02-L
                    (SEQ ID NO: 338)
LTPEQVVAIASHDGGKQALETVQRLLPVLCQAHGL

TPEQVVAIASHDGGKQALETVQRLLPVLCQAHGLT

PEQVVAIASHDGGKQALETVQRLLPVLCQAHGLTP

EQVVAIASNIGGKQALETVQALLPVLCQAHGLTPE

QVVAIASHDGGKQALETVQRLLPVLCQAHGLTPEQ

VVAIASHDGGKQALETVQRLLPVLCQAHGLTPEQV

VAIASHDGGKQALETVQRLLPVLCQAHGLTPQQVV

AIASNNGGKQALETVQRLLPVLCQAHGLTPEQVVA

IASNIGGKQALETVQALLPVLCQAHGLTPQQVVAI

ASNNGGKQALETVQRLLPVLCQAHGLTPQQVVAIA

SNNGGKQALETVQRLLPVLCQAHGLTPQQVVAIAS

NGGGKQALETVQRLLPVLCQAHGLTPEQVVAIASH

DGGKQALETVQRLLPVLCQAHGLTPQQVVAIASNN

GGKQALETVQRLLPVLCQAHGLTPEQVVAIASHDG

GKQALETVQRLLPVLCQAHGLTPQQVVAIASNGGG

```
Repeat TRBC T02-R
                                    (SEQ ID NO: 339)
LTPQQVVAIASNNGGKQALETVQRLLPVLCQAHGL

TPQQVVAIASNNGGKQALETVQRLLPVLCQAHGLT

PQQVVAIASNNGGKQALETVQRLLPVLCQAHGLTP

EQVVAIASNIGGKQALETVQALLPVLCQAHGLTPQ

QVVAIASNNGGKQALETVQRLLPVLCQAHGLTPEQ

VVAIASNIGGKQALETVQALLPVLCQAHGLTPQQV

VAIASNGGGKQALETVQRLLPVLCQAHGLTPEQVV

AIASHDGGKQALETVQRLLPVLCQAHGLTPQQVVA

IASNGGGKQALETVQRLLPVLCQAHGLTPEQVVAI

ASHDGGKQALETVQRLLPVLCQAHGLTPQQVVAIA

SNGGGKQALETVQRLLPVLCQAHGLTPQQVVAIAS

NNGGKQALETVQRLLPVLCQAHGLTPEQVVAIASH

DGGKQALETVQRLLPVLCQAHGLTPQQVVAIASNG

GGKQALETVQRLLPVLCQAHGLTPQQVVAIASNGG

GKQALETVQRLLPVLCQAHGLTPQQVVAIASNGGG

RPALE

Repeat CD52_T02-L
                                    (SEQ ID NO: 340)
LTPQQVVAIASNGGGKQALETVQRLLPVLCQAHGL

TPEQVVAIASHDGGKQALETVQRLLPVLCQAHGLT

PEQVVAIASHDGGKQALETVQRLLPVLCQAHGLTP

QQVVAIASNGGGKQALETVQRLLPVLCQAHGLTPE

QVVAIASHDGGKQALETVQRLLPVLCQAHGLTPEQ

VVAIASHDGGKQALETVQRLLPVLCQAHGLTPQQV

VAIASNGGGKQALETVQRLLPVLCQAHGLTPEQVV

AIASNIGGKQALETVQALLPVLCQAHGLTPEQVVA

IASHDGGKQALETVQRLLPVLCQAHGLTPQQVVAI

ASNGGGKQALETVQRLLPVLCQAHGLTPEQVVAIA

SHDGGKQALETVQRLLPVLCQAHGLTPEQVVAIAS

NIGGKQALETVQALLPVLCQAHGLTPEQVVAIASH

DGGKQALETVQRLLPVLCQAHGLTPEQVVAIASHD

GGKQALETVQRLLPVLCQAHGLTPEQVVAIASNIG

GKQALETVQALLPVLCQAHGLTPQQVVAIASNGGG

RPALE

Repeat CD52_T02-R
                                    (SEQ ID NO: 341)
LTPQQVVAIASNGGGKQALETVQRLLPVLCQAHGL

TPQQVVAIASNNGGKQALETVQRLLPVLCQAHGLT

PEQVVAIASHDGGKQALETVQRLLPVLCQAHGLTP

QQVVAIASNGGGKQALETVQRLLPVLCQAHGLTPE

QVVAIASHDGGKQALETVQRLLPVLCQAHGLTPQQ

VVAIASNGGGKQALETVQRLLPVLCQAHGLTPQQV

VAIASNGGGKQALETVQRLLPVLCQAHGLTPEQVV

AIASNIGGKQALETVQALLPVLCQAHGLTPEQVVA

IASHDGGKQALETVQRLLPVLCQAHGLTPEQVVAI

ASHDGGKQALETVQRLLPVLCQAHGLTPQQVVAIA

SNGGGKQALETVQRLLPVLCQAHGLTPQQVVAIAS

NNGGKQALETVQRLLPVLCQAHGLTPQQVVAIASN

GGGKQALETVQRLLPVLCQAHGLTPEQVVAIASNI

GGKQALETVQALLPVLCQAHGLTPEQVVAIASHDG

GKQALETVQRLLPVLCQAHGLTPQQVVAIASNGGG

RPALE
```

In another aspect, one another step of genetically modifying cell can be a method of expanding TCRα deficient T cells comprising introducing into the T cell pTα (also known as preTCRα) or a functional variant thereof and expanding the cells, optionally through stimulation of the CD3 complex. In some embodiments, the method comprises: a) transfecting the cells with nucleic acid encoding at least a fragment of pTα to support CD3 surface expression; b) expressing said pTα into the cells; and c) expanding the cells, optionally through stimulation of the CD3 complex.

Also provided are methods of preparing T cells for immunotherapy comprising steps of the method for expansion for T cell. In some embodiments, the pTα polynucleotide sequence can be introduced randomly or by homologous recombination. In some embodiments, the insertion can be associated with the inactivation of the TCRα gene. Different functional variants of pTα can be used. A "functional variant" of the peptide refers to a molecule substantially similar to either the entire peptide or a fragment thereof. A "fragment" of the pTα or functional variant thereof refers to any subset of the molecule, that is, a shorter peptide than the full-length pTα. In some embodiments, pTα or functional variants can be, for example, full-length pTα or a C-terminal truncated pTα version. C-terminal truncated pTα lacks in C-terminal end one or more residues. As non limiting examples, C-terminal truncated pTα version lacks 18, 48, 62, 78, 92, 110 or 114 residues from the C-terminus of the protein. Amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In preferred embodiment, at least one mutation is introduced in the different pTα versions as described above to affect dimerization. As non limiting example, mutated residue can be at least W46R, D22A, K24A, R102A or R117A of the human pTα protein or aligned positions using CLUSTALW method on pTα family or homologue member. Preferably pTα or variant thereof as described above comprise the mutated residue W46R or the mutated residues D22A, K24A, R102A and R117A. In some embodiments, said pTα or variants are also fused to a signal-transducing domain such as CD28, OX40, ICOS, CD27, CD137 (4-1 BB) and CD8 as non limiting examples. The extracellular domain of pTα or variants as described above can be fused to a fragment of the TCRα protein, particularly the transmembrane and intracellular domain of TCRα. pTα variants can also be fused to the intracellular domain of TCRα.

In some embodiments, pTα versions can be fused to an extracellular ligand-binding domain. In some embodiments, pTα or functional variant thereof is fused to a single chain antibody fragment (scFv) comprising the light and the heavy variable fragment of a target antigen specific monoclonal antibody joined by a flexible linker.

The term "TCRα deficient T cell" refers to an isolated T cell that lacks expression of a functional TCRα chain. This may be accomplished by different means, as non limiting examples, by engineering a T cell such that it does not express any functional TCRα on its cell surface or by engineering a T cell such that it produces very little functional TCRα chain on its surface or by engineering a T cell to express mutated or truncated form of TCRα chain. TCRα deficient cells can no longer be expanded through CD3 complex. Thus, to overcome this problem and to allow proliferation of TCRα deficient cells, pTα or functional variant thereof is introduced into the cells, thus restoring a functional CD3 complex. In some embodiments, the method further comprises introducing into said T cells rare-cutting endonucleases able to selectively inactivate by DNA cleavage one gene encoding one component of the T cell receptor (TCR). In some embodiments, the rare-cutting endonuclease is a TALE-nuclease.

In another aspect, engineered T cells obtained by the methods described herein can be contacted with bispecific antibodies. For example, the T cells can be contacted with bispecific antibodies ex vivo prior to administration to a patient, or in vivo following administration to a patient. Bispecific antibodies comprise two variable regions with distinct antigen properties that facilitate bringing the engineered cells into proximity to a target antigen. As a non-limiting example, a bispecific antibody can be directed against a tumor marker and lymphocyte antigen, such as for example without limitation CD3, and has the potential to redirect and activate any circulating T cells against tumors.

In some embodiments, polynucleotides encoding polypeptides according to the present invention can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transfecting T cell. In some embodiments, the method comprises: contacting a T cell with RNA and applying to T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transfecting T cell comprising contacting said T cell with RNA and applying to T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, as non limiting examples, an RNA encodes a rare-cutting endonuclease, one monomer of the rare-cutting endonuclease such as half-TALE-nuclease, a CAR, at least one component of the multi-chain chimeric antigen receptor, a pTα or functional variant thereof, an exogenous nucleic acid, and/or one additional catalytic domain.

Engineered Immune Cells

The invention also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g. retroviruses, adenoviruses), liposomes, and the like. Transient transformation methods include, for example without limitation, microinjection, electroporation or particle bombardment. Polynucleotides may be included in vectors, such as for example plasmid vectors or viral vectors.

Also provided herein are isolated cells and cell lines obtained by the above-described methods of engineering cells provided herein. In some embodiments, an isolated cell comprises at least one CAR as described above. In some embodiments, an isolated cell comprises a population of CARs, each CAR comprising different extracellular ligand-binding domains.

Also provided herein are isolated immune cells obtained according to any one of the methods described above. Any immune cell capable of expressing heterologous DNAs can be used for the purpose of expressing the CAR of interest. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+ T-lymphocytes and CD8+ T-lymphocytes.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer or from a patient diagnosed with an infection. In some embodiments, cells can be part of a mixed population of cells which present different phenotypic characteristics.

Also provided herein are cell lines obtained from a transformed T cell according to any of the above-described methods. Also provided herein are modified cells resistant to an immunosuppressive treatment. In some embodiments, an isolated cell according to the invention comprises a polynucleotide encoding a CAR.

The immune cells of the invention can be activated and expanded, either prior to or after genetic modification of the T cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFp, and TNF, or any other additives for the growth of cells known to the skilled artisan.

Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics In some embodiments, the cells of the invention can be expanded by co-culturing with tissue or cells. The cells can also be expanded in vivo, for example in the subject's blood after administrating the cell into the subject.

In some embodiments, an isolated cell according to the present invention comprises one inactivated gene selected from the group consisting of CD52, GR, PD-1, CTLA-4, LAG3, Tim3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present invention comprises two inactivated genes selected from the group consisting of: CD52 and GR, CD52 and TCRα, CDR52 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene.

In some embodiments, TCR is rendered not functional in the cells according to the invention by inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present invention. Modified cells disclosed herein can be used in for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are BCMA specific CAR-T cells comprising an inactivated dCK gene. In some embodiments, the dCK knockout cells are made by transfection of T cells using polynucleotides encoding specific TAL-nuclease directed against dCK genes by, for example, electroporation of mRNA. The dCK knockout BCMA specific CAR-T cells are resistant to PNAs, including for example clorofarabine and/or fludarabine, and maintain T cell cytotoxic activity toward BCMA-expressing cells.

In some embodiments, isolated cells or cell lines of the invention can comprise a pTα or a functional variant thereof. In some embodiments, an isolated cell or cell line can be further genetically modified by inactivating the TCRα gene.

In some embodiments, the CAR-T cell comprises a polynucleotide encoding a suicide polypeptide, such as for example RQR8. See, e.g., WO2013153391A, which is hereby incorporated by reference in its entirety. In CAR-T cells comprising the polynucleotide, the suicide polypeptide is expressed at the surface of a CAR-T cell. In some embodiments, the suicide polypeptide comprises the amino acid sequence shown in SEQ ID NO: 342.

```
                                          (SEQ ID NO: 342)
CPYSNPSLCSGGGGSELPTQGTFSNVSTNVSPAKPTTTACPY

SNPSLCSGGGGSPAPRPPTPAPTIASQPLSLRPEACRPAAGG

AVHTRGLDFACDIYIWAPLAGTCGVLLLSLVITLYCNHRN

RRRVCKCPRPVV
```

The suicide polypeptide may also comprise a signal peptide at the amino terminus. In some embodiments, the suicide polypeptide comprises the amino acid sequence shown in SEQ ID NO: 400.

```
                                          (SEQ ID NO: 400)
MGTSLLCWMALCLLGADHADACPYSNPSLCSGGGGSELPTQG

TFSNVSTNVSPAKPTTTACPYSNPSLCSGGGGSPAPRPPTPA

PTIASQPLSLRPEACRPAAGGAVHTRGLDFACDIYIWAPLAG

TCGVLLLSLVITLYCNHRNRRRVCKCPRPVV
```

When the suicide polypeptide is expressed at the surface of a CAR-T cell, binding of rituximab to the R epitopes of the polypeptide causes lysis of the cell. More than one molecule of rituximab may bind per polypeptide expressed at the cell surface. Each R epitope of the polypeptide may bind a separate molecule of rituximab. Deletion of BCMA specific CAR-T cells may occur in vivo, for example by administering rituximab to a patient. The decision to delete the transferred cells may arise from undesirable effects being detected in the patient which are attributable to the transferred cells, such as for example, when unacceptable levels of toxicity are detected.

In some embodiments, the CAR-T cell comprises a selected epitope within the scFv having a specificity to be recognized by a specific antibody. See, e.g., PCT application "mAb-DRIVEN CHIMERIC ANTIGEN RECEPTOR SYSTEMS FOR SORTING/DEPLETING ENGINEERED IMMUNE CELLS," filed on Jan. 25, 2016, which is hereby incorporated by reference in its entirety. Such an epitope facilitates sorting and/or depleting the CAR-T cells. The epitope can be selected from any number of epitopes known in the art. In some embodiments, the epitope can be a target of a monoclonal antibody approved for medical use, such as, for example without limitation, the CD20 epitope recognized by rituximab. In some embodiments, the epitope comprises the amino acid sequence shown in SEQ ID NO: 397.

```
                          (SEQ ID NO: 397)
CPYSNPSLC
```

In some embodiments, the epitope is located within the CAR. For example without limitation, the epitope can be located between the scFv and the hinge of a CAR. In some embodiments, two instances of the same epitope, separate by linkers, may be used in the CAR. For example, the polypeptide comprising the amino acid sequence shown in SEQ ID NO: 398 can be used within a CAR, located between the light chain variable region and the hinge.

```
                                          (SEQ ID NO: 398)
GSGGGGSCPYSNPSLCSGGGGSCPYSNPSLCSGGGGS
```

In some embodiments, the epitope-specific antibody may be conjugated with a cytotoxic drug. It is also possible to promote CDC cytotoxicity by using engineered antibodies on which are grafted component(s) of the complement system. In some embodiments, activation of the CAR-T cells can be modulated by depleting the cells using an antibody which recognizes the epitope.

Therapeutic Applications

Isolated cells obtained by the methods described above, or cell lines derived from such isolated cells, can be used as a medicament. In some embodiments, such a medicament can be used for treating cancer. In some embodiments, the cancer is multiple myeloma malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, or another B-cell related lymphomas.

In some embodiments, an isolated cell according to the invention, or cell line derived from the isolated cells, can be used in the manufacture of a medicament for treatment of a cancer in a patient in need thereof.

Also provided herein are methods for treating patients. In some embodiments the method comprises providing an immune cell of the invention to a patient in need thereof. In some embodiments, the method comprises a step of administrating transformed immune cells of the invention to a patient in need thereof.

In some embodiments, T cells of the invention can undergo robust in vivo T cell expansion and can persist for an extended amount of time.

Methods of treatment of the invention can be ameliorating, curative or prophylactic. The method of the invention may be either part of an autologous immunotherapy or part of an allogenic immunotherapy treatment. The invention is particularly suitable for allogeneic immunotherapy. T cells from donors can be transformed into non-alloreactive cells using standard protocols and reproduced as needed, thereby producing CAR-T cells which may be administered to one or several patients. Such CAR-T cell therapy can be made available as an "off the shelf" therapeutic product.

Cells that can be used with the disclosed methods are described in the previous section. Treatment can be used to treat patients diagnosed with, for example, cancer. Cancers that may be treated include, for example without limitation, cancers that involve B lymphocytes, including any of the above-listed cancers. Types of cancers to be treated with the CARs and CAR-T cells of the invention include, but are not limited to certain leukemia or lymphoid malignancies. Adult tumors/cancers and pediatric tumors/cancers are also included. In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be administrated into patients undergoing an immunosuppressive treatment. Indeed, the invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T cells according to the invention within the patient. The administration of the cells or population of cells according to the invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the invention are preferably administered by intravenous injection.

In some embodiments the administration of the cells or population of cells can comprise administration of, for example, about $10^4$ to about $10^9$ cells per kg body weight including all integer values of cell numbers within those ranges. In some embodiments the administration of the cells or population of cells can comprise administration of about $10^5$ to $10^6$ cells per kg body weight including all integer values of cell numbers within those ranges. The cells or population of cells can be administrated in one or more doses. In some embodiments, said effective amount of cells can be administrated as a single dose. In some embodiments, said effective amount of cells can be administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In some embodiments, an effective amount of cells or composition comprising those cells are administrated parenterally. In some embodiments, administration can be an intravenous administration. In some embodiments, administration can be directly done by injection within a tumor.

In some embodiments of the invention, cells are administered to a patient in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or nataliziimab treatment for MS patients or efaliztimab treatment for psoriasis patients or other treatments for PML patients. In some embodiments, BCMA specific CAR-T cells are administered to a patient in conjunction with one or more of the following: an anti-PD-1 antibody (e.g., nivolumab, pembrolizumab, or PF-06801591), an anti-PD-L1 antibody (e.g., avelumab, atezolizumab, or durvalumab), an anti-OX40 antibody (e.g., PF-04518600), an anti-4-1 BB antibody (e.g., PF-05082566), an anti-MCSF antibody (e.g., PD-0360324), an anti-GITR antibody, and/or an anti-TIGIT antibody. In some embodiments, a BCMA specific CAR comprising the amino acid sequence shown in SEQ ID NO: 396 is administered to a patient in conjunction with anti-PD-L1 antibody avelumab. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM-PATH, anti-CD3 antibodies or other antibody therapies, cytoxin, fludarabine, cyclosporin, FK506, rapamycin, mycoplienolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH, In some embodiments, the cell compositions of the invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the invention. In some embodiments, expanded cells are administered before or following surgery.

Kits

The invention also provides kits for use in the instant methods. Kits of the invention include one or more containers comprising a polynucleotide encoding a BCMA specific CAR, or an engineered immune cell comprising a polynucleotide encoding a BCMA specific CAR as described herein, and instructions for use in accordance with any of the methods of the invention described herein. Generally, these instructions comprise a description of administration of the engineered immune cell for the above described therapeutic treatments.

The instructions relating to the use of the engineered immune cells as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a BCMA antibody. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the invention in any way. Indeed, various modifications of the invention in addition to those shown and described herein will become apparent to those skilled in the art from the foregoing description and fall within the scope of the appended claims.

Representative materials of the present invention were deposited in the American Type Culture Collection (ATCC) on Feb. 9, 2016. The biological deposit having ATCC Accession No. PTA-122834 is a vector comprising a polynucleotide encoding a BCMA specific CAR. The deposit was made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Example 1

Determination of Kinetics and Affinity of BCMA/Human IgG Interactions at 25° C. and/or 37° C.

This example determines the kinetics and affinity of various anti-BCMA antibodies at 25° C. and 37° C.

All experiments were performed on a Bio-Rad Proteon XPR36 surface Plasmon resonance biosensor (Bio-Rad, Hercules, CA). An array of anti-BCMA antibodies was prepared using an amine-coupling method on a Bio-Rad GLC Sensor Chip similar to that described in Abdiche, et al., Anal. Biochem. 411, 139-151 (2011). The analysis temperature for the immobilization was 25° C. and the running buffer was HBS-T+ (10 mM HEPES, 150 mM NaCl, 0.05% Tween-20, pH 7.4). Channels were activated in the analyte (horizontal) direction by injecting a mixture of 1 mM ECD and 0.25 mM NHS for 3 minutes at a flow rate of 30 µL/min. IgGs were immobilized on the activated spots by injecting them in the ligand (vertical) direction at 20 µg/mL in 10 mM Acetate pH 4.5 buffer for 1.5 minutes at 30 µg/mL. The activated surfaces were blocked by injecting 1M ethanolamine, pH 8.5 in the analyte direction for 3 minutes at 30 µL/min.

The analysis temperature for the BCMA binding analysis was 3TC or 25° C. in a running buffer of HBS-T+, supplemented with 1 mg/mL BSA. A kinetic titration method was employed for the interaction analysis as described in Abdiche, et al. Human BCMA (huBCMA) or cynomolgus monkey BCMA (cyBCMA) analyte was injected in the analyte direction using a series of injections from low to high concentration. The concentrations used were 0.08 nM, 0.4 nM, 2 nM, 10 nM and 50 nM (a 5-membered series, with a 5-fold dilution factor and top concentration of 50 nM). The association time for a given analyte dilution was two minutes. Immediately after the 50 nM BCMA injection, dissociation was monitored for 2 hours. Prior to the BCMA analyte injections, buffer was injected 5 times using the same association and dissociation times at the BCMA analyte cycles to prepare a buffer blank sensorgram for double-referencing purposes (double referencing as described in Myszka, J. Mol. Recognit. 12, 279-284 (1999).

The sensorgrams were double-referenced and fit to a 1:1 Langmuir with mass transport kinetic titration model in BIAevaluation Software version 4.1.1 (GE Lifesciences, Piscataway, NJ). The kinetics and affinity parameters for various anti-BCMA antibodies of the invention are shown in Tables 4A-4C. The antibodies shown in Tables 4A-4C share the same VH and VL regions as the CARs shown in Table 1 having the same name.

TABLE 4A

| Sample | $k_a$ (1/Ms) | $k_d$ (1/s) | $t_{1/2}$ (min) | $K_D$ (pM) |
|---|---|---|---|---|
| A02_Rd4_6nM_C01 | 1.2E+06 | 2.8E-05 | 411 | 24 |
| A02_Rd4_6nM_C16 | 1.1E+06 | 6.2E-05 | 187 | 59 |
| Combo_Rd4_0.6nM_C29 | 6.6E+06 | 1.4E-04 | 83 | 21 |
| L3PY/H3TAQ | 2.6E+06 | 1.4E-04 | 84 | 53 |

TABLE 4B

| Antibody | ka (1/Ms) huBCMA @ 25° C. | kd (1/s) huBCMA @25° C. | T ½ (min) to huBCMA @25° C. | KD (nM) to huBCMA @ 25° C. |
|---|---|---|---|---|
| P6E01/P6E01 | 1.04E+06 | 4.15E-03 | 2.8 | 4.0 |
| P6E01/H3.AQ | 8.35E+05 | 3.45E-04 | 33.53 | 0.41 |
| L1.LGF/L3.KW/P6E01 | 8.31E+05 | 7.55E-03 | 1.53 | 9.08 |
| L1.LGF/L3.NY/P6E01 | 1.33E+06 | 4.40E-03 | 2.63 | 3.32 |
| L1.GDF/L3.NY/P6E01 | 1.60E+06 | 5.92E-03 | 1.95 | 3.70 |
| L1.LGF/L3.KW/H3.AL | 4.28E+05 | 1.23E-03 | 9.40 | 2.87 |
| L1.LGF/L3.KW/H3.AP | 9.28E+05 | 2.27E-03 | 5.10 | 2.44 |
| L1.LGF/L3.KW/H3.AQ | 5.24E+05 | 9.56E-04 | 12.09 | 1.82 |
| L1.LGF/L3.PY/H3.AP | 4.57E+05 | 9.69E-04 | 11.92 | 2.12 |
| L1.LGF/L3.PY/H3.AQ | 9.31E+05 | 8.86E-04 | 13.04 | 0.95 |
| L1.LGF/L3.NY/H3.AL | 7.63E+05 | 9.70E-04 | 11.91 | 1.27 |
| L1.LGF/L3.NY/H3.AP | 9.36E+05 | 5.33E-04 | 21.67 | 0.57 |
| L1.LGF/L3.NY/H3.AQ | 6.66E+05 | 2.99E-04 | 38.61 | 0.45 |
| L1.GDF/L3.KW/H3.AL | 4.45E+05 | 3.90E-03 | 2.96 | 8.76 |
| L1.GDF/L3.KW/H3.AP | 1.17E+06 | 4.61E-03 | 2.51 | 3.93 |
| L1.GDF/L3.KW/H3.AQ | 7.97E+05 | 3.48E-03 | 3.32 | 4.37 |
| L1.GDF/L3.PY/H3.AQ | 1.42E+06 | 1.35E-02 | 0.86 | 9.49 |
| L1.GDF/L3.NY/H3.AL | 9.07E+05 | 4.03E-03 | 2.87 | 4.44 |
| L1.GDF/L3.NY/H3.AP | 1.41E+06 | 1.41E-03 | 8.21 | 1.00 |
| L1.GDF/L3.NY/H3.AQ | 9.84E+05 | 7.22E-04 | 16.00 | 0.73 |
| L3.KW/P6E01 | 7.40E+05 | 3.15E-04 | 36.66 | 0.43 |
| L3.PY/P6E01 | 7.12E+05 | 2.28E-04 | 50.74 | 0.32 |
| L3.NY/P6E01 | 8.76E+05 | 3.84E-04 | 30.08 | 0.44 |

| Antibody | ka (1/Ms) huBCMA @ 37° C. | kd (1/s) huBCMA @37° C. | T ½ (min) to huBCMA @37° C. | KD (nM) to huBCMA @ 37° C. |
|---|---|---|---|---|
| L3.PY/L1.PS/P6E01 | 2.49E+06 | 1.13E-03 | 10.21 | 0.45 |
| L3.PY/L1.AH/P6E01 | 2.55E+06 | 1.26E-03 | 9.19 | 0.49 |
| L3.PY/L1.FF/P6E01 | 2.39E+06 | 1.41E-03 | 8.18 | 0.59 |
| L3.PY/L1.PH/P6E01 | 2.81E+06 | 9.13E-04 | 12.65 | 0.32 |
| L3.PY/L3.KY/P6E01 | 3.18E+06 | 1.09E-03 | 10.65 | 0.34 |
| L3.PY/L3.KF/P6E01 | 2.88E+06 | 2.08E-03 | 5.56 | 0.72 |
| L3.PY/H2.QR | 2.56E+06 | 1.19E-03 | 9.75 | 0.46 |
| L3.PY/H2.DY | 2.60E+06 | 1.38E-03 | 8.37 | 0.53 |
| L3.PY/H2.YQ | 2.58E+06 | 1.56E-03 | 7.41 | 0.60 |
| L3.PY/H2.LT | 2.40E+06 | 1.29E-03 | 8.95 | 0.54 |
| L3.PY/H2.HA | 2.43E+06 | 1.47E-03 | 7.89 | 0.60 |
| L3.PY/H2.QL | 2.64E+06 | 2.18E-03 | 5.31 | 0.82 |
| L3.PY/H3.YA | 3.15E+06 | 1.18E-03 | 9.82 | 0.37 |
| L3.PY/H3.AE | 3.29E+06 | 1.39E-03 | 8.32 | 0.42 |
| L3.PY/H3.AQ | 3.08E+06 | 1.73E-03 | 6.69 | 0.56 |
| L3.PY/H3.TAQ | 3.08E+06 | 1.14E-03 | 10.13 | 0.37 |
| L3.PY/P6E01 | 2.65E+06 | 1.96E-03 | 5.91 | 0.74 |
| L3.PY/L1.PS/H2.QR | 3.97E+06 | 1.03E-01 | 0.11 | 25.85 |
| L3.PY/L1.PS/H2.DY | 3.22E+06 | 3.61E-03 | 3.20 | 1.12 |
| L3.PY/L1.PS/H2.YQ | 3.35E+06 | 4.30E-03 | 2.69 | 1.28 |
| L3.PY/L1.PS/H2.LT | 3.40E+06 | 4.65E-03 | 2.49 | 1.37 |
| L3.PY/L1.PS/H2.HA | 3.30E+06 | 1.06E-02 | 1.09 | 3.21 |
| L3.PY/L1.PS/H2.QL | 1.52E+07 | 3.14E-01 | 0.04 | 20.64 |
| L3.PY/L1.PS/H3.YA | 3.07E+06 | 9.05E-03 | 1.28 | 2.95 |
| L3.PY/L1.PS/H3.AE | 3.14E+06 | 1.46E-03 | 7.93 | 0.46 |
| L3.PY/L1.PS/H3.AQ | 3.26E+06 | 1.79E-03 | 6.46 | 0.55 |
| L3.PY/L1.PS/H3.TAQ | 3.25E+06 | 2.46E-03 | 4.70 | 0.76 |
| L3.PY/L1.AH/H2.QR | 3.13E+06 | 1.81E-03 | 6.39 | 0.58 |
| L3.PY/L1.AH/H2.DY | 3.05E+06 | 1.52E-03 | 7.62 | 0.50 |
| L3.PY/L1.AH/H2.YQ | 2.42E+06 | 1.93E-03 | 6.00 | 0.80 |
| L3.PY/L1.AH/H2.LT | 3.16E+06 | 1.23E-03 | 9.38 | 0.39 |
| L3.PY/L1.AH/H2.HA | 3.33E+06 | 1.81E-03 | 6.37 | 0.54 |
| L3.PY/L1.AH/H2.QL | 3.04E+06 | 1.60E-03 | 7.22 | 0.53 |
| L3.PY/L1.AH/H3.YA | 3.00E+06 | 1.50E-03 | 7.73 | 0.50 |
| L3.PY/L1.AH/H3.AE | 3.32E+06 | 1.73E-03 | 6.70 | 0.52 |
| L3.PY/L1.AH/H3.AQ | 3.03E+06 | 1.97E-03 | 5.85 | 0.65 |
| L3.PY/L1.AH/H3.TAQ | 3.27E+06 | 1.19E-03 | 9.68 | 0.37 |
| L3.PY/L1.FF/H2.QR | 3.47E+06 | 1.77E-03 | 6.54 | 0.51 |
| L3.PY/L1.FF/H2.DY | 4.14E+06 | 2.71E-03 | 4.27 | 0.65 |
| L3.PY/L1.FF/H2.YQ | 3.32E+06 | 1.52E-03 | 7.61 | 0.46 |
| L3.PY/L1.FF/H2.LT | 3.30E+06 | 1.67E-03 | 6.92 | 0.51 |
| L3.PY/L1.FF/H2.HA | 3.49E+06 | 2.19E-03 | 5.29 | 0.63 |
| L3.PY/L1.FF/H2.QL | 3.48E+06 | 1.40E-03 | 8.28 | 0.40 |
| L3.PY/L1.FF/H3.YA | 3.50E+06 | 1.80E-03 | 6.41 | 0.51 |
| L3.PY/L1.FF/H3.AE | 3.82E+06 | 2.63E-03 | 4.39 | 0.69 |
| L3.PY/L1.FF/H3.AQ | 3.32E+06 | 1.54E-03 | 7.51 | 0.46 |
| L3.PY/L1.FF/H3.TAQ | 3.52E+06 | 1.89E-03 | 6.12 | 0.54 |
| L3.PY/L1.PH/H2.QR | 3.69E+06 | 2.36E-03 | 4.89 | 0.64 |
| L3.PY/L1.PH/H2.HA | 2.37E+06 | 1.16E-03 | 9.99 | 0.49 |
| L3.PY/L1.PH/H3.AE | 3.68E+06 | 1.34E-03 | 8.61 | 0.36 |
| L3.PY/L1.PH/H3.AQ | 3.08E+06 | 1.59E-03 | 7.27 | 0.52 |
| L3.PY/L1.PH/H3.TAQ | 3.58E+06 | 2.13E-03 | 5.43 | 0.59 |
| L3.PY/L3.KY/H2.QR | 2.95E+06 | 9.90E-04 | 11.67 | 0.34 |
| L3.PY/L3.KY/H2.DY | 3.19E+06 | 6.42E-04 | 18.00 | 0.20 |
| L3.PY/L3.KY/H2.YQ | 2.14E+06 | 1.65E-03 | 7.02 | 0.77 |
| L3.PY/L3.KY/H2.LT | 2.92E+06 | 9.06E-04 | 12.75 | 0.31 |
| L3.PY/L3.KY/H2.HA | 3.29E+06 | 1.63E-03 | 7.10 | 0.49 |
| L3.PY/L3.KY/H2.QL | 3.65E+06 | 2.08E-03 | 5.56 | 0.57 |
| L3.PY/L3.KY/H3.YA | 3.30E+06 | 9.12E-04 | 12.67 | 0.28 |
| L3.PY/L3.KY/H3.TAQ | 2.79E+06 | 6.49E-04 | 17.79 | 0.23 |
| L3.PY/L3.KF/H2.DY | 2.74E+06 | 1.82E-03 | 6.35 | 0.67 |
| L3.PY/L3.KF/H2.YQ | 1.96E+06 | 2.23E-03 | 5.18 | 1.14 |
| L3.PY/L3.KF/H2.LT | 2.75E+06 | 1.91E-03 | 6.05 | 0.69 |
| L3.PY/L3.KF/H2.QL | 2.07E+06 | 1.25E-03 | 9.26 | 0.60 |
| L3.PY/L3.KF/H3.YA | 3.12E+06 | 1.47E-03 | 7.85 | 0.47 |
| L3.PY/L3.KF/H3.AE | 3.07E+06 | 1.55E-03 | 7.44 | 0.51 |
| L3.PY/L3.KF/H3.AQ | 3.48E+06 | 2.27E-03 | 5.09 | 0.65 |
| L3.PY/L3.KF/H3.TAQ | 2.82E+06 | 1.62E-03 | 7.12 | 0.58 |

| Antibody | ka (1/Ms) cyBCMA @ 25° C. | kd (1/s) cyBCMA @25° C. | T ½ (min) to cyBCMA @25° C. | KD (nM) to cyBCMA @ 25° C. |
|---|---|---|---|---|
| P6E01/P6E01 | | 7.02E-02 | 0.16 | 115.4 |
| P6E01/H3.AQ | 1.08E+06 | 7.40E-03 | 1.6 | 6.9 |
| L1.LGF/L3.KW/P6E01 | 4.55E+05 | 1.95E-02 | 0.6 | 42.8 |
| L1.LGF/L3.NY/P6E01 | 9.20E+05 | 1.05E-02 | 1.1 | 11.4 |
| L1.GDF/L3.NY/P6E01 | 1.20E+06 | 7.67E-03 | 1.5 | 6.4 |
| L1.LGF/L3.KW/H3.AL | 2.90E+05 | 1.21E-02 | 1.0 | 41.8 |
| L1.LGF/L3.KW/H3.AP | 5.54E+05 | 1.54E-02 | 0.7 | 27.8 |
| L1.LGF/L3.KW/H3.AQ | 5.27E+05 | 3.55E-03 | 3.3 | 6.7 |
| L1.LGF/L3.PY/H3.AP | 3.64E+05 | 1.30E-02 | 0.9 | 35.8 |
| L1.LGF/L3.PY/H3.AQ | 1.00E+06 | 4.77E-03 | 2.4 | 4.8 |
| L1.LGF/L3.NY/H3.AL | 6.35E+05 | 1.48E-02 | 0.8 | 23.2 |
| L1.LGF/L3.NY/H3.AP | 8.30E+05 | 5.57E-03 | 2.1 | 6.7 |
| L1.LGF/L3.NY/H3.AQ | 7.51E+05 | 1.48E-03 | 7.8 | 2.0 |
| L1.GDF/L3.KW/H3.AL | 3.18E+05 | 1.80E-02 | 0.6 | 56.7 |
| L1.GDF/L3.KW/H3.AP | 8.14E+05 | 2.03E-02 | 0.6 | 24.9 |
| L1.GDF/L3.KW/H3.AQ | 8.02E+05 | 5.65E-03 | 2.0 | 7.0 |
| L1.GDF/L3.PY/H3.AQ | 1.55E+06 | 1.66E-02 | 0.7 | 10.7 |
| L1.GDF/L3.NY/H3.AL | 9.00E+05 | 2.19E-02 | 0.5 | 24.3 |
| L1.GDF/L3.NY/H3.AP | 1.36E+06 | 7.02E-02 | 1.6 | 5.2 |
| L1.GDF/L3.NY/H3.AQ | 1.18E+06 | 1.36E-02 | 8.5 | 1.2 |
| L3.KW/P6E01 | 7.63E+05 | 2.57E-02 | 4.5 | 3.4 |
| L3.PY/P6E01 | 8.55E+05 | 2.93E-03 | 3.9 | 3.4 |
| L3.NY/P6E01 | 1.01E+06 | 2.87E-03 | 4.0 | 2.8 |

| Antibody | ka (1/Ms) cyBCMA @ 37° C. | kd (1/s) cyBCMA @37° C. | T ½ (min) to cyBCMA @37° C. | KD (nM) to cyBCMA @ 37° C. |
|---|---|---|---|---|
| L3.PY/L1.PS/P6E01 | 2.17E+06 | 6.06E-03 | 1.91 | 2.79 |
| L3.PY/L1.AH/P6E01 | 2.16E+06 | 5.72E-03 | 2.02 | 2.65 |
| L3.PY/L1.FF/P6E01 | 2.45E+06 | 5.91E-03 | 1.96 | 2.41 |
| L3.PY/L1.PH/P6E01 | 2.17E+06 | 7.89E-03 | 1.46 | 3.63 |

TABLE 4B-continued

| | | | | |
|---|---|---|---|---|
| L3.PY/L3.KY/P6E01 | 2.27E+06 | 5.02E-03 | 2.30 | 2.21 |
| L3.PY/L3.KF/P6E01 | 2.39E+06 | 8.30E-03 | 1.39 | 3.48 |
| L3.PY/H2.QR | 2.18E+06 | 6.58E-03 | 1.76 | 3.02 |
| L3.PY/H2.DY | 2.24E+06 | 6.18E-03 | 1.87 | 2.76 |
| L3.PY/H2.YQ | 2.46E+06 | 6.21E-03 | 1.86 | 2.53 |
| L3.PY/H2.LT | 2.09E+06 | 7.57E-03 | 1.53 | 3.63 |
| L3.PY/H2.HA | 1.99E+06 | 7.55E-03 | 1.53 | 3.79 |
| L3.PY/H2.QL | 2.05E+06 | 1.26E-02 | 0.91 | 6.16 |
| L3.PY/H3.YA | 2.87E+06 | 5.40E-03 | 2.14 | 1.88 |
| L3.PY/H3.AE | 2.82E+06 | 5.04E-03 | 2.29 | 1.79 |
| L3.PY/H3.AQ | 2.77E+06 | 5.39E-03 | 2.14 | 1.94 |
| L3.PY/H3.TAQ | 2.57E+06 | 4.37E-03 | 2.64 | 1.70 |
| L3.PY/P6E01 | 2.20E+06 | 1.31E-02 | 0.88 | 5.96 |
| L3.PY/L1.PS/H2.QR | 5.25E+05 | 6.70E-04 | 17.23 | 1.28 |
| L3.PY/L1.PS/H2.DY | 1.90E+06 | 3.78E-03 | 3.06 | 1.99 |
| L3.PY/L1.PS/H2.YQ | 2.00E+06 | 3.74E-03 | 3.09 | 1.87 |
| L3.PY/L1.PS/H2.LT | 2.17E+06 | 4.11E-03 | 2.81 | 1.89 |
| L3.PY/L1.PS/H2.HA | 1.45E+06 | 2.69E-03 | 4.30 | 1.86 |
| L3.PY/L1.PS/H2.QL | 6.57E+05 | 6.36E-04 | 18.17 | 0.97 |
| L3.PY/L1.PS/H3.YA | 1.77E+06 | 9.98E-03 | 1.16 | 5.65 |
| L3.PY/L1.PS/H3.AE | 2.46E+06 | 4.13E-03 | 2.80 | 1.68 |
| L3.PY/L1.PS/H3.AQ | 2.52E+06 | 4.33E-03 | 2.67 | 1.72 |
| L3.PY/L1.PS/H3.TAQ | 2.58E+06 | 5.52E-03 | 2.09 | 2.14 |
| L3.PY/L1.AH/H2.QR | 2.20E+06 | 4.91E-03 | 2.35 | 2.23 |
| L3.PY/L1.AH/H2.DY | 2.32E+06 | 4.51E-03 | 2.56 | 1.95 |
| L3.PY/L1.AH/H2.YQ | 1.58E+06 | 4.31E-03 | 2.68 | 2.74 |
| L3.PY/L1.AH/H2.LT | 2.19E+06 | 2.96E-03 | 3.91 | 1.35 |
| L3.PY/L1.AH/H2.HA | 2.58E+06 | 4.39E-03 | 2.63 | 1.70 |
| L3.PY/L1.AH/H2.QL | 2.62E+06 | 9.55E-03 | 1.21 | 3.65 |
| L3.PY/L1.AH/H3.YA | 2.37E+06 | 5.26E-03 | 2.20 | 2.22 |
| L3.PY/L1.AH/H3.AE | 2.25E+06 | 3.56E-03 | 3.25 | 1.58 |
| L3.PY/L1.AH/H3.AQ | 2.24E+06 | 3.99E-03 | 2.90 | 1.78 |
| L3.PY/L1.AH/H3.TAQ | 2.28E+06 | 3.02E-03 | 3.83 | 1.32 |
| L3.PY/L1.FF/H2.QR | 2.55E+06 | 4.21E-03 | 2.75 | 1.65 |
| L3.PY/L1.FF/H2.DY | 2.66E+06 | 5.00E-03 | 2.31 | 1.88 |
| L3.PY/L1.FF/H2.YQ | 2.19E+06 | 3.26E-03 | 3.55 | 1.49 |
| L3.PY/L1.FF/H2.LT | 2.19E+06 | 3.41E-03 | 3.38 | 1.56 |
| L3.PY/L1.FF/H2.HA | 2.33E+06 | 4.17E-03 | 2.77 | 1.79 |
| L3.PY/L1.FF/H2.QL | 2.36E+06 | 4.49E-03 | 2.57 | 1.91 |
| L3.PY/L1.FF/H3.YA | 2.46E+06 | 4.16E-03 | 2.77 | 1.69 |
| L3.PY/L1.FF/H3.AE | 2.85E+06 | 5.01E-03 | 2.31 | 1.76 |
| L3.PY/L1.FF/H3.AQ | 2.18E+06 | 3.29E-03 | 3.51 | 1.51 |
| L3.PY/L1.FF/H3.TAQ | 2.32E+06 | 3.76E-03 | 3.07 | 1.62 |
| L3.PY/L1.PH/H2.QR | 2.42E+06 | 4.36E-03 | 2.65 | 1.80 |
| L3.PY/L1.PH/H2.HA | 1.61E+06 | 5.53E-03 | 2.09 | 3.44 |
| L3.PY/L1.PH/H3.AE | 2.61E+06 | 2.02E-03 | 5.72 | 0.77 |
| L3.PY/L1.PH/H3.AQ | 2.28E+06 | 3.41E-03 | 3.39 | 1.50 |
| L3.PY/L1.PH/H3.TAQ | 2.51E+06 | 3.20E-03 | 3.61 | 1.28 |
| L3.PY/L3.KY/H2.QR | 2.05E+06 | 7.74E-03 | 1.49 | 3.78 |
| L3.PY/L3.KY/H2.DY | 1.96E+06 | 2.43E-03 | 4.75 | 1.24 |
| L3.PY/L3.KY/H2.YQ | 1.27E+06 | 2.58E-03 | 4.47 | 2.04 |
| L3.PY/L3.KY/H2.LT | 1.82E+06 | 2.32E-03 | 4.98 | 1.27 |
| L3.PY/L3.KY/H2.HA | 2.28E+06 | 3.18E-03 | 3.63 | 1.40 |
| L3.PY/L3.KY/H2.QL | 2.75E+06 | 4.09E-03 | 2.83 | 1.49 |
| L3.PY/L3.KY/H3.YA | 1.84E+06 | 4.28E-03 | 2.70 | 2.33 |
| L3.PY/L3.KY/H3.TAQ | 1.81E+06 | 1.92E-03 | 6.03 | 1.06 |
| L3.PY/L3.KF/H2.DY | 2.08E+06 | 3.68E-03 | 3.14 | 1.77 |
| L3.PY/L3.KF/H2.YQ | 1.41E+06 | 5.01E-03 | 2.30 | 3.55 |
| L3.PY/L3.KF/H2.LT | 1.91E+06 | 4.13E-03 | 2.80 | 2.16 |
| L3.PY/L3.KF/H2.QL | 1.42E+06 | 3.10E-03 | 3.73 | 2.18 |
| L3.PY/L3.KF/H3.YA | 2.10E+06 | 7.96E-03 | 1.45 | 3.78 |
| L3.PY/L3.KF/H3.AE | 1.85E+06 | 5.64E-03 | 2.05 | 3.05 |
| L3.PY/L3.KF/H3.AQ | 2.55E+06 | 2.38E-03 | 4.85 | 0.93 |
| L3.PY/L3.KF/H3.TAQ | 2.01E+06 | 1.91E-03 | 6.05 | 0.95 |

TABLE 4C

| | Human BCMA | | | Cyno BCMA | | |
|---|---|---|---|---|---|---|
| Antibody | ka (1/Ms) | kd (1/s) | KD (pM) | ka (1/Ms) | kd (1/s) | KD (pM) |
| P5A2_VHVL (P5A) | 6.96E+06 | 3.87E-02 | 5567 | 1.61E+06 | 1.64E-02 | 10230 |
| A02_Rd4_0.6nM_C06 | 3.49E+06 | 7.37E-05 | 21 | 1.81E+06 | 1.05E-04 | 58 |
| A02_Rd4_0.6nM_C09 | 5.50E+06 | 9.75E-05 | 18 | 2.13E+06 | 1.74E-04 | 82 |
| A02_Rd4_6nM_C16 (P5AC16) | 1.56E+06 | 1.41E-04 | 90 | 1.34E+06 | 1.58E-04 | 118 |
| A02_Rd4_6nM_C03 | 1.69E+06 | 1.26E-04 | 75 | 1.17E+06 | 1.85E-04 | 158 |
| A02_Rd4_6nM_C01 | 3.11E+06 | 9.20E-05 | 30 | 1.45E+06 | 5.83E-04 | 401 |
| A02_Rd4_6nM_C26 | 4.26E+06 | 1.39E-04 | 33 | 2.21E+06 | 4.48E-04 | 203 |
| A02_Rd4_6nM_C25 | 2.75E+06 | 1.80E-04 | 65 | 1.50E+06 | 3.30E-04 | 220 |
| A02_Rd4_6nM_C22 | 3.38E+06 | 1.82E-04 | 54 | 1.84E+06 | 3.24E-04 | 176 |
| A02_Rd4_6nM_C19 | 3.00E+06 | 1.48E-04 | 49 | 2.54E+06 | 6.61E-04 | 260 |
| A02_Rd4_0.6nM_C03 | 4.27E+06 | 1.82E-04 | 43 | 2.12E+06 | 4.26E-04 | 201 |
| A02_Rd4_6nM_C07 | 1.48E+06 | 1.89E-04 | 128 | 6.91E+05 | 7.86E-04 | 1138 |
| A02_Rd4_6nM_C23 | 1.22E+07 | 2.55E-04 | 21 | 2.63E+06 | 4.14E-04 | 157 |
| A02_Rd4_0.6nM_C18 | 4.73E+06 | 2.29E-04 | 48 | 3.24E+06 | 6.39E-04 | 197 |
| A02_Rd4_6nM_C10 | 4.51E+06 | 3.15E-04 | 70 | 1.90E+06 | 8.98E-04 | 472 |
| A02_Rd4_6nM_C05 | 3.10E+06 | 3.08E-04 | 99 | 1.36E+06 | 1.29E-03 | 950 |
| A02_Rd4_0.6nM_C10 | 2.30E+06 | 2.96E-04 | 129 | 8.83E+05 | 1.63E-03 | 1842 |
| A02_Rd4_6nM_C04 | 4.47E+06 | 6.03E-04 | 135 | 2.18E+06 | 8.31E-04 | 381 |
| A02_Rd4_0.6nM_C26 | 7.26E+06 | 4.43E-04 | 61 | 2.71E+06 | 2.56E-03 | 941 |
| A02_Rd4_0.6nM_C13 | 8.53E+06 | 5.66E-04 | 66 | 2.29E+06 | 1.28E-03 | 560 |
| A02_Rd4_0.6nM_C01 (P5AC1) | 4.74E+06 | 9.15E-04 | 193 | 2.39E+06 | 1.57E-03 | 655 |
| A02_Rd4-6nM_C08 | 3.92E+06 | 7.38E-04 | 188 | 2.23E+06 | 1.13E-02 | 5072 |
| P5C1_VHVL (PC1) | 1.16E+07 | 6.92E-02 | 5986 | 3.53E+06 | 5.38E-02 | 15231 |
| C01_Rd4_6nM_C24 | 7.47E+06 | 3.48E-03 | 467 | 3.17E+06 | 8.91E-04 | 281 |
| C01_Rd4_6nM_C26 | 1.50E+07 | 1.36E-03 | 90 | 4.75E+06 | 1.99E-03 | 419 |
| C01_Rd4_6nM_C02 | 1.61E+07 | 1.44E-03 | 89 | 5.12E+06 | 2.18E-03 | 426 |
| C01_Rd4_6nM_C10 | 1.31E+07 | 2.12E-03 | 162 | 4.44E+06 | 2.19E-03 | 493 |
| C01_Rd4_0.6nM_C27 | 1.23E+07 | 3.74E-03 | 303 | 3.34E+06 | 2.85E-03 | 852 |
| C01_Rd4_6nM_C20 | 6.02E+06 | 2.76E-03 | 459 | 3.60E+06 | 6.25E-03 | 1737 |
| C01_Rd4_6nM_C12 | 1.21E+07 | 6.49E-03 | 535 | 4.51E+06 | 3.70E-03 | 820 |
| C01_Rd4_0.6nM_C16 | 1.55E+07 | 6.30E-03 | 407 | 4.95E+06 | 4.64E-03 | 939 |
| C01_Rd4_0.6nM_C09 | 1.51E+07 | 8.25E-03 | 545 | 5.28E+06 | 9.36E-03 | 1773 |
| C01_Rd4_6nM_C09 | 1.58E+07 | 1.28E-02 | 811 | 3.73E+06 | 8.68E-03 | 2328 |
| C01_Rd4_0.6nM_C03 | 1.55E+07 | 1.50E-02 | 964 | 4.72E+06 | 1.19E-02 | 2528 |
| C01_Rd4_0.6nM_C06 | 1.82E+07 | 1.54E-02 | 847 | 6.22E+06 | 1.21E-02 | 1948 |
| C01_Rd4_6nM_C04 | 2.33E+07 | 4.97E-02 | 2134 | 6.34E+06 | 3.27E-02 | 5156 |

TABLE 4C-continued

| Antibody | Human BCMA | | | Cyno BCMA | | |
|---|---|---|---|---|---|---|
| | ka (1/Ms) | kd (1/s) | KD (pM) | ka (1/Ms) | kd (1/s) | KD (pM) |
| COMBO_Rd4_0.6nM_C22 | 1.97E+06 | 7.15E-05 | 36 | 1.34E+06 | 6.66E-05 | 50 |
| COMBO_Rd4_6nM_C21 | 1.17E+07 | 7.34E-05 | 6 | 3.17E+06 | 2.48E-04 | 78 |
| COMBO_Rd4_6nM_C10 | 5.47E+06 | 9.72E-05 | 18 | 1.52E+06 | 1.60E-04 | 105 |
| COMBO_Rd4_0.6nM_C04 | 1.07E+07 | 1.58E-04 | 15 | 3.52E+06 | 1.37E-04 | 39 |
| COMBO_Rd4_6nM_C25 | 7.98E+06 | 1.13E-04 | 14 | 2.85E+06 | 2.26E-04 | 79 |
| COMBO_Rd4_0.6nM_C21 | 1.34E+07 | 1.15E-04 | 9 | 3.63E+06 | 3.04E-04 | 84 |
| COMBO_Rd4_6nM_C11 | 6.74E+06 | 1.24E-04 | 18 | 2.64E+06 | 4.12E-04 | 156 |
| COMBO_Rd4_0.6nM_C20 | 7.65E+06 | 1.46E-04 | 19 | 3.09E+06 | 2.84E-04 | 92 |
| COMBO_Rd4_6nM_C09 | 8.85E+06 | 1.43E-04 | 16 | 2.37E+06 | 3.18E-04 | 134 |
| COMBO_Rd4_6nM_C08 | 8.99E+06 | 1.69E-04 | 19 | 3.06E+06 | 4.28E-04 | 140 |
| COMBO_Rd4_0.6nM_C19 | 7.86E+06 | 1.55E-04 | 20 | 2.92E+06 | 9.79E-04 | 336 |
| COMBO_Rd4_0.6nM_C02 | 8.57E+06 | 1.85E-04 | 22 | 3.01E+06 | 4.94E-04 | 164 |
| COMBO_Rd4_0.6nM_C23 | 7.39E+06 | 2.10E-04 | 28 | 2.81E+06 | 5.31E-04 | 189 |
| COMBO_Rd4_0.6nM_C29 | 1.47E+07 | 2.77E-04 | 19 | 4.00E+06 | 3.36E-04 | 84 |
| COMBO_Rd4_0.6nM_C09 | 1.04E+07 | 3.19E-04 | 31 | 3.77E+06 | 3.46E-04 | 92 |
| COMBO_Rd4_6nM_C12 (PC1C12) | 1.38E+07 | 2.70E-04 | 20 | 3.29E+06 | 4.86E-04 | 148 |
| COMBO_Rd4_0.6nM_C30 | 4.35E+06 | 2.82E-04 | 65 | 1.68E+06 | 8.08E-04 | 481 |
| COMBO_Rd4_0.6nM_C14 | 8.66E+06 | 3.28E-04 | 38 | 3.48E+06 | 6.45E-04 | 185 |
| COMBO_Rd4_6nM_C07 | 1.05E+07 | 3.71E-04 | 35 | 3.94E+06 | 9.34E-04 | 237 |
| COMBO_Rd4_6nM_C02 | 1.05E+06 | 4.43E-04 | 422 | 7.95E+05 | 1.36E-03 | 1714 |
| COMBO_Rd4_0.6nM_C05 | 4.32E+06 | 4.97E-04 | 115 | 1.94E+06 | 1.72E-03 | 886 |
| COMBO_Rd4_0.6nM_C17 | 8.68E+06 | 8.01E-04 | 92 | 3.06E+06 | 1.01E-03 | 330 |
| COMBO_Rd4_6nM_C22 (COM22) | 3.03E+06 | 7.75E-04 | 256 | 1.70E+06 | 1.65E-03 | 972 |
| COMBO_Rd4_0.6nM_C11 | 5.11E+06 | 1.06E-03 | 207 | 2.20E+06 | 4.23E-03 | 1924 |

Example 2

BCMA Specific CAR-T Cells

This example demonstrates functional activity of BCMA specific CAR-T cells against BCMA positive (BCMA+) tumor cells.

Among all the BCMA specific CAR molecules generated, eight were selected for further activity tests based on affinity to BCMA, cross-reactivity to human BCMA and cyno BCMA, and epitope. The CAR molecules tested included: P5A, P5AC1, P5AC16, PC1, PC1C12, COM22, P6DY, and P6AP. Three different architectures were designed: version 1 (v1) comprises an FcγRIIIα hinge, version 2 (v2) comprises a CD8α hinge, and version 3 (v3) comprises and IgG1 hinge. The chimeric antigen receptors (CARs) shown in Table 5 were prepared and used and assessed for their degranulation activity towards BCMA+cells. Degranulation activity was determined upon transient expression of each CAR in human T cells.

TABLE 5

Exemplary BCMA specific CARs

| CAR | CAR Amino Acid Sequence | Components |
|---|---|---|
| P5A-V1 | MALPVTALLLPLALLLHAARPEVQLLESGGGLVQPGGSLRLSCA ASGFTFSSYAMNWVRQAPGKGLEWVSAISDSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSSSYLAWYQQKPGQAPRLLMYDASIRATGIPDRFS GSGSGTDFTLTISRLEPEDFAVYYCQQYGSWPLTFGQGTKVEIK GLAVSTISSFFPPGYQIYIWAPLAGTCGVLLLSLVITLYCKRGRK KLLYIFKQPFMRPVQTTQEEDGCSCRFPEEEEGGCELRVKFSRS ADAPAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR (SEQ ID NO: 343) | CD8α signal peptide; P5A2_VHVL VH (Table 1 SEQ ID NO: 33); GS linker; P5A2_VHVL VL (SEQ ID NO: 34); FcγRIIIα hinge; CD8α TM domain; 41BB ISD; CD3ζ ISD |
| P5A-V2 | MALPVTALLLPLALLLHAARPEVQLLESGGGLVQPGGSLRLSCA ASGFTFSSYAMNWVRQAPGKGLEWVSAISDSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSSSYLAWYQQKPGQAPRLLMYDASIRATGIPDRFS GSGSGTDFTLTISRLEPEDFAVYYCQQYGSWPLTFGQGTKVEIK TTTPAPRPPTPAPTIASQPLSLRPEACRPAAGGAVHTRGLDFAC DIYIWAPLAGTCGVLLLSLVITLYCKRGRKKLLYIFKQPFMRPV QTTQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR(SEQ ID NO: 344) | CD8α signal peptide; P5A2_VHVL VH; GS linker; P5A2_VHVL VL; CD8α hinge; CD8α TM domain; 41BB ISD; CD3ζ ISD |

TABLE 5-continued

Exemplary BCMA specific CARs

| CAR | CAR Amino Acid Sequence | Components |
|---|---|---|
| P5A-V3 | MALPVTALLLPLALLLHAARPEVQLLESGGGLVQPGGSLRLSCA ASGFTFSSYAMNWVRQAPGKGLEWVSAISDSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSSSYLAWYQQKPGQAPRLLMYDASIRATGIPDRFS GSGSGTDFTLTISRLEPEDFAVYYCQQYGSWPLTFGQGTKVEIK EPKSPDKTHTCPPCPAPPVAGPSVFLFPPKPKDTLMIARTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLTCLVKGFYPSDIAVEWESNGQPEN NYKTTPPVLDSDGSFFLYSKLTVDKSRWQQGNVFSCSVMHEAL HNHYTQKSLSLSPGKIYIWAPLAGTCGVLLLSLVITLYCKRGRKKL LYIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR(SEQ ID NO: 345) | CD8α signal peptide; P5A2_VHVL VH ; GS linker; P5A2_VHVL VL; IgG1 hinge; CD8α TM domain; 41BB ISD; CD3ζ ISD |
| P5AC1-V1 | MALPVTALLLPLALLLHAARPEVQLLESGGGLVQPGGSLRLSCA ASGFTFSSYAMNWVRQAPGKGLEWVSAILsSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRGGQSVSSSYLAWYQQKPGQAPRLLMYDASIRATGIPDRFS GSGSGTDFTLTISRLEPEDFAVYYCQQYQSWPLTFGQGTKVEIK GLAVSTISSFFPPGYQIYIWAPLAGTCGVLLLSLVITLYCKRGR LKKLYIFKQPFMRPVQTTQEEDGCSCRFPEEEEGGCELRVKFSR ASADPAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR (SEQ ID NO: 346) | CD8α signal peptide; A02_Rd4_0.6nM_C01 VH (SEQ ID NO: 72); GS linker; A02_Rd4_0.6nM_C01 VL (SEQ ID NO: 73); FcγRIIIα hinge; CD8α TM domain; 41BB ISD; CD3ζ ISD |
| P5AC1-V2 | MALPVTALLLPLALLLHAARPEVQLLESGGGLVQPGGSLRLSCA ASGFTFSSYAMNWVRQAPGKGLEWVSAILSSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRGGQSVSSSYLAWYQQKPGQAPRLLMYDASIRATGIPDRFS GSGSGTDFTLTISRLEPEDFAVYYCQQYQSWPLTFGQGTKVEIK TTTPAPRPPTPAPTIASQPLSLRPEACRPAAGGAVHTRGLDFAC DIYIWAPLAGTCGVLLLSLVITLYCKRGRKKLLYIFKQPFMRPV QTTQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR (SEQ ID NO: 347) | CD8α signal peptide; A02_Rd4_0.6nM_C01 VH; GS linker; A02_Rd4_0.6nM_C01 VL; CD8α hinge; CD8α TM domain; 41BB ISD; CD3ζ ISD |
| P5AC1-V2.1 | MALPVTALLLPLALLLHAARPEVQLLESGGGLVQPGGSLRLSCA ASGFTFSSYAMNWVRQAPGKGLEWVSAILSSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRGGQSVSSSYLAWYQQKPGQAPRLLMYDASIRATGIPDRFS GSGSGTDFTLTISRLEPEDFAVYYCQQYQSWPLTFGQGTKVEIK GSGGGGSCPYSNPSLCGGGGSCPYSNPSLCGGGGSTTTPAP RPPTPAPTIASQPLSLRPEACRPAAGGAVHTRGLDFACDIYIWA PLAGTCGVLLLSLVITLYCKRGRKKLLYIFKQPFMRPVQTTQEED GCSCRFPEEEEGGCELRVKFSRSADAPAYQQGQNQLYNELNLG RREEYDVLDKRRGRDPEMGGKPRRKNPQEGLYNELQKDKMA EAYSEIGMKGERRRGKGHDGLYQGLSTATKDTYDALHMQALP PR (SEQ ID NO: 396) | CD8α signal peptide; A02_Rd4_0.6nM_C01 VH; GS linker; A02_Rd4_0.6nM_C01 VL; rituximab epitope; CD8α hinge; CD8α TM domain; 41BB ISD; CD3ζ ISD |
| P5AC1-V3 | MALPVTALLLPLALLLHAARPEVQLLESGGGLVQPGGSLRLSCA ASGFTFSSYAMNWVRQAPGKGLEWVSAILsSGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRGGQSVSSSYLAWYQQKPGQAPRLLMYDASIRATGIPDRFS GSGSGTDFTLTISRLEPEDFAVYYCQQYQSWPLTFGQGTKVEIK EPKSPDKTHTCPPCPAPPVAGPSVFLFPPKPKDTLMIARTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGKIYIWAPLAGTCGVLLLSLVITLYCKRGRKKL LYIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR (SEQ ID NO: 348) | CD8α signal peptide; A02_Rd4_0.6nM_C01 VH; GS linker; A02_Rd4_0.6nM_C01 VL; IgG1 hinge; CD8α TM domain; 41BB ISD; CD3ζ ISD |

TABLE 5-continued

Exemplary BCMA specific CARs

| CAR | CAR Amino Acid Sequence | Components |
| --- | --- | --- |
| P5AC16-V1 | MALPVTALLLPLALLLHAARPEVQLLESGGGLVQPGGSLRLSCA ASGFTFSSYAMNWVRQAPGKGLEWVSAISdFGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSDIYLAWYQQKPGQAPRLLMYDASIRATGIPDRFS GSGSGTDFTLTISRLEPEDFAVYYCQQYQTWPLTFGQGTKVEIKG LAVSTISSFFPPGYQIYIWAPLAGTCGVLLLSLVITLYCKRGRKK LLYIFKQPFMRPVQTTQEEDGCSCRFPEEEEGGCELRVKFSRSAD APAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR (SEQ ID NO: 349) | CD8α signal peptide; A02_Rd4_6nM_C16 VH (SEQ ID NO: 39); GS linker; A02_Rd4_6nM_C16 VL (SEQ ID NO: 40); FcγRIIIα hinge; CD8α TM domain; 41BB ISD; CD3ζ ISD; |
| P5AC16-V2 | MALPVTALLLPLALLLHAARPEVQLLESGGGLVQPGGSLRLSCA ASGFTFSSYAMNWVRQAPGKGLEWVSAISdFGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSDIYLAWYQQKPGQAPRLLMYDASIRATGIPDRFS GSGSGTDFTLTISRLEPEDFAVYYCQQYQTWPLTFGQGTKVEIK TTTPAPRPPTPAPTIASQPLSLRPEACRPAAGGAVHTRGLDFAC DIYIWAPLAGTCGVLLLSLVITLYCKRGRKKLLYIFKQPFMRPV QTTQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR (SEQ ID NO: 350) | CD8α signal peptide; A02_Rd4_6nM_C16 VH; GS linker; A02_Rd4_6nM_C16 VL; CD8α hinge; CD8α TM domain; 41BB ISD; CD3ζ ISD |
| P5AC16-V3 | MALPVTALLLPLALLLHAARPEVQLLESGGGLVQPGGSLRLSCA ASGFTFSSYAMNWVRQAPGKGLEWVSAISdFGGSTYYADSVK GRFTISRDNSKNTLYLQMNSLRAEDTAVYYCARYWPMDIWGQ GTLVTVSSGGGGSGGGGSGGGGSEIVLTQSPGTLSLSPGERATL SCRASQSVSDIYLAWYQQKPGQAPRLLMYDASIRATGIPDRFS GSGSGTDFTLTISRLEPEDFAVYYCQQYQTWPLTFGQGTKVEIK EPKSPDKTHTCPPCPAPPVAGPSVFLFPPKPKDTLMIARTPEVT CVVVDVSHEDPEVKFNWYVDGVEVHNAKTKPREEQYNSTYRV VSVLTVLHQDWLNGKEYKCKVSNKALPAPIEKTISKAKGQPREP QVYTLPPSRDELTKNQVSLTCLVKGFYPSDIAVEWESNGQPEN NYKTTPPVLDSDGSFFLYSKLTVDKSRWQQGNVFSCSVMHEALH NHYTQKSLSLSPGKIYIWAPLAGTCGVLLLSLVITLYCKRGRKK LLYIFKQPFMRPVQTTQEEDGCSCRFPEEEEGGCELRVKFSRSA DAPAYQQGQNQLYNELNLGRREEYDVLDKRRGRDPEMGGKPR RKNPQEGLYNELQKDKMAEAYSEIGMKGERRRGKGHDGLYO GLSTATKDTYDALHMQALPPR (SEQ ID NO: 351) | CD8α signal peptide; A02_Rd4_6nM_C16 VH; GS linker; A02_Rd4_6nM_C16 VL; IgG1 hinge; CD8α TM domain; 41BB ISD; CD3ζ ISD |
| PC1-V1 | MALPVTALLLPLALLLHAARPEVQLLESGGGLVQPGGSLRLSCA ASGFTFSSYPMSWVRQAPGKGLEWVSAIGGSGGSTYYADSVK GRFTISRDNSKNTLYLQMNSLRAEDTAVYYCARYWPMDSWG QGTLVTVSSGGGGSGGGGSGGGGSEIVLTQSPGTLSLSPGERA TLSCRASQSVSSTYLAWYQQKPGQAPRLLIYDASSRAPGIPDRF SGSGSGTDFTLTISRLEPEDFAVYYCQQYSTSPLTFGQGTKVEIK GLAVSTISSFFPPGYQIYIWAPLAGTCGVLLLSLVITLYCKRGRK KLLYIFKQPFMRPVQTTQEEDGCSCRFPEEEEGGCELRVKFSRS ADAPAYQQGQNQLYNELNLGRREEYDVLDKRRGRDPEMGGKPR RKNPQEGLYNELQKDKMAEAYSEIGMKGERRRGKGHDGLYQ GLSTATKDTYDALHMQALPPR (SEQ ID NO: 352) | CD8α signal peptide; P5C1_VHVL VH (SEQ ID NO: 76); GS linker; P5C1_VHVL VL (SEQ ID NO: 77); FcγRIIIα hinge; CD8α TM domain; 41BB ISD; CD3ζ ISD |
| PC1-V2 | MALPVTALLLPLALLLHAARPEVQLLESGGGLVQPGGSLRLSCA ASGFTFSSYPMSWVRQAPGKGLEWVSAIGGSGGSTYYADSVK GRFTISRDNSKNTLYLQMNSLRAEDTAVYYCARYWPMDSWG QGTLVTVSSGGGGSGGGGSGGGGSEIVLTQSPGTLSLSPGERA TLSCRASQSVSSTYLAWYQQKPGQAPRLLIYDASSRAPGIPDRF SGSGSGTDFTLTISRLEPEDFAVYYCQQYSTSPLTFGQGTKVEIK TTTPAPRPPTPAPTIASQPLSLRPEACRPAAGGAVHTRGLDFAC DIYIWAPLAGTCGVLLLSLVITLYCKRGRKKLLYIFKQPFMRPV QTTQEEDGCSCRFPEEEEGGCELRVKFSRSADAPAYQQGQNQLY NELNLGRREEYDVLDKRRGRDPEMGGKPRRKNPQEGLYNELQ KDKMAEAYSEIGMKGERRRGKGHDGLYQGLSTATKDTYDALH MQALPPR (SEQ ID NO: 353) | CD8α signal peptide; P5C1_VHVL VH; GS linker; P5C1_VHVL VL; CD8α hinge; CD8α TM domain; 41BB ISD; CD3ζ ISD |
| PC1-V3 | MALPVTALLLPLALLLHAARPEVQLLESGGGLVQPGGSLRLSCA ASGFTFSSYPMSWVRQAPGKGLEWVSAIGGSGGSTYYADSVK GRFTISRDNSKNTLYLQMNSLRAEDTAVYYCARYWPMDSWG QGTLVTVSSGGGGSGGGGSGGGGSEIVLTQSPGTLSLSPGERA TLSCRASQSVSSTYLAWYQQKPGQAPRLLIYDASSRAPGIPDRF SGSGSGTDFTLTISRLEPEDFAVYYCQQYSTSPLTFGQGTKVEIK EPKSPDKTHTCPPCPAPPVAGPSVFLFPPKPKDTLMIARTPEVT CVVVDVSHEDPEVKFNWYVDGVEVHNAKTKPREEQYNSTYRV | CD8α signal peptide; P5C1_VHVL VH; GS linker; P5C1_VHVL VL; IgG1 hinge; CD8α TM domain; 41BB ISD; CD3ζ ISD |

TABLE 5-continued

Exemplary BCMA specific CARs

| CAR | CAR Amino Acid Sequence | Components |
|---|---|---|
| | VSVLTVLHQDWLNGKEYKCKVSNKALPAPIEKTISKAKGQPREP<br>QVYTLPPSRDELTKNQVSLTCLVKGFYPSDIAVEWESNGQPEN<br>NYKTTPPVLDSDGSFFLYSKLTVDKSRWQQGNVFSCSVMHEAL<br>HNHYTQKSLSLSPGKIYIWAPLAGTCGVLLLSLVITLYCKRGRK<br>LKLYIFKQPFMRPVQTTQEEDGCSCRFPEEEEGGCELRVKFSRS<br>ADAPAYQQGQNQLYNELNLGRREEYDVLDKRRGRDPEMGGKPR<br>RKNPQEGLYNELQKDKMAEAYSEIGMKGERRRGKGHDGLYQ<br>GLSTATKDTYDALHMQALPPR (SEQ ID NO: 354) | |
| PC1C12-V1 | MALPVTALLLPLALLLHAARPEVQLLESGGGLVQPGGSLRLSCA<br>ASGFTFSSYPMSWVRQAPGKGLEWVSAIGgSGGWSYYADSVK<br>GRFTISRDNSKNTLYLQMNSLRAEDTAVYYCARYWPMDSWG<br>QGTLVTVSSGGGGSGGGGSGGGGSEIVLTQSPGTLSLSPGERA<br>TLSCWLSQSVSSTYLAWYQQKPGQAPRLLIYDASSRAPGIPDRF<br>SGSGSGTDFTLTISRLEPEDFAVYYCQQYSEWPLTFGQGTKVEIK<br>GLAVSTISSFFPPGYQIYIWAPLAGTCGVLLLSLVITLYCKRGRK<br>KLLYIFKQPFMRPVQTTQEEDGCSCRFPEEEEGGCELRVKFSRS<br>ADAPAYQQGQNQLYNELNLGRREEYDVLDKRRGRDPEMGGKPR<br>RKNPQEGLYNELQKDKMAEAYSEIGMKGERRRGKGHDGLYQ<br>GLSTATKDTYDALHMQALPPR (SEQ ID NO: 355) | CD8α signal peptide;<br>C01_Rd4_6nM_C12 VH<br>(SEQ ID NO: 83);<br>GS linker;<br>C01_Rd4_6nM_C12 VL<br>(SEQ ID NO: 84);<br>FcγRIIIα hinge;<br>CD8α TM domain;<br>41BB ISD;<br>CD3ζ ISD |
| PC1C12-V2 | MALPVTALLLPLALLLHAARPEVQLLESGGGLVQPGGSLRLSCA<br>ASGFTFSSYPMSWVRQAPGKGLEWVSAIGgSGGWSYYADSVK<br>GRFTISRDNSKNTLYLQMNSLRAEDTAVYYCARYWPMDSWG<br>QGTLVTVSSGGGGSGGGGSGGGGSEIVLTQSPGTLSLSPGERA<br>TLSCWLSQSVSSTYLAWYQQKPGQAPRLLIYDASSRAPGIPDRF<br>SGSGSGTDFTLTISRLEPEDFAVYYCQQYSEWPLTFGQGTKVEIK<br>TTTPAPRPPTPAPTIASQPLSLRPEACRPAAGGAVHTRGLDFAC<br>DIYIWAPLAGTCGVLLLSLVITLYCKRGRKKLLYIFKQPFMRPV<br>QTTQEEDGCSCRFPEEEEGGCELRVKFSRSADAPAYQQGQNQLY<br>NELNLGRREEYDVLDKRRGRDPEMGGKPRRKNPQEGLYNELQ<br>KDKMAEAYSEIGMKGERRRGKGHDGLYQGLSTATKDTYDALH<br>MQALPPR (SEQ ID NO: 356) | CD8α signal peptide;<br>C01_Rd4_6nM_C12<br>VH;<br>GS linker;<br>C01_Rd4_6nM_C12 VL;<br>CD8α hinge;<br>CD8α TM domain;<br>41BB ISD;<br>CD3ζ ISD |
| PC1C12-V3 | MALPVTALLLPLALLLHAARPEVQLLESGGGLVQPGGSLRLSCA<br>ASGFTFSSYPMSWVRQAPGKGLEWVSAIGgSGGWSYYADSVK<br>GRFTISRDNSKNTLYLQMNSLRAEDTAVYYCARYWPMDSWG<br>QGTLVTVSSGGGGSGGGGSGGGGSEIVLTQSPGTLSLSPGERA<br>TLSCWLSQSVSSTYLAWYQQKPGQAPRLLIYDASSRAPGIPDRF<br>SGSGSGTDFTLTISRLEPEDFAVYYCQQYSEWPLTFGQGTKVEIK<br>EPKSPDKTHTCPPCPAPPVAGPSVFLFPPKPKDTLMIARTPEVT<br>CVVVDVSHEDPEVKFNWYVDGVEVHNAKTKPREEQYNSTYRV<br>VSVLTVLHQDWLNGKEYKCKVSNKALPAPIEKTISKAKGQPREP<br>QVYTLPPSRDELTKNQVSLTCLVKGFYPSDIAVEWESNGQPEN<br>NYKTTPPVLDSDGSFFLYSKLTVDKSRWQQGNVFSCSVMHEALHN<br>HYTQKSLSLSPGKIYIWAPLAGTCGVLLLSLVITLYCKRGRKKL<br>LYIFKQPFMRPVQTTQEEDGCSCRFPEEEEGGCELRVKFSRSAD<br>APAYQQGQNQLYNELNLGRREEYDVLDKRRGRDPEMGGKPR<br>RKNPQEGLYNELQKDKMAEAYSEIGMKGERRRGKGHDGLYQ<br>GLSTATKDTYDALHMQALPPR (SEQ ID NO: 357) | CD8α signal peptide;<br>C01_Rd4_6nM_C12<br>VH;<br>GS linker;<br>C01_Rd4_6nM_C12 VL;<br>IgG1 hinge;<br>CD8α TM domain;<br>41BB ISD;<br>CD3ζ ISD |
| COM22-V1 | MALPVTALLLPLALLLHAARPEVQLLESGGGLVQPGGSLRLSCA<br>ASGFTFSSYAMNWVRQAPGKGLEWVSAISdSGGSRWYADSV<br>KGRFTISRDNSKNTLYLQMNSLRAEDTAVYYCTRYWPMDIWG<br>QGTLVTVSSGGGGSGGGGSGGGGSEIVLTQSPGTLSLSPGERA<br>TLSCRASVRVSSTYLAWYQQKPGQAPRLLMYDASIRATGIPDRF<br>SGSGSGTDFTLTISRLEPEDFAVYYCQQYMKWPLTFGQGTKVEI<br>KGLAVSTISSFFPPGYQIYIWAPLAGTCGVLLLSLVITLYCKRGRK<br>KLLYIFKQPFMRPVQTTQEEDGCSCRFPEEEEGGCELRVKFSRS<br>ADAPAYQQGQNQLYNELNLGRREEYDVLDKRRGRDPEMGGK<br>PRRKNPQEGLYNELQKDKMAEAYSEIGMKGERRRGKGHDGLY<br>QGLSTATKDTYDALHMQALPPR (SEQ ID NO: 358) | CD8α signal peptide;<br>COMBO_Rd4_0.6nM_C<br>22 VH (SEQ ID NO: 92);<br>GS linker;<br>COMBO_Rd4_0.6nM_C<br>22 VL (SEQ ID NO: 93);<br>FcγRIIIα hinge;<br>CD8α TM domain;<br>41BB ISD;<br>CD3ζ ISD |
| COM22-V2 | MALPVTALLLPLALLLHAARPEVQLLESGGGLVQPGGSLRLSCA<br>ASGFTFSSYAMNWVRQAPGKGLEWVSAISdSGGSRWYADSV<br>KGRFTISRDNSKNTLYLQMNSLRAEDTAVYYCTRYWPMDIWG<br>QGTLVTVSSGGGGSGGGGSGGGGSEIVLTQSPGTLSLSPGERA<br>TLSCRASVRVSSTYLAWYQQKPGQAPRLLMYDASIRATGIPDRF<br>SGSGSGTDFTLTISRLEPEDFAVYYCQQYMKWPLTFGQGTKVEI<br>KTTTPAPRPPTPAPTIASQPLSLRPEACRPAAGGAVHTRGLDFA<br>CDIYIWAPLAGTCGVLLLSLVITLYCKRGRKKLLYIFKQPFMRPV<br>QTTQEEDGCSCRFPEEEEGGCELRVKFSRSADAPAYQQGQNQ<br>LYNELNLGRREEYDVLDKRRGRDPEMGGKPRRKNPQEGLYNE<br>LQKDKMAEAYSEIGMKGERRRGKGHDGLYQGLSTATKDTYDA<br>LHMQALPPR (SEQ ID NO: 359) | CD8α signal peptide;<br>COMBO_Rd4_0.6nM_C<br>22 VH;<br>GS linker;<br>COMBO_Rd4_0.6nM_C<br>22 VL;<br>CD8α hinge;<br>CD8α TM domain;<br>41BB ISD;<br>CD3ζ ISD |

TABLE 5-continued

Exemplary BCMA specific CARs

| CAR | CAR Amino Acid Sequence | Components |
|---|---|---|
| COM22-V3 | MALPVTALLLPLALLLHAARPEVQLLESGGGLVQPGGSLRLSCA ASGFTFSSYAMNWVRQAPGKGLEWVSAISdSGGSRWYADSV KGRFTISRDNSKNTLYLQMNSLRAEDTAVYYCTRYWPMDIWG QGTLVTVSSGGGGSGGGGSGGGGSEIVLTQSPGTLSLSPGERA TLSCRASVRVSSTYLAWYQQKPGQAPRLLMYDASIRATGIPDRF SGSGSGTDFTLTISRLEPEDFAVYYCQQYMKWPLTFGQGTKVEI KEPKSPDKTHTCPPCPAPPVAGPSVFLFPPKPKDTLMIARTPEV TCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSRDELTKNQVSLTCLVKGFYPSDIAVEWESNGQPE NNYKTTPPVLDSDGSFFLYSKLTVDKSRWQQGNVFSCSVMHE ALHNHYTQKSLSLSPGKIYIWAPLAGTCGVLLLSLVITLYCKRGRK KLLYIFKQPFMRPVQTTQEEDGCSCRFPEEEEGGCELRVKFSRS ADAPAYQQGQNQLYNELNLGRREEYDVLDKRRGRDPEMGGK PRRKNPQEGLYNELQKDKMAEAYSEIGMKGERRRGKHDGLY QGLSTATKDTYDALHMQALPPR (SEQ ID NO: 360) | CD8α signal peptide; COMBO_Rd4_0.6nM_C 22 VH; GS linker; COMBO_Rd4_0.6nM_C 22 VL; IgG1 hinge; CD8α TM domain; 41BB ISD; CD3ζ ISD |
| P6DY-V1 | MALPVTALLLPLALLLHAARPEVQLLESGGGLVQPGGSLRLSCA ASGFTFGSYAMTWVRQAPGKGLEWVSAIDYSGGNTFYADSVK GRFTISRDNSKNTLYLQMNSLRAEDTAVYYCARVSPIASGMDY WGQGTLVTVSSGGGGSGGGGSGGGGSEIVLTQSPGTLSLSPG ERATLSCRASQSVSSSYPSWYQQKPGQAPRLLIYGASSRATGIP DRFSGSGSGTDFTLTISRLEPEDFAVYYCQHYPYPPSFTFGQGTK VEIKGLAVSTISSFFPPGYQIYIWAPLAGTCGVLLLSLVITLYCK RGRKKLLYIFKQPFMRPVQTTQEEDGCSCRFPEEEEGGCELRVK FSRSADAPAYQQGQNQLYNELNLGRREEYDVLDKRRGRDPEMG GKPRRKNPQEGLYNELQKDKMAEAYSEIGMKGERRRGKGHD GLYQGLSTATKDTYDALHMQ (SEQ ID NO: 361) | CD8α signal peptide; L3.PY/H2.DYVH (SEQ ID NO: 25); GS linker; L3.PY/L1.PS/P6E01 VL (SEQ ID NO: 18); FcγRIIIα hinge; CD8α TM domain; 41BB ISD; CD3ζ ISD |
| P6DY-V2 CAR | MALPVTALLLPLALLLHAARPEVQLLESGGGLVQPGGSLRLSCA CAR Amino Acid Sequence ASGFTFGSYAMTWVRQAPGKGLEWVSAIDYSGGNTFYADSVK GRFTISRDNSKNTLYLQMNSLRAEDTAVYYCARVSPIASGMDY WGQGTLVTVSSGGGGSGGGGSGGGGSEIVLTQSPGTLSLSPG ERATLSCRASQSVSSSYPSWYQQKPGQAPRLLIYGASSRATGIP DRFSGSGSGTDFTLTISRLEPEDFAVYYCQHYPYPPSFTFGQGTK VEIKTTTPAPRPPTPAPTIASQPLSLRPEACRPAAGGAVHTRGLD FACDIYIWAPLAGTCGVLLLSLVITLYCKRGRKKLLYIFKQPFMRP VQTTQEEDGCSCRFPEEEEGGCELRVKFSRSADAPAYQQGQN QLYNELNLGRREEYDVLDKRRGRDPEMGGKPRRKNPQEGLYN ELQKDKMAEAYSEIGMKGERRRGKGHDGLYQGLSTATKDTYD ALHMQALPPR (SEQ ID NO: 362) | CD8α signal peptide; Components L3.PY/H2.DYVH; GS linker; L3.PY/L1.PS/P6E01 VL; CD8α hinge; CD8α TM domain; 41BB ISD; CD3ζ ISD |
| P6DY-V3 | MALPVTALLLPLALLLHAARPEVQLLESGGGLVQPGGSLRLSCA ASGFTFGSYAMTWVRQAPGKGLEWVSAIDYSGGNTFYADSVK GRFTISRDNSKNTLYLQMNSLRAEDTAVYYCARVSPIASGMDY WGQGTLVTVSSGGGGSGGGGSGGGGSEIVLTQSPGTLSLSPG ERATLSCRASQSVSSSYPSWYQQKPGQAPRLLIYGASSRATGIP DRFSGSGSGTDFTLTISRLEPEDFAVYYCQHYPYPPSFTFGQGTK VEIKEPKSPDKTHTCPPCPAPPVAGPSVFLFPPKPKDTLMIARTP EVTCVVVDVSHEDPEVKFNWYVDGVEVHNAKTKPREEQYNST YRVVSVLTVLHQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMH EALHNHYTQKSLSLSPGKIYIWAPLAGTCGVLLLSLVITLYCKRGR KKLLYIFKQPFMRPVQTTQEEDGCSCRFPEEEEGGCELRVKFSR SADAPAYQQGQNQLYNELNLGRREEYDVLDKRRGRDPEMGG KPRRKNPQEGLYNELQKDKMAEAYSEIGMKGERRRGKHDGL YQGLSTATKDTYDALHMQALPPR (SEQ ID NO: 363) | CD8α signal peptide; L3.PY/H2.DYVH; GS linker; L3.PY/L1.PS/P6E01 VL; IgG1 hinge; CD8α TM domain; 41BB ISD; CD3ζ ISD |
| P6AP-V1 | MALPVTALLLPLALLLHAARPEVQLLESGGGLVQPGGSLRLSCA ASGFTFGSYAMTWVRQAPGKGLEWVSAISGSGGNTFYADSVK GRFTISRDNSKNTLYLQMNSLRAEDTAVYYCARVSPIAAPMDY WGQGTLVTVSSGGGGSGGGGSGGGGSEIVLTQSPGTLSLSPG ERATLSCRASQLGSFYLAWYQQKPGQAPRLLIYGASSRATGIPD RFSGSGSGTDFTLTISRLEPEDFAVYYCQHYNYPPSFTFGQGTKV EIKGLAVSTISSFFPPGYQIYIWAPLAGTCGVLLLSLVITLYCKR GRKKLLYIFKQPFMRPVQTTQEEDGCSCRFPEEEEGGCELRVKF SRSADAPAYQQGQNQLYNELNLGRREEYDVLDKRRGRDPEMGG KPRRKNPQEGLYNELQKDKMAEAYSEIGMKGERRRGKHDGL YQGLSTATKDTYDALHMQA (SEQ ID NO: 364) | CD8α signal peptide; P6AP-V1 VH (SEQ ID NO: 8); GS linker; P6AP-V1 VL (SEQ ID NO: 80) FcγRIIIα hinge; CD8α TM domain; 41BB ISD; CD3ζ ISD |
| P6AP-V2 | MALPVTALLLPLALLLHAARPEVQLLESGGGLVQPGGSLRLSCA ASGFTFGSYAMTWVRQAPGKGLEWVSAISGSGGNTFYADSVK GRFTISRDNSKNTLYLQMNSLRAEDTAVYYCARVSPIAAPMDY WGQGTLVTVSSGGGGSGGGGSGGGGSEIVLTQSPGTLSLSPG | CD8α signal peptide; L1.LGF/L3.KW/H3.AP VH; GS linker; |

TABLE 5-continued

Exemplary BCMA specific CARs

| CAR | CAR Amino Acid Sequence | Components |
|---|---|---|
|  | ERATLSCRASQLGSFYLAWYQQKPGQAPRLLIYGASSRATGIPD<br>RFSGSGSGTDFTLTISRLEPEDFAVYYCQHYNYPPSFTFGQGTKV<br>EIKTTTPAPRPPTPAPTIASQPLSLRPEACRPAAGGAVHTRGLDF<br>ACDIYIWAPLAGTCGVLLLSLVITLYCKRGRKKLLYIFKQPFMRPV<br>QTTQEEDGCSCRFPEEEEGGCELRVKFSRSADAPAYQQGQNQ<br>LYNELNLGRREEYDVLDKRRGRDPEMGGKPRRKNPQEGLYNE<br>LQKDKMAEAYSEIGMKGERRRGKGHDGLYQGLSTATKDTYDA<br>LHMQALPPR (SEQ ID NO: 365) | P6AP-V1 VL;<br>CD8α hinge;<br>CD8α TM domain;<br>41BB ISD;<br>CD3ζ ISD |
| P6AP-V3 | MALPVTALLLPLALLLHAARPEVQLLESGGGLVQPGGSLRLSCA<br>ASGFTFGSYAMTWVRQAPGKGLEWVSAISGSGGNTFYADSVK<br>GRFTISRDNSKNTLYLQMNSLRAEDTAVYYCARVSPIAAPMDY<br>WGQGTLVTVSSGGGGSGGGGSGGGGSEIVLTQSPGTLSLSPG<br>ERATLSCRASQLGSFYLAWYQQKPGQAPRLLIYGASSRATGIPD<br>RFSGSGSGTDFTLTISRLEPEDFAVYYCQHYNYPPSFTFGQGTKV<br>EIKEPKSPDKTHTCPPCPAPPVAGPSVFLFPPKPKDTLMIARTPE<br>VTCVVVDVSHEDPEVKFNWYVDGVEVHNAKTKPREEQYNSTY<br>RVVSVLTVLHQDWLNGKEYKCKVSNKALPAPIEKTISKAKGQPR<br>EPQVYTLPPSRDELTKNQVSLTCLVKGFYPSDIAVEWESNGQPE<br>NNYKTTPPVLDSDGSFFLYSKLTVDKSRWQQGNVFSCSVMHE<br>ALHNHYTQKSLSLSPGKIYIWAPLAGTCGVLLLSLVITLYCKRGRK<br>KLLYIFKQPFMRPVQTTQEEDGCSCRFPEEEEGGCELRVKFSRS<br>ADAPAYQQGQNQLYNELNLGRREEYDVLDKRRGRDPEMGGK<br>PRRKNPQEGLYNELQKDKMAEAYSEIGMKGERRRGKGHDGLY<br>QGLSTATKDTYDALHMQALPPR (SEQ ID NO: 366) | CD8α signal peptide;<br>L1.LGF/L3.KW/H3.AP<br>VH;<br>GS linker;<br>P6AP-V1 VL;<br>IgG1 hinge;<br>CD8α TM domain;<br>41BB ISD;<br>CD3ζ ISD |

For the activity assays, T cells from thirteen healthy donors (Donors 1-13) were obtained. Briefly, the T cells were purified from buffy-coat samples and activated using CD3/CD28 beads. Cells were transiently transfected with mRNAs encoding the different CAR molecules at D11/12 after activation. CAR activity was assessed by measuring their degranulation capacity, the inteferon-γ (IFNγ) release, and the cytotoxic activity when co-cultured with (a) cells expressing BCMA (MM1S, KMS12BM, and L363), or (b) cells that do not express the BCMA protein (K562). Also included for each assay were mock transfected T cells (T cells in buffer) to determine baseline activity of T cells that do not express a CAR.

CAR detection was done using a fusion protein in which the extracellular domain of the human BCMA protein was fused to a mouse IgG1 derived Fc fragment. Binding of the CAR at the cell surface with the BCMA portion of the fusion protein was detected with anti-Fc PE-conjugated antibody and analyzed by flow cytometry.

Materials and Methods

Primary T Cell Cultures

T cells were purified from Buffy coat samples provided by EFS (Etablissement Français du Sang, Paris, France) using Ficoll gradient density medium (Ficoll Paque PLUS/GE Healthcare Life Sciences). The PBMC layer was recovered and T cells were purified using a commercially available T cell enrichment kit (Stem Cell Technologies). Purified T cells were activated in X-Vivo™-15 medium (Lonza) supplemented with 20 ng/mL Human IL-2 (Miltenyi Biotech), 5% Human Serum (Sera Laboratories), and Dynabeads Human T activator CD3/CD28 at a bead:cell ratio 1:1 (Life Technologies). After activation cells were grown and maintained in X-Vivo™-15 medium (Lonza) supplemented with 20 ng/mL Human IL-2 (Miltenyi Biotec) and 5% Human Serum (Sera Laboratories)

CAR mRNA Transfection

Transfections were done at Day 4/5 or Day 11/12 after T cell purification and activation. 5 millions of cells were transfected with 15 μg of mRNA encoding the different CAR constructs. CAR mRNAs were produced using the mMESSAGE mMACHINE T7 Kit (Life Technologies) and purified using RNeasy Mini Spin Columns (Qiagen). Transfections were done using PulseAgile™ Cytopulse technology, by applying two 0.1 mS pulses at 3000 V/cm followed by four 0.2 mS pulses at 325 V/cm in 0.4 cm gap cuvettes in a final volume of 200 μl of "Cytoporation buffer T" (BTX Harvard Apparatus). Cells were immediately diluted in X-Vivo™-15 media (Lonza) and incubated at 37° C. with 5% $CO_2$. IL-2 (from Miltenyi Biotec was added 2 h after electroporation at 20 ng/mL.

Degranulation Assay (CD107a Mobilization)

T cells were incubated in 96-well plates (50,000 cells/well), together with an equal amount of cells expressing or not the BCMA protein. Co-cultures were maintained in a final volume of 100 μl of X-Vivo™-15 medium (Lonza) for 6 hours at 37° C. with 5% $CO_2$. CD107a staining was done during cell stimulation, by the addition of a fluorescent anti-CD107a antibody (APC conjugated, from Miltenyi Biotec) at the beginning of the co-culture, together with 1 μg/ml of anti-CD49d (BD Pharmingen), 1 μg/ml of anti-CD28 (Miltenyi Biotec), and 1× Monensin solution (eBioscience). After the 6 h incubation period, cells were stained with a fixable viability dye (eFluor 780, from eBioscience) and fluorochrome-conjugated anti-CD8 (PE conjugated Miltenyi Biotec) and analyzed by flow cytometry. The degranulation activity was determined as the % of CD8+/CD107a+ cells, and by determining the mean fluorescence intensity signal (MFI) for CD107a staining among CD8+ cells. Degranulation assays were carried out 24 h after mRNA transfection. Results are summarized in the Tables 6A-9H and 9A-9C below. In the tables, the second column (labeled "CAR-T cell") indicates the BCMA specific CAR being expressed in the transfected T cells.

CD107a expression on cells is a marker of antigen specific activation. The percent and MFI of CD107a on CD8 T cells expressing BCMA specific CARs increase when incubated with BCMA high (H929), medium (MM1S) and low (KMS12BM, L363) expressing cells but not BCMA negative cells (K562 and Daudi) (Tables 6A-9H and 9A-9C). CD107a expression levels did not increase on mock transfected T cells contacted with BCMA. Thus, the BCMA specific CAR-T cells are activated in the presence of BCMA-expressing cells but not in the presence of cells that do not express BCMA.

These results demonstrate that T cells expressing BCMA specific CARs are activated when incubated with BCMA expressing cells, and that the activation is antigen-specific.

IFNγ Release Assay

T cells were incubated in 96-well plates (50,000 cells/well), together with (a) cells expressing BCMA (MM1S, KMS12BM, and L363) or (b) cells that do not express the BCMA protein (K562). Co-cultures were maintained in a final volume of 100 μl of X-Vivo™-15 medium (Lonza) for 24 hours at 37° C. with 5% $CO_2$. After this incubation period the plates were centrifuged at 1500 rpm for 5 minutes and the supernatants were recovered in a new plate. IFNγ detection in the cell culture supernatants was done by ELISA assay (Human IFNγ Quantikine ELISA Kit, from R&D Systems). The IFNγ release assays were carried by starting the cell co-cultures 24 h after mRNA transfection. Results are summarized in the Tables 8A-8D and 10 below.

As shown in Tables 8A-8D and 10, CD8 T cells expressing BCMA specific CARs produce IFNγ when incubated with either medium BCMA-expressing cells (MM1S) or low BCMA-expressing cells (KMS12BM, L363). In contrast, CD8 T cells expressing BCMA specific CARs produce negligible IFNγ when incubated with BCMA negative cells (K562).

These results demonstrate that T cells expressing BCMA specific CARs are activated when incubated with BCMA expressing cells, and that the activation is antigen-specific.

Cytotoxicity Assay

T cells were incubated in 96-well plates (100,000 cells/well), together with 10,000 target cells (expressing BCMA) and 10,000 control (BCMAneg) cells in the same well. Target and control cells were labeled with fluorescent intracellular dyes (CFSE or Cell Trace Violet, from Life Technologies) before co-culturing them with CAR+ T cells. The co-cultures were incubated for 4 hours at 37° C. with 5% $CO_2$. After this incubation period, cells were labeled with a fixable viability dye (eFluor 780, from eBioscience) and analyzed by flow cytometry. Viability of each cellular population (target cells or BCMAneg control cells) was determined and the % of specific cell lysis was calculated. Cytotoxicity assays were carried out 48 h after mRNA transfection. Results are summarized in the Tables 7A-7H below. In the tables, the cytotoxicity data are shown as percent viable cells, then calculated as a ratio of live BCMA positive cells/live BCMA negative cells. Cell lysis is calculated as 100—mock transfected T cells.

As shown in Tables 7A-7H, T cells expressing BCMA specific CARs exhibit killing activity when incubated with either medium BCMA-expressing cells (MM1S) or low BCMA-expressing cells (L363). In contrast, CD8 T cells expressing BCMA specific CARs do not exhibit killing activity when incubated with BCMA negative cells (K562).

In summary, T cells expressing the selected BCMA specific CARs shown in Table 5 are selectively activated upon contact with BCMA-expressing cells. While all versions of the BCMA specific CARs exhibited BCMA-specific activation, BCMA specific CARs comprising a CD8α hinge (v2) exhibited increased activation levels compared to BCMA specific CARs comprising a FcγRIIIα (v1) hinge or IgG1 (v3) hinge.

TABLE 6A

Degranulation Assay Results, Donor 1

| | | | MFI CD107a+ | % CD107a+ (in CD8+) |
|---|---|---|---|---|
| Donor 1 | mock transfected T cells | T cells | 410 | 2.45 |
| | | PMA/Iono | 4038 | 76.1 |
| | | MM1S | 547 | 6.78 |
| | | K562 | 610 | 7.55 |
| P6DY | v1 | T cells | 588 | 5.19 |
| | | PMA/Iono | 3758 | 75.1 |
| | | MM1S | 850 | 14.9 |
| | | K562 | 829 | 9.76 |
| | v2 | T cells | 756 | 6.86 |
| | | PMA/Iono | 4103 | 75.5 |
| | | MM1S | 3872 | 75.4 |
| | | K562 | 1130 | 20.7 |
| | v3 | T cells | 707 | 7.71 |
| | | PMA/Iono | 4336 | 78.7 |
| | | MM1S | 3665 | 72.6 |
| | | K562 | 612 | 7.7 |
| P6AP | v1 | T cells | 604 | 4.61 |
| | | PMA/Iono | 3526 | 72.8 |
| | | MM1S | 1847 | 46.4 |
| | | K562 | 503 | 4.28 |
| | v2 | T cells | 1380 | 27.8 |
| | | PMA/Iono | 2504 | 58 |
| | | MM1S | 5299 | 83.9 |
| | | K562 | 949 | 14.6 |
| | v3 | T cells | 856 | 12.6 |
| | | PMA/Iono | 2500 | 58.9 |
| | | MM1S | 3638 | 73 |
| | | K562 | 718 | 9.15 |

TABLE 6B

Degranulation Assay Results, Donor 2

| | | | MFI CD107a+ | % CD107a+ (in CD8+) |
|---|---|---|---|---|
| Donor 2 | mock transfected T cells | T cells | 270 | 1.66 |
| | | PMA/Iono | 3872 | 88.3 |
| | | MM1S | 499 | 11 |
| | | K562 | 492 | 8.78 |
| P5A | v1 | T cells | 423 | 7.2 |
| | | PMA/Iono | 6034 | 96.3 |
| | | MM1S | 2670 | 77.6 |
| | | K562 | 648 | 16.6 |
| | v2 | T cells | 428 | 7.14 |
| | | PMA/Iono | 4420 | 90.7 |
| | | MM1S | 5019 | 91.8 |
| | | K562 | 620 | 13.8 |
| | v3 | T cells | 451 | 8.87 |
| | | PMA/Iono | 4835 | 93.2 |
| | | MM1S | 4191 | 88.5 |
| | | K562 | 607 | 14.1 |
| P5A_C1 | v1 | T cells | 315 | 4.12 |
| | | PMA/Iono | 3567 | 85.8 |
| | | MM1S | 2193 | 68.6 |
| | | K562 | 537 | 10.1 |
| | v2 | T cells | 413 | 7.46 |
| | | PMA/Iono | 4423 | 91.1 |
| | | MM1S | 4575 | 90.6 |
| | | K562 | 660 | 17.2 |
| | v3 | T cells | 429 | 7.82 |
| | | PMA/Iono | 4442 | 93.5 |
| | | MM1S | 3710 | 84.4 |
| | | K562 | 597 | 13.9 |
| P5A_C16 | v1 | T cells | 424 | 7.95 |
| | | PMA/Iono | 4325 | 91.1 |
| | | MM1S | 1858 | 61.6 |
| | | K562 | 636 | 14.9 |

TABLE 6B-continued

Degranulation Assay Results, Donor 2

| | | | MFI CD107a+ | % CD107a+ (in CD8+) |
|---|---|---|---|---|
| | v2 | T cells | 401 | 5.69 |
| | | PMA/Iono | 3007 | 80 |
| | | MM1S | 4228 | 87.9 |
| | | K562 | 696 | 17.6 |
| | v3 | T cells | 372 | 5.25 |
| | | PMA/Iono | 3611 | 86.6 |
| | | MM1S | 3372 | 83.6 |
| | | K562 | 476 | 7.72 |

TABLE 6C

Degranulation Assay Results, Donor 3

| | | | | MFI CD107a+ | % CD107a+ (in CD8+) |
|---|---|---|---|---|---|
| Donor 3 | mock transfected T cells | | T cells | 338 | 3.61 |
| | | | PMA/Iono | 7111 | 98.1 |
| | | | MM1S | 464 | 9.44 |
| | | | K562 | 533 | 9.73 |
| | PC1 | v1 | T cells | 454 | 6.67 |
| | | | PMA/Iono | 5226 | 96.5 |
| | | | MM1S | 2178 | 75.6 |
| | | | K562 | 753 | 22.3 |
| | | v2 | T cells | 507 | 13 |
| | | | PMA/Iono | 4743 | 95.2 |
| | | | MM1S | 759 | 25.5 |
| | | | K562 | 649 | 15.5 |
| | | v3 | T cells | 463 | 6.84 |
| | | | PMA/Iono | 7092 | 98.1 |
| | | | MM1S | 2857 | 87.2 |
| | | | K562 | 665 | 15 |
| | PC1C12 | v1 | T cells | 373 | 3.35 |
| | | | PMA/Iono | 6214 | 97.2 |
| | | | MM1S | 1960 | 68.2 |
| | | | K562 | 513 | 7.61 |
| | | v2 | T cells | 579 | 11.5 |
| | | | PMA/Iono | 6341 | 97.5 |
| | | | MM1S | 4478 | 95.1 |
| | | | K562 | 680 | 15 |
| | | v3 | T cells | 533 | 10.1 |
| | | | PMA/Iono | 5785 | 97.4 |
| | | | MM1S | 3739 | 91 |
| | | | K562 | 648 | 13.2 |
| | COM22 | v1 | T cells | 354 | 2.74 |
| | | | PMA/Iono | 5894 | 96.7 |
| | | | MM1S | 2219 | 76.1 |
| | | | K562 | 445 | 5.62 |
| | | v2 | T cells | 401 | 6.52 |
| | | | PMA/Iono | 5802 | 94.6 |
| | | | MM1S | 2372 | 79.2 |
| | | | K562 | 534 | 8.9 |
| | | v3 | T cells | 501 | 10.4 |
| | | | PMA/Iono | 6387 | 97.6 |
| | | | MM1S | 2780 | 85.9 |
| | | | K562 | 648 | 13.8 |

TABLE 6D

Degranulation Assay Results, Donor 4

| | | | MFI CD107a+ | % CD107a+ (in CD8+) |
|---|---|---|---|---|
| Donor 4 (v3 only) | mock transfected T cells | T cells | 248 | 2.64 |
| | | PMA/Iono | 5750 | 94.9 |
| | | MM1S | 363 | 8.89 |
| | | K562 | 368 | 6.86 |
| | P5A | T cells | 335 | 3.82 |
| | | PMA/Iono | 6025 | 93 |
| | | MM1S | 3150 | 86.7 |
| | | K562 | 418 | 9.91 |
| | P5AC1 | T cells | 505 | 22.1 |
| | | PMA/Iono | 6950 | 98.3 |
| | | MM1S | 2975 | 84.7 |
| | | K562 | 575 | 23.3 |
| | P5AC16 | T cells | 368 | 6.2 |
| | | PMA/Iono | 5775 | 97.7 |
| | | MM1S | 3675 | 86.8 |
| | | K562 | 420 | 9.73 |
| | PC1 | T cells | 403 | 9.05 |
| | | PMA/Iono | 6975 | 97.8 |
| | | MM1S | 4625 | 93 |
| | | K562 | 543 | 15.8 |
| | PC1C12 | T cells | 485 | 12.9 |
| | | PMA/Iono | 6400 | 96.5 |
| | | MM1S | 3575 | 90.4 |
| | | K562 | 585 | 18.9 |
| | COM22 | T cells | 535 | 20.5 |
| | | PMA/Iono | 7250 | 98.3 |
| | | MM1S | 3725 | 91.4 |
| | | K562 | 533 | 16.9 |
| | P6DY | T cells | 313 | 3.08 |
| | | PMA/Iono | 5125 | 94.3 |
| | | MM1S | 2435 | 79.9 |
| | | K562 | 438 | 10.4 |
| | P6AP | T cells | 430 | 10.4 |
| | | PMA/Iono | 6100 | 94.2 |
| | | MM1S | 3800 | 91.7 |
| | | K562 | 478 | 14.6 |

TABLE 6E

Degranulation Assay Results, Donor 5

| | | | % CD107a+ (in CD8+) | MFI CD107a+ |
|---|---|---|---|---|
| Donor 5 (v3 only) | CAR-BCMA-P5A | L363 | 47 | 917 |
| | | MM1S | 65.3 | 1713 |
| | | K562 | 3.65 | 247 |
| | | T cells | 1.71 | 199 |
| | | PMA/iono | 98.6 | 4797 |
| | CAR-BCMA-P5AC1 | L363 | 50.6 | 1117 |
| | | MM1S | 65.5 | 1753 |
| | | K562 | 5.29 | 265 |
| | | T cells | 1.93 | 213 |
| | | PMA/iono | 99.1 | 5755 |
| | CAR-BCMA-P5AC16 | L363 | 57.2 | 1392 |
| | | MM1S | 73.9 | 2520 |
| | | K562 | 4.13 | 273 |
| | | T cells | 2.57 | 232 |
| | | PMA/iono | 98.1 | 5120 |
| | CAR-BCMA-PC1 | L363 | 71.9 | 2167 |
| | | MM1S | 82.9 | 2987 |
| | | K562 | 4.5 | 316 |
| | | T cells | 2.47 | 273 |
| | | PMA/iono | 98.5 | 5556 |
| | CAR-BCMA-PC1C12 | L363 | 57.8 | 1492 |
| | | MM1S | 71.5 | 2094 |
| | | K562 | 3.72 | 313 |
| | | T cells | 2.53 | 272 |
| | | PMA/iono | 98.2 | 4480 |

TABLE 6E-continued

Degranulation Assay Results, Donor 5

| | | % CD107a+ (in CD8+) | MFI CD107a+ |
|---|---|---|---|
| CAR-BCMA-COM22 | L363 | 61.3 | 1574 |
| | MM1S | 78.1 | 2602 |
| | K562 | 5.84 | 296 |
| | T cells | 5.26 | 284 |
| | PMA/iono | 98.3 | 4434 |
| CAR-BCMA-P6DY | L363 | 43.4 | 859 |
| | MM1S | 63.6 | 1624 |
| | K562 | 3.99 | 256 |
| | T cells | 1.95 | 228 |
| | PMA/iono | 98.1 | 4075 |
| CAR-BCMA-P6AP | L363 | 63.4 | 1745 |
| | MM1S | 77.8 | 2461 |
| | K562 | 4.81 | 310 |
| | T cells | 4.74 | 300 |
| | PMA/iono | 98.9 | 32 |
| mock transfected T cells | L363 | 2.54 | 200 |
| | MM1S | 5.19 | 233 |
| | K562 | 4.02 | 201 |
| | T cells | 1.95 | 192 |
| | PMA/iono | 97.7 | 3216 |

TABLE 6F

Degranulation Assay Results, Donor 6

| | | | MFI CD107a+ | % CD107a+ (in CD8+) |
|---|---|---|---|---|
| Donor 6 | BCMA_BC30_v3 (18) | Tcells alone | 121 | 1.04 |
| | | T cells PMA IONO | 5253 | 87.4 |
| | | T cells K562 | 230 | 3.21 |
| | | T cells MM1S | 1321 | 50.4 |
| | | T cells L363 | 986 | 41.8 |
| | CAR_BCMA_P5AC1_v2 | Tcells alone | 150 | 1.07 |
| | | T cells PMA IONO | 4701 | 83.2 |
| | | T cells K562 | 256 | 5.5 |
| | | T cells MM1S | 2193 | 63.8 |
| | | T cells L363 | 1400 | 50.9 |
| | CAR_BCMA_P5AC1_v3 | Tcells alone | 166 | 0.96 |
| | | T cells PMA IONO | 4518 | 80.2 |
| | | T cells K562 | 301 | 6.87 |
| | | T cells MM1S | 1101 | 40.7 |
| | | T cells L363 | 728 | 29.8 |
| | CAR_BCMA_PC1_v3 | Tcells alone | 217 | 1.63 |
| | | T cells PMA IONO | 4711 | 82.4 |
| | | T cells K562 | 329 | 6.36 |
| | | T cells MM1S | 2083 | 60.3 |
| | | T cells L363 | 1500 | 52.1 |
| | CAR_BCMA_PC1C12_v2 | Tcells alone | 209 | 2.01 |
| | | T cells PMA IONO | 5401 | 87.8 |
| | | T cells K562 | 332 | 7.7 |
| | | T cells MM1S | 2588 | 68.4 |
| | | T cells L363 | 1976 | 59.5 |
| | CAR_BCMA_PC1C12_v3 | Tcells alone | 162 | 1.72 |
| | | T cells PMA IONO | 5299 | 85.3 |
| | | T cells K562 | 266 | 6.25 |
| | | T cells MM1S | 669 | 28.8 |
| | | T cells L363 | 414 | 18.6 |
| | CAR_BCMA_COM22_v3 | Tcells alone | 193 | 3.23 |
| | | T cells PMA IONO | 4750 | 82.7 |
| | | T cells K562 | 288 | 5.13 |
| | | T cells MM1S | 814 | 35.7 |
| | | T cells L363 | 606 | 26.8 |
| | CAR_BCMA_P6AP_v2 | Tcells alone | 359 | 9.69 |
| | | T cells PMA IONO | 5521 | 87.4 |
| | | T cells K562 | 327 | 7.69 |
| | | T cells MM1S | 2289 | 63.8 |
| | | T cells L363 | 1876 | 56.9 |
| | CAR_BCMA_P6AP_v3 | Tcells alone | 284 | 4.87 |
| | | T cells PMA IONO | 4480 | 82.7 |
| | | T cells K562 | 331 | 5.9 |
| | | T cells MM1S | 1409 | 46.9 |
| | | T cells L363 | 926 | 35.3 |
| | mock transfected T cells | Tcells alone | 184 | 0.92 |
| | | T cells PMA IONO | 3955 | 78.6 |
| | | T cells K562 | 278 | 3.58 |
| | | T cells MM1S | 393 | 4.7 |
| | | T cells L363 | 190 | 1.12 |

TABLE 6G

Degranulation Assay Results, Donor 7

| | | | MFI CD107a+ | % CD107a+ (in CD8+) |
|---|---|---|---|---|
| Donor 7 | mock transfected T cells | Tcells alone | 68.3 | 1.55 |
| | | T cells PMA IONO | 3097 | 94.6 |
| | | T cells MM1S | 118 | 7.15 |
| | | T cells L363 | 90.3 | 2.63 |
| | | T cells K562 | 144 | 3.4 |
| | | T cells Daudi | 117 | 1.93 |
| | BCMA_BC30_v3 (18) | Tcells alone | 69.7 | 2.69 |
| | | T cells PMA IONO | 2864 | 94.9 |
| | | T cells MM1S | 1630 | 68.9 |
| | | T cells L363 | 529 | 43.8 |
| | | T cells K562 | 125 | 3.85 |
| | | T cells Daudi | 426 | 38.5 |
| | P5AC1_v2 | Tcells alone | 111 | 3.67 |
| | | T cells PMA IONO | 2859 | 95.6 |
| | | T cells MM1S | 2305 | 71.5 |
| | | T cells L363 | 877 | 53.1 |
| | | T cells K562 | 166 | 8.54 |
| | | T cells Daudi | 770 | 51.5 |
| | P5AC1_v3 | Tcells alone | 70.8 | 1.04 |
| | | T cells PMA IONO | 2740 | 94.6 |
| | | T cells MM1S | 526 | 43.3 |
| | | T cells L363 | 209 | 20.4 |
| | | T cells K562 | 118 | 8.32 |
| | | T cells Daudi | 450 | 35.9 |
| | PC1_v3 | Tcells alone | 61 | 1.37 |
| | | T cells PMA IONO | 2786 | 94.6 |
| | | T cells MM1S | 1027 | 56.3 |
| | | T cells L363 | 314 | 29.9 |
| | | T cells K562 | 140 | 12.1 |
| | | T cells Daudi | 536 | 39.6 |
| | PC1C12_v2 | Tcells alone | 98 | 5.95 |
| | | T cells PMA IONO | 3493 | 95.3 |
| | | T cells MM1S | 1917 | 73.7 |
| | | T cells L363 | 939 | 56.2 |
| | | T cells K562 | 192 | 11.5 |
| | | T cells Daudi | 1485 | 64.6 |
| | PC1C12_v3 | Tcells alone | 84.2 | 2.28 |
| | | T cells PMA IONO | 3017 | 95.2 |
| | | T cells MM1S | 342 | 28.2 |
| | | T cells L363 | 145 | 8.72 |
| | | T cells K562 | 186 | 7.53 |
| | | T cells Daudi | 223 | 11.8 |
| | COM22_v3 | Tcells alone | 93.6 | 5.32 |
| | | T cells PMA IONO | 2989 | 96.3 |
| | | T cells MM1S | 540 | 40 |
| | | T cells L363 | 154 | 12.5 |
| | | T cells K562 | 138 | 8.29 |
| | | T cells Daudi | 93.5 | 3.99 |
| | P6AP_v2 | Tcells alone | 164 | 13.7 |
| | | T cells PMA IONO | 3303 | 95.9 |
| | | T cells MM1S | 2755 | 76 |
| | | T cells L363 | 859 | 50.3 |
| | | T cells K562 | 287 | 15.8 |
| | | T cells Daudi | 1263 | 58.2 |
| | P6AP_v3 | Tcells alone | 114 | 10.5 |
| | | T cells PMA IONO | 3084 | 94.5 |
| | | T cells MM1S | 849 | 51.6 |
| | | T cells L363 | 380 | 30.9 |
| | | T cells K562 | 211 | 8.46 |
| | | T cells Daudi | 678 | 42.7 |

TABLE 6H

Degranulation Assay Results, Donor 8

| | | | MFI CD107a+ | % CD107a+ (in CD8+) |
|---|---|---|---|---|
| Donor 8 | mock transfected T cells | Tcells alone | 154 | 0.67 |
| | | T cells PMA IONO | 3777 | 66.2 |

TABLE 6H-continued

Degranulation Assay Results, Donor 8

|  |  | MFI CD107a+ | % CD107a+ (in CD8+) |
|---|---|---|---|
|  | T cells MM1S | 229 | 2.16 |
|  | T cells L363 | 166 | 1.51 |
|  | T cells K562 | 220 | 2.08 |
| BCMA_BC30_v3 (18) | Tcells alone | 210 | 1.05 |
|  | T cells PMA IONO | 4302 | 70.6 |
|  | T cells MM1S | 1661 | 42 |
|  | T cells L363 | 1049 | 26.5 |
|  | T cells K562 | 262 | 3.46 |
| P5AC1_v2 | Tcells alone | 207 | 0.86 |
|  | T cells PMA IONO | 4298 | 71.5 |
|  | T cells MM1S | 1648 | 40.8 |
|  | T cells L363 | 1099 | 26.5 |
|  | T cells K562 | 232 | 1.72 |
| P5AC1_v3 | Tcells alone | 187 | 0.84 |
|  | T cells PMA IONO | 3989 | 68.8 |
|  | T cells MM1S | 766 | 21.2 |
|  | T cells L363 | 521 | 14.2 |
|  | T cells K562 | 258 | 2.05 |
| PC1_v3 | Tcells alone | 242 | 1.23 |
|  | T cells PMA IONO | 4256 | 70.6 |
|  | T cells MM1S | 1046 | 23.1 |
|  | T cells L363 | 1183 | 27.4 |
|  | T cells K562 | 283 | 2.97 |
| PC1C12_v2 | Tcells alone | 257 | 1.87 |
|  | T cells PMA IONO | 3487 | 60.2 |
|  | T cells MM1S | 2463 | 51.2 |
|  | T cells L363 | 1657 | 35.4 |
|  | T cells K562 | 314 | 4.05 |
| PC1C12_v3 | Tcells alone | 166 | 0.86 |
|  | T cells PMA IONO | 4238 | 69.1 |
|  | T cells MM1S | 641 | 17.3 |
|  | T cells L363 | 507 | 14.2 |
|  | T cells K562 | 296 | 3.52 |
| COM22_v3 | Tcells alone | 283 | 2.55 |
|  | T cells PMA IONO | 4800 | 75.9 |
|  | T cells MM1S | 1035 | 27.9 |
|  | T cells L363 | 704 | 22.7 |
|  | T cells K562 | 334 | 4.82 |
| P6AP_v2 | Tcells alone | 545 | 8.33 |
|  | T cells PMA IONO | 4362 | 68.6 |
|  | T cells MM1S | 2273 | 46.7 |
|  | T cells L363 | 1671 | 34.7 |
|  | T cells K562 | 629 | 9.71 |
| P6AP_v3 | Tcells alone | 360 | 3.87 |
|  | T cells PMA IONO | 3584 | 61.5 |
|  | T cells MM1S | 1553 | 34.5 |
|  | T cells L363 | 1045 | 23 |
|  | T cells K562 | 595 | 7.4 |

TABLE 7A

Cytotoxicity Data, Donor 6

|  |  | Viability (mean) | | | |
|---|---|---|---|---|---|
|  | CAR | L363 | K562 | MM1S | K562 |
| Donor 6 | BC30_v3 | 22.93 | 89.90 | 16.30 | 88.43 |
|  | P5AC1_v2 | 27.27 | 90.07 | 21.47 | 90.17 |
|  | P5AC1_v3 | 36.03 | 89.30 | 19.80 | 88.50 |
|  | PC1_v3 | 19.03 | 88.23 | 13.57 | 87.50 |
|  | PC1C12_v2 | 19.60 | 86.13 | 14.67 | 84.67 |
|  | PC1C12_v3 | 55.50 | 89.33 | 41.33 | 88.67 |
|  | COM22_v3 | 42.00 | 90.33 | 25.67 | 88.30 |
|  | P6AP_v2 | 29.40 | 80.27 | 21.07 | 82.10 |
|  | P6AP_v3 | 48.53 | 85.20 | 25.57 | 81.30 |
|  | mock transfected T cells | 90.90 | 88.20 | 91.77 | 86.30 |

TABLE 7B

Cytotoxicity Data, Donor 6

|  | CAR | BCMA+/BCMA− | | Ratio to Mock transfected T cells | | Cell lysis | |
|---|---|---|---|---|---|---|---|
|  |  | L363 | MM1S | L363 | MM1S | L363 | MM1S |
| Donor 6 | BC30_v3 | 25.51 | 18.43 | 0.24752108 | 0.17333946 | 75.2 | 82.7 |
|  | P5AC1_v2 | 30.27 | 23.81 | 0.29374647 | 0.22389502 | 70.6 | 77.6 |
|  | P5AC1_v3 | 40.35 | 22.37 | 0.39152336 | 0.21040098 | 60.8 | 79.0 |
|  | PC1_v3 | 21.57 | 15.50 | 0.2093085 | 0.14581122 | 79.1 | 85.4 |
|  | PC1C12_v2 | 22.76 | 17.32 | 0.22079514 | 0.1629089 | 77.9 | 83.7 |
|  | PC1C12_v3 | 62.13 | 46.62 | 0.60281513 | 0.4383953 | 39.7 | 56.2 |
|  | COM22_v3 | 46.49 | 29.07 | 0.45113441 | 0.27335977 | 54.9 | 72.7 |
|  | P6AP_v2 | 36.63 | 25.66 | 0.35539949 | 0.24131177 | 64.5 | 75.9 |
|  | P6AP_v3 | 56.96 | 31.45 | 0.55272006 | 0.29573955 | 44.7 | 70.4 |
|  | mock transfected T cells | 103.06 | 106.33 | 1 | 1 | 0.0 | 0.0 |

TABLE 7C

Cytotoxicity Data, Donor 7

|  | CAR | Viability (mean) | | | |
|---|---|---|---|---|---|
|  |  | L363 | K562 | MM1S | K562 |
| Donor 7 | mock transfected T cells | 92.53 | 92.80 | 90.70 | 92.33 |
|  | BC30_v3 | 46.00 | 90.40 | 34.00 | 89.83 |
|  | P5AC1_v2 | 50.50 | 90.73 | 35.17 | 89.40 |
|  | P5AC1_v3 | 60.20 | 89.97 | 43.03 | 89.53 |
|  | PC1_v3 | 49.43 | 89.67 | 37.33 | 88.97 |
|  | PC1C12_v2 | 40.23 | 88.50 | 22.53 | 87.53 |
|  | PC1C12_v3 | 81.03 | 91.30 | 71.70 | 89.83 |
|  | COM22_v3 | 67.87 | 90.00 | 52.97 | 89.20 |
|  | P6AP_v2 | 57.33 | 89.93 | 32.87 | 87.10 |
|  | P6AP_v3 | 66.37 | 91.60 | 46.35 | 94.00 |

TABLE 7E

Cytotoxicity Data, Donor 8

|  | CAR | Viability (mean) | | | |
|---|---|---|---|---|---|
|  |  | L363 | K562 | MM1S | K562 |
| Donor 8 | mock transfected T cells | 93.97 | 91.13 | 95.97 | 88.07 |
|  | BC30_v3 | 67.97 | 86.80 | 46.40 | 78.87 |
|  | P5AC1_v2 | 69.80 | 85.37 | 47.13 | 79.17 |
|  | P5AC1_v3 | 77.90 | 88.77 | 62.70 | 84.40 |
|  | PC1_v3 | 61.67 | 86.60 | 41.67 | 78.97 |
|  | PC1C12_v2 | 62.43 | 85.27 | 35.27 | 78.20 |
|  | PC1C12_v3 | 85.17 | 85.27 | 78.87 | 77.77 |
|  | COM22_v3 | 76.70 | 87.87 | 56.40 | 84.50 |
|  | P6AP_v2 | 77.23 | 84.90 | 61.47 | 83.47 |
|  | P6AP_v3 | 83.23 | 85.67 | 72.57 | 84.63 |
|  | cell lines | 95.20 | 94.97 | 96.97 | 94.20 |

TABLE 7D

Cytotoxicity Data, Donor 7

|  | CAR | BCMA+/BCMA− | | Ratio to Mock transfected T cells | | Cell lysis | |
|---|---|---|---|---|---|---|---|
|  |  | L363 | MM1S | L363 | MM1S | L363 | MM1S |
| Donor 7 | mock transfected T cells | 99.71 | 98.23 | 1 | 1 | 0.0 | 0.0 |
|  | BC30_v3 | 50.88 | 37.85 | 0.51031598 | 0.38529434 | 49.0 | 61.5 |
|  | P5AC1_v2 | 55.66 | 39.34 | 0.55818001 | 0.40044688 | 44.2 | 60.0 |
|  | P5AC1_v3 | 66.91 | 48.06 | 0.67106507 | 0.48929577 | 32.9 | 51.1 |
|  | PC1_v3 | 55.13 | 41.96 | 0.55288988 | 0.4271896 | 44.7 | 57.3 |
|  | PC1C12_v2 | 45.46 | 25.74 | 0.45592406 | 0.26206149 | 54.4 | 73.8 |
|  | PC1C12_v3 | 88.76 | 79.81 | 0.89010798 | 0.81251777 | 11.0 | 18.7 |
|  | COM22_v3 | 75.41 | 59.38 | 0.7562472 | 0.60448985 | 24.4 | 39.6 |
|  | P6AP_v2 | 63.75 | 37.73 | 0.63934647 | 0.38413929 | 36.1 | 61.6 |
|  | P6AP_v3 | 72.45 | 49.31 | 0.7266149 | 0.50196463 | 27.3 | 49.8 |

TABLE 7F

Cytotoxicity Data, Donor 8

| | CAR | BCMA+/BCMA− | | Ratio to Mock transfected T cells | | Cell lysis | |
|---|---|---|---|---|---|---|---|
| | | L363 | MM1S | L363 | MM1S | L363 | MM1S |
| Donor 8 | mock transfected T cells | 1.03 | 0.95 | 1 | 1 | 0.0 | 0.0 |
| | BC30_v3 | 0.78 | 0.59 | 0.75941589 | 0.61953757 | 24.1 | 38.0 |
| | P5AC1_v2 | 0.82 | 0.60 | 0.79299515 | 0.62694429 | 20.7 | 37.3 |
| | P5AC1_v3 | 0.88 | 0.74 | 0.85112036 | 0.78229085 | 14.9 | 21.8 |
| | PC1_v3 | 0.71 | 0.53 | 0.69061501 | 0.5556331 | 30.9 | 44.4 |
| | PC1C12_v2 | 0.73 | 0.45 | 0.7101346 | 0.47489852 | 29.0 | 52.5 |
| | PC1C12_v3 | 1.00 | 1.01 | 0.96871004 | 1.06793091 | 3.1 | −6.8 |
| | COM22_v3 | 0.87 | 0.67 | 0.84659295 | 0.70285469 | 15.3 | 29.7 |
| | P6AP_v2 | 0.91 | 0.74 | 0.88226799 | 0.77547847 | 11.8 | 22.5 |
| | P6AP_v3 | 0.97 | 0.86 | 0.94229927 | 0.9028984 | 5.8 | 9.7 |
| | cell lines | 1.00 | 1.03 | 0.97223038 | 1.08396365 | 2.8 | −8.4 |

TABLE 7G

Cytotoxicity Data, Donor 9

| | CAR | Viability (mean) | | | |
|---|---|---|---|---|---|
| | | L363 | K562 | MM1S | K562 |
| Donor 9 | mock transfected T cells | 86.3 | 87.8 | 69.6 | 86.5 |
| | BC30_v3 | 27.1 | 86.6 | 16.0 | 86.6 |
| | P5AC1_v2 | 31.9 | 87.9 | 21.0 | 87.2 |
| | P5AC1_v3 | 46.9 | 85.1 | 36.3 | 84.0 |
| | PC1_v3 | 27.8 | 85.3 | 25.4 | 85.0 |
| | PC1C12_v2 | 29.3 | 88.7 | 15.0 | 86.0 |
| | COM22_v3 | 49.0 | 88.8 | 35.7 | 87.5 |
| | P6AP_v2 | 41.4 | 85.7 | 22.8 | 84.0 |
| | P6AP_v3 | 56.4 | 84.3 | 44.9 | 84.4 |
| | Cell lines | 92.3 | 91.7 | 83.5 | 91.8 |

TABLE 7H

Cytotoxicity Data, Donor 9

| | CAR | BCMA+/BCMA− | | Ratio to Mock transfected T cells | | Cell lysis | |
|---|---|---|---|---|---|---|---|
| | | L363 | MM1S | L363 | MM1S | L363 | MM1S |
| Donor 9 | mock transfected T cells | 0.98216319 | 0.80469954 | 1 | 1 | 0 | 0 |
| | BC30_v3 | 0.31331794 | 0.18444359 | 0.31900802 | 0.22920802 | 68.10 | 77.08 |
| | P5AC1_v2 | 0.3631539 | 0.24111578 | 0.36974905 | 0.29963455 | 63.03 | 70.04 |
| | P5AC1_v3 | 0.55133229 | 0.43231441 | 0.56134489 | 0.53723706 | 43.87 | 46.28 |
| | PC1_v3 | 0.32551778 | 0.29831439 | 0.33142942 | 0.37071525 | 66.86 | 62.93 |
| | PC1C12_v2 | 0.3298272 | 0.17473847 | 0.3358171 | 0.21714748 | 66.42 | 78.29 |
| | COM22_v3 | 0.55159475 | 0.40746382 | 0.56161212 | 0.50635523 | 43.84 | 49.36 |
| | P6AP_v2 | 0.48289269 | 0.27092424 | 0.49166238 | 0.33667751 | 50.83 | 66.33 |
| | P6AP_v3 | 0.66903915 | 0.53199052 | 0.68118939 | 0.66110454 | 31.88 | 33.89 |
| | Cell lines | 1.00690909 | 0.90889292 | 1.02519531 | 1.1294811 | −2.52 | −12.95 |

TABLE 8A

IFNγ Production (pg/mL), Donor 6
Donor 6

| CAR | | pg/ml |
|---|---|---|
| mock transfected T cells | Tcells alone | 155.1 |
| BCMA_BC30_v3 (18) | | 654.71 |
| P5AC1_v2 | | 174.035 |
| P5AC1_v3 | | 61.215 |
| PC1_v3 | | 255.045 |
| PC1C12_v2 | | 481.595 |
| PC1C12_v3 | | 463.08 |
| COM22_v3 | | 2996.305 |
| P6AP_v2 | | 1294.055 |
| P6AP_v3 | | 500.435 |
| mock transfected T cells | T cells PMA IONO | 81654.2 |
| BCMA_BC30_v3 (18) | | 49368.7 |
| P5AC1_v2 | | 49102.7 |
| P5AC1_v3 | | 66837.7 |
| PC1_v3 | | 70798.2 |
| PC1C12_v2 | | 56402.2 |
| PC1C12_v3 | | 121954.7 |
| COM22_v3 | | 125878.7 |
| P6AP_v2 | | 73577.2 |
| P6AP_v3 | | 51242.7 |
| mock transfected T cells | T cells K562 | −83.215 |
| BCMA_BC30_v3 (18) | | 265.565 |
| P5AC1_v2 | | −10.05 |

TABLE 8A-continued

IFNγ Production (pg/mL), Donor 6
Donor 6

| CAR | | pg/ml |
|---|---|---|
| P5AC1_v3 | | 36.475 |
| PC1_v3 | | −74.04 |
| PC1C12_v2 | | 344.72 |
| PC1C12_v3 | | 583.99 |
| COM22_v3 | | 610.97 |
| P6AP_v2 | | 40.66 |
| P6AP_v3 | | 36.775 |
| mock transfected T cells | T cells MM1S | 660.33 |
| BCMA_BC30_v3 (18) | | 8004.42 |
| P5AC1_v2 | | 5667.72 |
| P5AC1_v3 | | 2619.735 |
| PC1_v3 | | 6152.67 |
| PC1C12_v2 | | 8526.27 |
| PC1C12_v3 | | 1405.945 |
| COM22_v3 | | 3330.27 |
| P6AP_v2 | | 5436.27 |
| P6AP_v3 | | 3881.115 |
| mock transfected T cells | T cells L363 | 1287.38 |
| BCMA_BC30_v3 (18) | | 6363.72 |
| P5AC1_v2 | | 3116.725 |
| P5AC1_v3 | | 2720.52 |
| PC1_v3 | | 6661.97 |
| PC1C12_v2 | | 9478.72 |
| PC1C12_v3 | | 1707.885 |
| COM22_v3 | | 2397.83 |
| P6AP_v2 | | 5911.97 |
| P6AP_v3 | | 3470.38 |

TABLE 8B

IFNγ Production (pg/mL), Donor 7
Donor 7

| CAR | | pg/ml |
|---|---|---|
| mock transfected T cells | Tcells alone | −3.1 |
| BCMA_BC30_v3 (18) | | 64.1 |
| P5AC1_v2 | | −18.0 |
| P5AC1_v3 | | −73.0 |
| PC1_v3 | | 6.1 |
| PC1C12_v2 | | 156.5 |
| PC1C12_v3 | | 100.1 |
| COM22_v3 | | 182.9 |
| P6AP_v2 | | 564.7 |
| P6AP_v3 | | 107.0 |
| mock transfected T cells | T cells PMA IONO | 44970.8 |
| BCMA_BC30_v3 (18) | | 32725.3 |
| P5AC1_v2 | | 27476.6 |
| P5AC1_v3 | | 13100.5 |
| PC1_v3 | | 40824.4 |
| PC1C12_v2 | | 39884.6 |
| PC1C12_v3 | | 30245.2 |
| COM22_v3 | | 62690.4 |
| P6AP_v2 | | 69923.2 |
| P6AP_v3 | | 88578.4 |
| mock transfected T cells | T cells MM1S | 29.9 |
| BCMA_BC30_v3 (18) | | 4662.6 |
| P5AC1_v2 | | 3420.3 |
| P5AC1_v3 | | 1173.7 |
| PC1_v3 | | 2478.5 |
| PC1C12_v2 | | 5314.6 |
| PC1C12_v3 | | 809.9 |
| COM22_v3 | | 1344.6 |
| P6AP_v2 | | 3020.3 |
| P6AP_v3 | | 2166.7 |
| mock transfected T cells | T cells L363 | 15.6 |
| BCMA_BC30_v3 (18) | | 2360.2 |
| P5AC1_v2 | | 2576.3 |
| P5AC1_v3 | | 582.7 |
| PC1_v3 | | 1723.3 |
| PC1C12_v2 | | 2962.9 |
| PC1C12_v3 | | 136.6 |

TABLE 8B-continued

IFNγ Production (pg/mL), Donor 7
Donor 7

| CAR | | pg/ml |
|---|---|---|
| COM22_v3 | | 467.4 |
| P6AP_v2 | | 2081.4 |
| P6AP_v3 | | 1119.0 |
| mock transfected T cells | T cells K562 | −80.5 |
| BCMA_BC30_v3 (18) | | −127.2 |
| P5AC1_v2 | | −124.4 |
| P5AC1_v3 | | −47.9 |
| PC1_v3 | | −93.6 |
| PC1C12_v2 | | 21.8 |
| PC1C12_v3 | | −55.4 |
| COM22_v3 | | −36.1 |
| P6AP_v2 | | 83.8 |
| P6AP_v3 | | 83.8 |
| mock transfected T cells | | 335.1 |
| BCMA_BC30_v3 (18) | T cells Daudi | 7794.8 |
| P5AC1_v2 | | 8093.7 |
| P5AC1_v3 | | 3870.6 |
| PC1_v3 | | 6068.9 |
| PC1C12_v2 | | 10190.2 |
| PC1C12_v3 | | 1638.8 |
| COM22_v3 | | 4287.6 |
| P6AP_v2 | | 6971.6 |
| P6AP_v3 | | 5280.0 |

TABLE 8C

IFN-γ Production (pg/mL), Donor 8
Donor 8

| CAR | | pg/ml |
|---|---|---|
| mock transfected T cells | Tcells alone | −697.44 |
| BCMA_BC30_v3 (18) | | −660.92 |
| P5AC1_v2 | | −603.38 |
| P5AC1_v3 | | −543.44 |
| PC1_v3 | | −552.22 |
| PC1C12_v2 | | −399.26 |
| PC1C12_v3 | | −652.73 |
| COM22_v3 | | −530.09 |
| P6AP_v2 | | 17.24 |
| P6AP_v3 | | −289.82 |
| mock transfected T cells | T cells PMA IONO | 37206.73 |
| BCMA_BC30_v3 (18) | | 53311.73 |
| P5AC1_v2 | | 57732.14 |
| P5AC1_v3 | | 52577.56 |
| PC1_v3 | | 48925.48 |
| PC1C12_v2 | | 38310.06 |
| PC1C12_v3 | | 71881.73 |
| COM22_v3 | | 61941.73 |
| P6AP_v2 | | 82339.64 |
| P6AP_v3 | | 63337.14 |
| mock transfected T cells | T cells MM1S | −684.65 |
| BCMA_BC30_v3 (18) | | 2976.34 |
| P5AC1_v2 | | 2727.71 |
| P5AC1_v3 | | 769.05 |
| PC1_v3 | | 2682.98 |
| PC1C12_v2 | | 5019.05 |
| PC1C12_v3 | | −198.04 |
| COM22_v3 | | 1155.19 |
| P6AP_v2 | | 2945.65 |
| P6AP_v3 | | 671.21 |
| mock transfected T cells | T cells L363 | −664.74 |
| BCMA_BC30_v3 (18) | | 2934.77 |
| P5AC1_v2 | | 2342.50 |
| P5AC1_v3 | | 579.85 |
| PC1_v3 | | 2232.65 |
| PC1C12_v2 | | 3676.59 |
| PC1C12_v3 | | −303.86 |
| COM22_v3 | | 695.72 |
| P6AP_v2 | | 1612.74 |
| P6AP_v3 | | 311.07 |

TABLE 8C-continued

IFN-γ Production (pg/mL), Donor 8
Donor 8

| CAR | | pg/ml |
|---|---|---|
| mock transfected T cells | T cells K562 | −672.42 |
| BCMA_BC30_v3 (18) | | −583.71 |
| P5AC1_v2 | | −631.02 |
| P5AC1_v3 | | −650.83 |
| PC1_v3 | | −615.50 |
| PC1C12_v2 | | −501.18 |
| PC1C12_v3 | | −615.17 |
| COM22_v3 | | −596.02 |
| P6AP_v2 | | −393.94 |
| P6AP_v3 | | −476.71 |

TABLE 8D

IFN-γ Production (pg/mL), Donor 9
Donor 9

| CAR | | pg/ml |
|---|---|---|
| mock transfected T cells | Tcells alone | 93.2 |
| BCMA_BC30_v3 (18) | | 1225.2 |
| P5AC1_v2 | | 1344.5 |
| P5AC1_v3 | | 632.3 |
| PC1_v3 | | 2745.7 |
| PC1C12_v2 | | 48.1 |
| COM22_v3 | | 2656.9 |
| P6AP_v2 | | 566.5 |
| P6AP_v3 | | −335.8 |
| mock transfected T cells | T cells PMA IONO | 12505.8 |
| BCMA_BC30_v3 (18) | | 12312.2 |
| P5AC1_v2 | | 10607.5 |
| P5AC1_v3 | | 12014.7 |
| PC1_v3 | | 12829.9 |
| PC1C12_v2 | | 13829.5 |
| COM22_v3 | | 13489.5 |
| P6AP_v2 | | 13182.1 |
| P6AP_v3 | | 13506.3 |
| mock transfected T cells | T cells MM1S | 1006.4 |
| BCMA_BC30_v3 (18) | | 2376.8 |
| P5AC1_v2 | | −359.5 |
| P5AC1_v3 | | 97.8 |
| PC1_v3 | | 290.1 |
| PC1C12_v2 | | 752.7 |
| COM22_v3 | | −601.0 |
| P6AP_v2 | | −304.1 |
| P6AP_v3 | | −394.9 |
| mock transfected T cells | T cells L363 | −228.2 |
| BCMA_BC30_v3 (18) | | 3000.2 |
| P5AC1_v2 | | 2314.0 |
| P5AC1_v3 | | 1646.4 |
| PC1_v3 | | −15.4 |
| PC1C12_v2 | | 2796.5 |
| COM22_v3 | | 320.6 |
| P6AP_v2 | | −163.0 |
| P6AP_v3 | | −233.9 |
| mock transfected T cells | T cells K562 | −227.9 |
| BCMA_BC30_v3 (18) | | 2027.5 |
| P5AC1_v2 | | 3928.4 |
| P5AC1_v3 | | 300.2 |
| PC1_v3 | | 74.9 |
| PC1C12_v2 | | 1835.7 |
| COM22_v3 | | 45.0 |
| P6AP_v2 | | 51.4 |
| P6AP_v3 | | 158.3 |

TABLE 9A

Degranulation Assay Results, Donor 10

| Donor 10 | | MFI CD107a+ | % CD107a+ (in CD8+) |
|---|---|---|---|
| LT alone | mock transfected T cells | 82.2 | 1.95 |
| | 26859 P5AC1-V2 | 83.8 | 1.47 |
| | 26868 PC1C12-V2 | 94.2 | 3.21 |
| | 26871 COM22-V2 | 107 | 5.96 |
| PMA Iono | mock transfected T cells | 5933 | 99 |
| | 26859 P5AC1-V2 | 5863 | 99 |
| | 26868 PC1C12-V2 | 6366 | 99.4 |
| | 26871 COM22-V2 | 6149 | 99 |
| MM1S | mock transfected T cells | 211 | 16.5 |
| | 26859 P5AC1-V2 | 1377 | 74.4 |
| | 26868 PC1C12-V2 | 1760 | 79.1 |
| | 26871 COM22-V2 | 1470 | 76.5 |
| H929 | mock transfected T cells | 141 | 6.09 |
| | 26859 P5AC1-V2 | 1026 | 65.4 |
| | 26868 PC1C12-V2 | 1262 | 71.1 |
| | 26871 COM22-V2 | 784 | 59.2 |
| L363 | mock transfected T cells | 153 | 6.48 |
| | 26859 P5AC1-V2 | 793 | 60.1 |
| | 26868 PC1C12-V2 | 1054 | 67.3 |
| | 26871 COM22-V2 | 827 | 61.7 |
| MM1S GFP LUC | mock transfected T cells | 187 | 9.88 |
| | 26859 P5AC1-V2 | 1228 | 70.5 |
| | 26868 PC1C12-V2 | 1476 | 74.9 |
| | 26871 COM22-V2 | 1095 | 68.5 |
| H929 GFP LUC | mock transfected T cells | 153 | 9.48 |
| | 26859 P5AC1-V2 | 1648 | 77.8 |
| | 26868 PC1C12-V2 | 1960 | 84 |
| | 26871 COM22-V2 | 1029 | 69.4 |
| L363 GFP LUC | mock transfected T cells | 104 | 3.06 |
| | 26859 P5AC1-V2 | 753 | 60.7 |
| | 26868 PC1C12-V2 | 873 | 64.6 |
| | 26871 COM22-V2 | 766 | 61.1 |
| KMS12BM GFP LUC | mock transfected T cells | 91.3 | 2.67 |
| | 26859 P5AC1-V2 | 945 | 67.2 |
| | 26868 PC1C12-V2 | 1192 | 71.2 |
| | 26871 COM22-V2 | 961 | 67.2 |
| K562 | mock transfected T cells | 127 | 6.06 |
| | 26859 P5AC1-V2 | 136 | 9.1 |
| | 26868 PC1C12-V2 | 119 | 9.49 |
| | 26871 COM22-V2 | 135 | 9.55 |

TABLE 9B

Degranulation Assay Results, Donor 11

| Donor 11 | | MFI CD107a+ | % CD107a+ (in CD8+) |
|---|---|---|---|
| LT alone | mock transfected T cells | 69.9 | 0.57 |
| | 26859 P5AC1-V2 | 68.3 | 0.62 |
| | 26868 PC1C12-V2 | 67.2 | 0.88 |
| | 26871 COM22-V2 | 80.9 | 3.95 |
| PMA Iono | mock transfected T cells | 5511 | 91.7 |
| | 26859 P5AC1-V2 | 5360 | 97.4 |
| | 26868 PC1C12-V2 | 4741 | 96.1 |
| | 26871 COM22-V2 | 5066 | 95.7 |
| KMS12BM GFP LUC | mock transfected T cells | 77.8 | 1.81 |
| | 26859 P5AC1-V2 | 1304 | 68.3 |
| | 26868 PC1C12-V2 | 650 | 45.5 |
| | 26871 COM22-V2 | 986 | 62.5 |
| H929 GFP LUC | mock transfected T cells | 73 | 1.04 |
| | 26859 P5AC1-V2 | 738 | 49.6 |
| | 26868 PC1C12-V2 | 428 | 30.9 |
| | 26871 COM22-V2 | 468 | 35.5 |
| MM1S | mock transfected T cells | 121 | 2.67 |
| | 26859 P5AC1-V2 | 854 | 52 |
| | 26868 PC1C12-V2 | 399 | 26.4 |
| | 26871 COM22-V2 | 486 | 33.4 |

TABLE 9B-continued

Degranulation Assay Results, Donor 11

| Donor 11 | | MFI CD107a+ | % CD107a+ (in CD8+) |
|---|---|---|---|
| K562 | mock transfected T cells | 125 | 3.08 |
| | 26859 P5AC1-V2 | 140 | 3.35 |
| | 26868 PC1C12-V2 | 123 | 1.84 |
| | 26871 COM22-V2 | 161 | 4.11 |

TABLE 9C

Degranulation Assay Results, Donor 12

| Donor 11 | | MFI CD107a+ | % CD107a+ (in CD8+) |
|---|---|---|---|
| LT alone | mock transfected T cells | 69.9 | 0.57 |
| | 26859 P5AC1-V2 | 68.3 | 0.62 |
| | 26868 PC1C12-V2 | 67.2 | 0.88 |
| | 26871 COM22-V2 | 80.9 | 3.95 |
| PMA Iono | mock transfected T cells | 5511 | 91.7 |
| | 26859 P5AC1-V2 | 5360 | 97.4 |
| | 26868 PC1C12-V2 | 4741 | 96.1 |
| | 26871 COM22-V2 | 5066 | 95.7 |

TABLE 9C-continued

Degranulation Assay Results, Donor 12

| Donor 11 | | MFI CD107a+ | % CD107a+ (in CD8+) |
|---|---|---|---|
| KMS12BM GFP LUC | mock transfected T cells | 77.8 | 1.81 |
| | 26859 P5AC1-V2 | 1304 | 68.3 |
| | 26868 PC1C12-V2 | 650 | 45.5 |
| | 26871 COM22-V2 | 986 | 62.5 |
| H929 GFP LUC | mock transfected T cells | 73 | 1.04 |
| | 26859 P5AC1-V2 | 738 | 49.6 |
| | 26868 PC1C12-V2 | 428 | 30.9 |
| | 26871 COM22-V2 | 468 | 35.5 |
| MM1S | mock transfected T cells | 121 | 2.67 |
| | 26859 P5AC1-V2 | 854 | 52 |
| | 26868 PC1C12-V2 | 399 | 26.4 |
| | 26871 COM22-V2 | 486 | 33.4 |
| K562 | mock transfected T cells | 125 | 3.08 |
| | 26859 P5AC1-V2 | 140 | 3.35 |
| | 26868 PC1C12-V2 | 123 | 1.84 |
| | 26871 COM22-V2 | 161 | 4.11 |

TABLE 10

IFN gamma release assay results, Donor 10
Donor 10

| | | |
|---|---|---|
| mock transfected T cells | T cells alone | 871.8 pg/mL |
| pCLS26859 CAR_BCMA_P5AC1_v2 | | 1466.2 pg/mL |
| pCLS26868 CAR_BCMA_PC1C12_v2 | | 1172.2 pg/mL |
| pCLS26871 CAR_BCMA_COM22_v2 | | 1873.1 pg/mL |
| mock transfected T cells | MM1S LucGFP | 1436.5 pg/mL |
| pCLS26859 CAR_BCMA_P5AC1_v2 | | 12208.4 pg/mL |
| pCLS26868 CAR_BCMA_PC1C12_v2 | | 13695.3 pg/mL |
| pCLS26871 CAR_BCMA_COM22_v2 | | 10784.1 pg/mL |
| mock transfected T cells | MM1S | 5329.0 pg/mL |
| pCLS26859 CAR_BCMA_P5AC1_v2 | | 6060.3 pg/mL |
| pCLS26868 CAR_BCMA_PC1C12_v2 | | 6776.1 pg/mL |
| pCLS26871 CAR_BCMA_COM22_v2 | | 7827.0 pg/mL |
| mock transfected T cells | H929 LucGFP | 754.2 pg/mL |
| pCLS26859 CAR_BCMA_P5AC1_v2 | | 16589.9 pg/mL |
| pCLS26868 CAR_BCMA_PC1C12_v2 | | 15989.7 pg/mL |
| pCLS26871 CAR_BCMA_COM22_v2 | | 14410.4 pg/mL |
| mock transfected T cells | H929 | 809.8 pg/mL |
| pCLS26859 CAR_BCMA_P5AC1_v2 | | 18072.7 pg/mL |
| pCLS26868 CAR_BCMA_PC1C12_v2 | | 17948.1 pg/mL |
| pCLS26871 CAR_BCMA_COM22_v2 | | 14437.3 pg/mL |
| mock transfected T cells | L363 LucGFP | 1184.5 pg/mL |
| pCLS26859 CAR_BCMA_P5AC1_v2 | | 11556.9 pg/mL |
| pCLS26868 CAR_BCMA_PC1C12_v2 | | 13254.5 pg/mL |
| pCLS26871 CAR_BCMA_COM22_v2 | | 11384.1 pg/mL |
| mock transfected T cells | L363 | 1777.3 pg/mL |
| pCLS26859 CAR_BCMA_P5AC1_v2 | | 15685.1 pg/mL |
| pCLS26868 CAR_BCMA_PC1C12_v2 | | 14929.1 pg/mL |
| pCLS26871 CAR_BCMA_COM22_v2 | | 14995.7 pg/mL |
| mock transfected T cells | L363 LucGFP | 1184.5 pg/mL |
| pCLS26859 CAR_BCMA_P5AC1_v2 | | 11556.9 pg/mL |
| pCLS26868 CAR_BCMA_PC1C12_v2 | | 13254.5 pg/mL |
| pCLS26871 CAR_BCMA_COM22_v2 | | 11384.1 pg/mL |
| mock transfected T cells | KMS12BM LucGFP | 1283.2 pg/mL |
| pCLS26859 CAR_BCMA_P5AC1_v2 | | 9073.3 pg/mL |
| pCLS26868 CAR_BCMA_PC1C12_v2 | | 10060.6 pg/mL |
| pCLS26871 CAR_BCMA_COM22_v2 | | 10687.2 pg/mL |
| mock transfected T cells | K562 | 691.6 pg/mL |
| pCLS26859 CAR_BCMA_P5AC1_v2 | | 684.1 pg/mL |
| pCLS26868 CAR_BCMA_PC1C12_v2 | | 904.2 pg/mL |
| pCLS26871 CAR BCMA COM22 v2 | | 969.0 pg/mL |

Example 3

BCMA Specific CAR-T Cells Induce Tumor Regression in MM1.S Tumor Model

This example illustrates treatment of tumors with BCMA specific CAR-T cells using the MM1.S tumor model.

In vivo efficacy study of BCMA specific CAR-T cells was performed with MM1.S, expressing luciferase and GFP, orthotopic model. Five million MM1.S Luc2AGFP cells were injected intravenously through the tail vein into 6-8 weeks old female Nod/Scid/IL2Rg−/− (NSG) animals. Intraperitoneal injection of D-luciferin (Regis Technologies, Morton Grove, IL) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, CA).

Three different BCMA specific CAR-T cells were used in this study: T cells expressing the BCMA specific CAR constructs P5AC1-V2, PC1C12-V2, or COM22-V2 (see, Table 5 above). Non-transduced control T cells were used as the negative control. All T cells were engineered to be TCRα deficient.

When the total flux reached an average of 45E6 for all animals (day 20 post tumor implant), the animals were randomized into four groups. A single dose of human either BCMA specific CAR-T cells or non-transduced control T cells was administered through bolus tail vein injection. Animals were terminated when they exhibit hindlimb paralysis or a 20% loss of body weight, an endpoint for MM1.S orthotopic models.

Results of this study are summarized in FIG. 1. In FIG. 1, total flux [p/s] represents tumor progression. Treatment with BCMA specific CAR-T cells (triangles, diamonds, squares) resulted in lower total flux as compared to the negative control (circles). Thus, treatment with BCMA specific CAR-T cells inhibited tumor progression as compared to the negative control.

These results demonstrate BCMA specific CAR-T cells are effective to induce tumor regression.

Example 4

Treatment of Multiple Myeloma with BCMA Specific CAR-T Cells

This example illustrates treatment of multiple myeloma with BCMA specific CAR-T cells using the Molp8 orthotopic model.

In vivo efficacy study of BCMA specific CAR-T cells was performed with Molp8, expressing luciferase and GFP, orthotopic model. Two million Molp8 Luc2AGFP cells were injected intravenously through the tail vein into 6-8 weeks old female NSG animals. Intraperitoneal injection of D-luciferin (Regis Technologies, Morton Grove, IL) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, CA).

When the total flux reached an average of 30E6 for all animals (day 8 post tumor implant), the animals were randomized into three groups. Each group was administered one of the following cells: 1) non-transduced T cells TCR KO ("TCR KO") used as a control, 2) BCMA specific CAR-T cells expressing P5AC1-V2.1 ("P5AC1 V2 R2 TCR KO"), or 3) BCMA specific CAR-T cells expressing P5AC1-V2 and the RQR8 suicide polypeptide ("P5AC1 V2 RQR8 TCR KO"). All of cells 1-3 are TCRα deficient. The BCMA specific CAR-T cells were prepared as described in example above. BCMA specific CAR constructs P5AC1-V2.1 and P5AC1-V2 are shown in Table 5 above. A single dose of 3 million control (TCR KO) or BCMA specific CAR-T (P5AC1 V2 R2 TCR KO or P5AC1 V2 RQR8 TCR KO) cells were administered through bolus tail vein injection. Animals were terminated when they lose more than 15% of total body weight, an endpoint for Molp8 orthotopic models.

Figure 2:
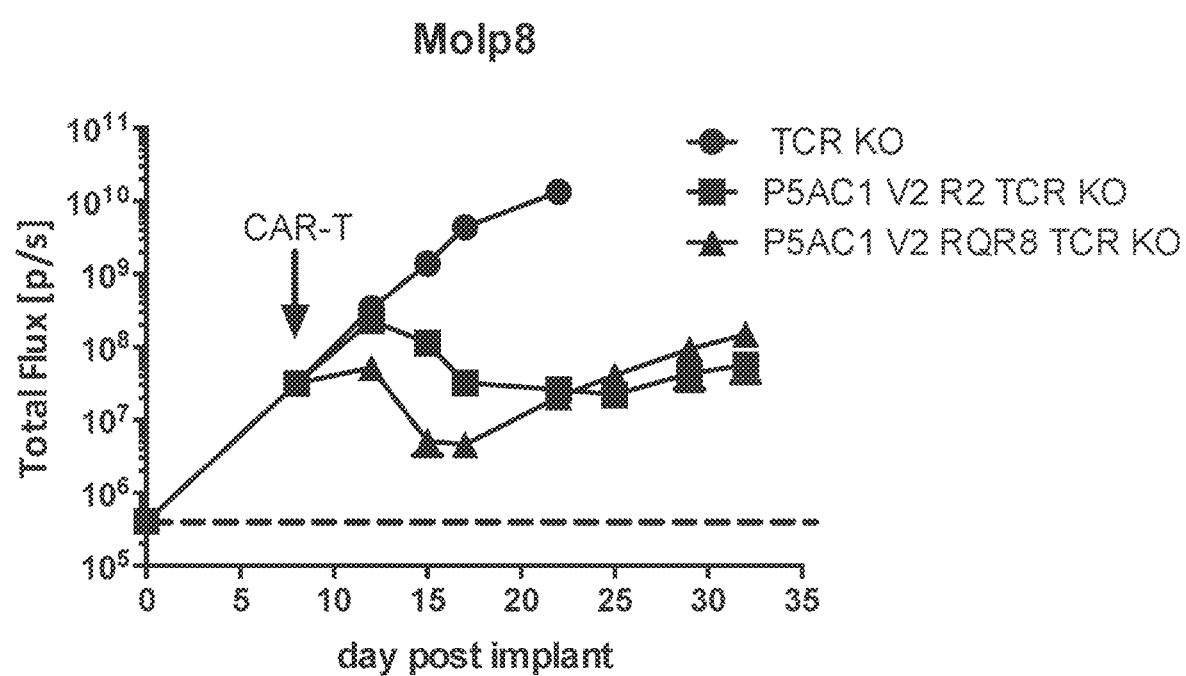
FIG. 2 depicts a graph summarizing the results of treatment with BCMA specific CAR-T cells in the Molp8 tumor model.

Results from the study are summarized in FIG. 2. A single dose of 3 million P5AC1 R2 TCRKO BCMA specific CAR-T cells (squares) or P5AC1 RQR8 TCRKO CAR-T cells (triangles) BCMA specific CAR-T cells resulted in lower total flux from days 10-35 post tumor implant as compared to the negative control (circles) (FIG. 2). Thus, treatment with BCMA specific CAR-T cells inhibited tumor progression as compared to the negative control.

These results demonstrate BCMA specific CAR-T cells are effective to inhibit tumor progression.

Example 5

Treatment of Multiple Myeloma with BCMA Specific CAR-T Cells

This example illustrates the therapeutic activity of BCMA specific CAR-T cells in orthotopic mouse models of multiple myeloma.

Two humanized mouse models were used to evaluate the efficacy of BCMA specific CAR-T cells against human myeloma cell lines expressing BCMA. Six (6) to eight (8) week old female Nod/Scid IL2rg−/− (NSG) mice were purchased from the Jackson Laboratories. All animals were housed in a pathogen free vivarium facility at Rinat and experiments were conducted according to the protocols in accordance with the Institutional Animal Care and Use Committee (IACUC) guidelines.

The MM1.S and Molp-8 cell lines were purchased from the American Type Culture Collection (ATCC.org) and the Deutsche Sammlung von Mikroorganismen and Zellkulturen GmbH (DSMZ.de). Cell lines were engineered to express a Luc-GFP fusion protein using lentiviral particles (amsbio). Cells were cultured in RPMI 1640 medium with L-glutamine supplemented with either 10% fetal calf serum for MM1.S or with 20% FCS for Molp-8 cells at 37° C. in 5% carbon dioxide ($CO_2$). Cells growing in an exponential growth phase were harvested and used for tumor inoculation.

Therapeutic BCMA specific CAR-T cells were produced as described. Healthy human donor cells, peripheral blood mononuclear cells (PBMC) or purified pan-T cells, are activated and transduced with lentiviral particles encoding a BCMA specific CAR and RQR8 driven by EF-1a promoter. Three different BCMA specific CARs were used in this study: P5AC1-V2, PC1C12-V2 and COM22-V2 (see, Table 5 above). T cells were gene edited for deletion of the TCRα gene. Cells were cultured for 14 to 17 days and then cryopreserved in 90% FCS/10% DMSO. For T cell injection, T cells were rapidly thawed in a 37° C. waterbath and washed twice with RPMI 1640 medium containing 25 mM Hepes. Cells were injected in 0.2 ml RPMI 1640 with 25 mM Hepes into the tail vein of tumor-bearing animals.

NSG mice were irradiated with 1 Gy total body irradiation (RAD Source Technologies) one day prior to tumor cell inoculation. $5 \times 10^6$ MM1.S/Luc2-EGFP cells or $2 \times 10^6$ Molp-8/Luc2-EGFP cells were injected into the tail vein in 0.1 ml of phosphate-buffered saline (PBS). Tumor burden was measured twice weekly using bioluminescence imaging. Mice were injected with 3 ug D-Luciferin dissolved in 0.2 ml PBS and anesthetized using isofluorane. 7 minutes after injection animals were imaged using a Perkin Elmer IVIS Spectrum camera system. The total body luminescence with the exception of the mouse tail was measured and tumor burden is reported as total flux (photons per second). Tumors were allowed to establish until exponential growth occurred. Animals were randomized into treatment groups based on total flux and treated with BCMA specific CAR-T cells or untransduced control T cells from the same donor. The effect of CAR-T treatment was assessed twice weekly using bioluminescence imaging and body weight measurements. The study endpoint was reached when the first animal exhibited end-stage disease as indicated by body weight loss (>20% of initial body weight), hindleg paralysis, or other signs of animal distress. Statistical analysis was performed using GraphPad Prism 6. Repeated measures one-way ANOVA with Tukey's correction was used to compare anti-tumor efficacy between all groups. P<0.05 was considered significant.

Results are summarized in Table 11 (MM1.S) and Table 12 (Molp-8) below ($\log_{10}$ values of total flux in photons per second +/−SEM). A suboptimal CAR-T cell dose was used to compare BCMA specific CAR-T cells having different scFvs. The BCMA specific CAR-T cell groups are P5AC1-V2, PC1C12-V2 and COM22-V2 (see, Table 5 above). In the MM1.S model, $3.5 \times 10^6$ CAR-expressing T cells were injected on day 17 after tumor implantation. In the Molp8 model, $4 \times 10^6$ CAR-expressing T cells were injected on day 7 after tumor implantation. Transduction efficiencies ranged from 19% to 29% for BCMA specific CAR-T cells dosed in MM1.S mouse model and 31% to 36% for BCMA specific CAR-T cells dosed in Molp8 mouse model. An equivalent total dose of untransduced T cells was used for the control group. The control T cell-treated group exhibited progressive tumor growth until the study endpoint was reached at day 35 for MM1.S and day 23 for Molp8. Statistical analysis of the tumor burden using the RM-ANOVA test with Dunnets correction showed that in all three BCMA specific CAR-T treated groups, tumor burden was significantly lower compared to the tumor burden in the control group (p<0.01) (Tables 11 and 12). For example, in the MM1.S tumor model, mean total flux in animals treated with P5AC1-V2 BCMA specific CAR-T cells was 6.44 log 10 photons/s at day 25, compared to 9.22 log 10 photons/s in animals given control T cells (Table 11). At day 35 post tumor implantation, mean total flux in animals treated with P5AC1-V2 BCMA specific CAR-T cells was 6.82 log 10 photons/s, compared to 10.18 log 10 photons/s in animals given control T cells (Table 11). In the Molp8 tumor model, mean total flux in animals treated with P5AC1-V2 BCMA specific CAR-T cells was 7.88 log 10 photons/s at day 14, compared to 9.39 log 10 photons/s in animals given control T cells (Table 12). At day 23 post tumor implantation, mean total flux in animals treated with P5AC1-V2 BCMA specific CAR-T cells was 9.29 log 10 photons/s, compared 10.37 log 10 photons/s in animals given control T cells (Table 12).

These results demonstrate that treatments with BCMA specific CAR-T cells are effective to induce tumor regression.

TABLE 11

Tumor bioluminescence measurements of orthotopic MM1.S tumor model

Group 1: Control T cells

| Days after tumor implantation | Mean total flux (log10 photons/s) | SEM | N |
|---|---|---|---|
| 17 | 7.84 | 0.04 | 10 |
| 21 | 8.16 | 0.19 | 10 |
| 25 | 9.22 | 0.02 | 10 |
| 28 | 9.53 | 0.02 | 10 |
| 32 | 9.96 | 0.05 | 10 |
| 35 | 10.18 | 0.07 | 10 |

| Days after tumor implantation | Mean total flux (log10) | SEM | N |
|---|---|---|---|
| Group 2: P5AC1-V2 BCMA specific CAR-T cells | | | |
| 17 | 7.84 | 0.03 | 10 |
| 21 | 8.14 | 0.11 | 10 |
| 25 | 6.44 | 0.16 | 10 |
| 28 | 6.51 | 0.09 | 10 |
| 32 | 6.72 | 0.10 | 10 |
| 35 | 6.82 | 0.09 | 10 |
| Group 3: PC1C12-V2 BCMA specific CAR-T cells | | | |
| 17 | 7.86 | 0.04 | 10 |
| 21 | 8.56 | 0.15 | 10 |
| 25 | 6.85 | 0.26 | 10 |
| 28 | 6.41 | 0.30 | 10 |
| 32 | 6.64 | 0.29 | 10 |
| 35 | 6.62 | 0.30 | 10 |
| Group 4: COM22-V2 BCMA specific CAR-T cells | | | |
| 17 | 7.84 | 0.04 | 10 |
| 21 | 8.49 | 0.10 | 10 |
| 25 | 6.55 | 0.08 | 10 |
| 28 | 6.40 | 0.09 | 10 |
| 32 | 6.98 | 0.14 | 10 |
| 35 | 6.87 | 0.22 | 10 |

TABLE 12

Tumor bioluminescence measurements of orthotopic Molp-8 tumor model

| Days after tumor implantation | Mean total flux (log10) | SEM | N |
|---|---|---|---|
| Group 1: T cell only control | | | |
| 0 | 5.80 | 0.02 | 10 |
| 7 | 7.48 | 0.04 | 10 |
| 10 | 8.24 | 0.06 | 10 |
| 14 | 9.39 | 0.04 | 10 |
| 17 | 9.88 | 0.03 | 10 |
| 21 | 10.12 | 0.04 | 10 |
| 23 | 10.37 | 0.03 | 10 |
| Group 2: P5AC1-V2 BCMA specific CAR-T cells | | | |
| 0 | 5.80 | 0.02 | 10 |
| 7 | 7.48 | 0.04 | 10 |
| 10 | 8.41 | 0.05 | 10 |
| 14 | 7.88 | 0.18 | 10 |
| 17 | 7.39 | 0.21 | 10 |
| 21 | 7.98 | 0.12 | 10 |
| 23 | 8.29 | 0.11 | 10 |

TABLE 12-continued

Tumor bioluminescence measurements
of orthotopic Molp-8 tumor model

Group 3: PC1C12-V2 BCMA specific CAR-T cells

| | | | |
|---|---|---|---|
| 0 | 5.80 | 0.02 | 10 |
| 7 | 7.51 | 0.04 | 10 |
| 10 | 8.31 | 0.07 | 10 |
| 14 | 7.07 | 0.21 | 10 |
| 17 | 6.51 | 0.15 | 10 |
| 21 | 7.37 | 0.13 | 10 |
| 23 | 7.75 | 0.13 | 10 |

Group 4: COM22-V2 BCMA specific CAR-T cells

| Days after tumor implantation | Mean total flux (log10 | SEM | N |
|---|---|---|---|
| 0 | 5.80 | 0.02 | 10 |
| 7 | 7.49 | 0.04 | 10 |
| 10 | 8.39 | 0.07 | 10 |
| 14 | 7.78 | 0.16 | 10 |
| 17 | 7.51 | 0.21 | 10 |
| 21 | 7.89 | 0.17 | 10 |
| 23 | 8.32 | 0.14 | 10 |

Example 6

Treatment of Multiple Myeloma with TCRα/dCK Knockout BCMA Specific CAR-T Cells

This example illustrates the therapeutic activity of BCMA specific CAR-T cells in orthotopic mouse models of multiple myeloma.

A humanized mouse model was used to evaluate the efficacy of BCMA CAR-T cells against human myeloma cell lines expressing BCMA. 6 to 8 week old female Nod/Scid IL2rg−/− (NSG) mice were purchased from the Jackson Laboratories. All animals were housed in a pathogen free vivarium facility at Rinat and experiments were conducted according to the protocols in accordance with the Institutional Animal Care and Use Committee (IACUC) guidelines.

The MM1.S cell lines was purchased from the American Type Culture Collection (ATCC.org). The Cell line was engineered to express a Luc-GFP fusion protein using lentiviral particles (amsbio) and gene edited using TALEN nucleases to disable the deoxycytidine (dCK) gene. Cells were cultured in RPMI 1640 medium with L-glutamine supplemented with 10% fetal calf serum at 37° C. in 5% carbon dioxide ($CO_2$). Cells growing in an exponential growth phase were harvested and used for tumor inoculation.

Therapeutic CAR-T cells were produced as described. Healthy human donor cells, peripheral blood mononuclear cells (PBMC) or purified pan-T cells, are activated and transduced with lentiviral particles encoding for BCMA scFV, CD8 hinge, CD8 transmembrane, 41BB and CD3ζ with RQR8 genes under the control of the EF-1a promoter. The BCMA specific CAR-T cells were gene edited to delete the TCRα and/or the dCK gene using a combination of TCRα and dCK TALEN, or TCRα TALEN alone. Transduction efficiency for all T cells was 70%. TCRα knockout T cells were purified using magnetic selection kits for CD3-positive cells (Miltenyi); dCK knockout T cells were purified by expansion in the presence of 0.5 µM clofarabine. Cells were cultured for 14 to 17 days and then cryopreserved in 90% FCS/10% DMSO. For T cell injection, T cells were rapidly thawed in a 37° C. water bath and washed twice with RPMI 1640 medium containing 25 mM Hepes. For treatment, T cells were injected in 0.2 ml RPMI 1640 with 25 mM Hepes into the tail vein of tumor-bearing animals.

For the mouse tumor model, animals were injected with MM1.S/dCK KO tumor cells. Mice were then treated with $2.5 \times 10^6$ BCMA specific CAR-T cells on day 18 post tumor cell implantation. An equivalent dose of untransduced T cells that received TCRα and dCK TALEN was used as control. Animals were treated with clofarabine or vehicle for five days after T cell injection.

Results: the control T cell-treated group exhibited progressive tumor growth until the study endpoint was reached at day 35 (Table 13, Group 1). Compared against control, groups treated with TCRα knockout BCMA specific CAR-T cells and vehicle exhibited a significant decrease in tumor burden (p<0.05) that was diminished upon coadministration of clofarabine (p<0.05) (Table 13, Groups 2 and 3). Tumor burden was significantly reduced in animals treated with TCRα/dCK double knockout CAR-T cells, irrespective of whether the animals received vehicle or clofarabine (p<0.05) (Table 13, Groups 4 and 5). Reduction of tumor burden in the groups receiving TCRα/dCK double knockout T cells did not differ from the group receiving TCRα single knockout T cells and vehicle (p>0.1) (Table 13, Groups 2, 4, and 5).

These results demonstrate that treatments with TCRα/dCK double knockout BCMA CAR-T cells are effective to induce tumor regression in the presence of nucleoside analog therapies such as fludarabine and clofarabine.

TABLE 13

Tumor bioluminescence measurements of nucleoside analog therapy-resistant orthotopic MM1.S tumor model.

Group 1: TCRα/dCK KO control T cells + clofarabine

| Days after T cell administration | Mean total flux (log10 photons/s) | SEM | N |
|---|---|---|---|
| 0 | 7.87 | 0.04 | 10 |
| 4 | 8.94 | 0.08 | 10 |
| 8 | 9.22 | 0.05 | 10 |
| 11 | 9.52 | 0.04 | 10 |
| 15 | 10.00 | 0.04 | 10 |
| 18 | 10.38 | 0.04 | 10 |

| Days after T cell administration | Mean total flux (log10) | SEM | N |
|---|---|---|---|

Group 2: TCRα KO BCMA specific CAR-T cells + vehicle

| | | | |
|---|---|---|---|
| 0 | 7.86 | 0.04 | 10 |
| 4 | 9.28 | 0.07 | 10 |
| 8 | 8.58 | 0.12 | 10 |
| 11 | 8.04 | 0.14 | 10 |
| 15 | 8.14 | 0.15 | 10 |
| 18 | 8.24 | 0.15 | 10 |

Group 3: TCRα KO BCMA specific CAR-T cells + clofarabine

| | | | |
|---|---|---|---|
| 0 | 7.87 | 0.04 | 10 |
| 4 | 9.33 | 0.07 | 10 |
| 8 | 9.17 | 0.07 | 10 |
| 11 | 8.95 | 0.14 | 10 |
| 15 | 9.36 | 0.08 | 10 |
| 18 | 9.50 | 0.07 | 10 |

TABLE 13-continued

Tumor bioluminescence measurements of nucleoside analog therapy-resistant orthotopic MM1.S tumor model.

| Group 4: TCRα/dCK KO BCMA specific CAR-T cells + vehicle | | | |
|---|---|---|---|
| 0 | 7.86 | 0.04 | 10 |
| 4 | 9.19 | 0.08 | 10 |
| 8 | 9.08 | 0.12 | 10 |
| 11 | 8.59 | 0.18 | 10 |
| 15 | 8.60 | 0.21 | 10 |
| 18 | 8.69 | 0.18 | 10 |
| Group 5: TCRα/dCK KO BCMA specific CAR-T cells + clofarabine | | | |
| 0 | 7.87 | 0.04 | 10 |
| 4 | 9.26 | 0.09 | 10 |
| 8 | 9.07 | 0.10 | 10 |
| 11 | 8.51 | 0.14 | 10 |
| 15 | 8.42 | 0.21 | 10 |
| 18 | 8.49 | 0.18 | 10 |

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

---

It is claimed:

1. A method of treating a condition associated with malignant cells expressing B-cell maturation antigen (BCMA) in a subject comprising:
    administering to a subject in need thereof an effective amount of a pharmaceutical composition comprising an engineered immune cell expressing at the surface a BCMA-specific chimeric antigen receptor (CAR) comprising an extracellular ligand-binding domain, a first transmembrane domain, and an intracellular signaling domain and wherein the extracellular ligand-binding domain comprises a single chain Fv fragment (scFv) comprising
    (i) a heavy chain variable (VH) region comprising the amino acid sequence shown in SEQ ID NO: 33 and a light chain variable (VL) region comprising the amino acid sequence shown in SEQ ID NO: 34;
    (ii) a heavy chain variable (VH) region comprising the amino acid sequence shown in SEQ ID NO: 112 and a light chain variable (VL) region comprising the amino acid sequence shown in SEQ ID NO: 38;
    (iii) a heavy chain variable (VH) region comprising the amino acid sequence shown in SEQ ID NO: 72 and a light chain variable (VL) region comprising the amino acid sequence shown in SEQ ID NO: 73;
    (iv) a heavy chain variable (VH) region comprising the amino acid sequence shown in SEQ ID NO: 39 and a light chain variable (VL) region comprising the amino acid sequence shown in SEQ ID NO: 40;
    (v) a heavy chain variable (VH) region comprising the amino acid sequence shown in SEQ ID NO: 76 and a light chain variable (VL) region comprising the amino acid sequence shown in SEQ ID NO: 77;
    (vi) a heavy chain variable (VH) region comprising the amino acid sequence shown in SEQ ID NO: 83 and a light chain variable (VL) region comprising the amino acid sequence shown in SEQ ID NO: 84;
    (vii) a heavy chain variable (VH) region comprising the amino acid sequence shown in SEQ ID NO: 92 and a light chain variable (VL) region comprising the amino acid sequence shown in SEQ ID NO: 93;
    (viii) a heavy chain variable (VH) region comprising the amino acid sequence shown in SEQ ID NO: 25 and a light chain variable (VL) region comprising the amino acid sequence shown in SEQ ID NO: 18; or
    (ix) a heavy chain variable (VH) region comprising the amino acid sequence shown in SEQ ID NO: 8 and a light chain variable (VL) region comprising the amino acid sequence shown in SEQ ID NO: 80,
    wherein the transmembrane domain comprises a CD8α chain transmembrane domain, and wherein the intracellular signaling domain comprises a CD3ξ signaling domain and/or a 4-1BB signaling domain.

2. The method of claim 1, wherein the VH region comprises the amino acid sequence shown in SEQ ID NO: 33 and the VL region comprises the amino acid sequence shown in SEQ ID NO: 34.

3. The method of claim 1, wherein the VH region comprises the amino acid sequence shown in SEQ ID NO: 112 and the VL region comprises the amino acid sequence shown in SEQ ID NO: 38.

4. The method of claim 1, wherein the BCMA specific CAR comprises the amino acid sequence shown in SEQ ID NO: 344.

5. The method of claim 4, wherein the BCMA specific CAR comprises a CD20 epitope.

6. The method of claim 5, wherein the CD20 epitope comprises the amino acid sequence shown in SEQ ID NO: 397 or SEQ ID NO: 398.

7. The method of claim 1,
    wherein the BCMA specific CAR comprises a CD8a signal peptide having the sequence of SEQ ID NO: 318; a VH region having the sequence of SEQ ID NO: 33; a GS linker having the sequence of SEQ ID NO: 333; a VL region having the sequence of SEQ ID NO: 34; a CD20 epitope having the sequence of SEQ ID NO: 398; a CD8a hinge having the sequence of SEQ ID NO: 320; a CD8α transmembrane domain having the sequence of SEQ ID NO: 322; a 4-1BB intracellular signaling domain having the sequence of SEQ ID NO: 323; and a CD3ζ intracellular signaling domain having the sequence of SEQ ID NO: 324;
    wherein the BCMA specific CAR further comprises a stalk domain between the extracellular ligand-binding domain and the first transmembrane domain;
    wherein the BCMA specific CAR further comprises a CD20 epitope;
    wherein the BCMA specific CAR further comprises another extracellular ligand-binding domain that is not specific for BCMA binding;
    wherein the engineered immune cell further comprises another CAR that is not specific for BCMA;
    wherein the engineered immune cell further comprises a polynucleotide encoding a suicide polypeptide; or
    wherein the engineered immune cell further comprises a disruption in one or more endogenous genes, wherein the endogenous gene encodes TCRα, TCRβ, CD52, glucocorticoid receptor (GR), deoxycytidine kinase (dCK), or an immune checkpoint protein.

8. The method of claim 7, wherein the stalk domain is selected from the group consisting of: a human CD8α hinge, an IgG1 hinge, and an FcγRIIIα hinge.

9. The method of claim 7, wherein the CD20 epitope comprises the amino acid sequence shown in SEQ ID NO: 397 or SEQ ID NO: 398.

10. The method of claim 7, wherein the endogenous gene encodes an immune checkpoint protein.

11. The method of claim 7, wherein the immune checkpoint protein is selected from the group consisting of PD-1, CTLA-4, LAG3, Tim3, BTLA, BY55, TIGIT, B7H5, LAIR1, SIGLEC10 and 2B4.

12. The method of claim 1,
wherein the engineered immune cell is selected from the group consisting of: a T cell, a dendritic cell, a killer dendritic cell, a mast cell, an NK-cell, and a B cell;
wherein the engineered immune cell is an inflammatory T-lymphocyte, a cytotoxic T-lymphocyte, a regulatory T-lymphocyte, or a helper T-lymphocyte; or
wherein the engineered immune cell is an autologous immune cell or an allogeneic immune cell.

13. A method of treating a condition associated with malignant cells expressing B-cell maturation antigen (BCMA) in a subject comprising:
administering to a subject in need thereof an effective amount of a pharmaceutical composition comprising an engineered immune cell expressing at the surface a BCMA-specific chimeric CAR comprising an extracellular ligand-binding domain, a first transmembrane domain, and an intracellular signaling domain, wherein the extracellular ligand-binding domain comprises a single chain Fv fragment (scFv) comprising
(i) a VH region comprising a VH complementarity determining region 1 (VH CDR1), a VH complementarity determining region 2 (VH CDR2), and a VH complementarity determining region 3 (VH CDR3), wherein the VH CDR1 comprises the amino acid sequence shown in SEQ ID NO: 150, 151, or 152; the VH CDR2 comprises the amino acid sequence shown in SEQ ID NO: 153 or 154; the VH CDR3 comprises the amino acid sequence shown in SEQ ID NO: 155, and
a VL region comprising a VL complementarity determining region 1 (VL CDR1), a VL complementarity determining region 2 (VL CDR2), and a VL complementarity determining region 3 (VL CDR3), wherein the VL CDR1 comprises the amino acid sequence shown in SEQ ID NO: 209; the VL CDR2 comprises the amino acid sequence shown in SEQ ID NO: 221; the VL CDR3 comprises the amino acid sequence shown in SEQ ID NO: 222;
(ii) a VH region comprising a VH CDR1, a VH CDR2, and a VH CDR3, wherein the VH CDR1 comprises the amino acid sequence shown in SEQ ID NO: 151, 156, or 157; the VH CDR2 comprises the amino acid sequence shown in SEQ ID NO: 158 or 159; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 209; the VL CDR2 comprises the amino acid sequence shown in SEQ ID NO: 221; the VL CDR3 comprises the amino acid sequence shown in SEQ ID NO: 225;
(iii) a VH region comprising a VH CDR1, a VH CDR2, and a VH CDR3, wherein the VH CDR1 comprises the amino acid sequence shown in SEQ ID NO: 150, 151, or 152; the VH CDR2 comprises the amino acid sequence shown in SEQ ID NO: 187 or 188; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 249; the VL CDR2 comprises the amino acid sequence shown in SEQ ID NO: 221; the VL CDR3 comprises the amino acid sequence shown in SEQ ID NO: 225;
(iv) a VH region comprising a VH CDR1, a VH CDR2, and a VH CDR3, wherein the VH CDR1 comprises the amino acid sequence shown in SEQ ID NO: 150, 151, or 152; the VH CDR2 comprises the amino acid sequence shown in SEQ ID NO: 165 or 166; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 226; the VL CDR2 comprises the amino acid sequence shown in SEQ ID NO: 221; the VL CDR3 comprises the amino acid sequence shown in SEQ ID NO: 227;
(v) a VH region comprising a VH CDR1, a VH CDR2, and a VH CDR3, wherein the VH CDR1 comprises the amino acid sequence shown in SEQ ID NO: 150, 151, or 152; the VH CDR2 comprises the amino acid sequence shown in SEQ ID NO: 159 or 162; the VH CDR3 comprises the amino acid sequence shown in SEQ ID NO: 161, and
a VL region comprising a VL CDR1, a VL CDR2, and a VL CDR3, wherein the VL CDR1 comprises the amino acid sequence shown in SEQ ID NO: 251; the VL CDR2 comprises the amino acid sequence shown in SEQ ID NO: 252; the VL CDR3 comprises the amino acid sequence shown in SEQ ID NO: 253;
(vi) a VH region comprising a VH CDR1, a VH CDR2, and a VH CDR3, wherein the VH CDR1 comprises the amino acid sequence shown in SEQ ID NO: 151, 156, or 157; the VH CDR2 comprises the amino acid sequence shown in SEQ ID NO: 190 or 191; the VH CDR3 comprises the amino acid sequence shown in SEQ ID NO: 161, and
a VL region comprising a VL CDR1, a VL CDR2, and a VL CDR3, wherein the VL CDR1 comprises the amino acid sequence shown in SEQ ID NO: 262; the VL CDR2 comprises the amino acid sequence shown in SEQ ID NO: 252; the VL CDR3 comprises the amino acid sequence shown in SEQ ID NO: 263;
(vii) a VH region comprising a VH CDR1, a VH CDR2, and a VH CDR3, wherein the VH CDR1 comprises the amino acid sequence shown in SEQ ID NO: 150, 151, or 152; the VH CDR2 comprises the amino acid sequence shown in SEQ ID NO: 154 or 169; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 271; the VL CDR2 comprises the amino acid sequence shown in SEQ ID NO: 221; the VL CDR3 comprises the amino acid sequence shown in SEQ ID NO: 272;
(viii) a VH region comprising a VH CDR1, a VH CDR2, and a VH CDR3, wherein the VH CDR1 comprises the amino acid sequence shown in SEQ ID NO: 129, 130, or 131; the VH CDR2 comprises the amino acid sequence shown in SEQ ID NO: 139 or 140; the VH CDR3 comprises the amino acid sequence shown in SEQ ID NO: 134, and
a VL region comprising a VL CDR1, a VL CDR2, and a VL CDR3, wherein the VL CDR1 comprises the amino acid sequence shown in SEQ ID NO: 217; the VL CDR2 comprises the amino acid sequence shown in SEQ ID NO: 210; the VL CDR3 comprises the amino acid sequence shown in SEQ ID NO: 216; or
(ix) a VH region comprising a VH CDR1, a VH CDR2, and a VH CDR3, wherein the VH CDR1 comprises the amino acid sequence shown in SEQ ID NO: 129, 130, or 131; the VH CDR2 comprises the amino acid sequence shown in SEQ ID NO: 132 or 133; the VH CDR3 comprises the amino acid sequence shown in SEQ ID NO: 137, and a VL region comprising a VL CDR1, a VL CDR2, and a VL CDR3, wherein the VL CDR1 comprises the amino acid sequence shown in SEQ ID NO: 377; the VL CDR2 comprises the amino acid sequence shown in SEQ ID NO: 210; the VL CDR3 comprises the amino acid sequence shown in SEQ ID NO: 214, wherein the transmembrane domain comprises a CD8α chain transmembrane domain, and wherein the intracellular signaling domain comprises a CD3ξ signaling domain and/or a 4-1BB signaling domain.

14. The method of claim 13, wherein the extracellular ligand-binding domain comprises a single chain Fv fragment (scFv) comprising
(i) a VH region comprising a VH CDR1, a VH CDR2, and a VH CDR3, wherein the VH CDR1 comprises the amino acid sequence shown in SEQ ID NO: 150, 151, or 152; the VH CDR2 comprises the amino acid sequence shown in SEQ ID NO: 153 or 154; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 209; the VL CDR2 comprises the amino acid sequence shown in SEQ ID NO: 221; the VL CDR3 comprises the amino acid sequence shown in SEQ ID NO: 222.

15. The method of claim 13, wherein the extracellular ligand-binding domain comprises a single chain Fv fragment (scFv) comprising
a VH region comprising a VH CDR1, a VH CDR2, and a VH CDR3, wherein the VH CDR1 comprises the amino acid sequence shown in SEQ ID NO: 151, 156, or 157; the VH CDR2 comprises the amino acid sequence shown in SEQ ID NO: 158 or 159; the VH CDR3 comprises the amino acid sequence shown in SEQ ID NO: 155, and
a VL region comprising a VL CDR1, a VL CDR2, and a VL CDR3, wherein the VL CDR1 comprises the amino acid sequence shown in SEQ ID NO: 209; the VL CDR2 comprises the amino acid sequence shown in SEQ ID NO: 221; the VL CDR3 comprises the amino acid sequence shown in SEQ ID NO: 225.

16. The method of claim 13, wherein the BCMA specific CAR comprises the amino acid sequence shown in SEQ ID NO: 344.

17. The method of claim 16, wherein the BCMA specific CAR comprises a CD20 epitope.

18. The method of claim 17, wherein the CD20 epitope comprises the amino acid sequence shown in SEQ ID NO: 397 or SEQ ID NO: 398.

19. The method of claim 13,
wherein the BCMA specific CAR comprises a CD8a signal peptide having the sequence of SEQ ID NO: 318; a VH region having the sequence of SEQ ID NO: 33; a GS linker having the sequence of SEQ ID NO: 333; a VL region having the sequence of SEQ ID NO: 34; a CD20 epitope having the sequence of SEQ ID NO: 398; a CD8a hinge having the sequence of SEQ ID NO: 320; a CD8α transmembrane domain having the sequence of SEQ ID NO: 322; a 4-1BB intracellular signaling domain having the sequence of SEQ ID NO: 323; and a CD3ζ intracellular signaling domain having the sequence of SEQ ID NO: 324;
wherein the BCMA specific CAR further comprises a stalk domain between the extracellular ligand-binding domain and the first transmembrane domain;
wherein the BCMA specific CAR further comprises a CD20 epitope;
wherein the BCMA specific CAR further comprises another extracellular ligand-binding domain that is not specific for BCMA binding;
wherein the engineered immune cell further comprises another CAR that is not specific for BCMA;
wherein the engineered immune cell further comprises a polynucleotide encoding a suicide polypeptide; or
wherein the engineered immune cell further comprises a disruption in one or more endogenous genes, wherein the endogenous gene encodes TCRα, TCRβ, CD52, glucocorticoid receptor (GR), deoxycytidine kinase (dCK), or an immune checkpoint protein.

20. The method of claim 19, wherein the stalk domain is selected from the group consisting of: a human CD8α hinge, an IgG1 hinge, and an FcγRIIIα hinge.

21. The method of claim 19, wherein the CD20 epitope comprises the amino acid sequence shown in SEQ ID NO: 397 or SEQ ID NO: 398.

22. The method of claim 19, wherein the endogenous gene encodes an immune checkpoint protein.

23. The method of claim 19, wherein the immune checkpoint protein is selected from the group consisting of PD-1, CTLA-4, LAG3, Tim3, BTLA, BY55, TIGIT, B7H5, LAIR1, SIGLEC10 and 2B4.

24. The method of claim 13,
wherein the engineered immune cell is selected from the group consisting of: a T cell, a dendritic cell, a killer dendritic cell, a mast cell, an NK-cell, and a B cell;
wherein the engineered immune cell is an inflammatory T-lymphocyte, a cytotoxic T-lymphocyte, a regulatory T-lymphocyte, or a helper T-lymphocyte; or
wherein the engineered immune cell is an autologous immune cell or an allogeneic immune cell.

* * * * *